United States Patent
Zhang et al.

(10) Patent No.: US 10,246,443 B2
(45) Date of Patent: *Apr. 2, 2019

(54) CYANOQUINOLINE DERIVATIVES

(71) Applicant: Tianjin Hemay Oncoloy Pharmaceutical Co., Ltd., Tianjin (CN)

(72) Inventors: Hesheng Zhang, Tianjin (CN); Yingwei Chen, Tianjin (CN); Qingchao He, Tianjin (CN)

(73) Assignee: TIANJIN HEMAY ONCOLOGY PHARMACEUTICAL CO., LTD., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,220

(22) Filed: Apr. 13, 2017

(65) Prior Publication Data
US 2017/0226093 A1 Aug. 10, 2017

Related U.S. Application Data

(63) Continuation of application No. 14/881,085, filed on Oct. 12, 2015, now Pat. No. 9,676,724, which is a continuation of application No. 13/702,987, filed as application No. PCT/CN2011/075464 on Jun. 8, 2011, now Pat. No. 9,187,458.

(30) Foreign Application Priority Data

Jun. 9, 2010 (CN) .......................... 2010 1 01994675

(51) Int. Cl.
| | | |
|---|---|---|
| C07D 217/26 | (2006.01) |
| C07D 401/12 | (2006.01) |
| C07D 401/14 | (2006.01) |
| C07D 405/12 | (2006.01) |
| C07D 405/14 | (2006.01) |
| C07D 409/14 | (2006.01) |

(52) U.S. Cl.
CPC ......... *C07D 405/14* (2013.01); *C07D 217/26* (2013.01); *C07D 401/12* (2013.01); *C07D 401/14* (2013.01); *C07D 405/12* (2013.01); *C07D 409/14* (2013.01)

(58) Field of Classification Search
CPC ... A61P 35/00; A61K 31/497; A61K 31/4709; A61K 31/5377; A61K 31/506; C07D 401/14; C07D 401/12; C07D 405/12; C07D 405/14; C07D 409/14
USPC .......................................... 514/312; 546/160
See application file for complete search history.

(56) References Cited

U.S. PATENT DOCUMENTS

| | | |
|---|---|---|
| 6,153,617 A | 11/2000 | Bridges |
| 6,972,288 B1 | 12/2005 | Himmelsbach et al. |
| 8,198,301 B2 | 6/2012 | Zhang |
| 9,187,458 B2 * | 11/2015 | Zhang .................. C07D 401/12 |
| 9,676,724 B2 * | 6/2017 | Zhang .................. C07D 401/12 |
| 2003/0212276 A1 | 11/2003 | Boschelli et al. |
| 2009/0105247 A1 | 4/2009 | Zhang |

FOREIGN PATENT DOCUMENTS

| | | |
|---|---|---|
| CN | 101824029 A | 9/2010 |
| WO | 00/68201 A1 | 11/2000 |

OTHER PUBLICATIONS

Banker, et al, "Modern Pharmaceutics," 3 ed., Marcel Dekker, New York, pp. 451 and 596 (1996).
Boschelli, et al., "7-Alkoxy-4-phenylamino-3-quinolinecarbonitriles as Dual Inhibitors of Src and Abl Kinases," *J. Med. Chem.*, vol. 47, pp. 1599-1601 (2004).
Eskins, et al., "A phase I dose escalation of BIBW 2992, an irreversible dual inhibitor of epidermal growth factor receptor 1 (EGFR) and 2 (HER2) tyrosine kinase in a 2-week on, 2-week off schedule in patients with advanced solid tumours," *British Journal of Cancer*, vol. 98, pp. 80-85 (2008).
Pannala, et al., "Synthesis and Structure-activity relationship of 4-(2-aryl-cyclopropylamino)-quinoline-3-carbonitriles as EGFR Tyrosine kinase inhibitors," *Bioorganic & Medicinal Chemistry*, vol. 17, pp. 5978-5982 (2007).
Thaimattam, et al, "3D-QSAR studies on c-Src Kinase inhibitors and docking analyses of a potent dual kinase inhibitor of c-Src and c-Abl kinases," *Bioorganic & Medicinal Chemistry*, vol. 13, pp. 4704-4712 (2005).
Tsou, et al., "6-Substituted-4-(3-bromophenylamino)quinazolines as Putative Irreversible Inhibitors of the Epidermal Growth Factor Growth Factor Receptor (EGFR) and Human Epidermal Gowth Factor Receptor (HER-2) Tyrosine Kinases with Enhanced Antitumor Activity.," *Med. Chem.*, vol. 44, pp. 2719-2734 (2001).
Wissner, et al., "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," *J. Med. Chem.*, vol. 46, pp. 49-63 (2003).

(Continued)

*Primary Examiner* — Daniel R Carcanague
(74) *Attorney, Agent, or Firm* — Kilpatrick Townsend & Stockton LLP

(57) ABSTRACT

Disclosed is a compound of formula I, a stereoisomer thereof, a cis-trans-isomer thereof, a tautomer thereof, or a mixture thereof, or a pharmaceutically acceptable salt thereof, a solvate thereof or a prodrug thereof,

I

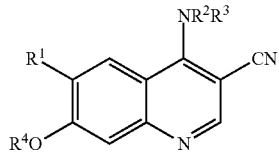

wherein $R^1$, $R^2$, $R^3$ and $R^4$ are each as defined in the present application.

20 Claims, No Drawings

(56) References Cited

OTHER PUBLICATIONS

Wolff, "Burger's Medicinal Chemistry, 5 ed., Part 1", John Wiley & Sons, pp. 975-977 (1995).
International Search Report dated Sep. 29, 2011, issued in related International Patent Application No. PCT/CN2011/075464, filed Jun. 8, 2010.

* cited by examiner

CYANOQUINOLINE DERIVATIVES

CROSS REFERENCE TO RELATED APPLICATIONS

This application is a continuation of U.S. application Ser. No. 14/881,085, filed Oct. 12, 2015, which is a continuation of U.S. application Ser. No. 13/702,987, filed May 3, 2013, now U.S. Pat. No. 9,187,458, which is a U.S. National Phase of PCT/CN2011/075464, filed Jun. 8, 2011, which claims priority to CN 201010199467.5, filed Jun. 9, 2010, the disclosures of which are incorporated herein by reference for all purposes.

FIELD

The present application is directed to organic chemistry and pharmaceutical chemistry.

BACKGROUND

In worldwide, the tumor, including cancer, is one of the major factors leading to death. Although there is a notable development in the discovery of novel methods for treating tumor, the major selections for therapy are still the surgery operation, chemotherapy and radiotherapy. The three therapeutic treatment methods can be used alone or in combination. However, the surgery operation and radiotherapy generally are useful for patients, of which the tumor type has been identified. There are limits of the surgery operation and radiotherapy for treating patients, of which the tumor has spread. The chemotherapy is generally useful for treating patients having metastatic cancer or diffuse carcinoma, such as leukemia. Although the chemotherapy has therapeutic values, it usually does not cure the diseases because cancer cells of patients are tolerant to the drugs of chemotherapy.

Therefore, there is a need for novel chemotherapeutants to treat tumor. In this regard, different researchers are doing continuous efforts to discover novel potential effective chemotherapeutic drugs.

SUMMARY

In one aspect, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof,

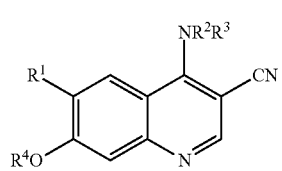

wherein:
$R^1$ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

$R^2$ and $R^3$ are each independently selected from the group consisting of hydrogen, substituted or unsubstituted aralkyl, substituted or unsubstituted aryl, and substituted or unsubstituted heteroaryl;

or $R^2$ and $R^3$ together with nitrogen atom to which they are attached form substituted or unsubstituted heterocyclyl; and $R^4$ is substituted or unsubstituted heterocyclyl, or substituted or unsubstituted heteroaryl.

In another aspect, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof,

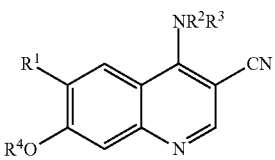

wherein:
$R^1$ is selected from the group consisting of $C_1$-$C_6$ alkylacylamino, $C_2$-$C_6$ alkenylacylamino, $C_2$-$C_6$ alkynylacylamino, $C_6$-$C_{18}$ arylacylamino, $C_1$-$C_6$ alkyl-substituted amino, $C_1$-$C_6$ alkoxy;

$R^2$ and $R^3$ are each independently selected from the group consisting of hydrogen, $C_7$-$C_{24}$ aralkyl, substituted or unsubstituted $C_6$-$C_{18}$ aryl, substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, $C_6$-$C_{18}$ aryloxy, and $C_5$-$C_{18}$ heteroaryloxy, and a substituent on the heteroaryl is selected from $C_7$-$C_{24}$ aralkyl, $C_6$-$C_{18}$ arylacylamino, $C_6$-$C_{18}$ arylsulfonylamino, $C_5$-$C_{18}$ heteroaryl acylamino, $C_3$-$C_{10}$ cycloalkylacylamino, $C_6$-$C_{18}$ arylaminoacyl, $C_7$-$C_{24}$ aralkyloxy, $C_6$-$C_{24}$ heteroaralkyloxy, and $C_6$-$C_{18}$ aryloxy;

or $R^2$ and $R^3$ together with nitrogen atom to which they are attached form substituted or unsubstituted $C_3$-$C_{18}$ heterocyclyl; and $R^4$ is $C_3$-$C_{18}$ heterocyclyl or $C_5$-$C_{18}$ heteroaryl.

In another aspect, the present application is directed to a pharmaceutical composition, comprising a therapeutically effective amount of a compound of formula I, a stereoisomer thereof, a cis-trans-isomer thereof, a tautomer thereof, or a mixture thereof, or a pharmaceutically acceptable salt thereof, a solvate thereof or prodrug thereof, and a pharmaceutically acceptable carrier.

In yet another aspect, the present application is directed to a method for treating and/or preventing a tumor in a mammal, comprising administering to the mammal in need thereof a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof.

In another aspect, the present application is directed to a method for inhibiting growth of tumor cells, comprising contacting the tumor cells with a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof.

In still another aspect, the present application is directed to a method for inhibiting overexpression or mutation of a receptor tyrosine kinase in a mammal, comprising contacting the receptor tyrosine kinase with a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof.

In still yet another aspect, the present application is directed to a method for treating and/or preventing physiological abnormity caused by overexpression or mutation of a receptor tyrosine kinase in a mammal, comprising administering to the mammal in need thereof a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof.

DETAILED DESCRIPTION

Definitions

Certain chemical groups named herein are preceded by a shorthand notation indicating the total number of carbon atoms that are to be found in the indicated chemical group. For example, $C_7$-$C_{12}$ alkyl describes an alkyl group, as defined below, having a total of 7 to 12 carbon atoms, and $C_3$-$C_{10}$ cycloalkyl describes a cycloaklyl group, as defined below, having a total of 3 to 10 carbon atoms. The total number of carbon atoms in the shorthand notation does not include the carbons that may exist in the substituents of the groups described.

Furthermore, as used in the specification and appended claims of the present application, unless specified to the contrary, the following terms have the meanings indicated:

"Amino" refers to the —$NH_2$ group. The amino group may be substituted with a group selected from alkyl, alkenyl, alkynyl, haloalkyl, haloalkenyl, haloalkynyl, hydroxyalkyl, aralkyl, cycloalkyl, cycloalkylalkyl, and the like.

"Cyano" refers to the —CN group.

"Hydroxy" refers to the —OH group.

"Imino" refers to =NH substituent.

"Nitro" refers to the —$NO_2$ group.

"Oxo" refers to =O substituent.

"Thio" refers to =S substituent.

"Trifluoromethyl" refers to the —$CF_3$ group.

"Alkyl" refers to a straight or branched hydrocarbon chain group consisting solely of carbon and hydrogen, containing no unsaturation, having from one to twelve carbon atoms, preferably one to eight or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (tert-butyl), 3-methylhexyl, 2-methylhexyl, and the like. Unless stated otherwise specifically in the specification, an alkyl group may be optionally substituted by one or more groups independently selected from the group consisting of alkyl, alkenyl, halo, haloalkenyl, cyano, nitro, aryl, cycloalkyl, heterocyclyl, heteroaryl, oxo, trimethylsilyl, —$OR^{14}$, —OC(O)—$R^{14}$, —$N(R^{14})_2$, —C(O)$R^{14}$, —C(O)O$R^{14}$, —C(O)N($R^{14}$)$_2$, —$N(R^{14})C(O)OR^{16}$, —$N(R^{14})C(O)R^{16}$, —$N(R^{14})S(O)_tR^{16}$ (wherein t is 1 to 2), —$S(O)_tOR^{16}$ (wherein t is 1 to 2), —$S(O)_tR^{16}$ (wherein t is 0 to 2), and —$S(O)_tN(R^{14})_2$ (wherein t is 1 to 2).

In some embodiments, the alkyl group is $C_1$-$C_{12}$ alkyl.

In some embodiments, the alkyl group is $C_1$-$C_8$ alkyl.

In some embodiments, the alkyl group is $C_1$-$C_6$ alkyl.

"Alkenyl" refers to a straight or branched hydrocarbon chain group consisting solely of carbon and hydrogen atoms, containing at least one double bond, having two to twelve carbon atoms, preferably two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted with one or more groups independently selected from the group consisting of alkyl, alkenyl, halo, haloalkenyl, cyano, nitro, aryl, cycloalkyl, heterocyclyl, heteroaryl, oxo, trimethylsilyl, —$OR^{14}$, —OC(O)—$R^{14}$, —$N(R^{14})_2$, —C(O)$R^{14}$, —C(O)O$R^{14}$, —C(O)N($R^{14}$)$_2$, —$N(R^{14})C(O)OR^{16}$, —$N(R^{14})C(O)R^{16}$, —$N(R^{14})S(O)_tR^{16}$ (wherein t is 1 to 2), —$S(O)_tOR^{16}$ (wherein t is 1 to 2), —$S(O)_tR^{16}$ (wherein t is 0 to 2), and —$S(O)_tN(R^{14})_2$ (wherein t is 1 to 2).

In some embodiments, the alkenyl group is $C_2$-$C_{12}$ alkenyl.

In some embodiments, the alkenyl group is $C_2$-$C_8$ alkenyl.

In some embodiments, the alkenyl group is $C_2$-$C_6$ alkenyl.

"Alkynyl" refers to a straight or branched hydrocarbon chain group consisting solely of carbon and hydrogen atoms, containing at least one triple bond, having two to twelve carbon atoms, preferably two to six carbon atoms and which is attached to the rest of the molecule by a single bond, e.g., ethynyl, propynyl, butynyl, pentynyl, hexynyl, and the like. Unless stated otherwise specifically in the specification, an alkynyl group may be optionally substituted with one or more groups independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroaralkyl, —$OR^{14}$, —OC(O)—$R^{14}$, —$N(R^{14})_2$, —C(O)$R^{14}$, —C(O)O$R^{14}$, —C(O)N($R^{14}$)$_2$, —$N(R^{14})C(O)OR^{16}$, —$N(R^{14})C(O)R^{16}$, —$N(R^{14})S(O)_tR^{16}$ (wherein t is 1 to 2), —$S(O)_tOR^{16}$ (wherein t is 1 to 2), —$S(O)_tR^{16}$ (wherein t is 0 to 2), and —$S(O)_tN(R^{14})_2$ (wherein t is 1 to 2).

In some embodiments, the alkynyl group is $C_2$-$C_{12}$ alkynyl.

In some embodiments, the alkynyl group is $C_2$-$C_8$ alkynyl.

In some embodiments, the alkynyl group is $C_2$-$C_6$ alkynyl.

"Alkylene" or "alkylene chain" refers to a straight or branched divalent hydrocarbon chain, linking the rest of the molecule of a group, consisting solely of carbon and hydrogen, containing no unsaturation and having one to twelve carbon atoms, e.g., methylene, ethylidene, propylidene, n-butylidene, and the like. The alkylene chain is attached to the rest of the molecule through a single bond and other groups through a single bond. The alkylene chain may be attached to the rest of the molecule and to the group through one carbon within the chain or through any two carbons within the chain. Unless stated otherwise specifically in the specification, the alkylidene chain may be optionally substituted with one or more groups independently selected from the group consisting of alkyl, alkenyl, halo, haloalkenyl, cyano, nitro, aryl, cycloalkyl, heterocyclyl, heteroaryl, oxo, trimethylsilyl, —$OR^{14}$, —OC(O)—$R^{14}$, —$N(R^{14})_2$, —C(O)$R^{14}$, —C(O)O$R^{14}$, —C(O)N($R^{14}$)$_2$, —$N(R^{14})C(O)OR^{16}$, —$N(R^{14})C(O)R^{16}$, —$N(R^{14})S(O)_tR^{16}$ (wherein t is 1 to 2), —$S(O)_tOR^{16}$ (wherein t is 1 to 2), —$S(O)_tR^{16}$ (wherein t is 0 to 2), and —$S(O)_tN(R^{14})_2$ (wherein t is 1 to 2).

In some embodiments, the alkylene group is $C_1$-$C_{12}$ alkylidene.

In some embodiments, the alkylene group is $C_1$-$C_8$ alkylidene.

In some embodiments, the alkylene group is $C_1$-$C_6$ alkylidene.

"Alkenylene" or "alkenylene chain" refers to a straight or branched divalent hydrocarbon chain linking the rest of the molecule to a group, consisting solely of carbon and hydrogen, containing at least one double bond and having two to twelve carbon atoms, e.g., such as ethenylene, propenylene, n-butenylene, and the like. The alkenylene chain is attached to the rest of the molecule through a single bond and to other groups through a double bond or a single bond. The points of attachments of the alkenylene to the rest of the molecule and to other groups can be through one carbon or any two carbons within the chain. Unless stated otherwise specifically in the specification, the alkenylene may be optionally substituted with one or more groups independently selected from the group consisting of alkyl, alkenyl, halo, haloalkenyl, cyano, nitro, aryl, cycloalkyl, heterocyclyl, heteroaryl, oxo, trimethylsilyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (wherein t is 1 to 2), —$S(O)_tOR^{16}$ (wherein t is 1 to 2), —$S(O)_tR^{16}$ (wherein t is 0 to 2), and —$S(O)_tN(R^{14})_2$ (wherein t is 1 to 2).

In some embodiments, the alkenylene group is $C_2$-$C_{12}$ alkenylidene.

In some embodiments, the alkenylene group is $C_2$-$C_8$ alkenylidene.

In some embodiments, the alkenylene group is $C_2$-$C_6$ alkenylidene.

"Alkoxy" refers to a group of the formula —$OR_a$, where $R_a$ is an alkyl group as defined above. The alkoxy group contains one to twelve carbon atoms, preferably one to six carbon atoms. The alkyl part of the alkoxy group may be optionally substituted as defined above for for an alkyl group.

"Alkoxylalkyl" refers to a group of the formula —$R_a$—O—$R_a$, where each $R_a$ is independently an alkyl group as defined above. The oxygen atom may be bonded to any carbon in either alkyl group. Each alkyl part of the alkoxylalkyl group may be optionally substituted as defined above for an alkyl group.

"Aryl" refers to aromatic monocyclic or multicyclic hydrocarbon ring system consisting solely of hydrogen and carbon and containing from six to eighteen carbon atoms, where the ring system may be partially saturated. Aryl groups include, but are not limited to the groups such as phenyl, naphthyl and fluorenyl. Unless stated otherwise specifically in the specification, the term "aryl" or the prefix "ar-" (such as in "aralkyl") is meant to include aryl groups optionally substituted with one or more substituents independently selected from the group consisting of alkyl, alkenyl, halo, haloalkyl, haloalkenyl, cyano, nitro, aryl, heteroaryl, heteroaralkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (wherein t is 1 to 2), —$R^{15}$—$S(O)_tOR^{16}$ (wherein t is 1 to 2), —$R^{15}$—$S(O)_tR^{16}$ (wherein t is 0 to 2), and —$R^{15}$—$S(O)_tN(R^{14})_2$ (wherein t is 1 to 2).

In some embodiments, the aryl group is $C_6$-$C_{18}$ aryl.
In some embodiments, the aryl group is $C_6$-$C_{12}$ aryl.
In some embodiments, the aryl group is $C_6$-$C_{10}$ aryl.

"Aralkyl" refers to a group of the formula —$R_aR_b$, where $R_a$ is an alkyl group as defined above and $R_b$ is one or more aryl groups as defined above, e.g., benzyl, diphenylmethyl, and the like. The aryl part may be optionally substituted as described above.

"Aryloxy" refers to a group of the formula —$OR_b$, where $R_b$ is an aryl group as defined above. The aryl part of the aryloxy group may be optionally substituted as defined above.

"Aralkyloxy" refers to a group of the formula —$OR_c$, where $R_c$ is an aralkyl group as defined above. The aralkyl part of the aralkyloxy group may be optionally substituted as defined above.

"Cycloalkyl" refers to a stable non-aromatic monocyclic or multicyclic hydrocarbon group consisting solely of carbon and hydrogen atoms, including fused or bridged ring systems and having three to eighteen carbon atoms, preferably three to fifteen carbon atoms, preferably three to ten carbon atoms, and which is saturated or unsaturated and attatched to the rest of the molecule by a single bond. The monocyclic group comprises, e.g., cyclopropyl, cyclobutyl, cyclopentyl, cyclohexyl, cycloheptyl and cyclooctyl. The multicyclic group comprises, e.g., adamantanyl, norcamphanyl, decalinyl, 7,7-dimethyl-biscyclo[2.2.1]heptyl, and the like. Unless stated otherwise specifically in the specification, the term "cycloalkyl" is meant to include cycloalkyl groups which are optionally substituted with one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocycylylalkyl, heteroaryl, heteroaralkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (wherein t is 1 to 2), —$R^{15}$—$S(O)_tOR^{16}$ (wherein t is 1 to 2), —$R^{15}$—$S(O)_tR^{16}$ (wherein t is 0 to 2), and —$R^{15}$—$S(O)_tN(R^{14})_2$ (wherein t is 1 to 2).

In some embodiments, the cycloalkyl group is $C_3$-$C_{18}$ cycloalkyl.

In some embodiments, the cycloalkyl group is $C_3$-$C_{15}$ cycloalkyl.

In some embodiments, the cycloalkyl group is $C_3$-$C_{10}$ cycloalkyl.

"Cycloalkylalkyl" refers to a group of the formula-$R_aR_d$, where $R_a$ is an alkyl group as defined above, and $R_d$ is a cycloalkyl group as defined above. The alkyl part and cycloalkyl part may be optionally substituted as defined above.

"Halo" refers to bromo, chloro, fluoro or iodo.

"Haloalkyl" refers to an alkyl group, as defined above, that is substituted by one or more halo groups, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl may be optionally substituted as defined above for an alkyl group.

"Heterocyclyl" refers to a stable 3- to 18-membered non-aromatic ring group, which contains three to eighteen carbon atoms and one to six heteroatoms selected from the group consisting of nitrogen, oxygen and sulphur. Unless stated otherwise specifically in the specification, the heterocyclyl group may be monocyclic, bicyclic, tricyclic or tetracyclic ring system, which may include fused or bridged ring systems. Moreover, the nitrogen, carbon or sulphur atom in the heterocyclyl group may be optionally oxidized, and the nitrogen atom may be optionally quaternized. The heterocyclyl group may be partially or fully saturated. Examples of such heteroyclyl groups include, but are not limited to, dioxolanyl, thiophene[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Unless stated otherwise specifically in the specification, the term "heterocyclyl" is meant to include the heterocyclyl groups which may be optionally substituted with one or more substituents independently selected from the group consisting of alkyl, alkenyl, halo, haloalkyl, haloalkenyl, alkoxy, cyano, oxo, thio, nitro, aryl, aralkyl, cycloalkyl, cycloalkylalkyl, heterocyclyl, heterocycylylalkyl, heteroaryl, heteroaralkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)$OR^{14}$, —$R^{15}$—C(O)N($R^{14}$)$_2$, —$R^{15}$—N($R^{14}$)C(O)$OR^{16}$, —$R^{15}$—N($R^{14}$)C(O)$R^{16}$, —$R^{15}$—N($R^{14}$)S(O)$_t R^{16}$ (wherein t is 1 to 2), —$R^{15}$—S(O)$_t OR^{16}$ (wherein t is 1 to 2), —$R^{15}$—S(O)$_t R^{16}$ (wherein t is 0 to 2), and —$R^{15}$—S(O)$_t$N($R^{14}$)$_2$ (wherein t is 1 to 2).

In some embodiments, the heterocyclyl group is $C_3$-$C_{18}$ heterocyclyl.

In some embodiments, the heterocyclyl group is $C_3$-$C_{12}$ heterocyclyl.

In some embodiments, the heterocyclyl group is $C_3$-$C_{10}$ heterocyclyl.

"Heterocyclylalkyl" refers to a group of the formula-$R_a R_e$, where $R_a$ is an alkyl group as defined above, and $R_e$ is a heterocyclyl group as defined above. Moreover, if the heterocyclyl is a nitrogen-containing heterocyclyl, then the heterocyclyl may be attached to the alkyl group at the nitrogen atom. The alkyl part of the heterocyclylalkyl group may be optionally substituted as defined above for an alkyl group. The heterocyclyl part of the heterocyclylalkyl group may be optionally substituted as defined above for a heterocyclyl group.

"Heteroaryl" refers to a 5- to 18-membered aromatic ring group, which contains one to seventeen carbon atoms and one to ten heteroatoms selected from the group consisting of nitrogen, oxygen and sulphur. For the purpose of the present invention, the heteroaryl group may be monocyclic, bicyclic, tricyclic or tetracyclic ring system, which may include fused or bridged ring systems. Moreover, the nitrogen, carbon or sulphur atom in the heteroaryl group may be optionally oxidized, and the nitrogen atom may be optionally quaternized. The examples include, but are not limited to, azepinyl, acridinyl, benzimidazolyl, benzothiazolyl, benzoindolyl, benzodioxolanyl, benzofuranyl, benzoxazolyl, benzothiazolyl, benzothiadiazolyl, benzo[b][1,4]dioxepanyl, 1,4-benzodioxanyl, benzonaphthofuranyl, benzodioxolanyl, benzodioxadienyl, benzopyranyl, benzopyronyl, benzofuranyl, benzofuranonyl, benzothienyl, benzotriazolyl, benzo[4,6]imidazo[1,2-a]pyridyl, carbazolyl, cinnolinyl, dibenzofuranyl, dibenzothienyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, 2,3-naphthyridinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolyl, quinuclidinyl, isoquinolyl, tetrahydroquinolyl, thiazolyl, thiadiazolyl, triazolyl, tetrazolyl, triazinyl and thiophenyl. Unless stated otherwise specifically in the specification, the term "heteroaryl" is meant to include the heteroaryl groups which may be optionally substituted with one or more substituents independently selected from the group consisting of alkyl, alkenyl, alkoxy, halo, haloalkyl, haloalkenyl, cyano, oxo, thio, nitro, aryl, aralkyl, cycloalkyl, cycloalkylalkyl, heterocyclyl, heterocycylylalkyl, heteroaryl, heteroaralkyl, —$R^{15}$—$OR^{14}$, —$R^{15}$—OC(O)—$R^{14}$, —$R^{15}$—N($R^{14}$)$_2$, —$R^5$—C(O)$R^{14}$, —$R^{15}$—C(O)$OR^4$, —$R^{15}$—C(O)N($R^{14}$)$_2$, —$R^{15}$—N($R^{14}$)C(O)$OR^{16}$, —$R^{15}$—N($R^{14}$)C(O)$R^{16}$, —$R^{15}$—N($R^{14}$)S(O)$_t R^{16}$ (wherein t is 1 to 2), —$R^{15}$—S(O)$_t OR^{16}$ (wherein t is 1 to 2), —$R^{15}$—S(O)$_t R^{16}$ (wherein t is 0 to 2), and —$R^{15}$—S(O)$_t$N($R^{14}$)$_2$ (wherein t is 1 to 2).

In some embodiments, the heteroaryl group is $C_5$-$C_{18}$ heteroaryl.

In some embodiments, the heteroaryl group is $C_5$-$C_{12}$ heteroaryl.

In some embodiments, the heteroaryl group is $C_5$-$C_{10}$ heteroaryl.

"Heteroarylalkyl" refers to a group of the formula —$R_a R_f$, where $R_a$ is an alkyl group as defined above, and $R_f$ is a heteroaryl group as defined above. The heteroaryl part of the heteroarylalkyl group may be optionally substituted as defined above for a heteroaryl group. The alkyl part of the heteroarylalkyl may be optionally substituted as defined above for an alkyl group.

In definition of groups as described above, each $R^{14}$ is independently hydrogen, alkyl, haloalkyl, cycloalkyl, cycloalkylalkyl, aryl optionally substituted with one or more halogens, aralkyl, heterocyclyl, heterocyclylalkyl, heteroaryl or heteroaralkyl; each $R^{15}$ is independently a direct bond or straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteraryl, or heteroaralkyl.

"Optional" or "optionally" means that the subsequently described event of circumstances may or may not occur, and that the specification includes instances where said event or circumstance occurs and instances in which it does not. For example, "optionally substituted aryl" means that the aryl may or may not be substituted and that the specification includes the substituted aryl and the aryl which is not substituted.

"Stable compound" and "stable structure" are meant to indicate a compound that is sufficient robust to survive isolation to a useful degree of purity from a reaction mixture, and formulation into an effecacious therapeutic agent.

"Pharmaceutically acceptable salt" includes both acid and base addition salt.

"Pharmaceutically acceptable acid addition salt" refers to those salts which retain the biological effectiveness and properties of free bases, which are not biologically or otherwise undesirable, and which are formed with inorganic acids such as, but not limited to hydrochloric acid, hydrobromic acid, sulfuric acid, nitric acid, phosphoric acid and the like; and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic base or an organic base into the free acid. Salts derived from inorganic bases include, but are not limited to, sodium, potassium, lithium, ammonium, calcium, magnesium, iron, zinc, copper, manganese, aluminum slats, and the like. Preferred inorganic salts are ammonium, sodium, potassium, calcium, and magnesium salts. Salts derived from organic bases include, but are not limited to, slats of primary, secondary and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resin and the like. Particularly preferred organic bases are isopropylamine, diethylamine, ethanolamine, trimethylamine, dicyclohexylamine, choline and caffeine.

Often crystallization produces a solvate of the compound of the invention. As used herein, the term "solvate" refers to an aggregate that comprises one or more molecules of a compound of the invention with one or more molecules of solvent. The solvent may be water, in which case the solvate may be hydrate. Alternatively, the solvent may be an organic solvent. Therefore, the compounds of the present invention may exist as a hydrate, including monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

An intermediate of a compound of the formula I and all polymorphs and crystal habits of the foregoing species are also included within the scope of the present invention.

The compounds of the invention or their pharmaceutically acceptable salts may contain one or more asymmetric centers and may therefore produce enantiomers, diastereoisomers and other stereoisomeric forms, that may be defined, in terms of absolute stereochemistry, as (R)- or (S)-, or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as chromatography and fractional crystallization. The conventional techniques for preparing/isolating a single enantiomer include chiral synthesis from a suitable optically pure precursor, or resolution of a racemate (or the racemate of a salt or derivative) by using such as chiral High Pressure Liquid Chromatography (HPLC). When the compounds described herein comprise olefinic double bonds or other centers of geometric asymmetry, unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomer", which refers to two stereoisomers whose molecules are nonsuperimposable mirror image of one another.

A "cis-trans-isomer" refers to a molecule having the molecular formula, in which a spacial configuration of different relative distance between the adjacent atoms or radicals exists due to the factors such as the presence of a double bond or a ring, which block the free rotation of a bond.

A "tautomer" refers to a proton shift from one atom of a molecule to another atom of the same molecule. The present invention includes tautomers of any said compounds.

The term "prodrug" is meant to indicate a compound that may be converted into a biologically active compound of the invention under physiological conditions or by solvolysis. Therefore, the term "prodrug" refers to a metabolic precursor of a compound of the invention that is pharmaceutically acceptable. A prodrug may be inactive when administrated to a subject in need thereof, but is converted in vivo into an active compound of the invention. Prodrugs are typically rapidly transformed in vivo to yield the parent compound of the present invention, for example, by hydrolysis in blood. The prodrug compound often provides advantages of solubility, tissue compatibility or controlled-release in organism of mammals (see Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems", A.C.S. Symposium Series, Vol. 14 and Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administrated to a mammal subject Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino, or mercapto group is bonded to any group that, when the prodrug of the compound of the invention is administered to a mammal subject, cleaves to form a free hydroxy, free amino or free mecapto group, respectively. Examples of prodrugs include, but are not limited to, acetate, formate and benzoate of alcohol functional group in the compounds of the present invention and the like.

The invention disclosed herein is also meant to encompass the in vivo metabolic products of the disclosed compounds. Such products may result from, for example, the oxidization, reduction, hydrolysis, amidation, esterification, and the like of the administered compounds, primarily due to enzyme processes. Therefore, the invention includes compounds produced by a process comprising contacting a compound of the invention with a mammal for a period time sufficient to yield a metabolic product thereof. Such products are typically identified by administering a radiolabelled compound of the invention in a detectable dose to an animal, such as rat, mouse, guinea pig, monkey, or to human, allowing sufficient time to occur, and isolating its conversion products from urine, blood or other biological samples.

"Mammal" includes humans and both domestic animals, such as laboratory animals and household pets (e.g. cats, dogs, swine, cattle, sheep, goats, horses, rabbits), and non-domestic animals such as wildlife and the like.

The term "pharmaceutical composition" refers to a formulation of a compound of the invention and a medium generally acceptable in the art for the delivery of the biologically active compound to a mammal e.g. humans. Such a medium includes all pharmaceutically acceptable carriers for use. The pharmaceutical composition is conducive to administration of a compound to an organism. There are various routes of administration of a compound in the art including, but not limited to oral administration, injection administration, aerosol administration, parenteral administration and topical administration. The pharmaceutical compositions can also be obtained by reacting a compound with an inorganic acid such as hydrochloric acid, hydrobromic acid, sulfuric acid, nitric acid, phosphoric acid, methanesulfonic acid, ethanesulfonic acid, p-toluenesulfonic acid, salicylic acid and the like, or with an organic acid.

The term "carrier" defines a compound that facilitates the incorporation of a compound into cells or tissues. For example, dimethylsulfoxide (DMSO) is generally used as a carrier, as it facilitates the uptake of many organic compounds into cells or tissues of an organism.

"Pharmaceutically acceptable carrier" includes without limitation to any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier which has been approved by the national drug regulatory authorities as being acceptable for use in humans or domestic animals.

The term "physiologically acceptable" defines a carrier or a diluent that does not abrogate the biological activities and properties of a compound.

"Therapeutically effective amount" refers to that amount of a compound of the invention which, when administered to a mammal, preferably a human, is sufficient to effect treatment, as defined below, of the tumor in the mammal, preferably a human. The amount of a compound of the invention which constitutes a "therapeutically effective amount" will vary depending on the compound, the condition and its severity, the administration mode and the age of the mammal to be treated, but can be determined routinely by one of ordinary skill in the art having regard to his own knowledge and to this disclosure.

"Treating" or "treatment" as used herein covers the treatment of the tumor in a mammal, preferably a human, having the tumor, and includes:

(i) preventing the tumor from occurring in a mammal, in particular, when such mammal is predisposed to the tumor but has not yet been diagnosed as having it;

(ii) inhibiting the tumor, i.e. arresting its development; or (iii) relieving the tumor, i.e. causing regression of the tumor; or (iv) relieving the symptoms caused by the tumor.

Specific Embodiments

In one aspect, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof,

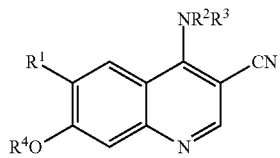

I wherein:

$R^1$ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

$R^2$ and $R^3$ are each independently selected from the group consisting of hydrogen, substituted or unsubstituted aralkyl, substituted or unsubstituted aryl, and substituted or unsubstituted heteroaryl;

or $R^2$ and $R^3$ together with nitrogen atom to which they are attached form substituted or unsubstituted heterocyclyl; and $R^4$ is substituted or unsubstituted heterocyclyl, or substituted or unsubstituted heteroaryl.

In another aspect, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof,

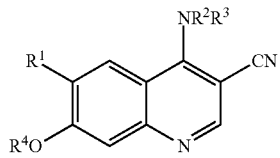

I wherein:

$R^1$ is selected from the group consisting of $C_1$-$C_6$ alkylacylamino, $C_2$-$C_6$ alkenylacylamino, $C_2$-$C_6$ alkynylacylamino, $C_6$-$C_{18}$ arylacylamino, $C_1$-$C_6$ alkyl-substituted amino, and $C_1$-$C_6$ alkoxy;

$R^2$ and $R^3$ are each independently selected from the group consisting of hydrogen, $C_7$-$C_{24}$ aralkyl, substituted or unsubstituted $C_6$-$C_{18}$ aryl, and substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, $C_6$-$C_{18}$ aryloxy, and $C_5$-$C_{18}$ heteroaryloxy, and a substituent on the heteroaryl is selected from the group consisting of $C_7$-$C_{24}$ aralkyl, $C_6$-$C_{18}$ arylacylamino, $C_6$-$C_{18}$ arylsulfonylamino, $C_5$-$C_{18}$ heteroarylacylamino, $C_3$-$C_{10}$ cycloalkylacylamino, $C_6$-$C_{18}$ arylaminoacyl, $C_7$-$C_{24}$ aralkyloxy, $C_6$-$C_{24}$ heteroaralkyloxy, and $C_6$-$C_{18}$ aryloxy;

or $R^2$ and $R^3$ together with nitrogen atom to which they are attached form substituted or unsubstituted $C_3$-$C_{18}$ heterocyclyl; and $R^4$ is $C_3$-$C_{18}$ heterocyclyl or $C_5$-$C_{18}$ heteroaryl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or prodrug thereof, wherein:

$R^1$ is selected from the group consisting of $C_1$-$C_6$ alkylacylamino, $C_2$-$C_6$ alkenylacylamino, $C_2$-$C_6$ alkynylacylamino, $C_6$-$C_{18}$ arylacylamino, $C_1$-$C_6$ alkyl-substituted amino, and $C_1$-$C_6$ alkoxy;

$R^2$ and $R^3$ are each independently selected from the group consisting of hydrogen, $C_7$-$C_{24}$ aralkyl, substituted or unsubstituted $C_6$-$C_{18}$ aryl, and substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, $C_6$-$C_{18}$ aryloxy, and $C_5$-$C_{18}$ heteroaryloxy, and a substituent on the heteroaryl is selected from the group consisting of $C_7$-$C_{24}$ aralkyl, $C_6$-$C_{18}$ arylacylamino, $C_6$-$C_{18}$ arylsulfonylamino, $C_5$-$C_{18}$ heteroarylacylamino, $C_3$-$C_{10}$ cycloalkylacylamino, $C_6$-$C_{18}$ arylaminoacyl, $C_7$-$C_{24}$ aralkyloxy, $C_6$-$C_{24}$ heteroaralkyloxy, and $C_6$-$C_{18}$ aryloxy;

or $R^2$ and $R^3$ together with nitrogen atom to which they are attached form substituted or unsubstituted $C_3$-$C_{18}$ heterocyclyl; and $R^4$ is tetrahydrofuranyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is selected from the group consisting of $C_1$-$C_6$ alkylacylamino, $C_2$-$C_6$ alkenylacylamino, $C_2$-$C_6$ alkynylacylamino, $C_6$-$C_{18}$ arylacylamino, $C_1$-$C_6$ alkyl-substituted amino, and $C_1$-$C_6$ alkoxy;

one of $R^2$ and $R^3$ is H, while the other one is selected from the group consisting of $C_7$-$C_{24}$ aralkyl, substituted or unsubstituted $C_6$-$C_{18}$ aryl, and substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, $C_6$-$C_{18}$ aryloxy, and $C_5$-$C_{18}$ heteroaryloxy, and a substituent on the heteroaryl is selected from the group consisting of $C_7$-$C_{24}$ aralkyl, $C_6$-$C_{18}$ arylacylamino, $C_6$-$C_{18}$ arylsulfonylamino, $C_5$-$C_{18}$ heteroarylacylamino, $C_3$-$C_{10}$ cycloalkylacylamino, $C_6$-$C_{18}$ arylaminoacyl, $C_7$-$C_{24}$ aralkyloxy, $C_6$-$C_{24}$ heteroaralkyloxy, and $C_6$-$C_{18}$ aryloxy; and $R^4$ is tetrahydrofuranyl.

In some embodiments, the present application is directed to a compound of formula I, a stereoisomer thereof, a cis-trans isomer thereof, a tautomer thereof, or a mixture thereof, or a pharmaceutically acceptable salt thereof, a solvate thereof or a prodrug thereof, wherein:

$R^1$ is selected from the group consisting of $C_1$-$C_6$ alkylacylamino, $C_2$-$C_6$ alkenylacylamino, and $C_6$-$C_{18}$ arylacylamino;

one of $R^2$ and $R^3$ is H, while the other one is selected from the group consisting of $C_7$-$C_{24}$ aralkyl, and substituted or unsubstituted $C_6$-$C_{18}$ aryl, wherein a substituent on the aryl is selected from the group consisting of $C_2$-$C_6$ alkynyl, halogen, $C_7$-$C_{24}$ aralkyloxy, $C_6$-$C_{18}$ aryloxy, $C_5$-$C_8$ heteroaryloxy, and $C_6$-$C_{24}$ heteroaralkyloxy; and $R^4$ is tetrahydrofuranyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is $C_2$-$C_6$ alkenylacylamino;

one of $R^2$ and $R^3$ is H, while the other one is selected from the group consisting of $C_7$-$C_{24}$ aralkyl, and substituted or unsubstituted $C_6$-$C_{18}$ aryl, wherein a substituent on the aryl is selected from the group consisting of $C_2$-$C_6$ alkynyl, halogen, $C_7$-$C_{24}$ aralkyloxy, and $C_6$-$C_{24}$ heteroaralkyloxy; and $R^4$ is tetrahydrofuranyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is selected from the group consisting of 4-(dimethylamino)-but-2-enamido, 4-(diethylamino)-but-2-enamido, 4-(piperidin-1-yl)-but-2-enamido, 4-(morpholin-4-yl)-but-2-enamido, 4-(tert-butylamino)-but-2-enamido, 4-(benzylamino)-but-2-enamido, 4-(6-hydroxyhexylamino)-but-2-enamido, 4-(2-methoxyethylamino)-but-2-enamido, 2-(piperidin-4-ylidene)acetamido, 2-(1-methylpiperidin-4-ylidene)acetamido, 4-(diethanolamino)-but-2-enamido, 4-(N-methylmethoxylethyl amino)-but-2-enamido, 4-(N-methylethanolamino)-but-2-enamido, 4-(dimethoxyl ethyl amino)-but-2-enamido, 4-(N-methyl-6-amino-1-hexanolyl)-but-2-enamido, 4-(N-methylbenzylamino)-but-2-enamido, 2-(1-ethylpiperidin-4-ylidene)acetamido, 2-(1-(2-methoxylethyl)piperidin-4-ylidene)acetamido, acrylamido, but-2-enamido, 3-methyl-but-2-enamido, and 2-(pyrrolidin-3-ylidene)acetamido;

one of $R^2$ and $R^3$ is H, while the other one is selected from the group consisting of $C_7$-$C_{24}$ aralkyl, and substituted or unsubstituted $C_6$-$C_{18}$ aryl, wherein a substituent on the aryl is selected from the group consisting of $C_2$-$C_6$ alkynyl, halogen, $C_7$-$C_{24}$ aralkyloxy, and $C_6$-$C_{24}$ heteroaralkyloxy; and $R^4$ is tetrahydrofuranyl.

In some embodiments, the present application is directed to a compound of formula I, a stereoisomer thereof, a cis-trans isomer thereof, a tautomer thereof, or a mixture thereof, or a pharmaceutically acceptable salt thereof, a solvate thereof or a prodrug thereof, wherein:

$R^1$ is selected from the group consisting of $C_1$-$C_6$ alkylacylamino, $C_2$-$C_6$ alkenylacylamino, and $C_6$-$C_{18}$ arylacylamino;

one of $R^2$ and $R^3$ is H, while the other one is substituted or unsubstituted $C_6$-$C_{18}$ aryl, wherein a substituent on the aryl is selected from the group consisting of halogen, $C_6$-$C_{24}$ heteroaralkyloxy, $C_2$-$C_6$ alkynyl, and $C_7$-$C_{24}$ aralkyloxy; and $R^4$ is tetrahydrofuranyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is $C_2$-$C_6$ alkenylacylamino;

$R^2$ and $R^3$ together with nitrogen atom to which they are attached form substituted or unsubstituted $C_3$-$C_{18}$ heterocyclyl; and $R^4$ is tetrahydrofuranyl.

In some embodiments, the present application is directed to a compound of formula I, a stereoisomer thereof, a cis-trans isomer thereof, a tautomer thereof, or a mixture thereof, or a pharmaceutically acceptable salt thereof, a solvate thereof or a prodrug thereof, wherein:

$R^1$ is 2-(piperidin-4-ylidene)acetamido;

$R^2$ and $R^3$ together with nitrogen atom to which they are attached form substituted or unsubstituted $C_3$-$C_{18}$ heterocyclyl; and $R^4$ is tetrahydrofuranyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is $C_2$-$C_6$ alkenylacylamino;

one of $R^2$ and $R^3$ is H, while the other one is selected from the group consisting of substituted or unsubstituted $C_6$-$C_{18}$ aryl, and substituted or unsubstituted $C_5$-$C_8$ heteroaryl, wherein a substituent on the aryl is selected from the group consisting of $C_2$-$C_6$ alkynyl, halogen, $C_7$-$C_{24}$ aralkyloxy, and $C_6$-$C_{18}$ aryloxy, and a substituent on the heteroaryl is selected from the group consisting of $C_7$-$C_{24}$ aralkyloxy, and $C_6$-$C_{18}$ aryloxy; and $R^4$ is hexahydropyridinyl optionally substituted with $C_1$-$C_6$ alkyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is 2-(piperidin-4-ylidene)acetamido;

one of $R^2$ and $R^3$ is H, while the other one is selected from the group consisting of substituted or unsubstituted $C_6$-$C_{18}$ aryl, and substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, and $C_6$-$C_{18}$ aryloxy, and a substituent on the heteroaryl is $C_7$-$C_{24}$ aralkyloxy; and $R^4$ is hexahydropyridinyl optionally substituted with $C_1$-$C_6$ alkyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is 2-(pyrrolidin-3-ylidene)acetamido;

one of $R^2$ and $R^3$ is H, while the other one is $C_5$-$C_8$ heteroaryl substituted with aryloxy; and $R^4$ is hexahydropyridyl optionally substituted with $C_1$-$C_6$ alkyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is $C_2$-$C_6$ alkenylacylamino;

one of $R^2$ and $R^3$ is H, while the other one is selected from the group consisting of substituted or unsubstituted $C_6$-$C_{18}$ aryl, and substituted or unsubstituted $C_5$-$C_8$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, and $C_6$-$C_{18}$ aryloxy, and a substituent on the heteroaryl is selected from the group consisting of $C_7$-$C_{24}$ aralkyloxy, and $C_6$-$C_{18}$ aryloxy; and $R^4$ is pyridinyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is 2-(piperidin-4-ylidene)acetamido;

one of $R^2$ and $R^3$ is H, while the other one is selected from the group consisting of substituted or unsubstituted $C_6$-$C_{18}$ aryl, and substituted or unsubstituted $C_5$-$C_{18}$ heteroaryl, wherein a substituent on the aryl is selected from the group consisting of $C_2$-$C_6$ alkynyl, halogen, $C_7$-$C_{24}$ aralkyloxy, $C_6$-$C_{24}$ heteroaralkyloxy, and $C_6$-$C_{18}$ aryloxy, and a substituent on the heteroaryl is selected from the group consisting of $C_7$-$C_{24}$ aralkyloxy, and $C_6$-$C_{18}$ aryloxy; and $R^4$ is pyridinyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is 2-(pyrrolidin-3-ylidene)acetamido;

one of $R^2$ and $R^3$ is H, while the other one is $C_5$-$C_8$ heteroaryl substituted with $C_6$-$C_{18}$ aryloxy; and $R^4$ is pyridinyl.

In some embodiments, the present application is directed to a compound of formula I, a stereoisomer thereof, a cis-trans-isomer thereof, a tautomer thereof, or a mixture thereof, or a pharmaceutically acceptable salt thereof, a solvate thereof or a prodrug thereof, wherein:

$R^1$ is 4-(diethyl amino)-but-2-enamido;

one of $R^2$ and $R^3$ is H, while the other one is $C_6$-$C_{18}$ aryl substituted with halogen; and $R^4$ is pyridinyl.

The specific embodiments of a compound of formula I are more detailedly described in the following preparations of the compound of the present invention.

Methods of Use

The present application provides a method for treating a patient having a tumor or protecting a patient from development of a tumor, comprising administering to an animal in need thereof, such as a mammal, especially a human patient, a therapeutically effective amount of a compound of the present invention or a pharmaceutical composition comprising a compound of the invention.

The compounds of the invention can be used to treat and/or prevent tumor. Therefore, for example, the compounds of the invention can be used to treat, prevent development of a tumor, relieve growth of tumor cells, or kill tumor cells. In some embodiments, the compounds of the invention are administered to a subject having a tumor. In one embodiment, the subject is human. In some embodiments, the tumor cells are contacted with one or more compounds of the invention.

As will be understood by a person having ordinary skill in the art, "need" is not an absolute term and merely implies that the patient can benefit from the treatment of the anti-tumor agent. By "patient" what is meant is an organism which benefits by the use of the anti-tumor agent. For example, any organism with the cancer, such as a colorectal carcinoma, a prostate carcinoma, a breast adenocarcinoma, a non-small cell lung carcinoma, an ovarian carcinoma, multiple myelomas, a melanoma, and the like, may benefit from the application of the anti-tumor agent that may in turn reduce the amount of the cancer present in the patient. In one embodiment, the patient's health may not require that an anti-tumor agent be administered, but the patient may still obtain some benefit by the reduction of the level of the tumor cells present in the patient, and thus be in need. In some embodiment, the anti-tumor agent is effective against one type of the tumor, but not against other types, therefore, allowing a high degree of selectivity in the treatment of the patient. In choosing such an anti-tumor agent, the methods and results disclosed in the examples can be useful.

The term "anti-tumor agent" as used herein refers to a compound or composition including the compound that reduces the likelihood of survival of a tumor cell. In one embodiment, the likelihood of survival is determined as a function of an individual tumor cell. Therefore, the anti-tumor agent will increase the chance that an individual tumor cell will die. In one embodiment, the likelihood of survival is determined as a function of a polulation of tumor cells. Therefore, the anti-tumor agent will increase the chances that there will be a decrease in the population of tumor cells. In one embodiment, the anti-tumor agent means the chemotherapeutant (chemotherapeutic agent) and other similar terms.

The term "chemotherapeutic agent" as used herein refers to a compound useful in the treatment of the neoplastic disease, such as cancer. Examples of the chemotherapeutic agents include alkylating agent, such as a nitrogen mustard, an ethyleneimine and a methylmelamine, an alkyl sulfonate, a nitrosourea and a triazene, folic acid antagonists, antimetabolites of nucleic acid metabolism, antibiotics, pyrimidine analogs, 5-fluorouracil, cisplatin, purine nucleosides, amines, amino acids, triazole nucleosides, corticosteroids, a natural product such as a vinca alkaloid, an epipodophyllotoxin, an antibiotic, an enzyme, a taxane, and a biological response modifier; miscellaneous reagents, such as a platinum coordination complex, an anthraquinone, an anthracycline, a substituted urea, a methyl hydrazine derivative, or an adrenocortical suppressant; or a hormone or an antagonist such as an adrenocorticosteroid, a progesterone, an estrogen, an antiestrogen, an androgen, an antiandrogen, or a gouadotropin-releasing hormone analog. Specific examples include doxorubicin, 14-hydroxy daunorubicin, 5-fluorouracil, cytosine arabinoside ("Ara-C"), cyclophosphamide, thiotepa, busulfan, cytotoxin, taxol, Toxotere, methotrexate, cisplatin, melphalan, vinblastine, bleomycin, etoposide, ifosfamide, mitomycin C, mitoxantrone, vincristine, vinorelbine, carboplatin, teniposide, daunorubicin, 10-demethylated daunorubicin, aminopterin, dactinomycin, mitomycin, esperamicin, melphalan, and other related nitrogen mustards. Also included in this definition are hormone reagents that act to regulate or inhibit hormone action on tumors, such as tamoxifen and onapristone.

The anti-tumor agent may act directly on a tumor cell to kill the cell, induce death of the cell, to prevent division of the cell, and the like. Alternatively, the anti-tumor agent may act indirectly on a tumor cell, such as by limiting nutrient or blood supply to the cell. Such anti-tumor agents are capable of destroying or suppressing the growth or reproduction of the tumor cells, such as a colon carcinoma, a prostate carcinoma, a breast adenocarcinoma, a non-small cell lung carcinoma, an ovarian carcinoma, multiple myelomas, a melanoma, and the like.

The term "neoplastic disease" or "neoplasm" as used herein refers to a cell or a population of cells, including a tumor or tissue (including cell suspensions such as bone marrow cell and fluids such as blood or serum), that exhibits abnormal growth by cellular proliferation greater than normal tissue. Neoplasms can be benign or malignant.

The methods of treatment disclosed herein can be used for any patient suspectable of having benign or malignant tumor growth, cancer or other tumorigenesis growth (the "tumor" or "tumors" as used herein covers tumor, solid tumor, cancer, disseminated tumor formative cell and topical tumorigenesis growth). Examples of the growth include, but are not limited to, breast cancer; osteosarcoma, angiosarcoma, fibrosarcoma, and other sarcoma; leukemia; sinus tumor; cancers of ovarian, ureter, bladder, prostate and other urogenital system; cancers of colon, esophageal and gastric and other gastrointestinal cancer; lung cancer; lymphoma; myeloma; pancreatic cancer; liver cancer; kidney cancer; endocrine cancer; skin cancer; melanoma; hemangioma; and brain or central nervous system (CNS; glioma) cancer. Generally, the tumor or growth to be treated can be any primary or secondary tumor or cancer.

In some embodiments, the cancer may be, for example, breast cancer, sarcoma, leukemia, ovarian cancer, ureter cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, hemangioma, and brain or central nervous system (CNS) cancer.

In some aspects, the cancer may be drug-resistant cancer. The drug-resistant cancer may exhibit, for example, one of: Bcl-2-overexpression, boosted level of the P-glycoprotein efflux pump, an increased expression of the multidrug-resistance related protein 1 encoded by MRP1, reduced drug intakes, the change of the drug target, or increased repairing of the drug induced DNA damage, the change of the apoptosis pathway, or activation of the cytochrome P450 enzyme. The drug-resistant cancer may be, for example, multiple myeloma, sarcoma, lymphoma (including non-Hodgkin's lymphoma), leukemia or any other drug-resistant cancer. The cancer may be, for example, naturally drug-resistant, or resistant to chemotherapy, biological therapy, radiotherapy, or immunotherapy. The cancer may be resistant to rituximab monoclonal antibody, Gleevac, velcade, Gleveec, Revlimid, Avastin, Tarceva, Erbitux, bortezomib, thalidomide and the like. Other specific examples of the drug-resistant cell line include MES-SA cell line, and multidrug-resistant derivative thereof, such as MES-SA/Dx5, HL-60 and HL-60/MX2.

Pharmaceutical Compositions

In one aspect, the present application is directed to a pharmaceutical composition, comprising a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof, and a pharmaceutically acceptable carrier,

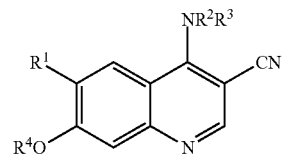

wherein:

$R^1$ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

$R^2$ and $R^3$ are each independently selected from the group consisting of hydrogen, substituted or unsubstituted aralkyl, substituted or unsubstituted aryl, and substituted or unsubstituted heteroaryl;

or $R^2$ and $R^3$ together with nitrogen atom to which they are attached form substituted or unsubstituted heterocyclyl; and $R^4$ is substituted or unsubstituted heterocyclyl, or substituted or unsubstituted heteroaryl.

In some embodiments, the pharmaceutical composition of the present application comprises a physiologically acceptable surfactants, carriers, diluents, excipients, smoothing agents, suspending agents, film forming substances, and coating assistants, or a combination thereof, and a compound of the invention. Acceptable carriers or diluents for therapeutic use are well-known in the art, and are described, for example, in Remington's Pharmaceutical Sciences, 18th Ed., Mack Publishing Co., Easton, Pa. (1990), which is incorporated herein by reference in its entirety.

Preservatives, stabilizers, dyes, sweeteners, flavoring agents, fragrances, and the like, may be provided in the pharmaceutical composition. For example, sodium benzoate, ascorbic acid and esters of p-hydroxybenzoic acid may be added as preservatives. Furthermore, antioxidants and suspending agents may be used.

In various embodiments, alcohols, esters, sulfating aliphatic alcohols, and the like may be used as surfactants; sucrose, glucose, lactose, starch, crystalline cellulose, mannitol, light anhydrous silicate, magnesium aluminate, methyl magnesium silicate aluminate, synthetic aluminum silicate, calcium carbonate, calcium bicarbonate, calcium hydrogenphosphate, calcium hydroxymethyl cellulose and the like may be used as excipients; magnesium stearate, talc, hardened oil may be used as smoothing agents; coconut oil, olive oil, sesame oil, peanut oil, soybean may be used as suspending agents or lubricants; cellulose acetate phthalate as a derivative of a carbohydrate such as cellulose or sugar, or methylacetate-metharylate copolymer as a derivative of polyethylene may be used as suspending agents; and plasticizers such as ester phthalates and the like may be used as suspending agents.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal or intraocular injections. The compound can be administered in sustained or controlled release dosage froms, including depot injections, osmotic pumps, pills, transdermal (including electromigrating) patches, and the like for prolonged and/or timed, pulsed administration at a predetermined rate.

Pharmaceutical compositions of the present application may be manufacture in manner that is itself known, for example, by means of conventional mixing, dissolving, granulating, dragee-making, levigating, emulsifying, encapsulating, entrapping, or tabletting processes.

Pharmaceutical compositions for use in accordance with the present application thus may be formulated by a conventional manner using one or more physiologically acceptable carriers comprising excipients and auxiliaries which facilitate processing the active compounds into preparation which can be used pharmaceutically. Proper formulation is dependent on the route of administration chosen. Any of the well-known techniques, carriers and excipients may be used as suitable and as understood in the art.

Injectables can be prepared in conventional forms, either as liquid solutions or suspensions, solid forms suitable for solution or suspension in liquid prior to injection, or as emulsions. Suitable excipients are, for example, water, saline, glucose, mannitol, lactose, lecithin, albumin, sodium glutamate, cysteine hydrochloride, and the like. Furthermore, if desired, the injectable pharmaceutical compositions may contain minor amounts of nontoxic auxiliary substances, such as wetting agents, pH buffering agents, and the like. Physiologically compatible buffers include, but are not limited to, Hank's solution, Ringer's solution or physiological saline buffer. If desired, absorption enhancing preparations (such as liposomes) may be used.

For transmucosal administration, penetrants suitable for the barrier to be permeated may be used in the formulation.

Pharmaceutical formulations for parenteral administration, e.g., by bolus injection or continuous infusion, include aqueous solution of the active compounds in water-soluable form. Furthermore, suspensions of the active compounds may be prepared as appropriate oily injection suspensions. Suitable lipotropic solvents or vehicles include fatty oil such as sesame oil, or other organic oils such as soybean oil, grapefruit oil or almond oil, or synthetic fatty acid esters, such as ethyl oleate or triglyceride, or liposomes. Aqueous injection suspension may contain substances which increase the viscosity of the suspension, such as sodium carboxymethylcellulose, sorbitol or dextran. Optionally, the suspension may also contain suitable stabilizers or agents that increase the solubility of the compounds to allow for the preparation of highly concentrated solutions. Formations for injection may be presented in unit dosage form, e.g., in ampoules or in multi-dose containers with an added preservative. The compositions may take such forms as suspensions, solutions or emulsions in oily or aqueous vehicles, and may contain formulatory agents such as suspending agents, stabilizing and/or dispersing agents. Alternatively, the active ingredient may be in powder form for constitution with a suitable carrier, e.g., sterile pyrogen-free water, before use.

For oral administration, the compound can be formulated readily by combining the active compound with pharmaceutically acceptable carriers well known in the art. Such carriers enable the compound of the invention to be formulated as tablets, pills, dragees, capsules, liquids, gels, syrups, ointments, suspensions, and the like, for oral ingestion by a patient to be treated. Pharmaceutical preparation for oral use can be obtained by combining the active compound with solid excipient, optionally grinding a resultant mixture, and processing the mixture of granules, after adding suitable auxiliaries, if desired, to obtain tablets or dragee cores. Suitable excipients are, in particular, fillers such as sugars, including lactose, saccharose, mannitol or sorbitol; cellulose preparations such as, for example, maize starch, wheat starch, rice starch, potato starch, gelatin, gum tragacanth, methylcellulose, hydroxypropyl methylcellulose, sodium carboxymethylcellulose, and/or polyvinylpyrrolidone (PVP). If desired, disintegrating agents may be added, such as the crosslinked polyvinylpyrrolidone, agar, or alginic acid or a salt thereof such as sodium alginate. Dragee cores are provided with suitabe coatings. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures. Dyestuffs or pigments may be added into the tablets or dagree coatings for identification or to characterizing different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures. Dyestuffs or pigments may be added into the tablets or dagree coatings for identification or to characterizing different combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain active ingredients in admixture with filler such as sugar, binders such as starches, and/or lubricants such as talc or magnesium stearate and, optionally, stabilizers. In soft capsules, the active ingredients may be dissolved or suspended in suitable liquids, such as fatty oil, liquid paraffin, or liquid polyethylene glycols. Furthermore, stabilizers may be added. All formulations for oral administration should be in dosages suitable for such administration.

For buccal administration, the compositions may take the form of tablets or lozenges formulated in conventional manner.

For administration by inhalation, the compound for the invention is conveniently delivered in the form of an aerosol spray presentation from the pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solution of the active compounds in water-soluble form, such as eyedrops, or in gellan gum or hydrogels; ophthalmic ointments; ophthalmic suspensions, such as microparticulates, drug-containing small polymeric particles that are suspended in a liquid carrier medium, lipid-soluble formulations, and microspheres; and ocular inserts. Suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As well known to a person having ordinary skill in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound may also be formulated in rectal compositions such as suppositories or retention enemas, e.g., including conventional suppository bases such as cocoa butter or other glycerides.

In addition to the formulations described previously, the compound may also be formulated as a depot preparation. Such long acting formulations may be administered by implantation (for example subcutaneously or intramuscularly) or by intramuscular injection. Therefore, for example, the compound may be formulated with suitable polymeric or hydrophobic materials (for example as an emulsion in an acceptable oil) or ion exchange resins, or s sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system may be varied considerably without destroying its solubility and toxicity. Furthermore, the identity of the co-solvent may be varied, for example, other low-toxicity nonpolar surfactants may be used instead of POLYSORBATE 80™; the fraction size of polyethylene glycol may be varied; other biocompatible polymers may replace polyethylene glycol, e.g., polyethylene pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethyl sulfoxide also may be employed, although usually at the cost of greater toxicity. Furthermore, the compounds may be delivered using a sustained-release system, such as semipermeable matrices of solid hydrophobic polymers containing the therapeutic agent. Various sustained-release materials have been established and are well known by a person having ordinary skill in the art. Sustained-release capsules may, depending on their chemical nature, release the compound fore a few weeks up to over 100 days.

Agents intended to be administered intracellularly may be administered using techniques well known to a person having ordinary skill in the art. For example, such agents may be encapsulated in liposomes. All molecules present in an aqueous solution at the time of liposome formation are incorporated into the aqueous interior. The liposome contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desirable organ. Alternatively, small hydrophobic organic molecules may be directly administered intracellularly.

Methods of Treatment and Use

In one aspect, the present application is directed to a method for treating and/or preventing tumor in a mammal, comprising administering to the mammal in need thereof a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof,

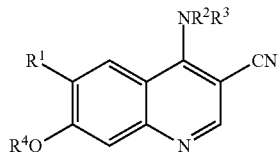

I wherein:

$R^1$ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

R² and R³ are each independently selected from the group consisting of hydrogen, substituted or unsubstituted aralkyl, substituted or unsubstituted aryl, and substituted or unsubstituted heteroaryl;

or R² and R³ together with nitrogen atom to which they are attached form substituted or unsubstituted heterocyclyl; and R⁴ is substituted or unsubstituted heterocyclyl, or substituted or unsubstituted heteroaryl.

In some embodiments, the mammal in the method for treating and/or preventing tumor is a human.

In some embodiment, the receptor tyrosine kinase in the method for treating and/or preventing tumor in a mammal occurs overexpression or mutation.

In some embodiments, the receptor tyrosine kinase in the method for treating and/or preventing tumor in a mammal is erbB family.

In some embodiments, the erbB family in the method for treating and/or preventing tumor in a mammal is selected from EGFR and/or Her2.

In another aspect, the present application is directed to a method for inhibiting growth of tumor cells, comprising contacting the tumor cells with a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof,

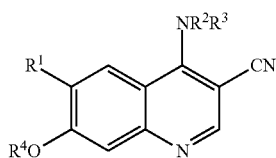

I wherein:

R¹ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

R² and R³ are each independently selected from the group consisting of hydrogen, substituted or unsubstituted aralkyl, substituted or unsubstituted aryl, and substituted or unsubstituted heteroaryl;

or R² and R³ together with nitrogen atom to which they are attached form substituted or unsubstituted heterocyclyl; and R⁴ is substituted or unsubstituted heterocyclyl, or substituted or unsubstituted heteroaryl.

In some embodiment, the receptor tyrosine kinase in the method for inhibiting growth of tumor cells occurs overexpression or mutation.

In some embodiments, the receptor tyrosine kinase in the method for inhibiting growth of tumor cells is erbB family.

In some embodiments, the erbB family in the method for inhibiting growth of tumor cell is selected from EGFR and/or Her2.

In yet another aspect, the present application is directed to a method for inhibiting overexpression or mutation of a receptor tyrosine kinase in a mammal, comprising contacting the receptor tyrosine kinase with a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof,

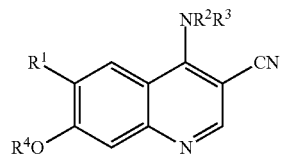

I wherein:

R¹ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

R² and R³ are each independently selected from the group consisting of hydrogen, substituted or unsubstituted aralkyl, substituted or unsubstituted aryl, and substituted or unsubstituted heteroaryl;

or R² and R³ together with nitrogen atom to which they are attached form substituted or unsubstituted heterocyclyl; and R⁴ is substituted or unsubstituted heterocyclyl, or substituted or unsubstituted heteroaryl.

In some embodiments, the receptor tyrosine kinase in the method for inhibiting overexpression or mutation of a receptor tyrosine kinase in a mammal is erbB family.

In some embodiments, the erbB family in the method for inhibiting overexpression or mutation of a receptor tyrosine kinase in a mammal is selected from EGFR and/or Her2.

In yet another aspect, the present application is directed to a method for treating and/or preventing physiological abnormity caused by overexpression or mutation of a receptor tyrosine kinase in a mammal, comprising administering to the mammal in need thereof a therapeutically effective amount of a compound of formula I, a stereoisomer thereof, a cis-trans-isomer thereof, a tautomer thereof, or a mixture thereof, or a pharmaceutically acceptable salt thereof, a solvate thereof or a prodrug thereof,

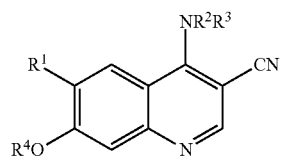

I wherein:

R¹ is selected from the group consisting of substituted or unsubstituted alkylacylamino, substituted or unsubstituted alkenylacylamino, substituted or unsubstituted alkynylacylamino, substituted or unsubstituted arylacylamino, substituted or unsubstituted amino, and substituted or unsubstituted alkoxy;

R² and R³ are each independently selected from the group consisting of hydrogen, substituted or unsubstituted aralkyl, substituted or unsubstituted aryl, and substituted or unsubstituted heteroaryl;

or $R^2$ and $R^3$ together with nitrogen atom to which they are attached form substituted or unsubstituted heterocyclyl; and $R^4$ is substituted or unsubstituted heterocyclyl, or substituted or unsubstituted heteroaryl.

In some embodiments, the receptor tyrosine kinase in the method for treating and/or preventing physiological abnormity caused by overexpression or mutation of a receptor tyrosine kinase in a mammal is erbB family.

In some embodiments, the erbB family in the method for treating and/or preventing physiological abnormity caused by overexpression or mutation of a receptor tyrosine kinase in a mammal is selected from EGFR and/or Her2.

In some embodiments, the physiological abnormity in the method for treating and/or preventing physiological abnormity caused by overexpression or mutation of a receptor tyrosine kinase in a mammal is tumor.

Methods of Administration

The compound or pharmaceutical compositions may be administered to the patient in any suitable means. Non-limiting examples of methods of administration include, among other, (a) administration through oral pathways, which include administration in capsule, tablet, granule, spray, syrup, or other such forms; (b) administration through non-oral pathways, such as rectal, vaginal, intraurethral, intraocular, intranasal, or intraauricular, which include administration as an aqueous suspension, an oily preparation or the like or as a drip, spray, suppository, salve, ointment or the lise; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by a person having ordinary skill in the art for bringing the compound of the invention into contact with living tissue.

The most suitable route depends on the nature and severity of the condition to be treated. A person having ordinary skill in the art also knows determination of methods of administration (buccal, intravenous, inhalation subcutaneous, rectal and the like), dosage form, suitable pharmaceutical excipients and other events regarding delivering the compound to a subject in need thereof.

Pharmaceutical compositions suitable for administration include the compositions where the active ingredient is contained in an effective amount to achieve its intended purpose. The therapeutically effective amount of the pharmaceutical composition disclosed herein required as a dose depends on the route of administration, the type of the animal, including human, being treated, and the physical characteristics of the specific animal under consideration. The does can be tailored to achieve a desired effect, but will depend on such factors as weight, diet, concurrent medication and other factors which those skilled in the medical arts will recognize. More specifically, a therapeutically effective amount means an amount of the compound effective to prevent, alleviate or ameliorate symptoms of disease or prolongs the survival of the subject being treated. Determination of a therapeutically effective amount is well within the capacity of a person having ordinary skill in the art, especially in light of the detailed disclosure provided herein.

As will be readily apparent to one skilled in the art, the useful in vivo dosage to be administered and particular mode of administration will vary depending on the age, weight and f mammal species treated, and the specific use for which the compound are employed. The determination of effective amount level, that is, the dosage levels necessary to achieve the desired results, can be accomphlished by a person having ordinary skill in the art using routine pharmacological methods. Typically, human clinical applications of the compound are commenced at lower dosage levels, with dosage level being increased until the desired effect is achieved. Alternatively, acceptable in vitro study can be used to establish useful doses and routes of administration of the compositions identified by the present methods using established pharmacological methods.

In non-human animal studies, applications of potential compounds are commenced at higher dosage levels, with dosage being decreased until the desired effect is no longer achieved or the adverse side effects disappear. The dosage may range broadly, depending on the desired effects and the therapeutic indication. Typically, the dosage may be between about 10 µg/kg and 500 mg/kg body weight, preferably between about 100 µg/kg and 200 mg/kg body weight. Alternatively, dosages may be based and calculated upon the surface area of the patient, as understood by a person having ordinary skill in the art.

The exact formulation, route of administration and dosage of the pharmaceutical compositions of the invention can be chosed by the individual physician in view of the patient's condition. Typically, the dose range of the composition administered to the patient can be from about 0.5 mg/kg to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and about 500%, more preferred between 25% to 250% of the established human dosage. Where no human dosage is established, as well be the case for newly-discovered pharmaceutical compounds, a suitable human dosage can be inferred from $ED_{50}$ or $ID_{50}$ values, or other appropriate values derived from in vitro or in vivo studies, as quantified by toxicity studies and efficacy study in animals.

It should be noted that the attending physician would know how to and when to terminate, interrupt, or adjust the administration due to toxicity and organs dysfunction. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg to 2000 mg of each active ingredient, preferably between 1 mg to 1000 mg of each active ingredient, e.g., 5 mg to 500 mg of each active ingredient. In other embodiments, an intravenous, subcutaneous or intramuscular dosage of each active ingredient of between 0.01 mg and 1000 mg, preferably between 0.1 mg and 800 mg, e.g. 1 mg to 200 mg is used. In cases of administration of a pharmaceutically acceptable salt, dosages may be calculated as the free base. In some embodiments, the compound is administered one to four times per day. Alternatively, the compositions of the present invention may be administered by continuous intravenous infusion, preferably at a dose of each active ingredient up to 1000 mg per day. As will be understood by a person having ordinary skill in the art, in certain situations, it may be necessary to administer the compound disclosed in the present invention in amounts that exceed, or even far exceed, the above preferred dosage range in order to effectively and aggressively treat particularly aggressive diseases or infections. In some embodiments, the compound will be administered for a period of continuous therapy, for example a week or more, or for months or years.

Dosage amount and interval may be adjusted individually to provide plasma levels of the active moiety which are sufficient to maintain the modulating effects, or minimal effective concentration (MEC). The MEC will vary for each compound, but the MEC can be estimated from in vitro data. Dosage necessary to achieve the MEC will depend on individual characteristics of route of administration. However, HPLC assays or biological assay can be used to determine plasma concentrations.

Dosage intervals can be also determined using MEC value. Compositions can be administered using regimen which maintains plasma levels above the MEC for 10-90% of the time, preferably for 30-90% of the time and more preferably for 50-90% of the time.

In case of local administration or selective uptake, the effective local concentration of the drug may not be related to plasma concentration.

The amount of the composition administered may be dependent on the subject being treated, on the subject's weight, the severity of the affliction, the manner of administration and the judgement of the prescribing physician.

Compounds disclosed in the present application can be evaluated for efficacy and toxicity using known methods. For example, the toxicology of a particular compound, or of a subset of the compounds, sharing certain chemical moieties, can be established by determining in vitro toxicity towards a cell line, such as a mammalian cell line, and preferably a human cell line. The results of such studies are often predicitive of toxicity in animals, such as mammals, or more specifically, humans. Alternatively, the toxicity of particular compounds in an animal model, such as mice, rats, rabbits or monkeys and the like can be determined using known methods. The efficacy of a particular compound can be established using several art recognized methods, such as in vitro methods, animal models, or human clinical trials. Art-recognized in vitro models exist for nearly every class of condition, including but not limited to cancer, cardiovascular disease, and various immune dysfunctions. Similarly, acceptable animal models can be used to establish efficacy of chemicals to treat such conditions. When selecting a model to determine efficacy, the skilled artisan can be guided by the state of the art to choose an appropriate model, dose, and route of administration, and regimen. Of course, human clinical trials can also be used to determine the efficacy of a compound in humans.

The compositions may, if desired, be presented in a pack or dispenser device which may contain one or more unit dosage forms containing the active ingredient. The pack may, for example, comprise metal or plastic foil, such as a blister pack. The pack or dispenser may be accompanied with instructions for administration. The pack or dispenser may be also accompanied with a notice associated with the container in form prescribed by a governmental agency regulating the manufacture, use, or sale of pharmaceuticals, which notice is reflective of approval by the agency of the form of the drug for of human or veterinary administration. Such notice, for example, may be the labeling approved by the United State Food and Drug Administration for prescription drugs, or the approved product insert. Compositions comprising the compound of the invention formulated in a compatible pharmaceutical carrier may also be prepared, placed in an appropriate container, and labeled for treatment of an indicated condition.

Preparation of Compounds

The process for preparing a compound of the present invention is exemplarily illustrated in the following reaction scheme. The compound is a compound of formula I, a stereoisomer thereof, a cis-trans-isomer thereof, a tautomer thereof, or a mixture thereof, or a pharmaceutically acceptable salt thereof, a solvate thereof or a prodrug thereof,

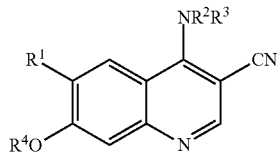

wherein $R^1$, $R^2$, $R^3$ and $R^4$ are each as defined in the present application.

It is understood that the following description, combinations of substituents and/or the variables of the depicted formulae are permissible only if such contributions result in stable compounds.

It will also be appreciated by a person having ordinary skill in the art that in the process described below the functional groups of intermediate compounds may be needed to be protected by suitable protecting group. Such functional groups include hydroxy, amino, mercapto and carboxylic acid. Suitable protecting groups for hydroxyl include trialkylsilyl or diarylalkylsilyl (such as tert-butyldimethylsilyl, tert-butyldiphenylsilyl or trimethylsilyl), tetrahydropyranyl, benzyl, and the like. Suitable protecting groups for amino, amidino and guanidino include tert-butylcarbonyl, carboxybenzyl, fluorenylmethoxy carbony, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or aralkyl esters.

Protecting group may be added or removed in accordance with the standard techniques, which are well-known by a person having ordinary skill in the art and as described herein.

The use of protecting groups is described in detail in Green, T. W. and P. G. M. Wuts, *Protective Groups in Organic Synthesis* (1999), 3rd Ed., Wiley. The protecting group may be polymer resin such as Wang resin or 2-chlorotrityl-chloride resin.

It will also appreciated by a person having ordinary skill in the art, although such protected derivatives of compound of this invention may not possess pharmacological activity as such, they may be administered to a mammal and thereafter metabolized in the body to form compounds of the invention which are pharmacologically active. Such derivatives may therefore be described as "prodrug". All prodrugs of compounds of this invention are included within the scope of the invention.

The following Reaction Scheme illustrates methods to make compounds of this invention. It is understood that a person having ordinary skill in the art would be able to make these compounds by similar methods or by methods known to the one skilled in the art. It is also understood that a person having ordinary skill in the art would use suitable starting components in the similar way as described below, and modify the synthesis parameters as required, in order to manufacture other compounds of formula I which are not explicitly illustrated hereinafter. In general, starting components may be obtained from the common commercial sources or synthesized according to sources known to a person having ordinary skill in the art or prepared as described in this invention.

$R^1$, $R^2$, $R^3$ and $R^4$ are defined in the following reaction scheme as in the Specification.

In general, the compounds of formula I can be synthesized following the general procedure as described in the Reaction Scheme 1.

ably a mixed acid. It is well-known for a person having ordinary skill in the art how to select conditions of a nitration reaction.

The compound of formula (102) reacts with alcohol of formula $R^4OH$ in the presence of a base. The resulting compound is treated with concentrated sulfuric acid, concentrated hydrochloric acid, concentrated phosphoric acid, and the like, to obtain the compound of formula (103). A base that can be used in the present invention includes, but is not limited to LiOH, NaOH, KOH, sodium ethoxide, potassium tert-butoxide, and the like.

The compound of formula (103) reacts with ethyl 2-cyano-3-ethoxy acrylate in a solvent to obtain the compound of formula (104). The solvent that can be used in this reaction includes, but is not limited to dichloromethane, toluene, and the like.

Reaction Scheme 1

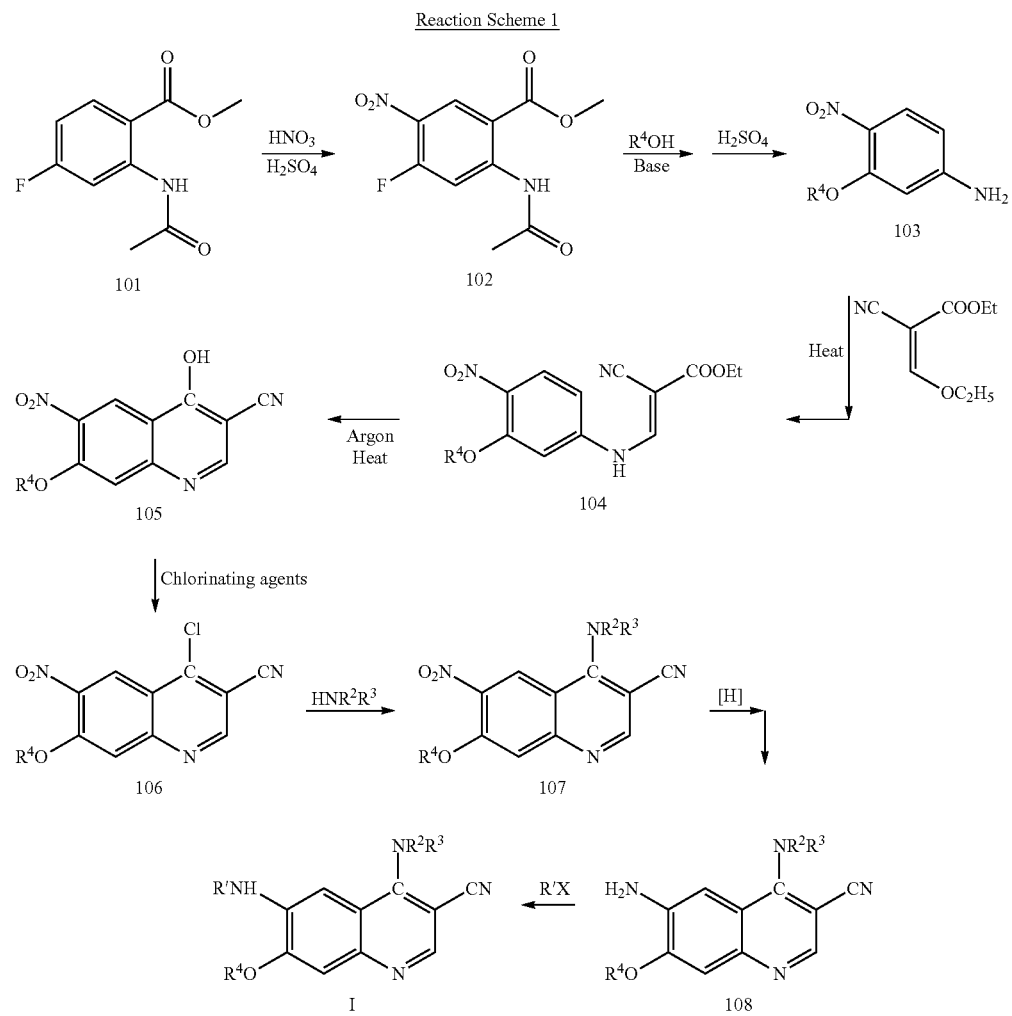

In Reaction Scheme 1, R' represents $C_1$-$C_6$ alkylacyl, $C_2$-$C_6$ alkenylacyl, $C_2$-$C_6$ alkynylacyl, $C_6$-$C_{18}$ arylacylamino, or $C_1$-$C_6$ alkyl. All the compounds may be present as a stereoisomer, a cis-trans-isomer, a tautomer or a mixture thereof.

As described below, the compound of formula (101) is subject to nitration to obtain the nitrated derivative of formula (102). Nitrating agent may be a mixed acid of nitric acid and sulfuric acid, concentrated nitric acid, and prefer- The compound of formula (104) is heated in a solvent in the presence of inert gas to obtain the compound of formula (105). The solvent that can be used in this reaction includes, but is not limited to Dowtherm A, and the like.

The compound of formula (105) reacts with a chlorinating agent to obtain the compound of formula (106). The chlorinating agent that can be used in the present invention includes, but is not limited to HCl, $SOCl_2$, $PCl_3$, $PCl_5$, $POCl_3$, $COCl_2$, and the like.

The compound of formula (106) reacts with an amine of formula HNR²R³ to obtain the compound of formula (107). The nitro group in the compound of formula (107) is reduced to an amino group with a reduction reaction to obtain the compound of formula (108). The reducing agent that can be used in this reaction includes, but is not limited to hydrogen, Zn/CH₃COOH, SnCl₂, Na₂Sₓ, NaSO₃, hydrazine and the like. Alternatively, electrochemical reduction process may be used.

The compound of formula (108) reacts with R'X, in which X represents Cl, Br, F, OMs or OTs to obtain the compound of formula I of the present invention.

In the following preparations for preparing intermediates of a compound of general formula I and the following examples regarding a compound of formula I, the used serial numbers of the compounds do not correspond to the serial numbers of the compounds described in the above Reaction Scheme.

Abbreviations in the following description of the preparation methods are as follows: Dowtherm A: a mixture of biphenyl and biphenyl ether; DCM: dichloromethane; THF: tetrahydrofuran; DIEA: diisopropylethylamine; DMF: N,N-dimethyl carboxamide; NBS: bromosuccinimide; DMAP: 4-dimethylaminopyridine; DCC: dicyclohexylcarbodiimide; Boc: tert-butoxycarbonyl; Fmoc: 9-fluorenylmethoxycarbonyl; Ms: methanesulfonyl; Ts: p-toluene sulfonyl; Su: succinylimide; At: 7-azobenzotriazol-1-yl; Bt: benzotriazol-1-yl; CBZ: benzyloxycarbonyl; Tyr: tyrosine; Glu: glutamate.

Unless specifically indicated, all H¹-NMR spectrum measuring instruments used in the examples in the present application are 400 MHz nuclear magnetic resonance spectrometer.

Preparation 1

METHYL 2-ACETYLAMINO-4-FLUORO-5-NITRO-BENZOATE

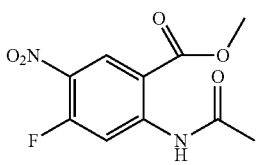 [SMILES: COC(=O)c1cc([N+](=O)[O-])c(F)cc1NC(C)=O]

To a three-neck flask (2,000 ml) was added concentrated nitric acid (500 ml). The mixture was cooled in an ice-water bath. Concentrated sulfuric acid (500 ml) was dropwise added to the mixture under mechanical stirring. After addition, the temperature of the resulting mixture was maintained below 15° C. Methyl 2-acetylamino-4-fluoro-benzoate (105.5 g, 0.5 mol) was slowly added. The resultant mixture was kept in an ice-water bath for 40 min with stirring. Then the mixture was poured into ice water (8 L). A large number of yellow solids precipitated. The mixture was stood for 10 min and filtered in vacuo. The filter cake was washed with lots of water and then transferred in water (2 L). The pH of the solution was adjusted to 7 with ammonia liquor under stirring and filtered in vacuo. The filter cake was dried by baking and recrystalized with ethyl acetate.

Preparation 2

4-NITRO-3-(TETRAHYDROFURAN-3-YL-OXY)-BENZENAMINE

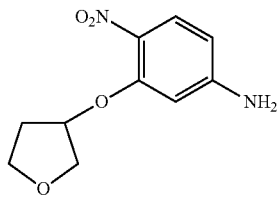 [SMILES: Nc1ccc([N+](=O)[O-])c(OC2CCOC2)c1]

To a single-neck reaction flask (100 ml) was added 3-hydroxytetrahydrofuran (27 ml, 400 mmol) under argon atmosphere. To the flask was added potassium tert-butoxide (15.9 g, 150 mmol) in batch under stirring. The resulting mixture was warmed to the temperature of 75° C. and stirred. After 15 min, the white solid substantially disappeared. Methyl 2-acetylamino-4-fluoro-5-nitro-benzoate (25.6 g, 100 mmol) was slowly added in batch to the solution. After addition, the resultant mixture was heated and stirred for further 50 min. The reaction was stopped. The mixture was slightly cooled and poured into water (500 ml). A large number of red solids precipitated. The pH of the solution was adjusted to 3 with hydrochloric acid (2N). The solids became yellow. The solution was extracted with ethyl acetate three times (total 800 mL). The aqueous layer was discarded. The layers of ethyl acetate were combined and washed once with water (300 mL) and once with saturated NaCl solution (300 mL). The organic layer was dried over MgSO₄ for half-hour, filtered and rotary-evaporated to dryness. The resultant substance was dried with an oil pump to give a tawny foam.

Concentrated sulfuric acid (200 mL) was dropwise added into water (300 mL) in an ice-water bath. The resultant acid was poured into the tawny foam. The mixture was stirred for 4.5 h in an oil bath at the temperature of 110° C. The reaction was stopped. The reaction solution was poured into ice water (2 L). The mixture was stirred in an ice water bath. The pH of the resulting solution was adjusted to 9 with ammonia liquor. The resultant mixture was extracted with ethyl acetate three times. The ethyl acetate layers were combined and washed with water (500 mL), saturated NaHCO₃ solution (500 mL), and saturated NaCl solution (500 mL), successively. The resultant organic layer was dried over MgSO₄ for half-hour. The mixture was filtered and rotary-evaporated to dryness. The resultant substance was purified with column chromatography (eluent: dichloromethane:ethyl acetate=2:5) to give a yellow solid. Yield: 11.5 g, 51%.

Preparation 3

(E/Z)-ETHYL 2-CYANO-3-(4-NITRO-3-(TETRAHYDROFURAN-3-YL-OXY)-PHENYLAMINO)-ACRYLATE

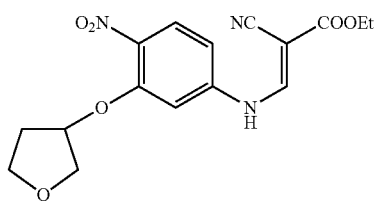 [SMILES: CCOC(=O)/C(C#N)=C/Nc1ccc([N+](=O)[O-])c(OC2CCOC2)c1]

To a single-neck reaction flask (250 mL) were added 4-nitro-3-(tetrahydrofuran-3-yl-oxy)-benzenamine (7.966 g, 35.722 mmol), (E/Z)-ethyl 2-cyano-3-ethoxy acrylate (8.452 g, 50.0 mmol) and toluene (146 mL). The mixture was stirred and refluxed for 16 hr in an oil bath at the temperature of 115° C. The reaction was stopped. The resultant mixture was cooled in an ice-water bath and filtered in vacuo. The filter cake was washed with mother liquor, toluene (200 mL) and anhydrous ethyl ether, successively. The filter cake was pumped to dryness to give a yellow solid (11.5 g). The resultant substance was recrystalized with ethylene glycol monomethyl ether to give a yellow crystal (9.95 g). Yield: 80.5%.

Preparation 4a

4-HYDROXY-6-NITRO-7-(TETRAHYDRO-FURAN-3-YL-OXY)QUINOLINE-3-CARBONITRILE

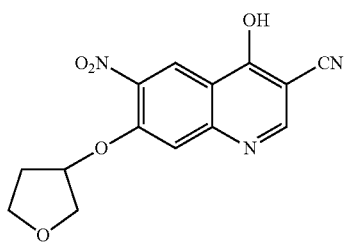

To a three-neck flask (2000 mL) under argon atmosphere was added (E/Z)-ethyl 2-cyano-3-(4-nitro-3-(tetrahydrofuran-3-yl-oxy)phenylamino)-acrylate (17.09 g, 49.251 mmol). To the flask was added Dowtherm A (600 mL) under argon atmosphere. After 10 min, the mixture was heated. The mixture was stirred at the temperature of about 256° C. for 2 hr. The resultant mixture was stood to cool to the room temperature. Yellow solids precipitated. Anhydrous ethyl ether (360 mL) was added to the mixture. The resulting mixture was stirred for 15 min at the room temperature and filtered in vacuo. The filter cake was washed with anhydrous ethyl ether and dried in the air. The fiter cake was dissolved in THF (40 mL). The solution was stirred and refluxed at the temperature of 85° C. for 1 hr, cooled to the room temperature and filtered in vacuo. The resultant filter cake was washed with mother liquor and dried in the air. The resultant substance was recrystalized with ethylene glycol monomethyl ether to give a gray solid (6.485 g). Yield: 43.7%.

Preparation 4b

7-FLUORO-4-HYDROXY-6-NITROQUINOLINE-3-CARBONITRILE

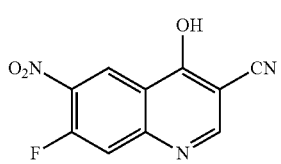 [SMILES: N#Cc1cnc2cc(F)c([N+](=O)[O-])cc2c1O]

The titled compound was prepared with 3-fluoro-4-nitrobenzenamine as starting material according to the processes of the Preparation 3 and Preparation 4a.

Preparation 4c (S)-4-HYDROXY-6-NITRO-7-(TETRAHYDRO-FURAN-3-YL-OXY)QUINOLINE-3-CARBONITRILE

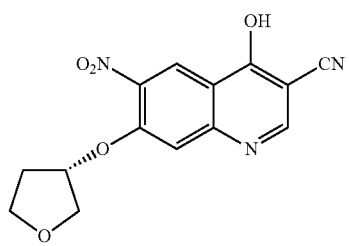

The titled compound was prepared with (S)-4-hydroxy-6-nitro-7-(tetrahydrofuran-3-yl-oxy)quinoline-3-carbonitrile as starting material according to the processes of the Preparation 3 and Preparation 4a.

Preparation 4d (R)-4-HYDROXY-6-NITRO-7-(TETRAHYDRO-FURAN-3-YL-OXY)QUINOLINE-3-CARBONITRILE

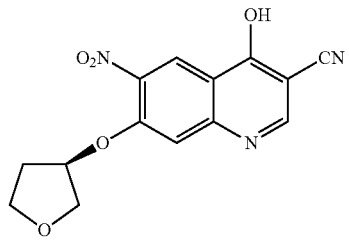

The titled compound was prepared with (R)-4-hydroxy-6-nitro-7-(tetrahydrofuran-3-yl-oxy)quinoline-3-carbonitrile as starting material according to the processes of the Preparation 3 and Preparation 4a.

Preparation 5a

4-CHLORO-6-NITRO-7-(TETRAHYDROFURAN-3-YL-OXY)QUINOLINE-3-CARBONITRILE

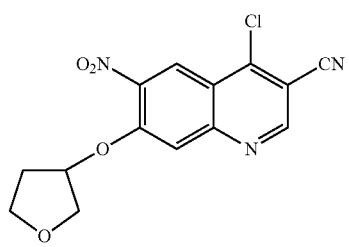 [SMILES: N#Cc1cnc2cc(OC3CCOC3)c([N+](=O)[O-])cc2c1Cl]

To a single-neck reaction flask (100 ml) were added 4-hydroxy-6-nitro-7-(tetrahydrofuran-3-yl-oxy)quinoline-3-carbonitrile (1.8 g, 3 mmol) and POCl$_3$ (10 mL) under argon atmosphere. The mixture was warmed to the temperature of 105° C. The reaction mixture was stirred for 2.5 hr. Then the reaction was stopped. The resultant mixture was rotary-evaporated to dryness. DCM (20 mL) was added to dissolve the resultant mixture. The solution was poured into a cooled mixture solution of DCM (200 mL) and saturated $K_2CO_3$ solution (60 mL). The resultant mixture was stirred for 10 min. The solution was extracted and the aqueous layer was discarded. The DCM layer was washed with water (150 mL) and staturated NaCl solution (150 mL), successively. The resultant substance was dried over $MgSO_4$ for half-hour, filtered, rotary-evaporated to dryness, and dried in vacuo to give a yellow solid (1.771 g). Yield: 92.7%.

The compounds of Preparation 5b and Preparation 5c were prepared with the compounds obtained from Preparation 4c and Preparation 4d as starting materials, respectively, according to the process of Preparation 5a.

Preparation 5b (S)-4-CHLORO-6-NITRO-7-(TETRAHYDRO-FURAN-3-YL-OXY)QUINOLINE-3-CARBONITRILE

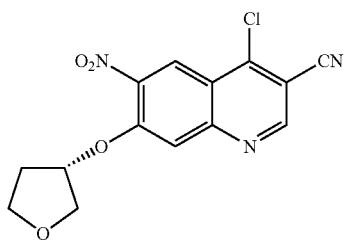 [SMILES: N#Cc1cnc2cc(O[C@H]3CCOC3)c([N+](=O)[O-])cc2c1Cl]

Preparation 5c (R)-4-CHLORO-6-NITRO-7-(TETRAHYDRO-FURAN-3-YL-OXY)QUINOLINE-3-CARBONITRILE

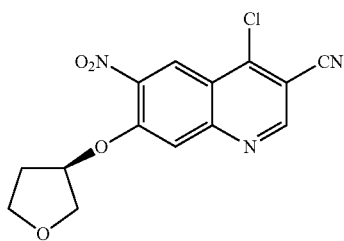 [SMILES: N#Cc1cnc2cc(O[C@@H]3CCOC3)c([N+](=O)[O-])cc2c1Cl]

Preparation 6a

3-CHLORO-4-(PYRIDIN-2-YL-METHOXY)BENZENAMINE

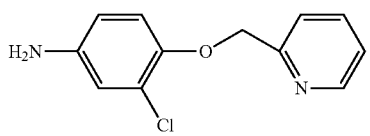

To a reaction flask were added 2-chloro-4-tert-butylcarbonylamino-phenol (24.35 g, 100 mmol), 2-chloromethyl-pyridine hydrochloride (32.8 g, 200 mmol), potassium carbonate (41.4 g, 300 mmol) and tetrabutyl amimonium iodide (1.107 g, 3 mmol). To the flask was added DMF (100 ml). The reaction mixture was stirred. After the reaction finished, the reaction solution was poured into water (1 L). The mixture was extracted with ethyl acetate three times. The ethyl acetate layers were combined. The resultant organic layer was washed with water (500 ml) and staturated saline solution (500 ml), successively. The resulting mixture was dried over anhydrous magnesium sulfate for 30 min, filtered and rotary-evaporated to dryness. The resultant substance was purified with column chromatography (eluent: ethyl acetate:petroleum ether=1:) to give N-(3-chloro-4-(pyridin-2-yl-methoxy)phenyl)-tert-butoxyacylamine.

To a reaction flask was added N-(3-chloro-4-(pyridin-2-yl-methoxy) phenyl)-tert-butoxyacylamine. N-(3-chloro-4-(pyridin-2-yl-methoxy)phenyl)-tert-butoxy acylamine was dissolved with 20% TFA in DCM (50 ml). The mixture was stirred at the room temperature. After the reaction finished, the solvent was rotary-evaporated. The residue was dissolved in DCM (200 ml). The resulting solution was washed with saturated sodium carbonate three times (200 ml×3), with water (200 ml) once, with saturated saline solution (200 ml) once, successively. The resultant substance was dried over anhydrous magnesium sulfate and filtered. The solvent was rotary-evaporated to give the target product.

The compounds of Preparations 6b to Preparation 6g were prepared with different starting materials according to a process similar to that of Preparation 6a.

Preparation 6b

1-BENZYL-1H-INDOLE-5-AMINE

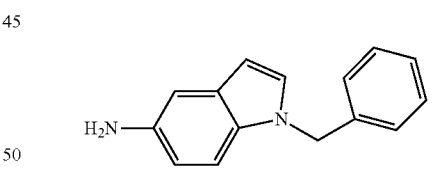

Preparation 6c 3-((5-AMINO-1H-INDOL-1-YL)METHYL)BENZONITRILE

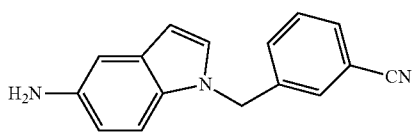 [SMILES: N#Cc1cccc(Cn2ccc3cc(N)ccc32)c1]

Preparation 6d 1-(3-METHOXYBENZYL)-1H-INDOL-5-AMINE

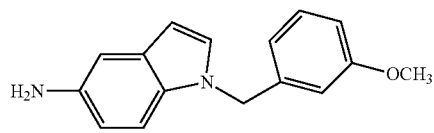 [SMILES: COc1cccc(Cn2ccc3cc(N)ccc32)c1]

Preparation 6e 1-(3-CHLOROBENZYL)-1H-INDOL-5-AMINE

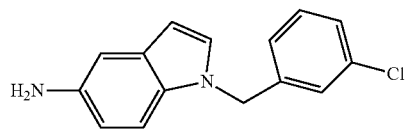 [SMILES: Nc1ccc2c(ccn2Cc2cccc(Cl)c2)c1]

Preparation 6f 6-(BENZYLOXY)-INDOLINE

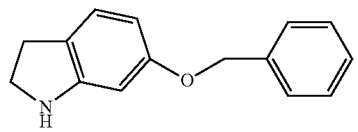 [SMILES: c1ccc(COc2ccc3c(c2)NCC3)cc1]

Preparation 6g 6-(BENZYLOXY)PYRIDIN-3-AMINE

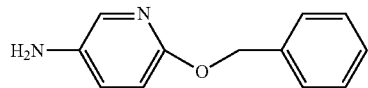 [SMILES: Nc1ccc(OCc2ccccc2)nc1]

Preparation 6h 4-(2-CHLOROBENZYLOXY)-3-CHLOROBENZENAMINE

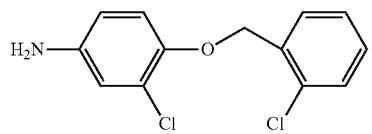

To a reaction flask were added 2-chloro-4-nitrophenol (5.205 g, 30 mmol), 2-chlorobenzyl chloride (5.313 g, 33 mmol), potassium carbonate (4.554 g, 33 mmol) and DMF (40 ml). The reaction mixture was heated to the temperature of 100° C. After the reaction finished, the reaction solution was poured into water (400 ml). The mixture was extracted with ethyl acetate (300 ml). The ethyl acetate layer was washed with saturated saline solution (200 ml) once and dried over anhydrous magnesium sulfate. The organic layer was filtered and the solvent was rotary-evaporated to dryness. The resultant substance was recrystalized with ethyl acetate to give 1-(2-chlorobenzyloxy)-2-chloro-4-nitrobenzene (8.567 g).

To a three-neck flask (500 ml) was added 1-(2-chlorobenzyloxy)-2-chloro-4-nitrobenzene (8.567 g). To the flask were added THF (100 ml) and methanol (50 ml). The solution was mechanically stirred and heated under reflux. Glacial acetic acid (17 ml) and reduced iron powders (16.8 g) were added into the solution. The mixture reacted for 1 hr. After the reaction finished, the resultant substance was filtered in vacuo and the filtrate was rotary-evaporated to dryness. To the resultant crude product was added HCl (4N, 200 ml). The mixture was sufficiently vibrated and then filtered in vacuo. To the resultant filter cake was added water (100 ml). The pH of the mixture was adjusted to 12 with 5% sodium hydroxide. Ethyl acetate (700 ml) was added. The solution was sufficiently vibrated and separated. The ethyl acetate layer was washed with saturated sodium carbonate (200 ml), water (200 ml) and staturated saline solution (200 ml), successively. The organic layer was dried over anhydrous magnesium sulfate and filtered. The solvent was rotary-evaporated to dryness. The resultant substance was recrystalized with ethyl acetate to give the target compound.

The compounds of Preparation 6i to Preparation 6aa were prepared according to the process of Preparation 6h.

Preparation 6i 4-(2-FLUOROBENZYLOXY)-3-CHLOROBENZENAMINE

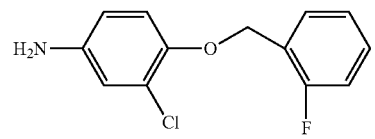 [SMILES: Nc1ccc(OCc2ccccc2F)c(Cl)c1]

Preparation 6j 4-(3-FLUOROBENZYLOXY)-3-CHLOROBENZENAMINE

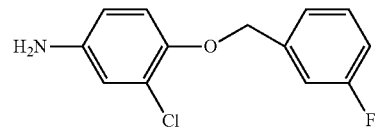

Preparation 6k 4-(4-FLUOROBENZYLOXY)-3-CHLOROBENZENAMINE

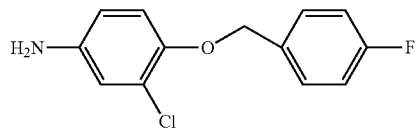

Preparation 6l 4-(3-CHLOROBENZYLOXY)-3-CHLOROBENZENAMINE

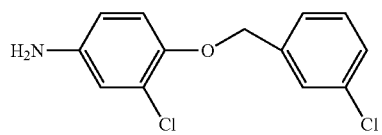

Preparation 6m 4-(4-CHLOROBENZYLOXY)-3-CHLOROBENZENAMINE

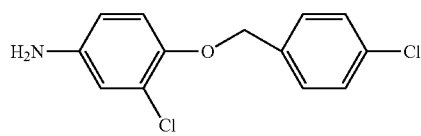

Preparation 6n 4-(2-METHYLBENZYLOXY)-3-CHLOROBENZENAMINE

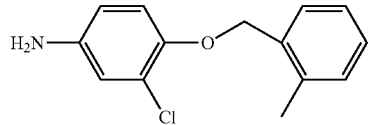 [SMILES: Cc1ccccc1COc1ccc(N)cc1Cl]

Preparation 6o 4-(3-METHYLBENZYLOXY)-3-CHLOROBENZENAMINE

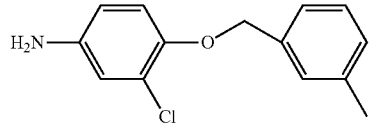

Preparation 6p 4-(4-METHYLBENZYLOXY)-3-CHLOROBENZENAMINE

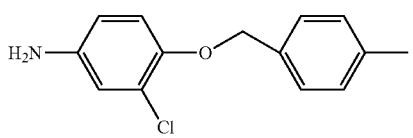 [SMILES: Cc1ccc(COc2ccc(N)cc2Cl)cc1]

Preparation 6q 4-(2-METHOXYBENZYLOXY)-3-CHLOROBENZENAMINE

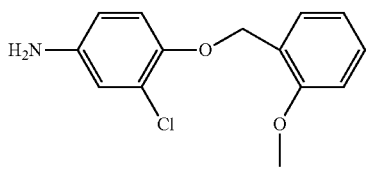 [SMILES: COc1ccccc1COc1ccc(N)cc1Cl]

Preparation 6r 4-(3-METHOXYBENZYLOXY)-3-CHLOROBENZENAMINE

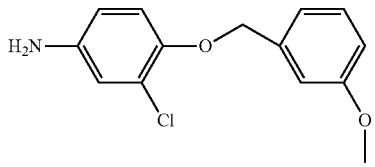 [SMILES: COc1cccc(COc2ccc(N)cc2Cl)c1]

Preparation 6s 4-(4-METHOXYLBENZYLOXY)-3-CHLOROBENZENAMINE

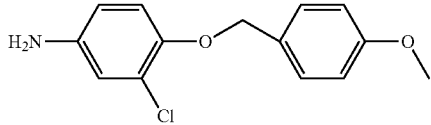

Preparation 6t 2-((4-AMINO-2-CHLOROPHENOXY)METHYL)BENZONITRILE

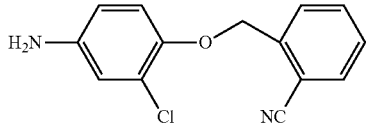 [SMILES: N#Cc1ccccc1COc1ccc(N)cc1Cl]

Preparation 6u 3-((4-AMINO-2-CHLOROPHENOXY)METHYL)BENZONITRILE

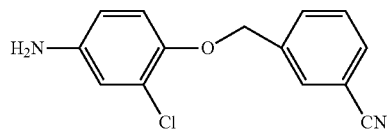 [SMILES: N#Cc1cccc(COc2ccc(N)cc2Cl)c1]

Preparation 6v 4-((4-AMINO-2-CHLOROPHENOXY)METHYL)BENZONITRLE

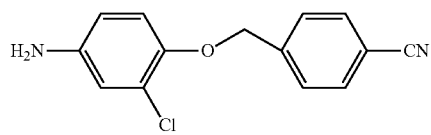 [SMILES: N#Cc1ccc(COc2ccc(N)cc2Cl)cc1]

Preparation 6w 4-(4-TERT-BUTYLBENZYLOXY)-3-CHLOROBENZENAMINE

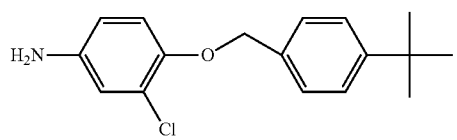 [SMILES: CC(C)(C)c1ccc(COc2ccc(N)cc2Cl)cc1]

Preparation 6x 4-(BENZYLOXY)-3-CHLOROBENZENAMINE

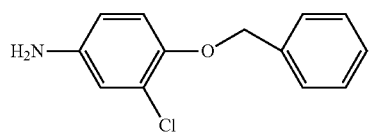 [SMILES: Nc1ccc(OCc2ccccc2)c(Cl)c1]

Preparation 6y 4-(2-CHLOROBENZYLOXY)-3-FLUOROBENZENAMINE

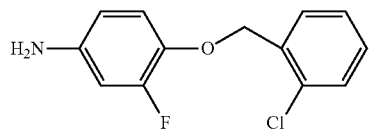 [SMILES: Nc1ccc(OCc2ccccc2Cl)c(F)c1]

Preparation 6z 4-(3-CHLOROBENZYLOXY)-3-FLUOROBENZENAMINE

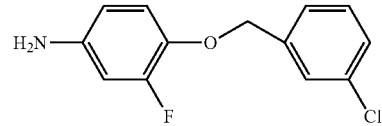

Preparation 6aa 4-(4-CHLOROBENZYLOXY)-3-FLUOROBENZENAMINE

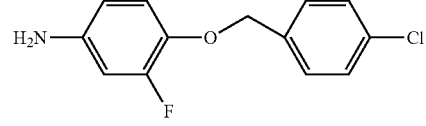

Preparation 6ab 4-(4-BROMOBENZYLOXY)-3-CHLOROBENZENAMINE

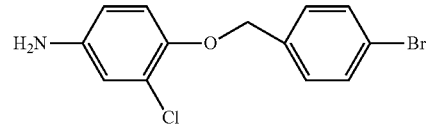

Preparation 6ac 4-(4-ETHYLBENZYLOXY)-3-CHLOROBENZENAMINE

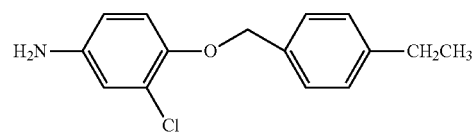 [SMILES: CCc1ccc(COc2ccc(N)cc2Cl)cc1]

Preparation 6ad 4-(4-ETHOXYBENZYLOXY)-3-CHLOROBENZENAMINE

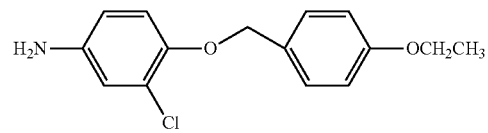 [SMILES: CCOc1ccc(COc2ccc(N)cc2Cl)cc1]

Preparation 6ah 6-(3-CHLOROBENZYLOXY)PYRIDINE-3-AMINE

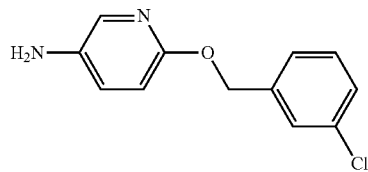 [SMILES: Nc1ccc(OCc2cccc(Cl)c2)nc1]

Preparation 6ai 4-(3-METHOXYBENZYLOXY)BENZENAMINE

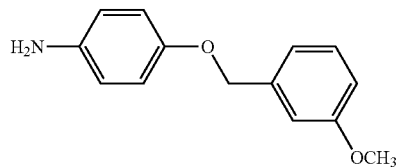 [SMILES: COc1cccc(COc2ccc(N)cc2)c1]

Preparation 6aj

4-BENZYLOXYBENZENAMINE

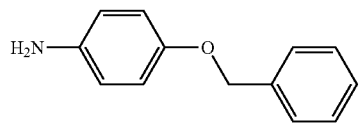

Preparation 6ak

2-AMINO-5-(N-BENZOYL)-AMINO-PYRIMIDINe

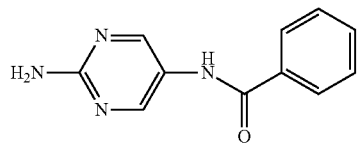 [SMILES: Nc1ncc(NC(=O)c2ccccc2)cn1]

To a three-neck flask were added 2-amino-5-nitropyrimidine (1.4 g, 10 mmol), (Boc)$_2$O (2.18 g, 10 mmol), sodium bicarbonate (1.4 g), THF (15 ml) and water (15 ml). The mixture was stirred at the room temperature for 4 hr. After the reaction finished, the resultant mixture was exacted with chloroform three times (20 ml*3). The organic phases were combined and washed once with saturated sodium chloride solution (20 ml). The organic phase was dried over anhydrous magnesium sulfate. After half-hour, the drying agent was discarded and the filtrate was concentrated in vacuo to give 5-nitro-2-(N-tert-butoxycarbonyl)-aminopyrimidine as a solid (2.3 g).

5-nitro-2-(N-tert-butoxycarbonyl)-aminopyrimidine (2.3 g) was dissolved in THF solution (20 ml). 10% palladium on carbon (230 mg) was added to the solution. The mixture was hydrogenated for 6 hr. The solution was filtered with silica gel-sand panel funnel. The filtrate was retained and the solvent was evaporated in vacuo. The resultant substance was purified by flash chromatography with silica gel column and eluated with chloroform:methanol=9:1 to give 5-amino-2-(N-tert-butoxycarbonyl)-aminopyrimidine (1.5 g).

5-amino-2-(N-tert-butoxycarbonyl)-aminopyrimidine (1.5 g) was dissolved in redistilled DCM (15 ml). Redistilled triethylamine (1.2 ml, 8.6 mmol) was added. The solution was cooled in an ice water bath under nitrogen atmosphere. After 20 min, a solution of benzoyl chloride (1 ml) in DCM (5 ml) was dropwise added into the solution. The ice water bath was removed after the addition finished. The solution was stirred overnight. To the solution was added water (100 ml). The resultant solution was extracted and separated. The organic phase was retained and washed once with of saturated sodium chloride (20 ml) and dried over anhydrous magnesium sulfate. After 0.5 hr, the solution was filtered. The filtrate was concentrated in vacuo. The resulting substance was purified by flash chromatography with silica gel column and eluated with chloroform:methanol=95:5 to give 2-(N-tert-butoxycarbonyl)-amino-5-(N-benzoyl)-aminopyrimidine (1.6 g).

2-(N-tert-butoxycarbonyl)-amino-5-(N-benzoyl)-aminopyrimidine (1.6 g) was dissolved in DCM (20 ml). Trifluoroacetic acid (1.5 ml, 5.8 mmol) was added under stirring at the room temperature. The mixture was stirred at the room temperature. After 2 hr, the reaction was stopped. The solvent was rotary-evaporated to dryness in vacuo. To the resultant substance was added ethyl acetate (20 ml) and 2N HCl (20 ml). The mixture was extracted and separated. The aqueous phase was retained and the pH was adjusted to 10 with 10% sodium hydroxide solution. The resulting mixture was extracted three times with ethyl acetate (25 ml*3) and the ethyl acetate layers were combined. The resultant organic phase was washed with saturated sodium chloride (20 ml) once and dried over anhydrous magnesium sulfate. After 0.5 hr, the solution was filtered and the filtrate was concentrated in vacuo to give 2-amino-5-(N-benzoyl)-amino-pyrimidine (0.7 g).

The compounds of Preparation 6al to Preparation 6an were prepared according to the process of Preparation 6ak.

Preparation 6al

2-AMINO-5-(N-4-DIMETHYLAMINO-BENZOYL)-AMINO-PYRIMIDINE

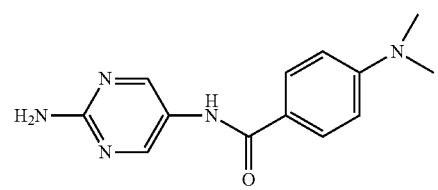 [SMILES: CN(C)c1ccc(C(=O)Nc2cnc(N)nc2)cc1]

Preparation 6am

2-AMINO-5-(N-4-METHOXY-BENZOYL)-AMINO-PYRIMIDINE

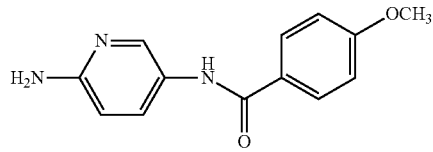 [SMILES: COc1ccc(C(=O)Nc2ccc(N)nc2)cc1]

Preparation 6an

2-AMINO-5-(N-BENZENESULFONYL)-AMINO-PYRIMIDINE

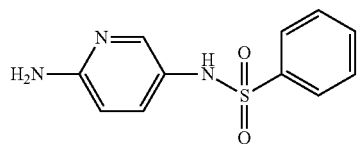 [SMILES: Nc1ccc(NS(=O)(=O)c2ccccc2)cn1]

Preparation 6ao 2-(N-BENZOYL)-AMINO-5-AMINO-PYRIMIDINE

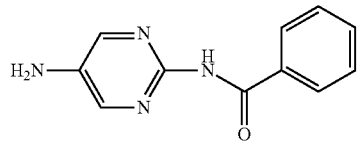 [SMILES: Nc1cnc(NC(=O)c2ccccc2)nc1]

To stirred solution of 2-amino-5-nitropyrimidine (1.0 g, 7.14 mmol) in pyridine (20 ml) was added benzoyl chloride (0.92 ml, 7.93 mmol). The mixture was refluxed for 4 hr under nitrogen atmosphere. The reactant mixture was cooled to the room temperature and poured into 200 ml water. The resulting mixture was stirred overnight and then filtered in vacuo. The filter cake was washed with water (20 ml*3) and dried in vacuo to give 2-(N-benzoyl)amino-5-nitropyrimidine as a white solid (790 mg).

2-(N-benzoyl)amino-5-nitropyrimidine (790 mg) was added into ethanol (100 ml). 80 mg of 10% palladium on carbon was added to the solution under stirring at the room temperature. The reactant was hydrogenated and stirred for 4 hr. The solution was filtered through silica gel-sand panel funnel. The filtrate was retained and the solvent was evaporated in vacuo. The resultant substance was purified by flash chromatography with silica gel column and eluted with chloroform:methanol=95:5 to give 2-(N-benzoyl)amino-5-aminopyrimidine (200 mg).

The compounds of Preparation 6ap to Preparation 6as were prepared according to the process of Preparation 6ao.

Preparation 6ap 2-(N-4-METHOXY-BENZOYL)-AMINO-5-AMINO-PYRIMIDINE

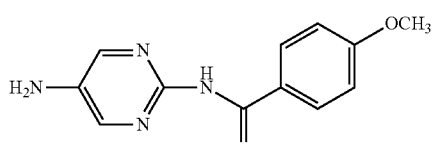

Preparation 6aq 2-(N-CYCLOHEXYL-1-BENZOYL)-AMINO-5-AMINO-PYRIMIDINE

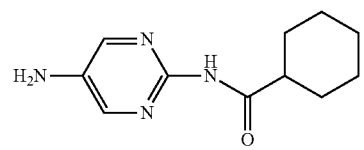 [SMILES: Nc1cnc(NC(=O)C2CCCCC2)nc1]

Preparation 6ar 2-(N-2-FORMYL-THIOPHENYL)-AMINO-5-AMINO-PYRIMIDINE

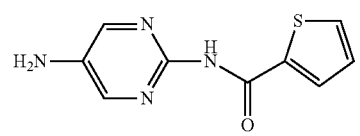 [SMILES: Nc1cnc(NC(=O)c2cccs2)nc1]

Preparation 6as 2-(N-2-FORMYL-FURANYL)-AMINO-5-AMINO-PYRIMIDINE

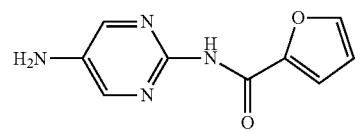 [SMILES: Nc1cnc(NC(=O)c2ccco2)nc1]

Preparation 7a 4-(3-CHLORO-4(PYRIDIN-2-YL-METHOXY) PHENYLAMINO)-6-NITRO-7-(TETRAHYDRO-FURAN-3-YL-OXY)QUINOLINE-3-CARBONITRILE

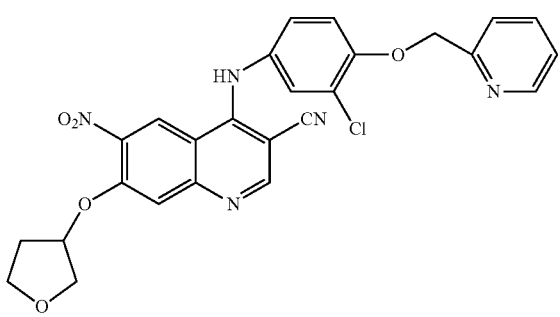

To a single-neck reaction flask (500 ml) were added 4-chloro-6-nitro-7-(tetrahydrofuran-3-yl-oxy)quinoline-3-carbonitrile (5 g, 15.649 mmol), 3-chloro-4-(pyridin-2-yl-methoxy)benzenamine (4.037 g, 17.214 mmol) and pyridine hydrochloride (421 mg). To the flask was added isopropanol (150 ml). The mixture was stirred and refluxed for 2 hr at the temperature of 85° C. The reaction was stopped and cooled to the room temperature. The resultant mixture was filtered in vacuo. The filter cake was washed with mother liquor and dried in vacuo to give a yellow solid (5.988 g). Yield: 73.9%.

The compounds of Preparation 7b to Preparation 7bh were prepared with different starting materials according to the process of Preparation 7a.

Preparation 7b 4-(3-CHLORO-4-FLUOROPHENYLAMINO)-6-NITRO-7-(TETRAHYDROFURAN-3-YL-OXY) QUINOLINE-3-CARBONITRILE

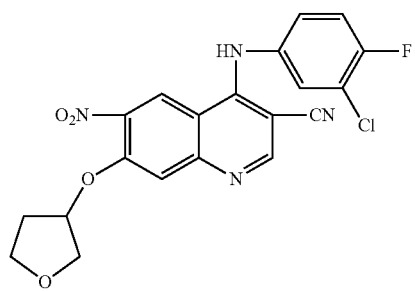

Preparation 7c 4-(3-ALKYNYLPHENYLAMINO)-6-NITRO-7-(TETRAHYDROFURAN-3-YL-OXY) QUINOLINE-3-CARBONITRILE

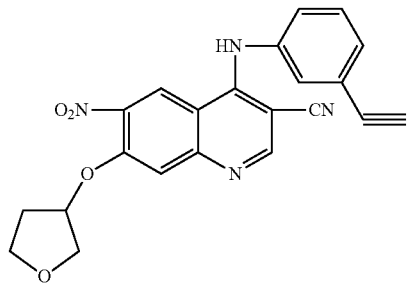

Preparation 7d 4-(3-BROMOPHENYLAMINO)-6-NITRO-7-(TETRAHYDROFURAN-3-YL-OXY) QUINOLINE-3-CARBONITRILE

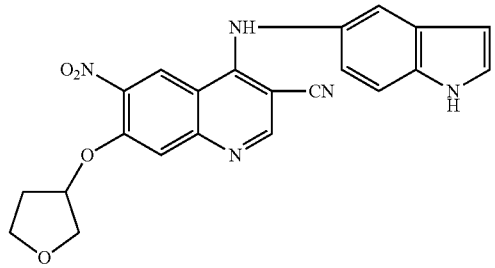 [SMILES: N#Cc1cnc2cc(OC3CCOC3)c([N+](=O)[O-])cc2c1Nc1ccc2[nH]ccc2c1]

Preparation 7e

6-NITRO-4-(1H-INDOL-5-YL-AMINO)-7-(TETRAHYDROFURAN-3-YL-OXY) QUINOLINE-3-CARBONITRILE

Preparation 7f 4-(4-(2-FLUOROBENZYLOXY)-3-FHLOROPHE-
NYLAMINO)-6-NITRO-7-(TETRAHYDRO-
FURAN-3-YL-OXY)QUINOLINE-3-CARBONI-
TRILE

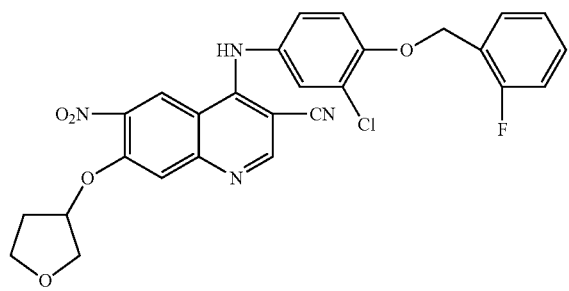

Preparation 7g 4-(4-(3-FLUOROBENZYLOXY)-3-CHLOROPHE-
NYLAMINO)-6-NITRO-7-(TETRAHYDRO-
FURAN-3-YL-OXY) QUINOLINE-3-CARBONI-
TRILE

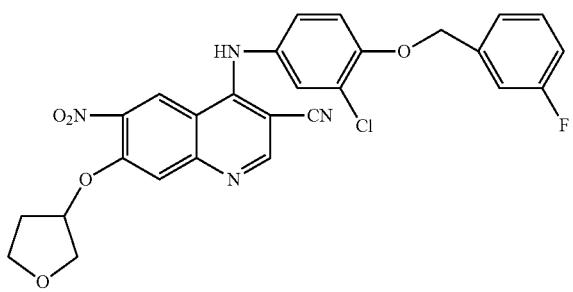

Preparation 7h 4-(4-(4-FLUOROBENZYLOXY)-3-CHLOROPHE-
NYLAMINO)-6-NITRO-7-(TETRAHYDRO-
FURAN-3-YL-OXY)QUINOLINE-3-CARBONI-
TRILE

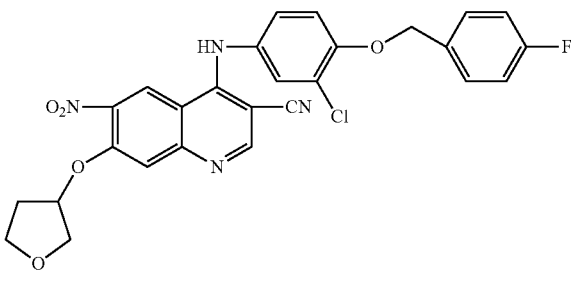 [SMILES: N#Cc1cnc2cc(OC3CCOC3)c([N+](=O)[O-])cc2c1Nc1ccc(OCc2ccc(F)cc2)c(Cl)c1]

Preparation 7i 4-(4-(2-CHLOROBENZYLOXY)-3-CHLOROPHE-
NYLAMINO)-6-NITRO-7-(TETRAHYDRO-
FURAN-3-YL-OXY)QUINOLINE-3-CARBONI-
TRILE

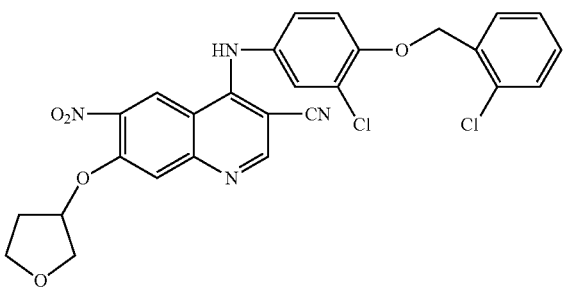

Preparation 7j 4-(4-(3-CHLOROBENZYLOXY)-3-CHLOROPHE-
NYLAMINO)-6-NITRO-7-(TETRAHYDRO-
FURAN-3-YL-OXY)QUINOLINE-3-CARBONI-
TRILE

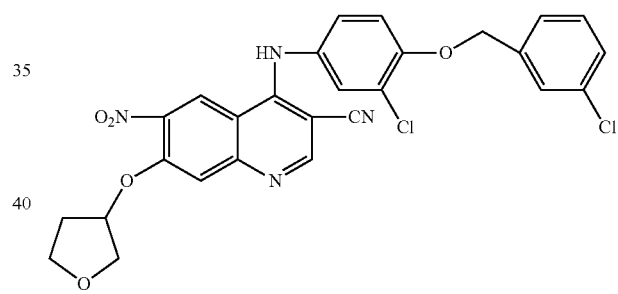

Preparation 7k 4-(4-(4-CHLOROBENZYLOXY)-3-CHLOROPHE-
NYLAMINO)-6-NITRO-7-(TETRAHYDRO-
FURAN-3-YL-OXY)QUINOLINE-3-CARBONI-
TRILE

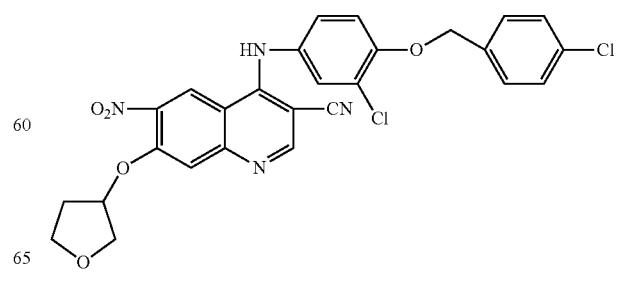

Preparation 7l 4-(4-(2-METHYLBENZYLOXY)-3-CHLOROPHE-
NYLAMINO)-6-NITRO-7-(TETRAHYDRO-
FURAN-3-YL-OXY)QUINOLINE-3-CARBONI-
TRILE

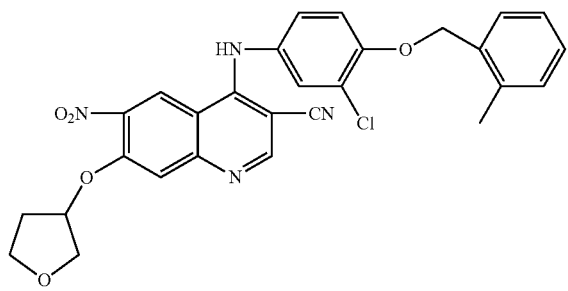

Preparation 7m 4-(4-(3-METHYLBENZYLOXY)-3-CHLOROPHE-
NYLAMINO)-6-NITRO-7-(TETRAHYDRO-
FURAN-3-YL-OXY)QUINOLINE-3-CARBONI-
TRILE

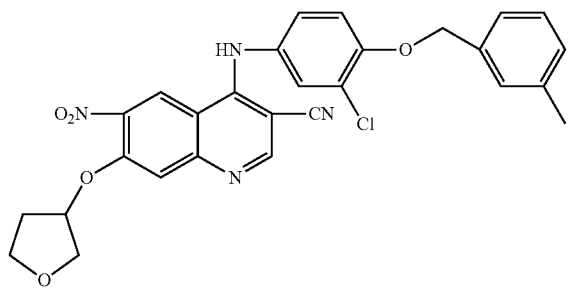 [SMILES: Cc1cccc(COc2ccc(Nc3c(C#N)cnc4cc(OC5CCOC5)c([N+](=O)[O-])cc34)cc2Cl)c1]

Preparation 7n 4-(4-(4-NETHYLBENZYLOXY)-3-CHLOROPHE-
NYLAMINO)-6-NITRO-7-(TETRAHYDRO-
FURAN-3-YL-OXY)QUINOLINE-3-CARBONI-
TRILE

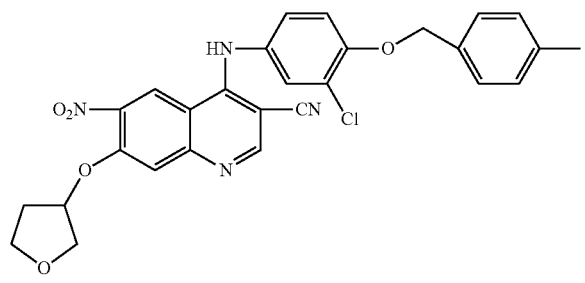

Preparation 7o 4-(4-(2-METHOXYBENZYLOXY)-3-CHLORO-
PHENYLAMINO)-6-NITRO-7-(TETRAHYDRO-
FURAN-3-YL-OXY)QUINOLINE-3-CARBONI-
TRILE

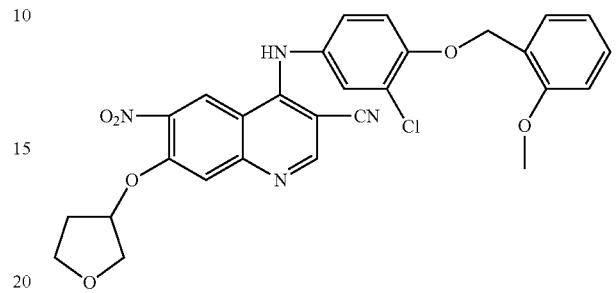

Preparation 7p 4-(4-(3-METHOXYBENZYLOXY)-3-CHLORO-
PHENYLAMINO)-6-NITRO-7-(TETRAHYDRO-
FURAN-3-YL-OXY)QUINOLINE-3-CARBONI-
TRILE

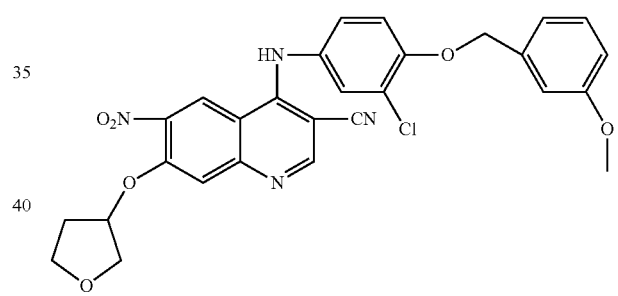

Preparation 7q 4-(4-(4-METHOXYBENZYLOXY)-3-CHLORO-
PHENYLAMINO)-6-NITRO-7-(TETRAHYDRO-
FURAN-3-YL-OXY)QUINOLINE-3-CARBONI-
TRILE

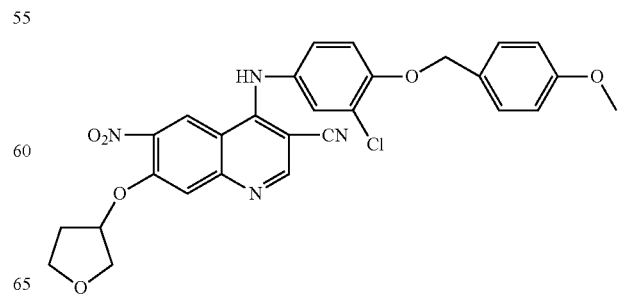

Preparation 7r 4-(4-(2-CYANOBENZYLOXY)-3-CHLOROPHE-
NYLAMINO)-6-NITRO-7-(TETRAHYDRO-
FURAN-3-YL-OXY)QUINOLINE-3-CARBONI-
TRILE

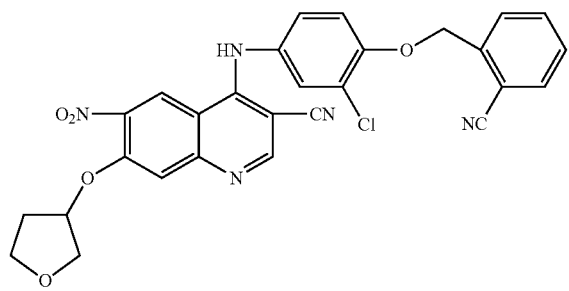

Preparation 7s 4-(4-(3-CYANOBENZYLOXY)-3-CHLOROPHE-
NYLAMINO)-6-NITRO-7-(TETRAHYDRO-
FURAN-3-YL-OXY)QUINOLINE-3-CARBONI-
TRILE

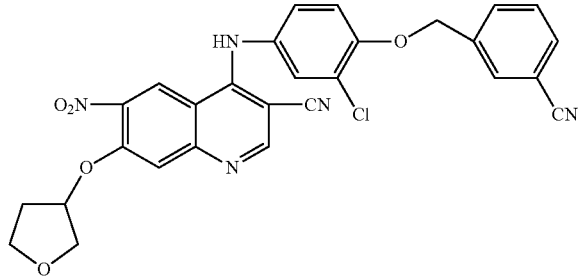 [SMILES: N#Cc1cccc(COc2ccc(Nc3c(C#N)cnc4cc(OC5CCOC5)c([N+](=O)[O-])cc34)cc2Cl)c1]

Preparation 7t 4-(4-(4-CYANOBENZYLOXY)-3-CHLOROPHE-
NYLAMINO)-6-NITRO-7-(TETRAHYDRO-
FURAN-3-YL-OXY)QUINOLINE-3-CARBONI-
TRILE

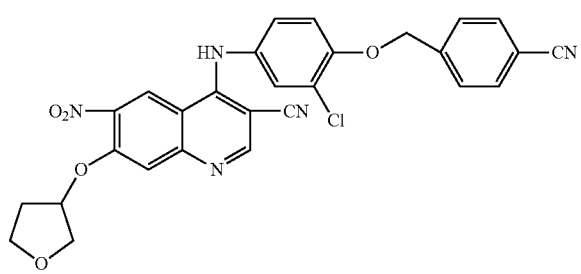 [SMILES: N#Cc1ccc(COc2ccc(Nc3c(C#N)cnc4cc(OC5CCOC5)c([N+](=O)[O-])cc34)cc2Cl)cc1]

Preparation 7u 4-(4-(4-TERT-BUTYLBENZYLOXY)-3-CHLORO-
PHENYLAMINO)-6-NITRO-7-(TETRAHYDRO-
FURAN-3-YL-OXY)QUINOLINE-3-CARBONI-
TRILE

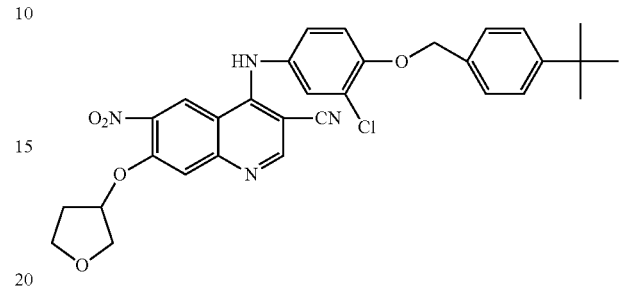

Preparation 7v 4-(4-BENZYLOXY-3-CHLOROPHENYLAMINO)-
6-NITRO-7-(TETRAHYDROFURAN-3-YL-OXY)
QUINOLINE-3-CARBONITRILE

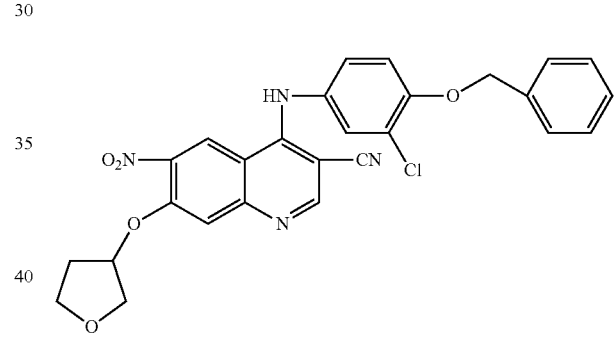

Preparation 7x 4-(4-(2-CHLOROBENZYLOXY)-3-FLUOROPHE-
NYLAMINO)-6-NITRO-7-(TETRAHYDRO-
FURAN-3-YL-OXY)QUINOLINE-3-CARBONI-
TRILE

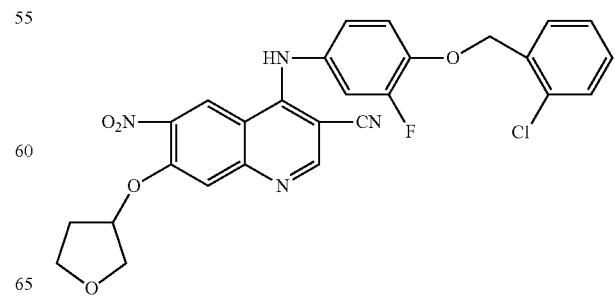

55

Preparation 7y 4-(4-(3-CHLOROBENZYLOXY)-3-FLUOROPHE-
NYLAMINO)-6-NITRO-7-(TETRAHYDRO-
FURAN-3-YL-OXY)QUINOLINE-3-CARBONI-
TRILE

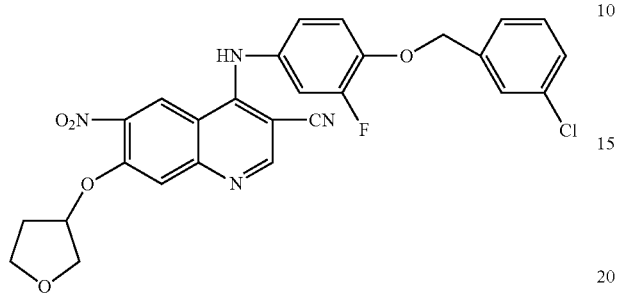

Preparation 7z 4-(4-(4-CHLOROBENZYLOXY)-3-FLUOROPHE-
NYLAMINO)-6-NITRO-7-(TETRAHYDRO-
FURAN-3-YL-OXY)QUINOLINE-3-CARBONI-
TRILE

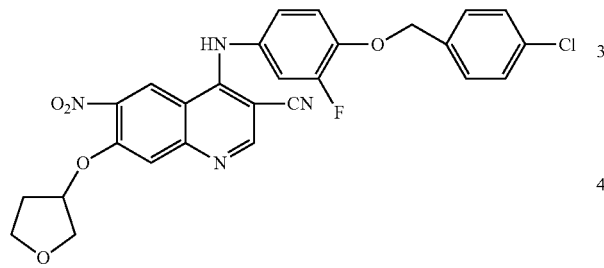

Preparation 7aa

6-NITRO-4-((S)-1-PHENYLETHYLAMINO)-7-
(TETRAHYDROFURAN-3-YL-OXY) QUINO-
LINE-3-CARBONITRILE

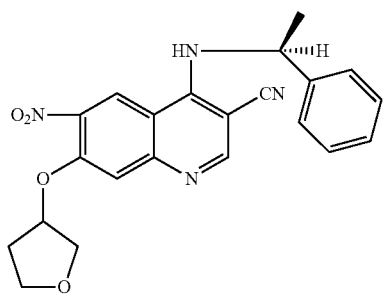 [SMILES: C[C@H](Nc1c(C#N)cnc2cc(OC3CCOC3)c([N+](=O)[O-])cc12)c1ccccc1]

56

Preparation 7ab

6-NITRO-4-((R)-1-PHENYLETHYLAMINO)-7-
(TETRAHYDROFURAN-3-YL-OXY) QUINO-
LINE-3-CARBONITRILE

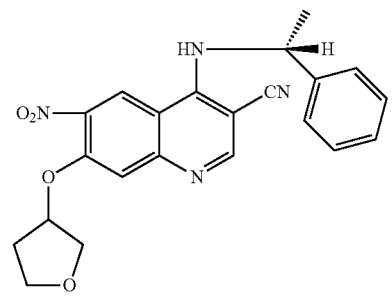 [SMILES: C[C@@H](Nc1c(C#N)cnc2cc(OC3CCOC3)c([N+](=O)[O-])cc12)c1ccccc1]

Preparation 7ac 4-(1-BENZYL-1H-INDOL-5-YLAMINE)-6-NI-
TRO-7-(TETRAHYDROFURAN-3-YL-OXY)QUI-
NOLINE-3-CARBONITRILE

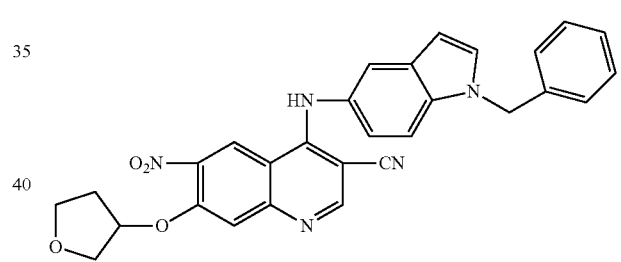

Preparation 7ad 4-(1-(3-CYANOBENZYL)-1H-INDOL-5-YL-
AMINO)-6-NITRO-7-(TETRAHYDROFURAN-3-
YL-OXY)QUINOLINE-3-CARBONITRILE

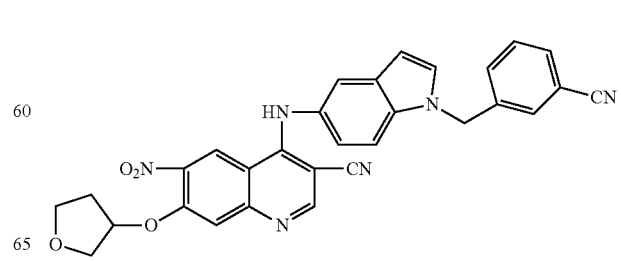

Preparation 7ae 4-(1-(3-METHOXYBENZYL)-1H-INDOL-5-YL-AMINO)-6-NITRO-7-(TETRAHYDROFURAN-3-YL-OXY)QUINOLINE-3-CARBONITRILE

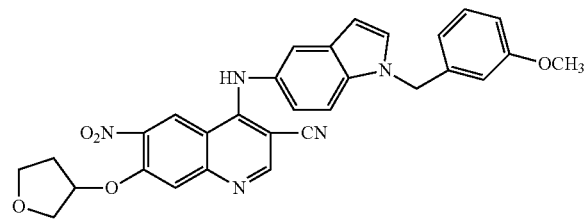

Preparation 7af 4-(1-(3-CHLOROBENZYL)-1H-INDOL-5-YL-AMINO)-6-NITRO-7-(TETRAHYDROFURAN-3-YL-OXY)QUINOLINE-3-CARBONITRILE

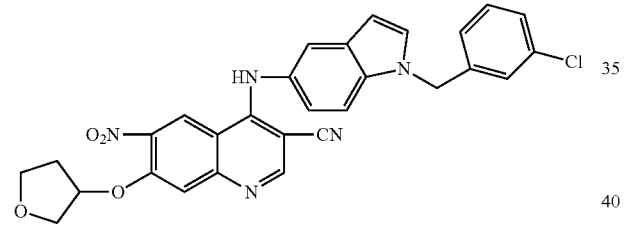

Preparation 7ag 4-(INDOLIN-1-YL)-6-NITRO-7-(TETRAHYDROFURAN-3-YL-OXY)QUINOLINE-3-CARBONITRILE

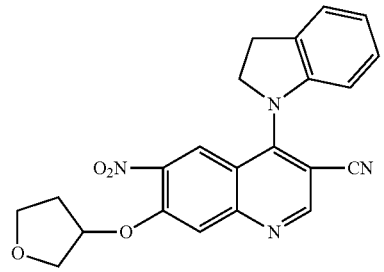 [SMILES: N#Cc1cnc2cc(OC3CCOC3)c([N+](=O)[O-])cc2c1N1CCc2ccccc21]

Preparation 7ah 4-(6-CHLOROINDOLIN-1-YL)-6-NITRO-7-(TETRAHYDROFURAN-3-YL-OXY) QUINOLINE-3-CARBONITRILE

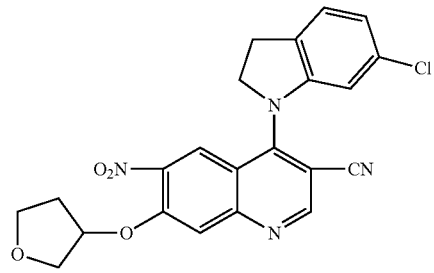

Preparation 7ai 4-(6-FLUOROINDOLIN-1-YL)-6-NITRO-7-(TETRAHYDROFURAN-3-YL-OXY) QUINOLINE-3-CARBONITRILE

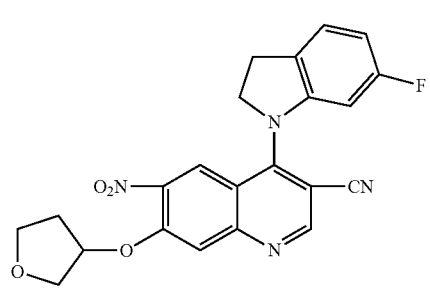 [SMILES: N#Cc1cnc2cc(OC3CCOC3)c([N+](=O)[O-])cc2c1N1CCc2ccc(F)cc21]

Preparation 7aj 4-(4-CHLOROINDOLIN-1-YL)-6-NITRO-7-(TETRAHYDROFURAN-3-YL-OXY) QUINOLINE-3-CARBONITRILE

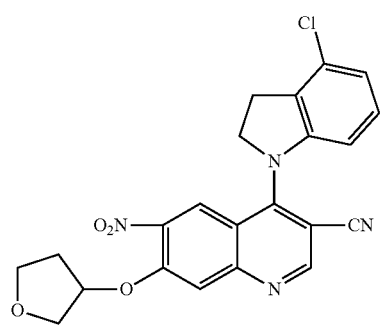 [SMILES: N#Cc1cnc2cc(OC3CCOC3)c([N+](=O)[O-])cc2c1N1CCc2c(Cl)cccc21]

Preparation 7ak 4-(3,4-DIHYDROQUINOLIN-1 (2H)-YL)-6-NITRO-7-(TETRAHYDROFURAN-3-YL-OXY)QUINOLINE-3-CARBONITRILE

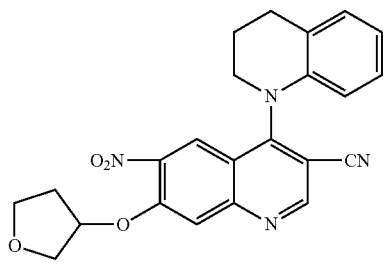 [SMILES: N#Cc1cnc2cc(OC3CCOC3)c([N+](=O)[O-])cc2c1N1CCCc2ccccc21]

Preparation 7al 4-(6-METHYL-3,4-DIHYDROQUINOLIN-1 (2H)-YL)-6-NITRO-7-(TETRAHYDROFURAN-3-YL-OXY)QUINOLINE-3-CARBONITRILE

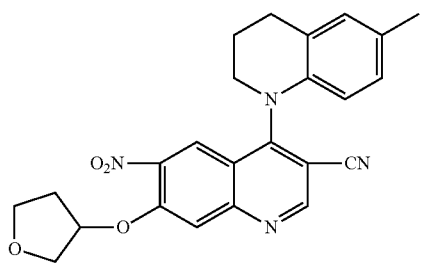 [SMILES: Cc1ccc2c(c1)CCCN2c1c(C#N)cnc2cc(OC3CCOC3)c([N+](=O)[O-])cc12]

Preparation 7am

6-NITRO-7-(TETRAHYDROFURAN-3-YL-OXY)-4-(7-(TRIFLUOROMETHYL)-3,4-DIHYDROQUINOLIN-1 (2H)-YL)QUINOLINE-3-CARBONITRILE

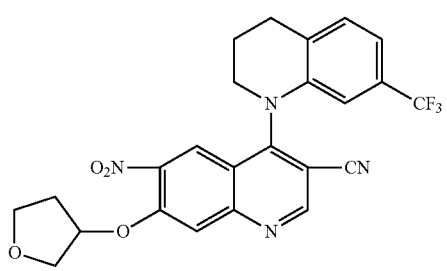 [SMILES: N#Cc1cnc2cc(OC3CCOC3)c([N+](=O)[O-])cc2c1N1CCCc2ccc(C(F)(F)F)cc21]

Preparation 7an 4-(6-(BENZYLOXY)INDOLIN-1-YL)-6-NITRO-7-(TETRAHYDROFURAN-3-YL-OXY)QUINOLINE-3-CARBONITRILE

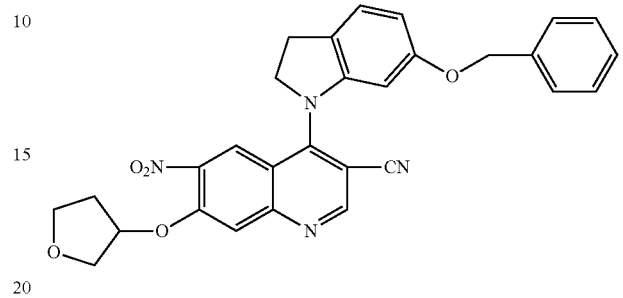

Preparation 7ao

Methyl 1-(3-CYANO-6-NITRO-7-(TETRAHYDROFURAN-3-YL-OXY)QUINOLIN-4YL) INDOLINE-2-CARBOXYLATE

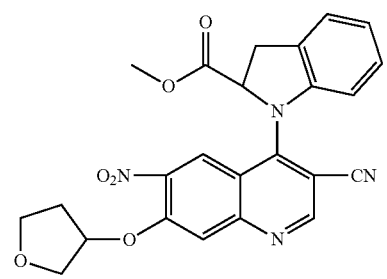 [SMILES: COC(=O)C1Cc2ccccc2N1c1c(C#N)cnc2cc(OC3CCOC3)c([N+](=O)[O-])cc12]

Preparation 7ap 4-(2-(HYDROXYMETHYL)INDOLIN-1-YL)-6-NITRO-7-(TETRAHYDROFURAN-3-YL-OXY) QUINOLINE-3-CARBONITRILE

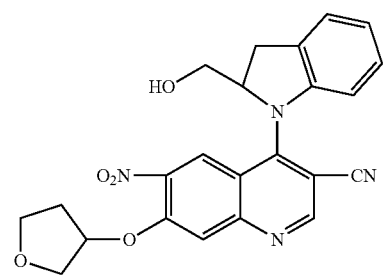 [SMILES: N#Cc1cnc2cc(OC3CCOC3)c([N+](=O)[O-])cc2c1N1c2ccccc2CC1CO]

Preparation 7aq 4-(6-(1H-PYRROL-1-YL)INDOLIN-1-YL)-6-NITRO-7-(TETRAHYDROFURAN-3-YL-OXY)QUINOLINE-3-CARBONITRILE

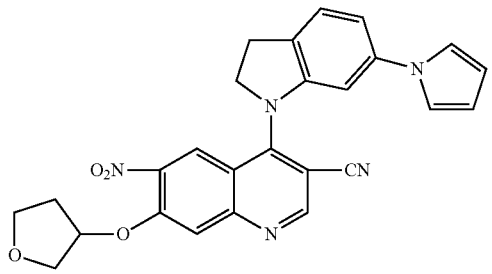 [SMILES: N#Cc1cnc2cc(OC3CCOC3)c([N+](=O)[O-])cc2c1N1CCc2ccc(-n3cccc3)cc21]

Preparation 7ar

6-NITRO-4-(OCTAHYDROINDOL-1-YL)-7-(TETRAHYDROFURAN-3-YL-OXY) QUINOLINE-3-CARBONITRILE

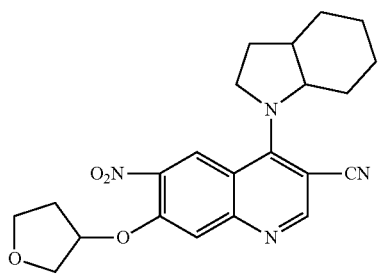 [SMILES: N#Cc1cnc2cc(OC3CCOC3)c([N+](=O)[O-])cc2c1N1CCC2CCCCC21]

Preparation 7as

6-NITRO-4-(PYRIMIDIN-2-YL-AMINO)-7-(TETRAHYDROFURAN-3-YL-OXY) QUINOLINE-3-CARBONITRILE

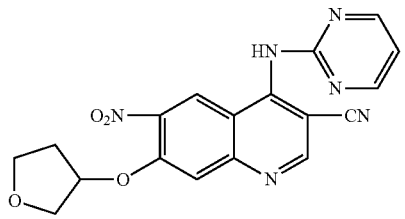 [SMILES: N#Cc1cnc2cc(OC3CCOC3)c([N+](=O)[O-])cc2c1Nc1ncccn1]

Preparation 7at

N-(2-(3-CYANO-6-NITRO-7-(TETRAHYDROFURAN-3-YL-OXY)QUINOLIN-4-YL-AMINO)PYRIMIDIN-5-YL)BENZAMIDE

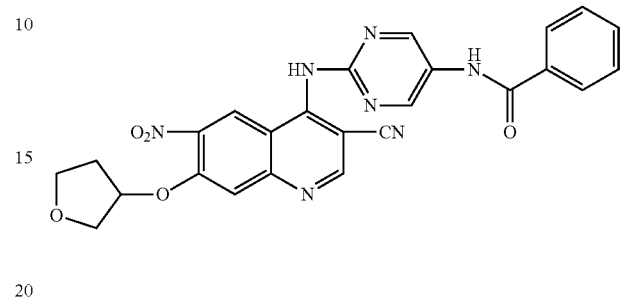

Preparation 7au

N-(2-(3-CYANO-6-NITRO-7-(TETRAHYDROFURAN-3-YL-OXY)QUINOLIN-4-YL-AMINO)PYRIMIDIN-5-YL)-4-(DIMETHYLAMINO)BENZAMIDE

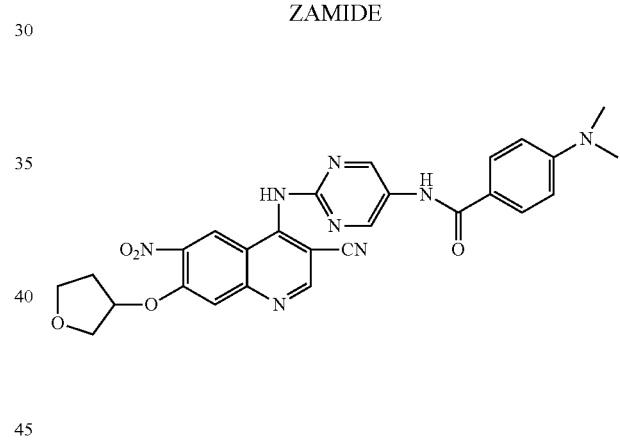

Preparation 7av

N-(2-(3-CYANO-6-NITRO-7-(TETRAHYDROFURAN-3-YL-OXY)QUINOLIN-4-YL-AMINO)PYRIMIDIN-5-YL)BENZENESULFONAMIDE

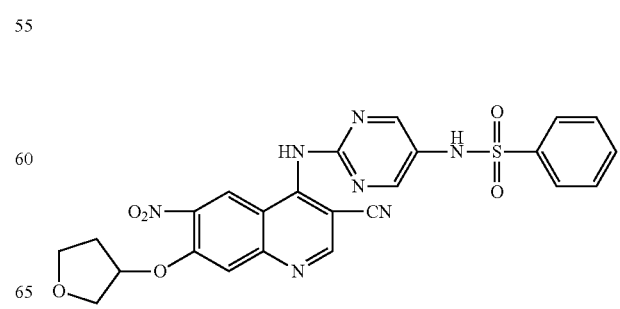

63

Preparation 7aw

N-(5-(3-CYANO-6-NITRO-7-(TETRAHYDRO-FURAN-3-YL-OXY)QUINOLIN4-4-YL-AMINO) PYRIMIDIN-2-YL)BENZAMIDE

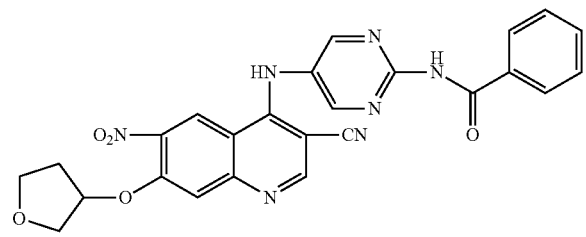 [SMILES: N#Cc1cnc2cc(OC3CCOC3)c([N+](=O)[O-])cc2c1Nc1cnc(NC(=O)c2ccccc2)nc1]

Preparation 7ax

N-(5-(3-CYANO-6-NITRO-7-(TETRAHYDRO-FURAN-3-YL-OXY)QUINOLIN4-4-YL-AMINO) PYRIMIDIN-2-YL)FURAN-2-CARBOXAMIDE

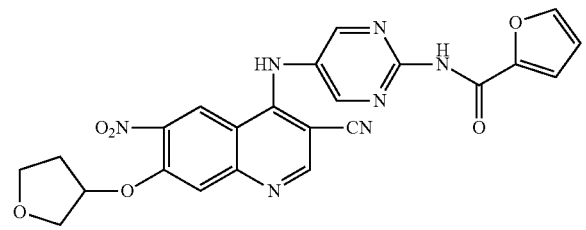 [SMILES: N#Cc1cnc2cc(OC3CCOC3)c([N+](=O)[O-])cc2c1Nc1cnc(NC(=O)c2ccco2)nc1]

Preparation 7ay

N-(5-(3-CYANO-6-NITRO-7-(TETRAHYDRO-FURAN-3-YL-OXY)QUINOLIN4-4-YL-AMINO) PYRIMIDIN-2-YL)THIOPHENE-2-CARBOXAMIDE

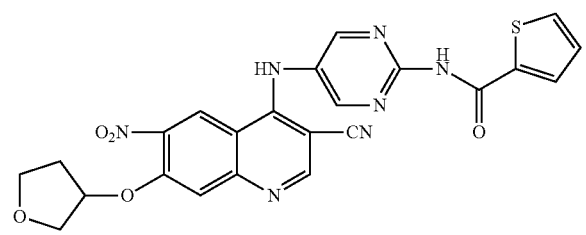 [SMILES: N#Cc1cnc2cc(OC3CCOC3)c([N+](=O)[O-])cc2c1Nc1cnc(NC(=O)c2cccs2)nc1]

64

Preparation 7az

N-(5-(3-CYANO-6-NITRO-7-(TETRAHYDRO-FURAN-3-YL-OXY)QUINOLIN-4-YL-AMINO) PYRIMIDIN-2-YL)CYCLOHEXYLCARBOXAMIDE

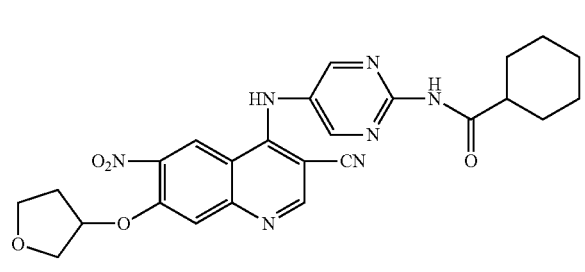 [SMILES: N#Cc1cnc2cc(OC3CCOC3)c([N+](=O)[O-])cc2c1Nc1cnc(NC(=O)C2CCCCC2)nc1]

Preparation 7ba 5-(3-CYANO-6-NITRO-7-(TETRAHYDRO-FURAN-3-YL-OXY)QUINOLIN-4-YL-AMINO)-N-(4-METHOXYPHENYL)PYRIMIDINE-2-CARBOXAMIDE

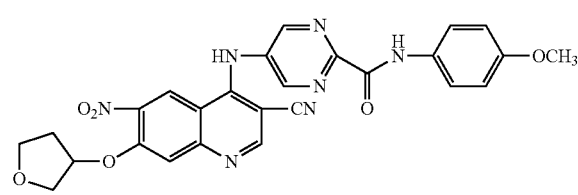 [SMILES: COc1ccc(NC(=O)c2ncc(Nc3c(C#N)cnc4cc(OC5CCOC5)c([N+](=O)[O-])cc34)cn2)cc1]

Preparation 7bb

6-NITRO-4-(PYRIDIN-2-YL-AMINO)-7-(TETRAHYDROFURAN-3-YL-OXY) QUINOLINE-3-CARBONITRILE

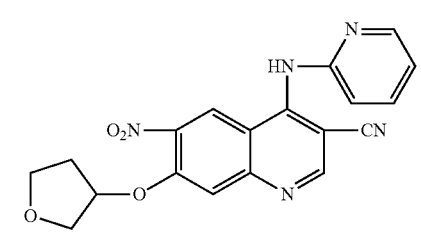

65

Preparation 7bc 6-(3-CYANO-6-NITRO-7-(TETRAHYDRO-
FURAN-3-YL-OXY)QUINOLIN-4-YL-AMINO)-
N-(4-METHOXYPHENYL)NICOTINAMIDE

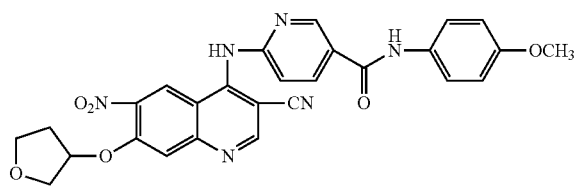

Preparation 7bd

6-NITRO-4-(PYRIDIN-3-YL-AMINO)-7-(TETRA-
HYDROFURAN-3-YL-OXY) QUINOLINE-3-
CARBONITRILE

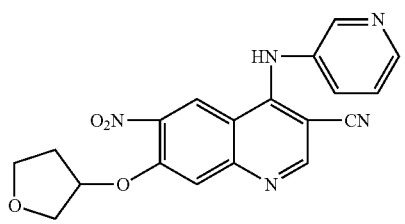 [SMILES: N#Cc1cnc2cc(OC3CCOC3)c([N+](=O)[O-])cc2c1Nc1cccnc1]

Preparation 7be

6-NITRO-4-(PYRIDIN-4-YL-AMINO)-7-(TETRA-
HYDROFURAN-3-YL-OXY) QUINOLINE-3-
CARBONITRILE

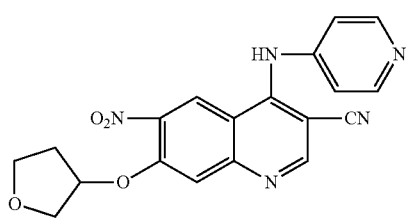

66

Preparation 7bf 4-(6-(BENZYLOXY)PYRIDIN-3-YL-AMINO)-6-
NITRO-7-(TETRAHYDROFURAN-3-YL-OXY)
QUINOLINE-3-CARBONITRILE

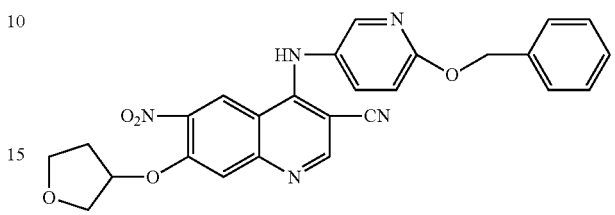

Preparation 7bg

6-NITRO-4-(PYRAZIN-2-YL-AMINO)-7-(TETRA-
HYDROFURAN-3-YL-OXY) QUINOLINE-3-
CARBONITRILE

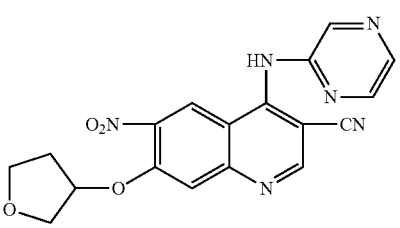

Preparation 7bh 4-(3-CHLORO-4-FLUOROPHENYLAMINO)-7-
FLUORO-6-NITROQUINOLINE-3-CARBONI-
TRILE

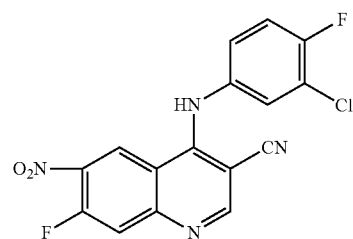 [SMILES: N#Cc1cnc2cc(F)c([N+](=O)[O-])cc2c1Nc1ccc(F)c(Cl)c1]

Preparation 7bi

4-(3-CHLORO-4-FLUOROPHENYLAMINO)-7-(1-METHYLPIPERIDIN-4-YL-OXY)-6-NITROQUINOLINE-3-CARBONITRILE

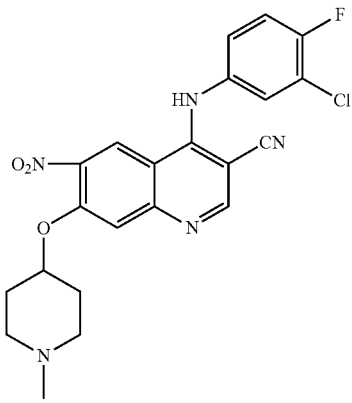

The compound was obtained according to the process of Preparation 2 with 4-(3-chloro-4-fluorophenylamino)-7-fluoro-6-nitroquinoline-3-carbonitrile and 4-hydroxy-1-methylpiperidine as starting materials.

The compounds of Preparation 7bj to Preparation 7by were prepared according to the process of Preparation 7bi.

Preparation 7bj

4-(3-ETHYNYLPHENYLAMINO)-7-(1-METHYLPIPERIDIN-4-YL-OXY)-6-NITROQUINOLINE-3-CARBONITRILE

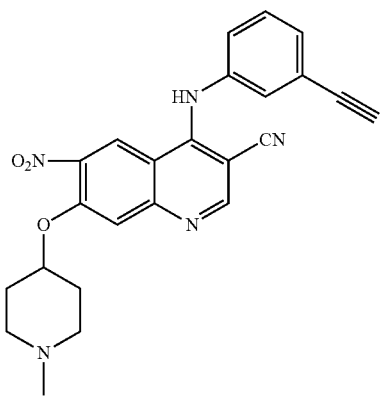

Preparation 7bk

4-(4-BENZYLOXY-3-CHLOROPHENYLAMINO)-7-(1-METHYLPIPERIDIN-4-YL-OXY)-6-NITROQUINOLINE-3-CARBONITRILE

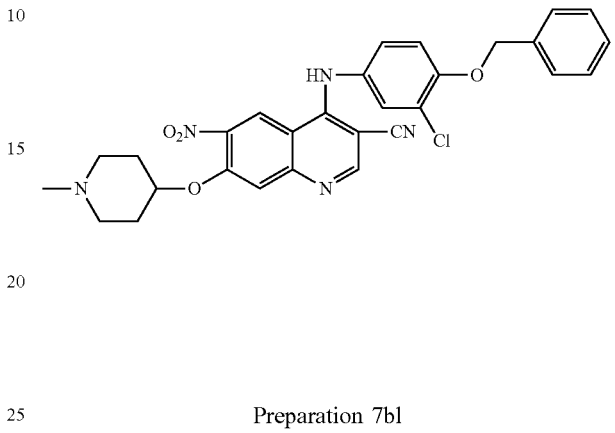

Preparation 7bl

4-(4-(2-CHLOROBENZYLOXY)-3-CHLOROPHENYLAMINO)-7-(1-METHYLPIPERIDIN-4-YL-OXY)-6-NITROQUINOLINE-3-CARBONITRILE

Preparation 7bm

4-(4-(3-CHLOROBENZYLOXY)-3-CHLOROPHENYLAMINO)-7-(1-METHYLPIPERIDIN-4-YL-OXY)-6-NITROQUINOLINE-3-CARBONITRILE

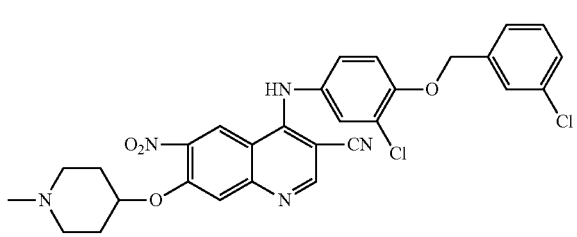 [SMILES: CN1CCC(Oc2cc3ncc(C#N)c(Nc4ccc(OCc5cccc(Cl)c5)c(Cl)c4)c3cc2[N+](=O)[O-])CC1]

69

Preparation 7bn 4-(4-(4-CHLOROBENZYLOXY)-3-CHLOROPHE-
NYLAMINO)-7-(1-METHYLPIPERIDIN-4-YL-
OXY)-6-NITROQUINOLINE-3-CARBONITRILE

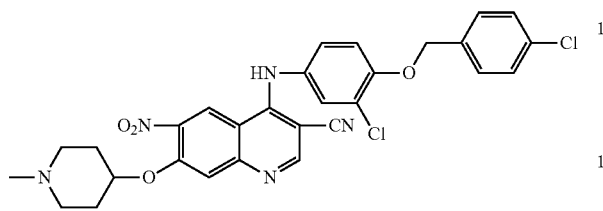

Preparation 7bo 4-(4-(4-BROMOBENZYLOXY)-3-CHLOROPHE-
NYLAMINO)-7-(1-METHYLPIPERIDIN-4-YL-
OXY)-6-NITROQUINOLINE-3-CARBONITRILE

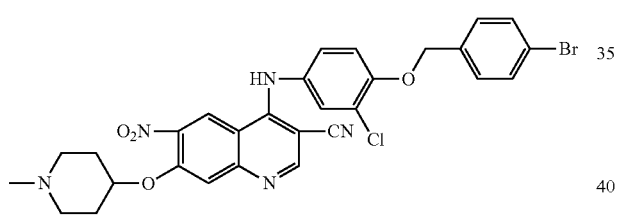

Preparation 7bp 4-(4-(4-METHYLBENZYLOXY)-3-CHLOROPHE-
NYLAMINO)-7-(1-METHYLPIPERIDIN-4-YL-
OXY)-6-NITROQUINOLINE-3-CARBONITRILE

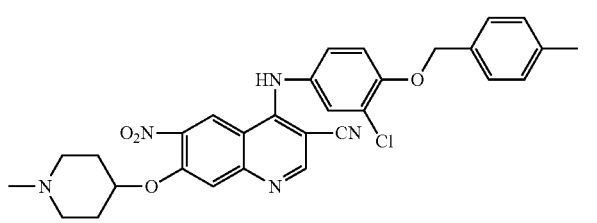

70

Preparation 7bq 4-(4-(4-METHOXYBENZYLOXY)-3-CHLORO-
PHENYLAMINO)-7-(1-METHYLPIPERIDIN-4-
YL-OXY)-6-NITROQUINOLINE-3-CARBONI-
TRILE

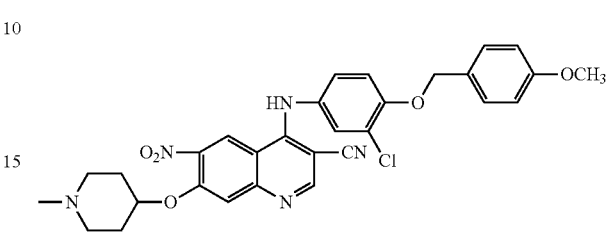

Preparation 7br 4-(4-(4-CYANOBENZYLOXY)-3-CHLOROPHE-
NYLAMINO)-7-(1-METHYLPIPERIDIN-4-YL-
OXY)-6-NITROQUINOLINE-3-CARBONITRILE

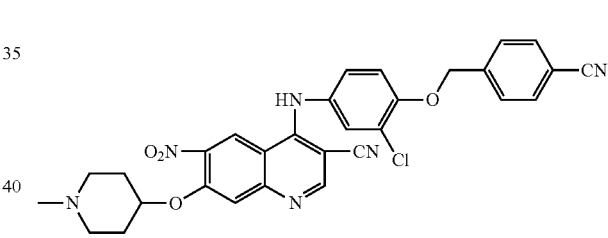

Preparation 7bs 4-(4-(4-ETHYLBENZYLOXY)-3-CHLOROPHE-
NYLAMINO)-7-(1-METHYLPIPERIDIN-4-YL-
OXY)-6-NITROQUINOLINE-3-CARBONITRILE

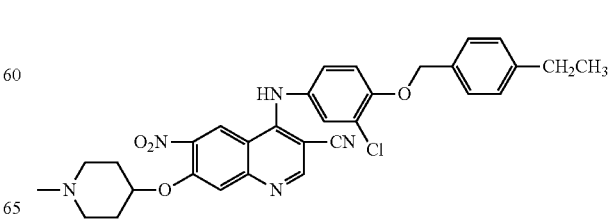

Preparation 7bt 4-(4-(4-ETHOXYBENZYLOXY)-3-CHLOROPHE-
NYLAMINO)-7-(1-METHYLPIPERIDIN-4-YL-
OXY)-6-NITROQUINOLINE-3-CARBONITRILE

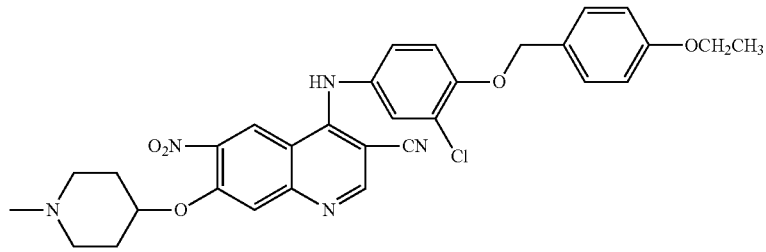 [SMILES: CCOc1ccc(COc2ccc(Nc3c(C#N)cnc4cc(OC5CCN(C)CC5)c([N+](=O)[O-])cc34)cc2Cl)cc1]

Preparation 7bu 4-(3-CHLORO-4-PHENOXYPHENYLAMINO)-7-
(1-METHYLPIPERIDIN-4-YL-OXY)-6-NITRO-
QUINOLINE-3-CARBONITRILE

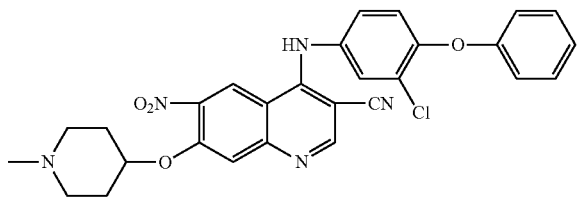 [SMILES: CN1CCC(Oc2cc3ncc(C#N)c(Nc4ccc(Oc5ccccc5)c(Cl)c4)c3cc2[N+](=O)[O-])CC1]

Preparation 7bv 7-(1-METHYLPIPERIDIN-4-YL-OXY)-6-NITRO-
4-(PYRIDIN-2-YL-AMINO) QUINOLINE-3-CAR-
BONITRILE

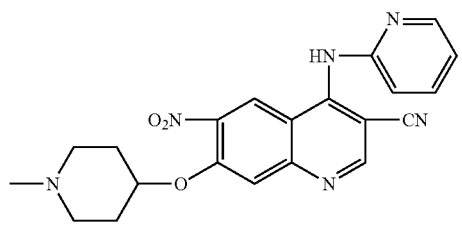 [SMILES: CN1CCC(Oc2cc3ncc(C#N)c(Nc4ccccn4)c3cc2[N+](=O)[O-])CC1]

Preparation 7bw 7-(1-METHYLPIPERIDIN-4-YL-OXY)-6-NITRO-
4-(PYRIDIN-3-YL-AMINO) QUINOLINE-3-CAR-
BONITRILE

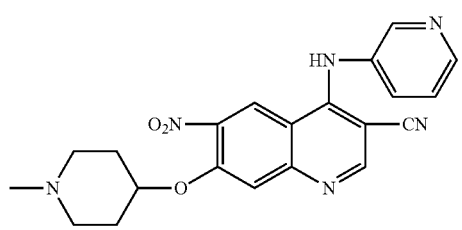 [SMILES: CN1CCC(Oc2cc3ncc(C#N)c(Nc4cccnc4)c3cc2[N+](=O)[O-])CC1]

Preparation 7bx 7-(1-METHYLPIPERIDIN-4-YL-OXY)-6-NITRO-
4-(PYRIDIN-4-YL-AMINO) QUINOLINE-3-CAR-
BONITRILE

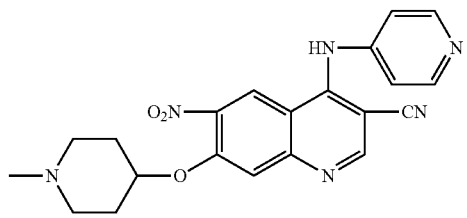 [SMILES: CN1CCC(Oc2cc3ncc(C#N)c(Nc4ccncc4)c3cc2[N+](=O)[O-])CC1]

Preparation 7by 4-(6-(BENZYLOXY)PYRIDIN-3-YL-AMINO)-7-
(1-METHYLPIPERIDIN-4-YL-OXY)-6-NITRO-
QUINOLINE-3-CARBONITRILE

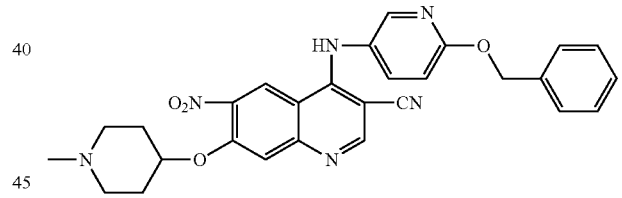

Preparation 7bz 4-(3-CHLORO-4-FLUOROPHENYLAMINO)-6-
NITRO-7-(PYRIDIN-4-YL-OXY) QUINOLINE-3-
CARBONITRILE

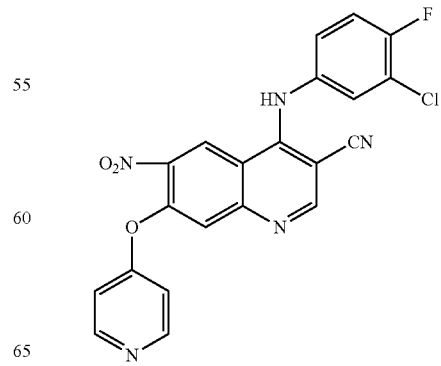

The compound was prepared according to the process of Preparation 2 and with 4-(3-chloro-4-fluorophenylamino)-7-fluoro-6-nitroquinoline-3-carbonitrile and 4-hydroxypyridine as starting materials.

The compounds of Preparation 7ca to Preparation 7cl were prepared according to the process of Preparation 7bz.

Preparation 7ca 4-(3-ETHYNYLPHENYLAMINO)-6-NITRO-7-(PYRIDIN-4-YL-OXY)QUINOLINE-3-CARBONITRILE

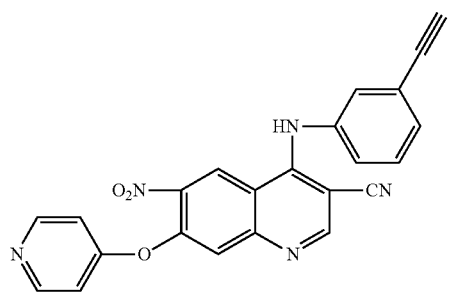 [SMILES: C#Cc1cccc(Nc2c(C#N)cnc3cc(Oc4ccncc4)c([N+](=O)[O-])cc23)c1]

Preparation 7cb

6-NITRO-4-(4-PHENOXYPHENYLAMINO)-7-(PYRIDIN-4-YL-OXY)QUINOLINE-3-CARBONITRILE

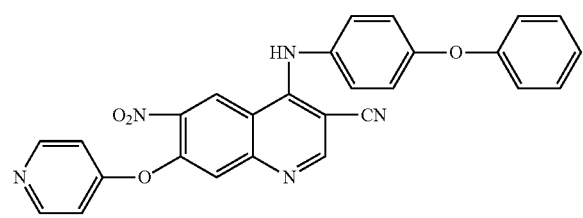 [SMILES: N#Cc1cnc2cc(Oc3ccncc3)c([N+](=O)[O-])cc2c1Nc1ccc(Oc2ccccc2)cc1]

Preparation 7cc 4-(4-(BENZYLOXY)PHENYLAMINO)-6-NITRO-7-(PYRIDIN-4-YL-OXY) QUINOLINE-3-CARBONITRILE

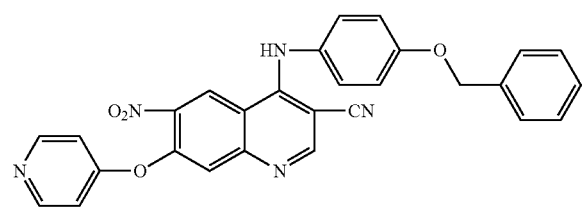 [SMILES: N#Cc1cnc2cc(Oc3ccncc3)c([N+](=O)[O-])cc2c1Nc1ccc(OCc2ccccc2)cc1]

Preparation 7cd 4-(4-(2-CHLOROBENZYLOXY)-3-CHLOROPHENYLAMINO)-6-NITRO-7-(PYRIDIN-4-YL-OXY) QUINOLINE-3-CARBONITRILE

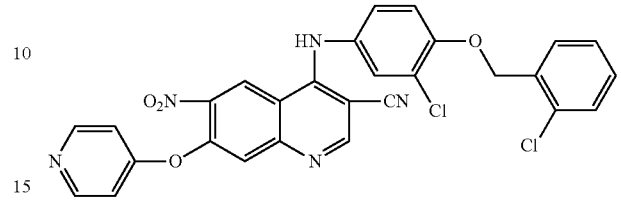

Preparation 7ce 4-(4-(4-METHYLBENZYLOXY)-3-CHLOROPHENYLAMINO)-6-NITRO-7-(PYRIDIN-4-YL-OXY) QUINOLINE-3-CARBONITRILE

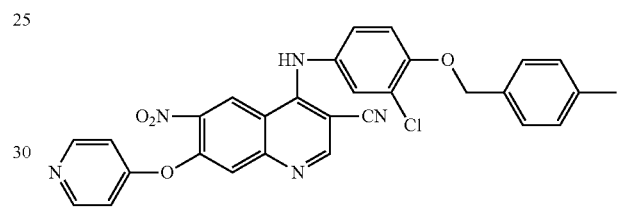

Preparation 7cf 4-(4-(4-METHOXYBENZYLOXY)PHENYLAMINO)-6-NITRO-7-(PYRIDIN-4-YL-OXY) QUINOLINE-3-CARBONITRILE

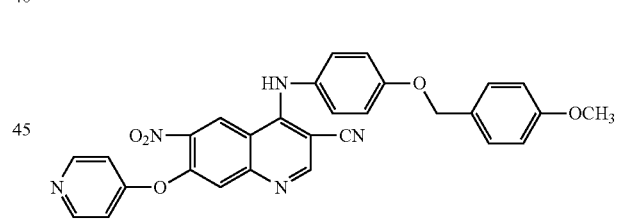

Preparation 7cg 4-(4-(3-CYANOBENZYLOXY)-3-CHLOROPHENYLAMINO)-6-NITRO-7-(PYRIDIN-4-YL-OXY) QUINOLINE-3-CARBONITRILE

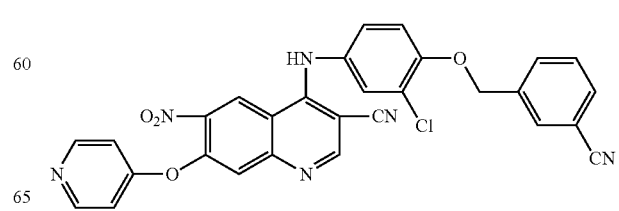

Preparation 7ch

6-NITRO-4-(PYRIDIN-2-YL-AMINO)-7-(PYRIDIN-4-YL-OXY)QUINOLINE-3-CARBONITRILE

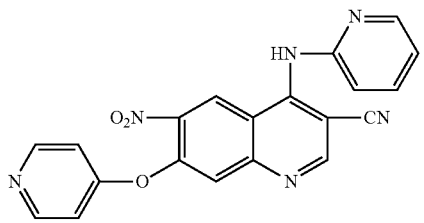 [SMILES: N#Cc1cnc2cc(Oc3ccncc3)c([N+](=O)[O-])cc2c1Nc1ccccn1]

Preparation 7ci

6-NITRO-7-(PYRIDIN-4-YL-OXY)-4-(PYRIMIDIN-2-YL-AMINO)QUINOLINE-3-CARBONITRILE

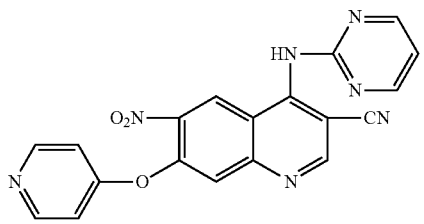 [SMILES: N#Cc1cnc2cc(Oc3ccncc3)c([N+](=O)[O-])cc2c1Nc1ncccn1]

Preparation 7cj 4-(6-(BENZYLOXY)PYRIDIN-3-YL-AMINO)-6-NITRO-7-(PYRIDIN-4-YL-OXY) QUINOLINE-3-CARBONITRILE

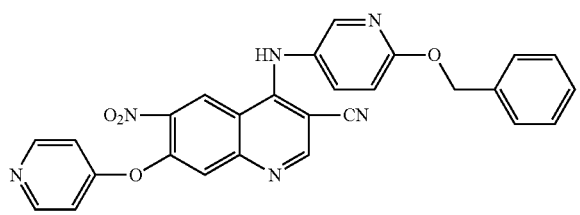

Preparation 7ck 4-(6-(3-CHLOROBENZYLOXY)PYRIDIN-3-YL-AMINO)-6-NITRO-7-(PYRIDIN-4-YL-OXY)QUINOLINE-3-CARBONITRILE

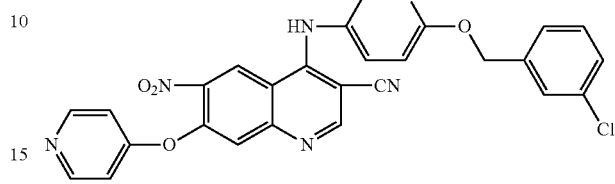

Preparation 7cl

6-NITRO-4-(6-PHENOXYPYRIDIN-3-YL-AMINO)-7-(PYRIDIN-4-YL-OXY) QUINOLINE-3-CARBONITRILE

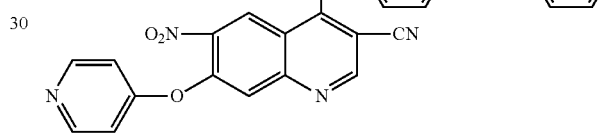

Preparation 8a

6-AMINO-4-(3-CHLORO-4-(PYRIDIN-2-YL-METHOXY)PHENYLAMINO)-7-(TETRAHYDROFURAN-3-YL-OXY)QUINOLINE-3-CARBONITRILE

To a single-neck flask (500 mL) were added 4-(3-chloro-4-(pyridin-2-yl-methoxy)benzenamide)-6-nitro-7-(tetrahydrofuran-3-yl-oxy) quinoline-3-carbonitrile (5.950 g, 11.498 mmol) and $SnCl_2 \cdot 2H_2O$ (12.935 g). To the flask was added anhydrous ethanol (250 mL). The mixture was stirred under reflux at the temperature of 85° C. After 1.5 hr, the reaction finished. The resultant mixture was rotary-evaporated to dryness. To the resulting mixture was added water (150 mL). The resultant mixture was ultrasonically treated and rotary-evaporated to dryness. The resulting product was poured into water (300 mL). The pH of the mixture was adjusted to 8 with saturated NaHCO$_3$ solution. The solution was extracted with chloroform three times (700 mL in total) and then extracted with ethyl acetate three times. The ethyl acetate layers were combined and washed with saturated NaCl solution (300 mL). The resultant organic phase was dried over anhydrous MgSO$_4$ for half-hour, filtered and rotary-evaporated to dryness. The resultant products were combined and purified by column chromatography (chloroform:methanol=95:5) to give a yellow solid (2.881 g). Yield: 51.4%.

The compounds of Preparation 8b to Preparation 8ck were prepared according to the process of Preparation 8a.

Preparation 8b

6-AMINO-4-(3-CHLORO-4-FLUOROPHENYLAMINO)-7-(TETRAHYDROFURAN-3-YL-OXY)QUINOLINE-3-CARBONITRILE

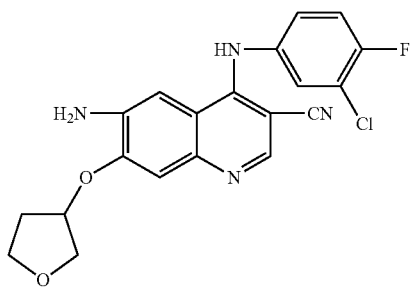 [SMILES: N#Cc1cnc2cc(OC3CCOC3)c(N)cc2c1Nc1ccc(F)c(Cl)c1]

Preparation 8c

6-AMINO-4-(3-ETHYNYLPHENYLAMINO)-7-(TETRAHYDROFURAN-3-YL-OXY) QUINOLINE-3-CARBONITRILE

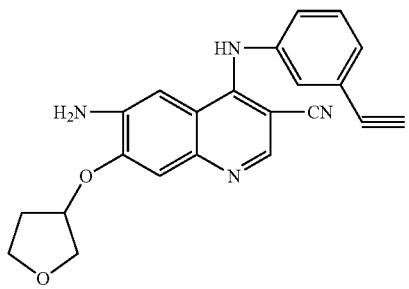 [SMILES: C#Cc1cccc(Nc2c(C#N)cnc3cc(OC4CCOC4)c(N)cc23)c1]

Preparation 8d

6-AMINO-4-(3-BROMOPHENYLAMINO)-7-(TETRAHYDROFURAN-3-YL-OXY) QUINOLINE-3-CARBONITRILE

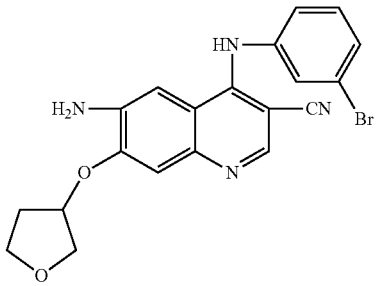 [SMILES: N#Cc1cnc2cc(OC3CCOC3)c(N)cc2c1Nc1cccc(Br)c1]

Preparation 8e

6-AMINO-4-(1H-INDOL-5-YL-AMINO)-7-(TETRAHYDROFURAN-3-YL-OXY) QUINOLINE-3-CARBONITRILE

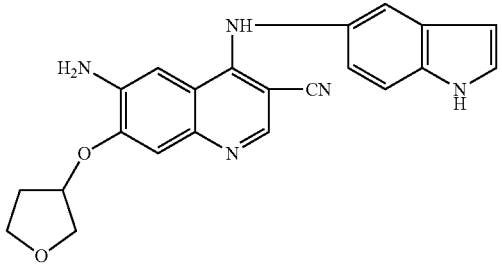 [SMILES: N#Cc1cnc2cc(OC3CCOC3)c(N)cc2c1Nc1ccc2[nH]ccc2c1]

Preparation 8f 4-(4-(2-FLUOROBENZYLOXY)-3-CHLOROPHENYLAMINO)-6-AMINO-7-(TETRAHYDROFURAN-3-YL-OXY)QUINOLINE-3-CARBONITRILE

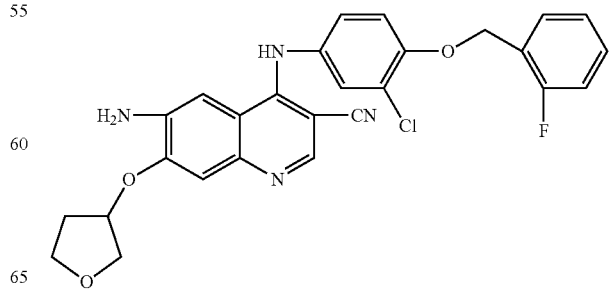

Preparation 8g 4-(4-(3-FLUOROBENZYLOXY)-3-CHLOROPHE-
NYLAMINO)-6-AMINO-7-(TETRAHYDRO-
FURAN-3-YL-OXY)QUINOLINE-3-CARBONI-
TRILE

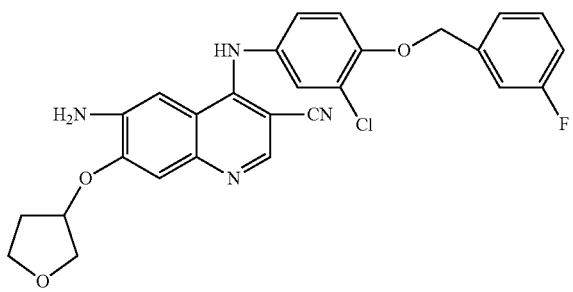 [SMILES: N#Cc1cnc2cc(OC3CCOC3)c(N)cc2c1Nc1ccc(OCc2cccc(F)c2)c(Cl)c1]

Preparation 8h 4-(4-(4-FLUOROBENZYLOXY)-3-CHLOROPHE-
NYLAMINO)-6-AMINO-7-(TETRAHYDRO-
FURAN-3-YL-OXY)QUINOLINE-3-CARBONI-
TRILE

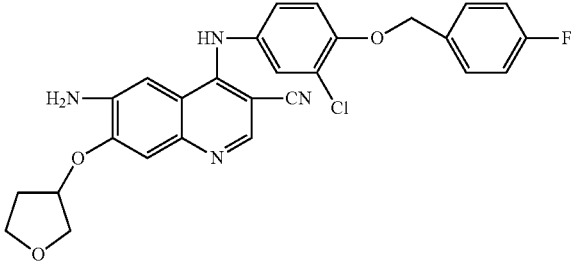

Preparation 8i 4-(4-(2-CHLOROBENZYLOXY)-3-CHLOROPHE-
NYLAMINO)-6-AMINO-7-(TETRAHYDRO-
FURAN-3-YL-OXY)QUINOLINE-3-CARBONI-
TRILE

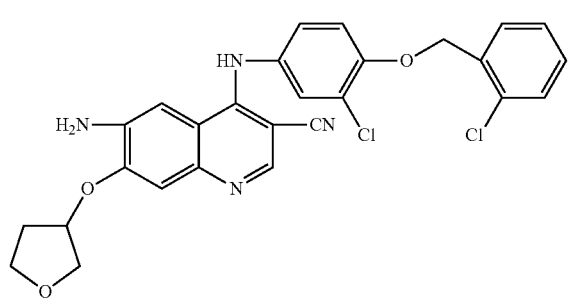 [SMILES: N#Cc1cnc2cc(OC3CCOC3)c(N)cc2c1Nc1ccc(OCc2ccccc2Cl)c(Cl)c1]

Preparation 8j 4-(4-(3-CHLOROBENZYLOXY)-3-CHLOROPHE-
NYLAMINO)-6-AMINO-7-(TETRAHYDRO-
FURAN-3-YL-OXY)QUINOLINE-3-CARBONI-
TRILE

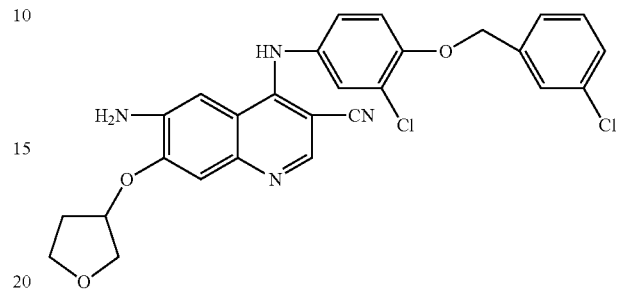

Preparation 8k 4-(4-(4-CHLOROBENZYLOXY)-3-CHLOROPHE-
NYLAMINO)-6-AMINO-7-(TETRAHYDRO-
FURAN-3-YL-OXY)QUINOLINE-3-CARBONI-
TRILE

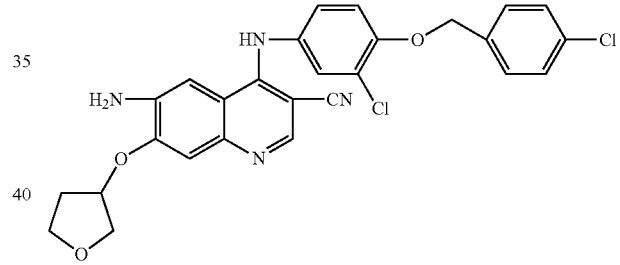

Preparation 8l 4-(4-(2-METHYLBENZYLOXY)-3-CHLOROPHE-
NYLAMINO)-6-AMINO-7-(TETRAHYDRO-
FURAN-3-YL-OXY)QUINOLINE-3-CARBONI-
TRILE

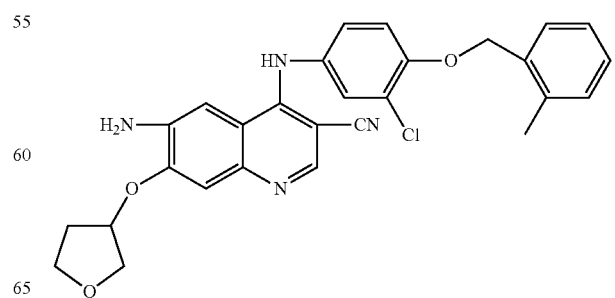

Preparation 8m 4-(4-(3-METHYLBENZYLOXY)-3-CHLOROPHE-
NYLAMINO)-6-AMINO-7-(TETRAHYDRO-
FURAN-3-YL-OXY)QUINOLINE-3-CARBONI-
TRILE

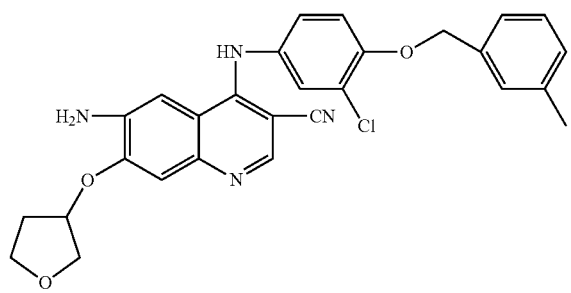

Preparation 8n 4-(4-(4-METHYLBENZYLOXY)-3-CHLOROPHE-
NYLAMINO)-6-AMINO-7-(TETRAHYDRO-
FURAN-3-YL-OXY)QUINOLINE-3-CARBONI-
TRILE

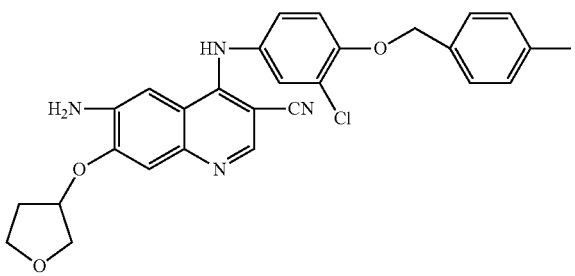 [SMILES: Cc1ccc(COc2ccc(Nc3c(C#N)cnc4cc(OC5CCOC5)c(N)cc34)cc2Cl)cc1]

Preparation 8o 4-(4-(2-METHOXYBENZYLOXY)-3-CHLORO-
PHENYLAMINO)-6-AMINO-7-(TETRAHYDRO-
FURAN-3-YL-OXY)QUINOLINE-3-CARBONI-
TRILE

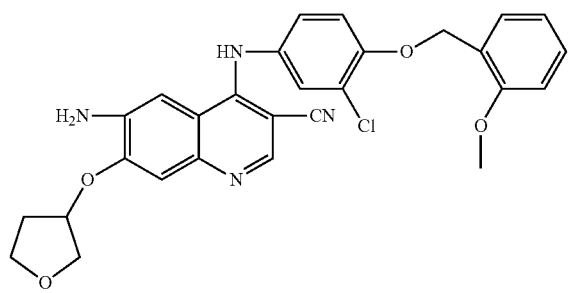 [SMILES: COc1ccccc1COc1ccc(Nc2c(C#N)cnc3cc(OC4CCOC4)c(N)cc23)cc1Cl]

Preparation 8p 4-(4-(3-METHOXYBENZYLOXY)-3-CHLORO-
PHENYLAMINO)-6-AMINO-7-(TETRAHYDRO-
FURAN-3-YL-OXY)QUINOLINE-3-CARBONI-
TRILE

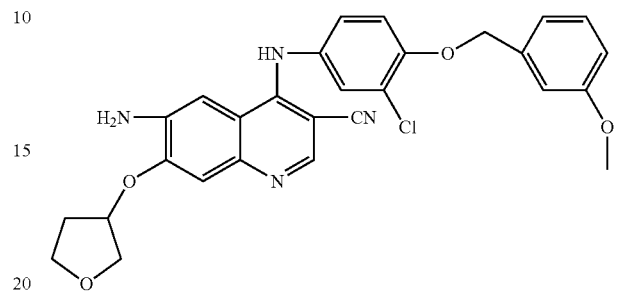

Preparation 8q 4-(4-(4-METHOXYBENZYLOXY)-3-CHLORO-
PHENYLAMINO)-6-AMINO-7-(TETRAHYDRO-
FURAN-3-YL-OXY)QUINOLINE-3-CARBONI-
TRILE

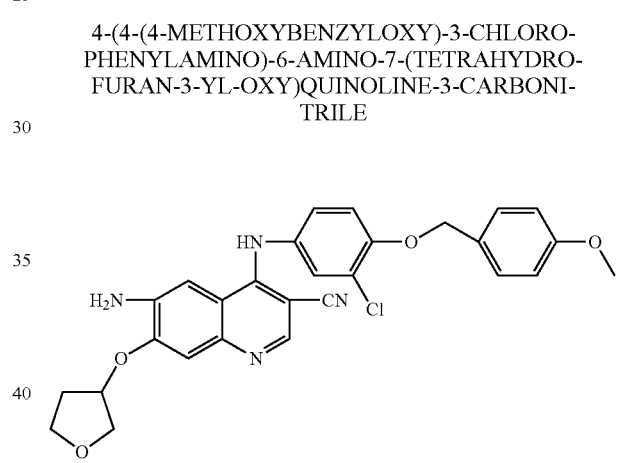

Preparation 8r 4-(4-(2-CYANOBENZYLOXY)-3-CHLOROPHE-
NYLAMINO)-6-AMINO-7-(TETRAHYDRO-
FURAN-3-YL-OXY)QUINOLINE-3-CARBONI-
TRILE

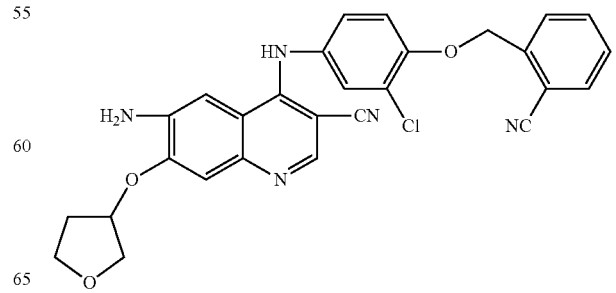

Preparation 8 s 4-(4-(3-CYANOBENZYLOXY)-3-CHLOROPHE-NYLAMINO)-6-AMINO-7-(TETRAHYDRO-FURAN-3-YL-OXY)QUINOLINE-3-CARBONI-TRILE

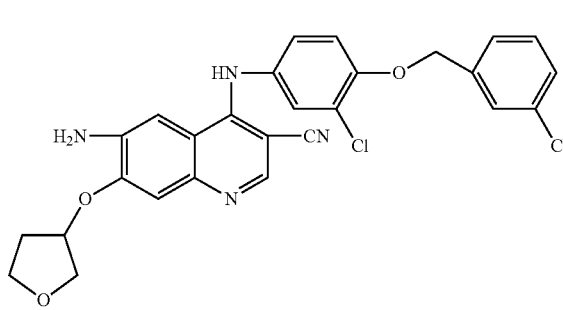

Preparation 8t 4-(4-(4-CYANOBENZYLOXY)-3-CHLOROPHE-NYLAMINO)-6-AMINO-7-(TETRAHYDRO-FURAN-3-YL-OXY)QUINOLINE-3-CARBONI-TRILE

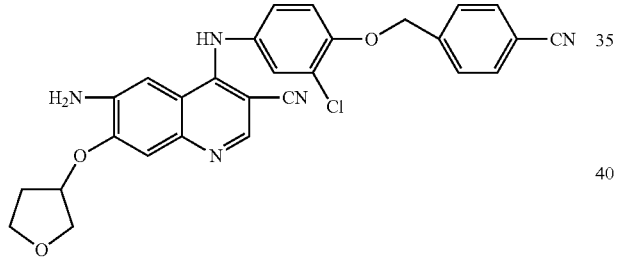

Preparation 8u 4-(4-(4-TERT-BUTYLBENZYLOXY)-3-CHLORO-PHENYLAMINO)-6-AMINO-7-(TETRAHYDRO-FURAN-3-YL-OXY)QUINOLINE-3-CARBONI-TRILE

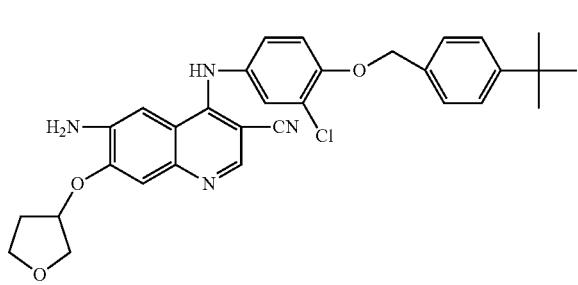 [SMILES: CC(C)(C)c1ccc(COc2ccc(Nc3c(C#N)cnc4cc(OC5CCOC5)c(N)cc34)cc2Cl)cc1]

Preparation 8v

6-AMINO-4-(4-(BENZYLOXY)-3-CHLOROPHE-NYLAMINO)-7-(TETRAHYDROFURAN-3-YL-OXY)QUINOLINE-3-CARBONITRILE

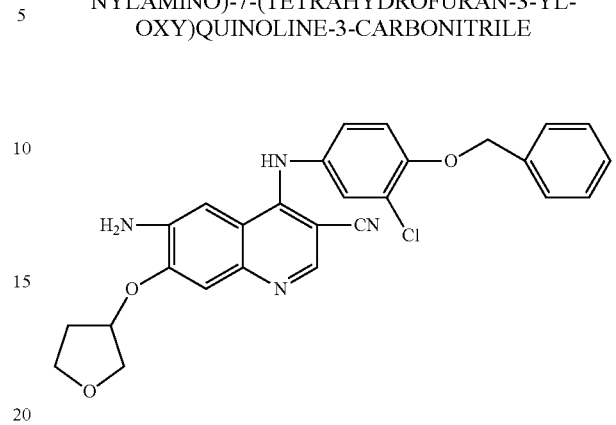

Preparation 8x 4-(4-(2-CHLOROBENZYLOXY)-3-FLUOROPHE-NYLAMINO)-6-AMINO-7-(TETRAHYDRO-FURAN-3-YL-OXY)QUINOLINE-3-CARBONI-TRILE

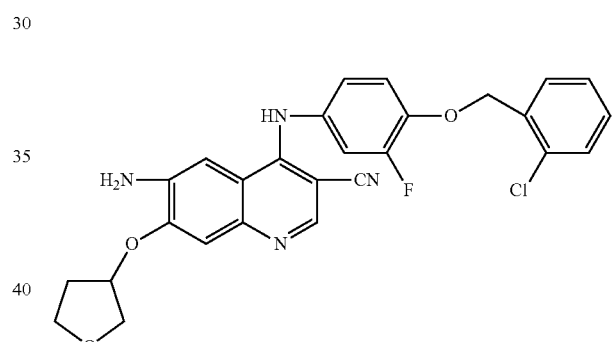

Preparation 8y 4-(4-(3-CHLOROBENZYLOXY)-3-FLUOROPHE-NYLAMINO)-6-AMINO-7-(TETRAHYDRO-FURAN-3-YL-OXY)QUINOLINE-3-CARBONI-TRILE

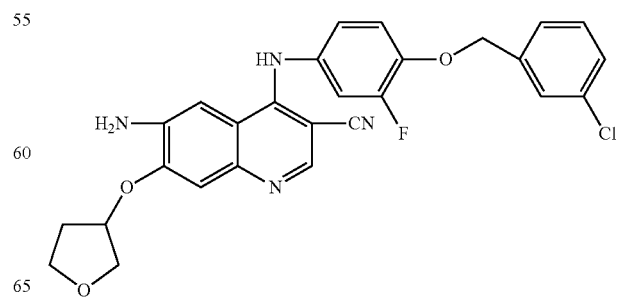

85

Preparation 8z 4-(4-(4-CHLOROBENZYLOXY)-3-FLUOROPHE-
NYLAMINO)-6-AMINO-7-(TETRAHYDRO-
FURAN-3-YL-OXY)QUINOLINE-3-CARBONI-
TRILE

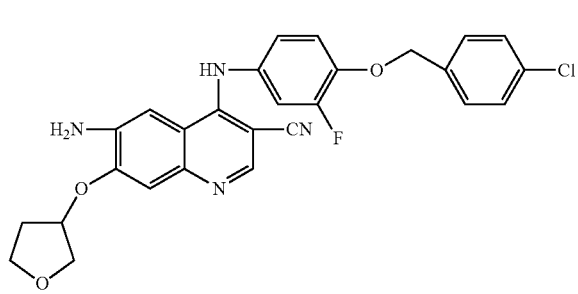

Preparation 8aa

6-AMINO-4-((S)-1-PHENYLETHYLAMINO)-7-
(TETRAHYDROFURAN-3-YL-OXY) QUINO-
LINE-3-CARBONITRILE

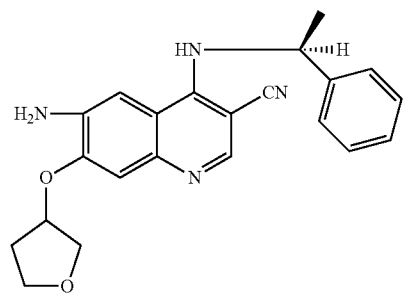 [SMILES: C[C@H](Nc1c(C#N)cnc2cc(OC3CCOC3)c(N)cc12)c1ccccc1]

Preparation 8ab

6-AMINO-4-((R)-1-PHENYLETHYLAMINO)-7-
(TETRAHYDROFURAN-3-YL-OXY) QUINO-
LINE-3-CARBONITRILE

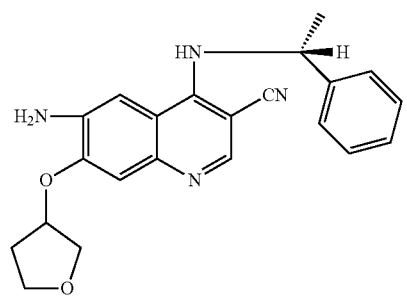 [SMILES: C[C@@H](Nc1c(C#N)cnc2cc(OC3CCOC3)c(N)cc12)c1ccccc1]

86

Preparation 8ac

6-AMINO-4-(1-BENZYL-1H-INDOL-5-YL-
AMINO)-7-(TETRAHYDROFURAN-3-YL-OXY)
QUINOLINE-3-CARBONITRILE

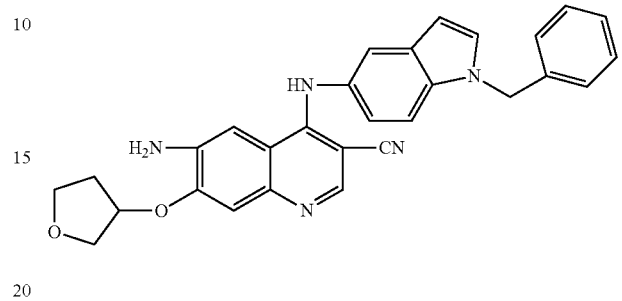

Preparation 8ad 4-(1-(3-CYANOBENZYL)-1H-INDOL-5-YL-
AMINO)-6-AMINO-7-(TETRAHYDROFURAN-3-
YL-OXY)QUINOLINE-3-CARBONITRILE

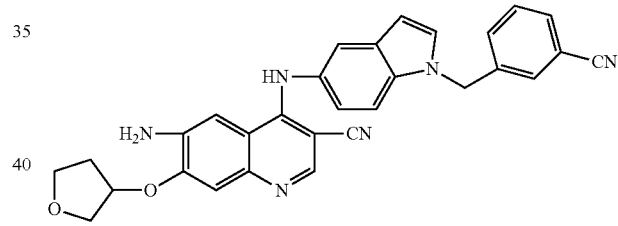

Preparation 8ae 4-(1-(3-METHOXYBENZYL)-1H-INDOL-5-YL-
AMINO)-6-AMINO-7-(TETRAHYDROFURAN-3-
YL-OXY)QUINOLINE-3-CARBONITRILE

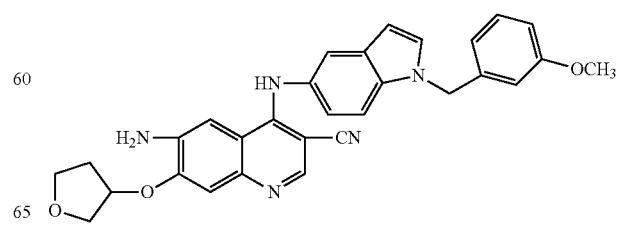

87

Preparation 8af 4-(1-(3-CHLOROBENZYL)-1H-INDOL-5-YL-AMINO)-6-AMINO-7-(TETRAHYDROFURAN-3-YL-OXY)QUINOLINE-3-CARBONITRILE

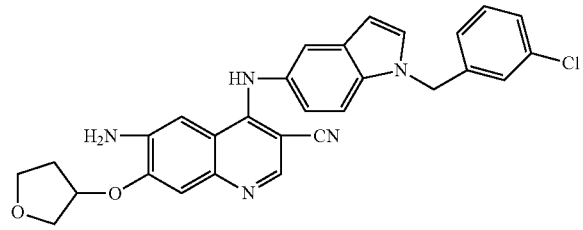 [SMILES: N#Cc1cnc2cc(OC3CCOC3)c(N)cc2c1Nc1ccc2c(ccn2Cc2cccc(Cl)c2)c1]

Preparation 8ag

6-AMINO-4-(INDOLIN-1-YL)-7-(TETRAHYDROFURAN-3-YL-OXY)QUINOLINE-3-CARBONITRILE

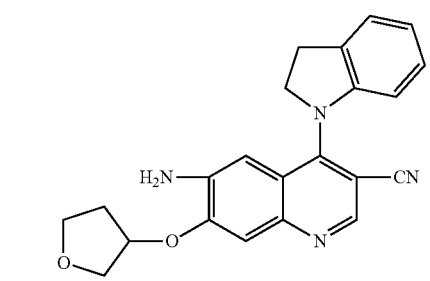

Preparation 8ah

6-AMINO-4-(6-CHLOROINDOLIN-1-YL)-7-(TETRAHYDROFURAN-3-YL-OXY) QUINOLINE-3-CARBONITRILE

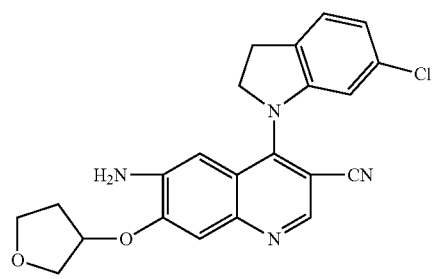

88

Preparation 8ai

6-AMINO-4-(6-FLUOROINDOLIN-1-YL)-7-(TETRAHYDROFURAN-3-YL-OXY) QUINOLINE-3-CARBONITRILE

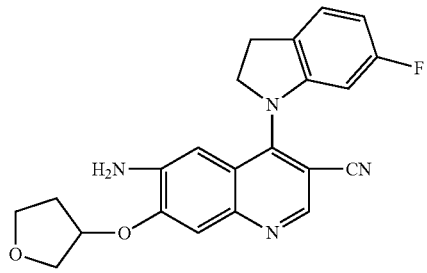 [SMILES: N#Cc1cnc2cc(OC3CCOC3)c(N)cc2c1N1CCc2ccc(F)cc21]

Preparation 8aj

6-AMINO-4-(4-CHLOROINDOLIN-1-YL)-7-(TETRAHYDROFURAN-3-YL-OXY) QUINOLINE-3-CARBONITRILE

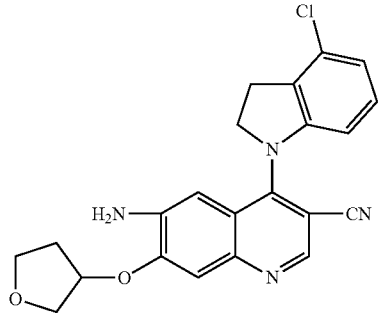

Preparation 8ak

6-AMINO-4-(3,4-DIHYDROQUINOLIN-1 (2H)-YL)-7-(TETRAHYDROFURAN-3-YL-OXY) QUINOLINE-3-CARBONITRILE

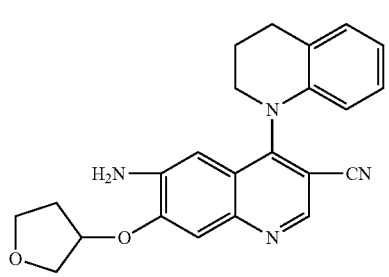

Preparation 8al

6-AMINO-4-(6-METHYL-3,4-DIHYDROQUINO-LIN-1 (2H)-YL)-7-(TETRAHYDROFURAN-3-YL-OXY)QUINOLINE-3-CARBONITRILE

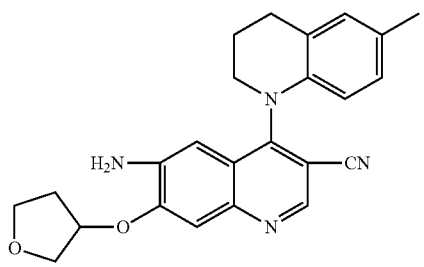

Preparation 8am

6-AMINO-7-(TETRAHYDROFURAN-3-YL-OXY)-4-(7-(TRIFLUOROMETHYL)-3,4-DIHYD-ROQUINOLIN-1 (2H)-YL)QUINOLINE-3-CAR-BONITRILE

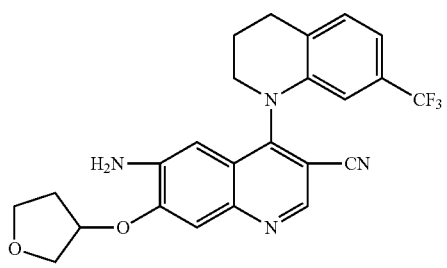

Preparation 8an

6-AMINO-4-(6-(BENZYLOXY)INDOLIN-1-YL)-7-(TETRAHYDROFURAN-3-YL-OXY)QUINO-LINE-3-CARBONITRILE

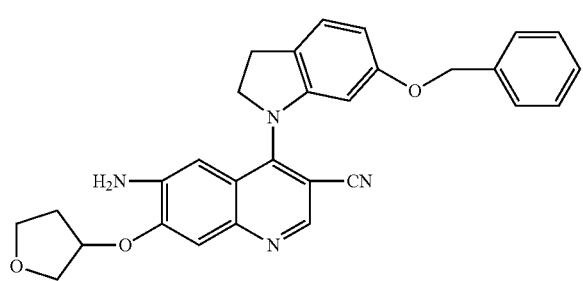

Preparation 8ao

METHYL 1-(6-AMINO-3-CYANO-7-(TETRAHY-DROFURAN-3-YL-OXY) QUINOLIN-4-YL)IN-DOLINE-2-CARBOXYLATE

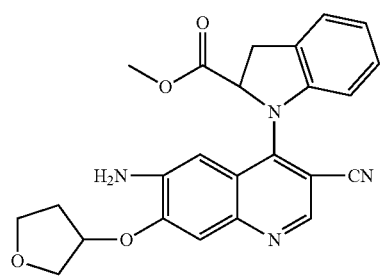

Preparation 8ap

6-AMINO-4-(2-(HYDROXYMETHYL)INDOLIN-1-YL)-7-(TETRAHYDROFURAN-3-YL-OXY) QUINOLINE-3-CARBONITRILE

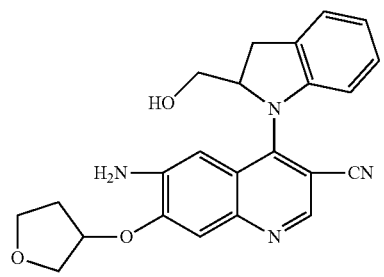 [SMILES: N#Cc1cnc2cc(OC3CCOC3)c(N)cc2c1N1c2ccccc2CC1CO]

Preparation 8aq 4-(6-(1H-PYRROL-1-YL)INDOLIN-1-YL)-6-AMINO-7-(TETRAHYDROFURAN-3-YL-OXY) QUINOLINE-3-CARBONITRILE

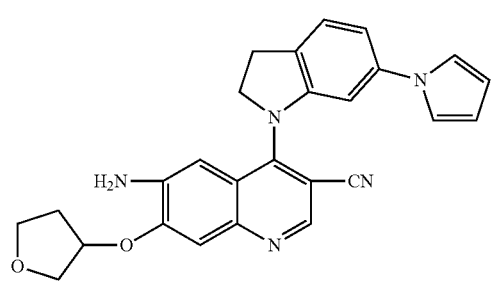

91

Preparation 8ar

6-AMINO-4-(OCTAHYDROINDOL-1-YL)-7-(TETRAHYDROFURAN-3-YL-OXY) QUINOLINE-3-CARBONITRILE

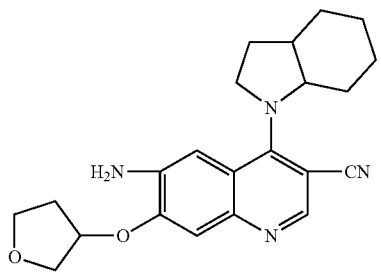

Preparation 8as

6-AMINO-4-(PYRIMIDIN-2-YL-AMINO)-7-(TETRAHYDROFURAN-3-YL-OXY) QUINOLINE-3-CARBONITRILE

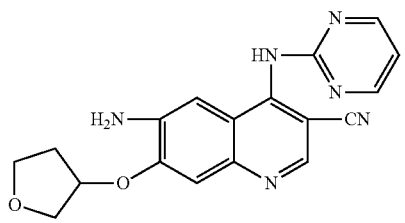

Preparation 8at

N-(2-(6-AMINO-3-CYANO-7-(TETRAHYDROFURAN-3-YL-OXY)QUINOLIN-4-YL-AMINO)PYRIMIDIN-5-YL)BENZAMIDE

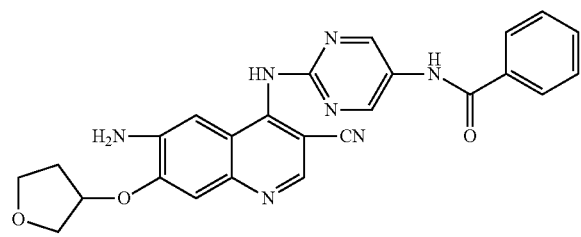

92

Preparation 8au

N-(2-(6-AMINO-3-CYANO-7-(TETRAHYDROFURAN-3-YL-OXY)QUINOLIN-4-YL-AMINO)PYRIMIDIN-5-YL)-4-(DIMETHYLAMINO)BENZAMIDE

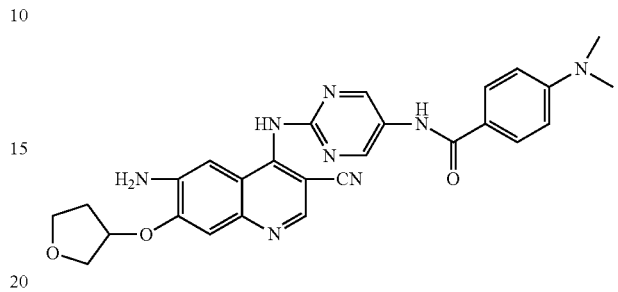

Preparation 8av

N-(2-(6-AMINO-3-CYANO-7-(TETRAHYDROFURAN-3-YL-OXY)QUINOLIN-4-YL-AMINO)PYRIMIDIN-5-YL)BENZENESULFONAMIDE

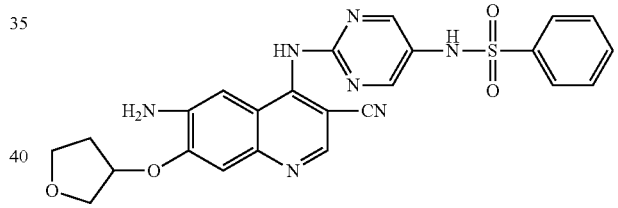

Preparation 8aw

N-(5-(6-AMINO-3-CYANO-7-(TETRAHYDROFURAN-3-YL-OXY)QUINOLIN-4-YL-AMINO)PYRIMIDIN-2-YL)BENZAMIDE

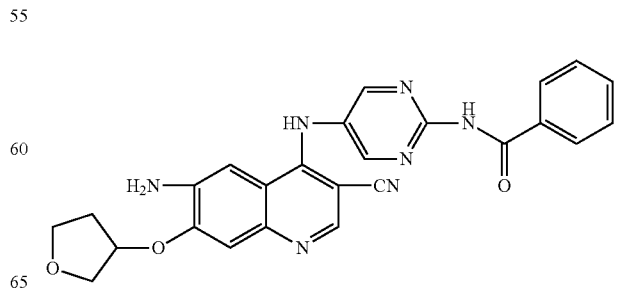

Preparation 8ax

N-(5-(6-AMINO-3-CYANO-7-(TETRAHYDRO-FURAN-3-YL-OXY)QUINOLIN-4-YL-AMINO)PYRIMIDIN-2-YL)FURAN-2-CARBOXAMIDE

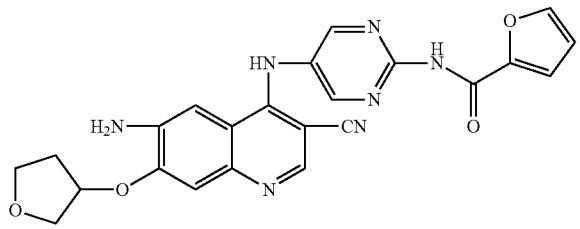

Preparation 8ay

N-(5-(6-AMINO-3-CYANO-7-(TETRAHYDRO-FURAN-3-YL-OXY)QUINOLIN-4-YL-AMINO)PYRIMIDIN-2-YL)THIOPHENE-2-CARBOXAMIDE

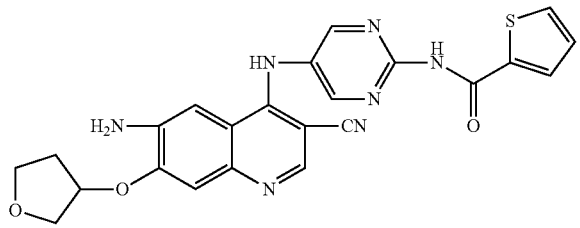

Preparation 8az

N-(5-(6-AMINO-3-CYANO-7-(TETRAHYDRO-FURAN-3-YL-OXY)QUINOLIN-4-YL-AMINO)PYRIMIDIN-2-YL)CYCLOHEXYLCARBOXAMIDE

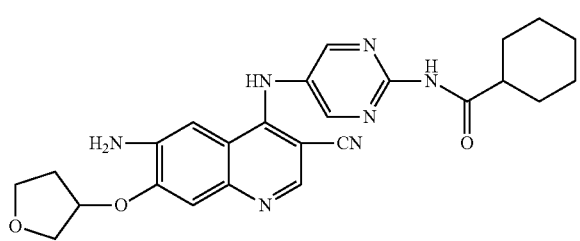

Preparation 8ba 5-(6-AMINO-3-CYANO-7-(TETRAHYDRO-FURAN-3-YL-OXY)QUINOLIN4-4-YL-AMINO)-N-(4-METHOXYPHENYL)PYRIMIDIN-2-YL-CARBOXAMIDE

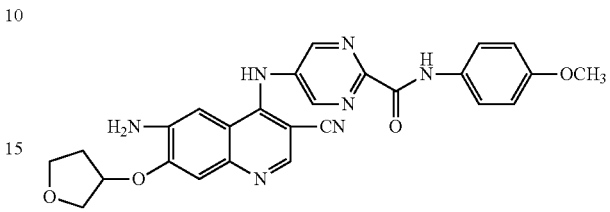

Preparation 8bb

6-AMINO-4-(PYRIDIN-2-YL-AMINO)-7-(TETRAHYDROFURAN-3-YL-OXY) QUINOLINE-3-CARBONITRILE

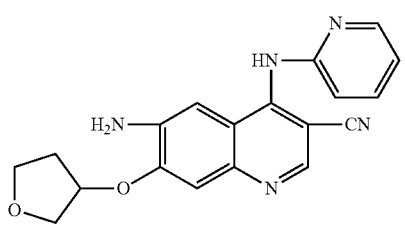 [SMILES: N#Cc1cnc2cc(OC3CCOC3)c(N)cc2c1Nc1ccccn1]

Preparation 8bc 6-(6-AMINO-3-CYANO-7-(TETRAHYDRO-FURAN-3-YL-OXY)QUINOLIN-4-YL-AMINO)-N-(4-METHOXYPHENYL)NICOTINAMIDE

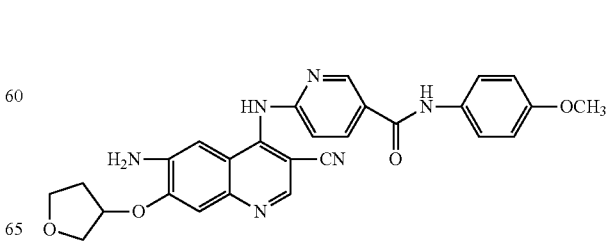

Preparation 8bd

6-AMINO-4-(PYRIDIN-3-YL-AMINO)-7-(TETRAHYDROFURAN-3-YL-OXY)QUINOLINE-3-CARBONITRILE

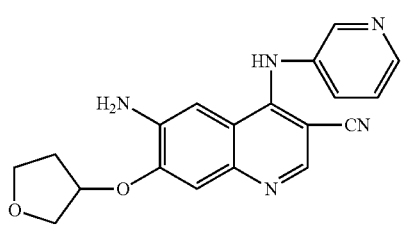 [SMILES: N#Cc1cnc2cc(OC3CCOC3)c(N)cc2c1Nc1cccnc1]

Preparation 8be

6-AMINO-4-(PYRIDIN-4-YL-AMINO)-7-(TETRAHYDROFURAN-3-YL-OXY)QUINOLINE-3-CARBONITRILE

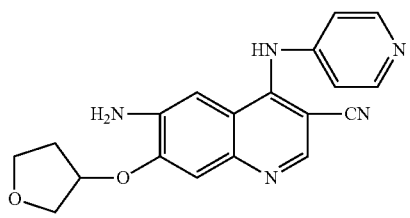 [SMILES: N#Cc1cnc2cc(OC3CCOC3)c(N)cc2c1Nc1ccncc1]

Preparation 8bf

6-AMINO-4-(6-(BENZYLOXY)PYRIDIN-3-YL-AMINO)-7-(TETRAHYDROFURAN-3-YL-OXY)QUINOLINE-3-CARBONITRILE

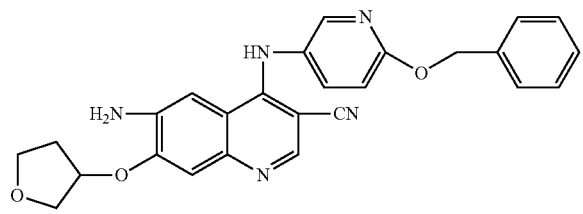

Preparation 8bg

6-AMINO-4-(PYRAZIN-2-YL-AMINO)-7-(TETRAHYDROFURAN-3-YL-OXY)QUINOLINE-3-CARBONITRILE

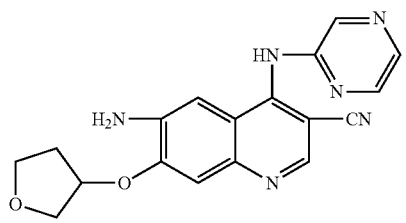 [SMILES: N#Cc1cnc2cc(OC3CCOC3)c(N)cc2c1Nc1cnccn1]

Preparation 8bh

6-AMINO-4-(3-CHLORO-4-FLUOROPHENYLAMINO)-7-(1-METHYLPIPERIDIN-4-YL-OXY)-QUINOLINE-3-CARBONITRILE

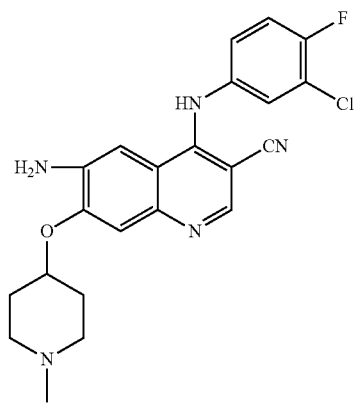 [SMILES: CN1CCC(Oc2cc3ncc(C#N)c(Nc4ccc(F)c(Cl)c4)c3cc2N)CC1]

Preparation 8bi

6-AMINO-4-(3-ETHYNYLPHENYLAMINO)-7-(1-METHYLPIPERIDIN-4-YL-OXY) QUINOLINE-3-CARBONITRILE

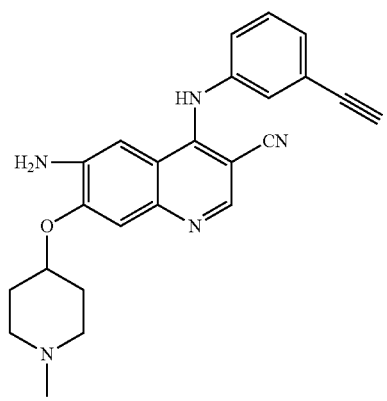 [SMILES: C#Cc1cccc(Nc2c(C#N)cnc3cc(OC4CCN(C)CC4)c(N)cc23)c1]

Preparation 8bj

6-AMINO-4-(4-(BENZYLOXY)-3-CHLOROPHE-NYLAMINO)-7-(1-METHYLPIPERIDIN-4-YL-OXY)QUINOLINE-3-CARBONITRILE

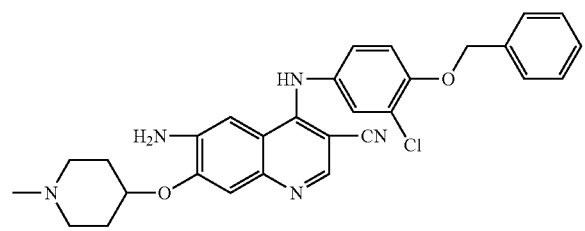

Preparation 8bk 4-(4-(2-CHLOROBENZYLOXY)-3-CHLOROPHE-NYLAMINO)-6-AMINO-7-(1-METHYLPIPERI-DIN-4-YL-OXY)QUINOLINE-3-CARBONITRILE

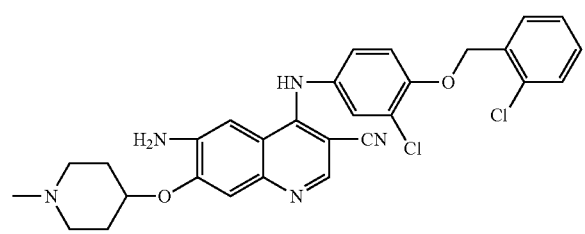 [SMILES: CN1CCC(Oc2cc3ncc(C#N)c(Nc4ccc(OCc5ccccc5Cl)c(Cl)c4)c3cc2N)CC1]

Preparation 8bl 4-(4-(3-CHLOROBENZYLOXY)-3-CHLOROPHE-NYLAMINO)-6-AMINO-7-(1-METHYLPIPERI-DIN-4-YL-OXY)QUINOLINE-3-CARBONITRILE

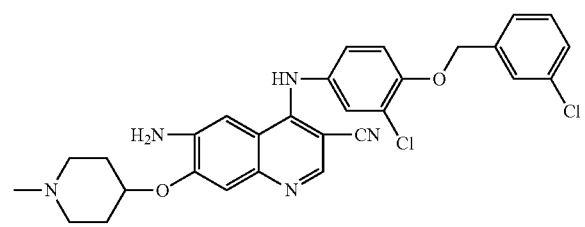

Preparation 8bm 4-(4-(4-CHLOROBENZYLOXY)-3-CHLOROPHE-NYLAMINO)-6-AMINO-7-(1-METHYLPIPERI-DIN-4-YL-OXY)QUINOLINE-3-CARBONITRILE

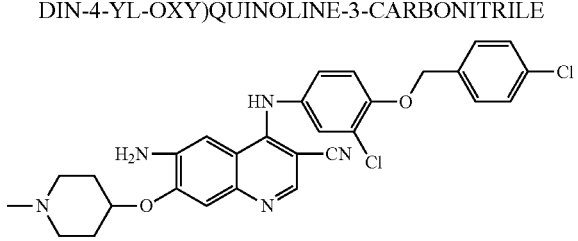

Preparation 8bn 4-(4-(4-BROMOBENZYLOXY)-3-CHLOROPHE-NYLAMINO)-6-AMINO-7-(1-METHYLPIPERI-DIN-4-YL-OXY)QUINOLINE-3-CARBONITRILE

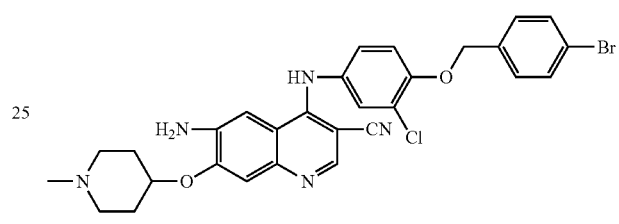

Preparation 8bo 4-(4-(4-METHYLBENZYLOXY)-3-CHLOROPHE-NYLAMINO)-6-AMINO-7-(1-METHYLPIPERI-DIN-4-YL-OXY)QUINOLINE-3-CARBONITRILE

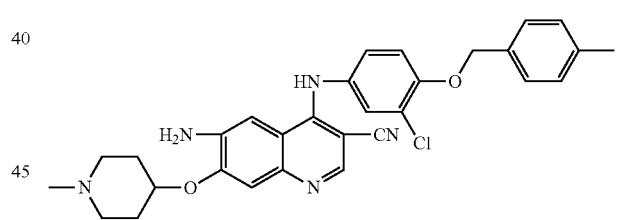

Preparation 8bp 4-(4-(4-METHOXYBENZYLOXY)-3-CHLORO-PHENYLAMINO)-6-AMINO-7-(1-METHYLPIP-ERIDIN-4-YL-OXY)QUINOLINE-3-CARBONI-TRILE

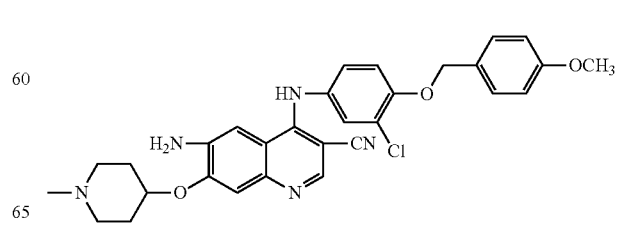

Preparation 8bq 4-(4-(4-CYANOBENZYLOXY)-3-CHLOROPHE-NYLAMINO)-6-AMINO-7-(1-METHYLPIPERI-DIN-4-YL-OXY)QUINOLINE-3-CARBONITRILE

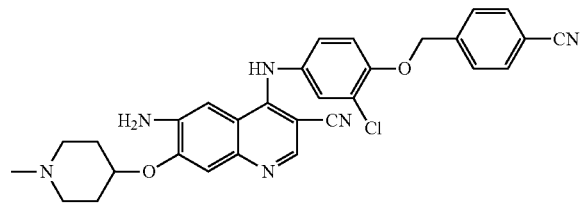

Preparation 8br 4-(4-(4-ETHYLBENZYLOXY)-3-CHLOROPHE-NYLAMINO)-6-AMINO-7-(1-METHYLPIPERI-DIN-4-YL-OXY)QUINOLINE-3-CARBONITRILE

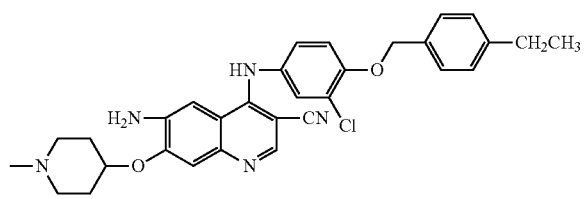

Preparation 8bs 4-(4-(4-ETHOXYBENZYLOXY)-3-CHLOROPHE-NYLAMINO)-6-AMINO-7-(1-METHYLPIPERI-DIN-4-YL-OXY)QUINOLINE-3-CARBONITRILE

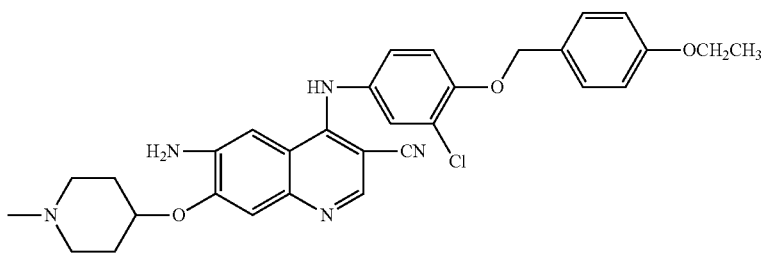

Preparation 8bt

6-AMINO-4-(3-CHLORO-4-PHENOXYPHE-NYLAMINO)-7-(1-METHYLPIPERIDIN-4-YL-OXY)QUINOLINE-3-CARBONITRILE

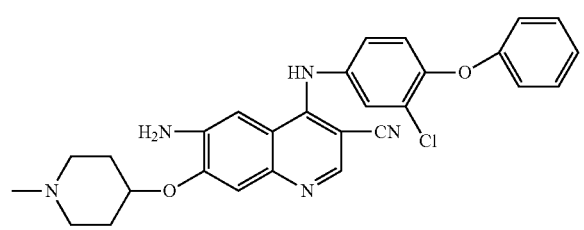 [SMILES: CN1CCC(Oc2cc3ncc(C#N)c(Nc4ccc(Oc5ccccc5)c(Cl)c4)c3cc2N)CC1]

Preparation 8bu

6-AMINO-7-(1-METHYLPIPERIDIN-4-YL-OXY)-4-(PYRIDIN-2-YL-AMINO)QUINOLINE-3-CARBONITRILE

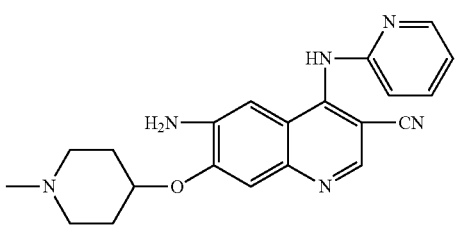

Preparation 8bv

6-AMINO-7-(1-METHYLPIPERIDIN-4-YL-OXY)-4-(PYRIDIN-3-YL-AMINO)QUINOLINE-3-CARBONITRILE

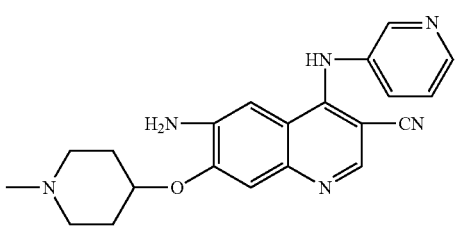 [SMILES: CN1CCC(Oc2cc3ncc(C#N)c(Nc4cccnc4)c3cc2N)CC1]

Preparation 8bw

6-AMINO-7-(1-METHYLPIPERIDIN-4-YL-OXY)-4-(PYRIDIN-4-YL-AMINO)QUINOLINE-3-CARBONITRILE

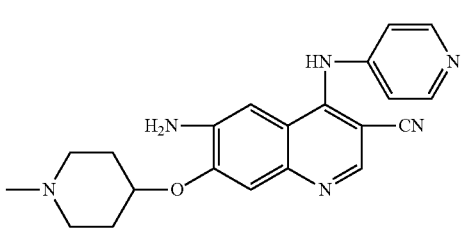

101

Preparation 8bx

6-AMINO-4-(6-(BENZYLOXY)PYRIDIN-3-YL-AMINO)-7-(1-METHYLPIPERIDIN-4-YL-OXY)QUINOLINE-3-CARBONITRILE

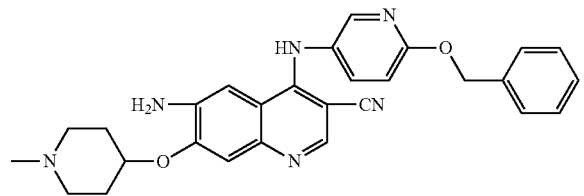

Preparation 8by

6-AMINO-4-(3-CHLORO-4-FLUOROPHE-NYLAMINO)-7-(PYRIDIN-4-YL-OXY)QUINO-LINE-3-CARBONITRILE

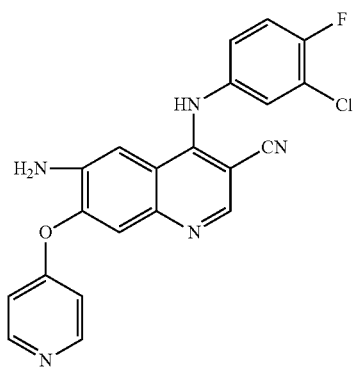

Preparation 8bz

6-AMINO-4-(3-ETHYNYLPHENYLAMINO)-7-(PYRIDIN-4-YL-OXY) QUINOLINE-3-CARBO-NITRILE

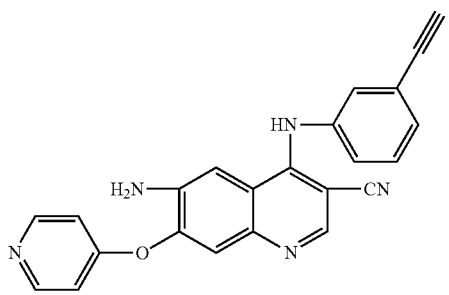

102

Preparation 8ca

6-AMINO-4-(4-PHENOXYPHENYLAMINO)-7-(PYRIDIN-4-YL-OXY)QUINOLINE-3-CARBONI-TRILE

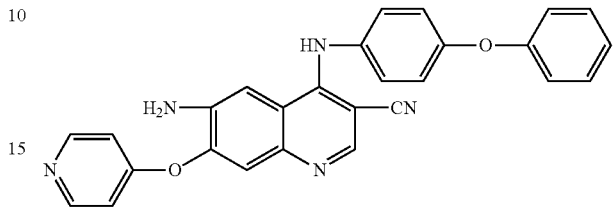

Preparation 8cb

6-AMINO-4-(4-(BENZYLOXY)PHENYLAMINO)-7-PYRIDIN-4-YL-OXY)QUINOLINE-3-CARBO-NITRILE

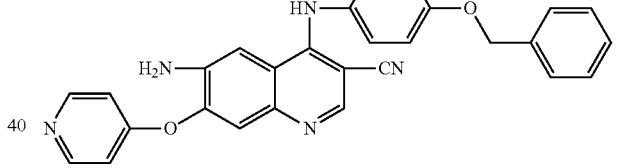

Preparation 8cc 4-(4-(2-CHLOROBENZYLOXY)-3-CHLOROPHE-NYLAMINO)-6-AMINO-7-(PYRIDIN-4-YL-OXY)QUINOLINE-3-CARBONITRILE

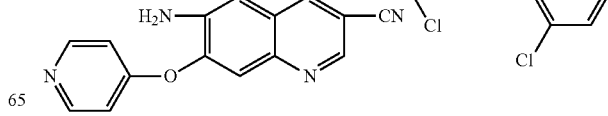

Preparation 8cd 4-(4-(4-METHYLBENZYLOXY)-3-CHLOROPHE-NYLAMINO)-6-AMINO-7-(PYRIDIN-4-YL-OXY) QUINOLINE-3-CARBONITRILE

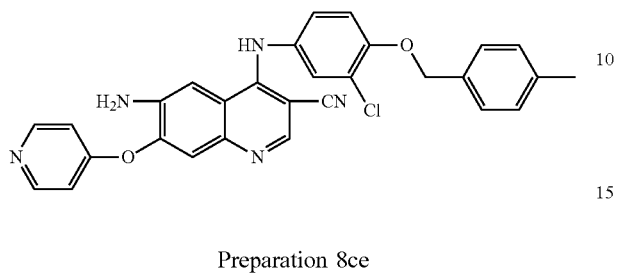

Preparation 8ce 4-(4-(4-METHOXYBENZYLOXY)PHE-NYLAMINO)-6-AMINO-7-(PYRIDIN-4-YL-OXY) QUINOLINE-3-CARBONITRILE

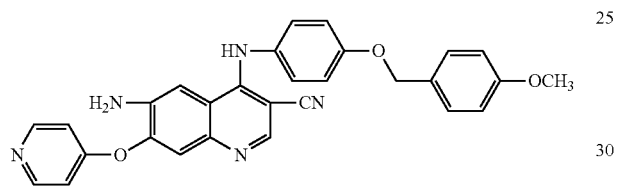

Preparation 8cf 4-(4-(3-CYANOBENZYLOXY)-3-CHLOROPHE-NYLAMINO)-6-AMINO-7-(PYRIDIN-4-YL-OXY) QUINOLINE-3-CARBONITRILE

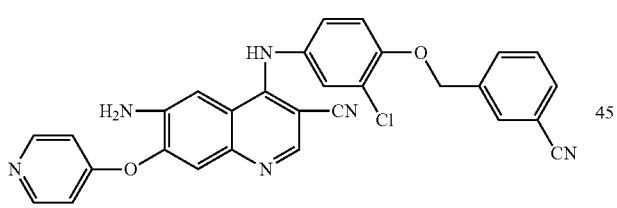

Preparation 8cg

6-AMINO-4-(PYRIDIN-2-YL-AMINO)-7-(PYRI-DIN-4-YL-OXY)QUINOLINE-3-CARBONITRILE

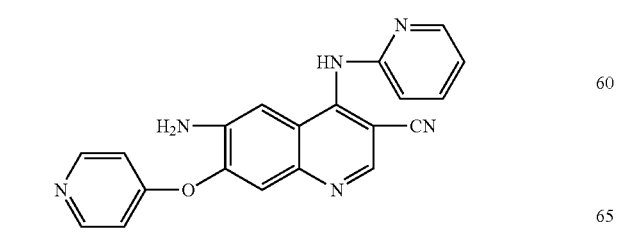

Preparation 8ch

6-AMINO-7-(PYRIDIN-4-YL-OXY)-4-(PYRIMI-DIN-2-YL-AMINO)QUINOLINE-3-CARBONI-TRILE

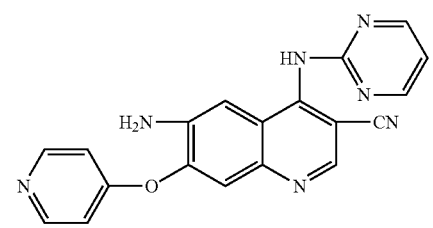

Preparation 8ci

6-AMINO-4-(6-(BENZYLOXY)PYRIDIN-3-YL-AMINO)-7-(PYRIDIN-4-YL-OXY)QUINOLINE-3-CARBONITRILE

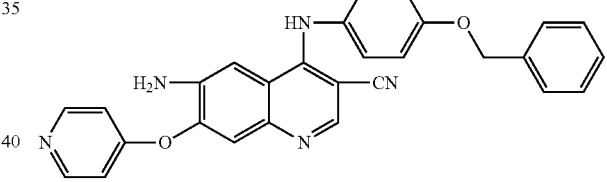

Preparation 8cj 4-(6-(3-CHLOROBENZYLOXY)PYRIDIN-3-YL-AMINO)-6-AMINO-7-(PYRIDIN-4-YL-OXY)QUI-NOLINE-3-CARBONITRILE

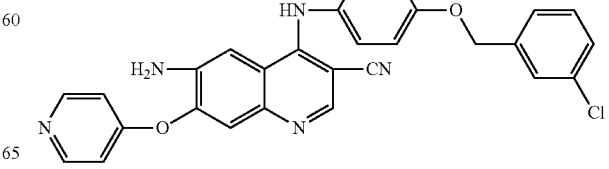

Preparation 8ck

6-AMINO-4-(6-PHENOXYPYRIDIN-3-YL-AMINO)-7-(PYRIDIN-4-YL-OXY)QUINOLINE-3-CARBONITRILE

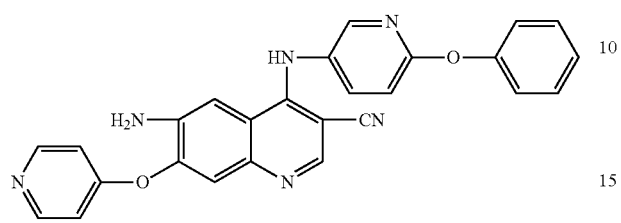

Preparation 9

(E)-TRIMETHYLSILYL 4-BROMO-2-BUTENOATE

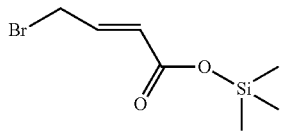

To a single-neck reaction flask (250 mL) were added of crotonic acid (10.750 g, 0.125 mol), anhydrous ethyl ether (125 mL) and trimethyl chlorosilane (19 mL, 0.150 mol). The mixture was stirred for 5 min. Pyridine (12 mL, 0.150 mol) was dropwise added into the resulting mixture under stirring at the temperature of 35° C. After the addition finished, the mixture was warmed up to the temperature of 38° C. and stirred under relux for 3 hr. The white solid was filtered in vacuo. Ethyl ether was evaporated under atmospheric pressure. The resultant was distilled under reduced pressure to collect the fraction under 10 mmHg at the temperature of 46° C.-48° C. to give (E)-trimethylsilyl 2-butenoate as a colorless liquid (12.242 g). Yield: 62.0%.

To a single-neck reaction flask (250 mL) were added (E)-trimethylsilyl 2-butenoate (12.242 g, 77.481 mmol), NBS (16.550 g, 92.977 mmol), (PhCO$_2$)$_2$ (310 mg) and carbon tetrachloride (100 mL). The mixture was stirred under reflux for 3.5 hr. The resulting mixture was cooled in an ice-water bath. The insoluble substance was filtered. The residue was rotatory-evaporated and concentrated until no liquid dropped. The concentrate was distilled under reduced pressure to collect the fraction under 9 mmHg at the temperature of 100° C.-102° C. to give the target compound as a colorless transparent liquid.

Preparation 10

(E/Z)-TRIMETHYLSILYL 4-BROMO-2-BUTENOATE

The compound was prepared according to the process of Preparation 9 with 2-butenoic acid as starting material.

The compounds of Preparations 11, 12 and 13 were prepared according to the preparation process disclosed in Chinese patent No. CN 200610138377.9.

Preparation 11

2-(1-(TERT-BUTOXYCARBONYL)PIPERIDIN-4-YLIDENE)-ACETIC ACID

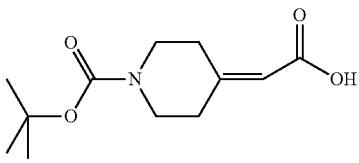 [SMILES: CC(C)(C)OC(=O)N1CCC(=CC(=O)O)CC1]

Preparation 12

2-(1-(2-METHOXYETHYL)-PIPERIDIN-4-YLIDENE)-ACETIC ACID

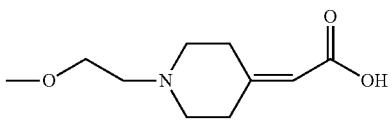

Preparation 13

(E)-2-(1-(TERT-BUTOXYCARBONYL)PYRROLIN-3-YLIDENE)ACETIC ACID

Example 1

(E)-4-BROMO-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-BUT-2-ENAMIDE

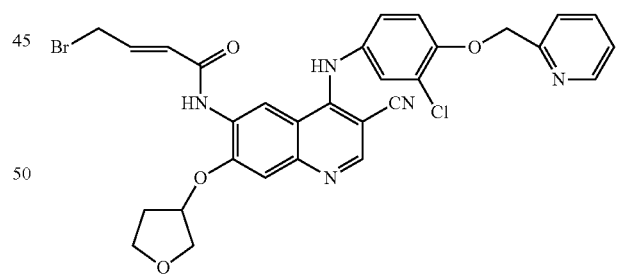

a) After a single-neck reaction flask (100 mL) was blown with argon for 5 min, to the reaction flask was added (E)-trimethylsilyl 4-bromo-2-butenoate (1.363 g, 5.75 mmol). DCM (treated with molecular sieves) (3 mL) was added under argon atmosphere. To the mixture were added oxalyl chloride (0.55 mL, 6.325 mmol) and one drop of DMF (chromatographically pure) under stirring. Lots of bubbles produced. After 1 min, the bubbles reduced. The resulting mixture was continuously stirred for 2 hr at the room temperature and then rotary-evaporated to dryness.

b) 6-amino-4-(3-chloro-4-(pyridin-2-yl-methoxy)phenylamino)-7-(tetrahydro furan-3-yl-oxy)quinolin-3-carbonitrile (2.44 g, 5 mmol) was dissolved in THF (redistilled) (36 mL) under argon atmosphere. The solution was cooled in an ice-water bath. DIEA (1.73 mL, 10 mmol) was added. The resulting solution was stirred for 10 min. The rotary-evaporated product from a) was dissolved in THF (redistilled) (14 mL). The resultant solution was dropwise added into the reaction solution. The mixture was stirred in an ice-water bath overnight. The resultant mixture was rotary-evaporated to dryness. Ethyl acetate (200 mL) and saturated $Na_2CO_3$ solution (150 mL) were added. The solution was stirred for 10 min at the room temperature. After separation, the aqueous layer was extracted once with ethyl acetate (100 mL). The ethyl acetate layers were combined. The organic phase was washed with water (200 mL) and saturated NaCl solution (200 mL), dried over $MgSO_4$ for half-hour, filtered and rotary-evaporated to dryness. The resultant substance was purified with column chromatography (eluent: chloroform:methanol=9:1) to give a yellow solid (2.381 g). Yield: 75.0%.

MS (M+1): 634.

$H^1$-NMR ($CDCl_3$): δ 2.222-2.270 (m, 1H); 2.346-2.476 (m, 1H); 3.431-3.458 (m, 1H); 3.925-3.955 (m, 1H); 4.012-4.247 (m, 4H); 5.158 (br, 1H); 5.281 (d, 2H, J=4.8); 6.114-6.422 (m, 2H); 6.905-7.198 (m, 3H); 7.535 (br, 1H); 7.648 (d, 1H, J=6.6); 7.765 (t, 1H, J=6.8); 8.154 (d, 1H, J=76.9); 8.485 (s, 1H); 8.596 (d, 2H, J=3.8); 9.109 (d, 1H, J=42.4).

Example 2

(E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

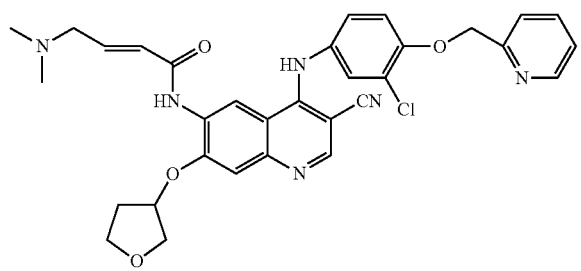 [SMILES: CN(C)C/C=C/C(=O)Nc1cc2c(Nc3ccc(OCc4ccccn4)c(Cl)c3)c(C#N)cnc2cc1OC1CCOC1]

(E)-4-bromo-N-(4-(3-chloro-4-(pyridin-2-yl-methoxy) phenylamino)-3-cyano-7-(tetrahydrofuran-3-yl-oxy)quinolin-6-yl)-2-butenamide (2.35 g, 3.704 mmol) was dissolved in DMF (chromatographically pure) (40 mL). The solution was cooled in an ice-water bath under argon atmosphere. To the solution was added NaI (278 mg, 1.852 mmol). The mixture was stirred for 30 min. To the mixture were added dimethylamine hydrochloride (604 mg, 7.408 mmol), potassium carbonate (2.556 g, 18.519 mmol) and tetrabutyl ammonium iodide (59 mg, 0.185 mmol). The resultant mixture was stirred at the room temperature overnight. After the reaction finished, the reaction solution was poured into staturated $NaHCO_3$ solution (400 mL) to precipitate a yellow solid. The solid was extracted with ethyl acetate three times (550 mL in total). The ethyl acetate layers were combined. The organic phase was washed with water (300 mL) and saturated NaCl solution (300 mL), successively. The resultant organic phase was dried over anhydrous $MgSO_4$ for half-hour, filtered and rotary-evaporated to dryness. The resultant substance was purified with column chromatography (eluent: chloroform:methanol=9:1) to give a yellow solid (1.375 g). Yield: 62.0%.

MS (M+1): 599.

$H^1$-NMR (DMSO-$d_6$, $CH_3OH$-$d_4$): δ 2.167-2.219 (m, 1H); 2.354-2.452 (m, 1H); 2.782 (s, 6H); 3.794 (dd, 1H, $J_1$=8.0; $J_2$=14.0); 3.949-4.074 (m, 5H); 5.258 (br, 1H); 5.546 (s, 2H); 6.795-6.914 (m, 2H); 7.387 (d, 1H, J=8.8); 7.551 (s, 1H); 7.674 (s, 1H); 7.845 (t, 1H, J=6.4); 8.000 (d, 1H, J=7.8); 8.406 (t, 1H, J=7.6); 8.851 (d, 1H, J=5.2); 9.043 (s, 1H); 9.231 (s, 1H).

Example 3

(E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE HYDROCHLORIDE

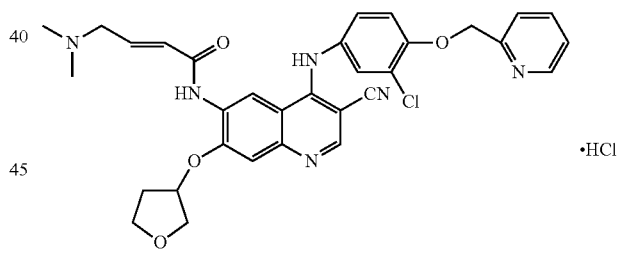

(E)-N-(4-(3-chloro-4-(pyridin-2-yl-methoxy)phenylamino)-3-cyano-7-(tetrahy drofuran-3-yl-oxy)quinolin-6-yl)-4-(dimethylamino)-2-butenamide was dissolved in redistilled methanol (10 mL). A solution of HCl in ethyl ether (5 mL, 1.8 N) was dropwise added into the resultant solution under stirring. The resulting mixture was stirred for 10 min and rotary-evaporated to dryness. The resultant substance was recrystalized with a mixed solution of anhydrous methanol and hydrochloric acid (2 N) to give a crystal of (E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-2-butenamide as hydrochloride (1.163 g).

MS (M+1): 599.

The compounds of Examples 4-21 were prepared according to the process for preparing the compound of Example 2.

Example 4

(E)-N-(4-(3-CHLORO-4-FLUOROPHE-NYLAMINO)-3-CYANO-7-(TETRAHYDRO-FURAN-3-YL-OXY)QUINOLIN-6-YL)-4-(DIM-ETHYLAMINO)-BUT-2-ENAMIDE

MS (M+1): 510

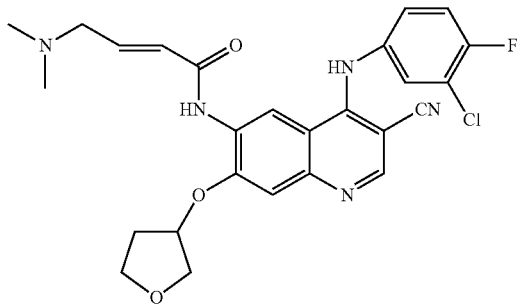

Example 5

(E)-N-(3-CYANO-4-(3-ETHYNYLPHE-NYLAMINO)-7-(TETRAHYDROFURAN-3-YL-OXY)QUINOLIN-6-YL)-4-(DIMETHYLAMINO)-BUT-2-ENAMIDE

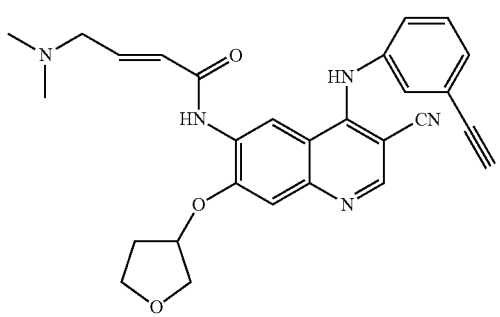 [SMILES: C#Cc1cccc(Nc2c(C#N)cnc3cc(OC4CCOC4)c(NC(=O)/C=C/CN(C)C)cc23)c1]

MS (M+1): 482

The compound was prepared as hydrochloride according to the process of Example 3 to determine $H^1$-NMR (DMSO-$d_6$): δ 2.173-2.218 (m, 1H); 2.405-2.468 (m, 1H); 2.746 (s, 3H); 2.755 (s, 3H); 3.774-3.831 (m, 1H); 3.956-4.103 (m, 5H); 4.315 (s, 1H); 5.270 (br, 1H); 6.826-6.968 (m, 2H); 7.500 (s, 3H); 7.559 (s, 1H); 7.768 (s, 1H); 9.074 (s, 1H); 9.219 (s, 1H); 10.037 (s, 1H); 11.340 (br, 2H).

Example 6

(E)-N-(4-(4-(BENZYLOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 564

Example 7

(E)-N-(4-(3-BROMOPHENYLAMINO)-3-CYANO-7-(TETRAHYDROFURAN-3-YL-OXY)QUINO-LIN-6-YL)-4-(DIMETHYLAMINO)-BUT-2-ENA-MIDE

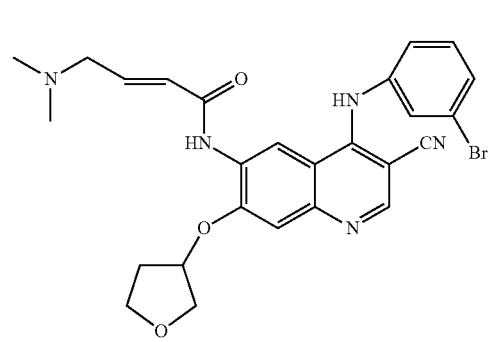 [SMILES: CN(C)C/C=C/C(=O)Nc1cc2c(Nc3cccc(Br)c3)c(C#N)cnc2cc1OC1CCOC1]

MS (M+1): 536

The compound was prepared as hydrochloride according to the process of Example 3 to determine $H^1$-NMR (DMSO-$d_6$): δ 2.157-2.216 (m, 1H); 2.385-2.456 (m, 1H); 2.741 (s, 3H); 2.753 (s, 3H); 3.803 (dd, 1H, $J_1$=8.0, $J_2$=13.6); 3.939-4.103 (m, 5H); 5.266 (br, 1H); 6.826-6.968 (m, 2H); 7.431-7.466 (m, 2H); 7.587-7.608 (m, 1H); 7.718 (s, 1H); 7.786 (s, 1H); 9.110 (s, 1H); 9.222 (s, 1H); 10.052 (s, 1H); 11.345 (br, 2H).

111

Example 8

(E)-N-(4-(4-(2-FLUOROBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

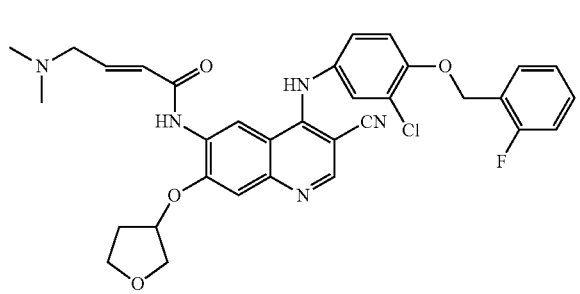 [SMILES: CN(C)C/C=C/C(=O)Nc1cc2c(Nc3ccc(OCc4ccccc4F)c(Cl)c3)c(C#N)cnc2cc1OC1CCOC1]

MS (M+1): 616

The compound was prepared as hydrochloride according to the process of Example 3 to determine H$^1$-NMR (DMSO-d$_6$): δ 2.148-2.211 (m, 1H); 2.380-2.452 (m, 1H); 2.744 (s, 3H); 2.755 (s, 3H); 3.803 (dd, 1H, J$_1$=8.0, J$_2$=13.6); 3.943-4.098 (m, 5H); 5.256 (br, 1H); 5.310 (s, 2H); 6.816-6.971 (m, 2H); 7.258-7.321 (m, 2H); 7.417-7.473 (m, 3H); 7.607-7.652 (m, 2H); 7.750 (s, 1H); 9.082 (s, 1H); 9.203 (s, 1H); 10.056 (s, 1H); 11.312 (br, 2H).

Example 9

(E)-N-(4-(4-(3-FLUOROBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

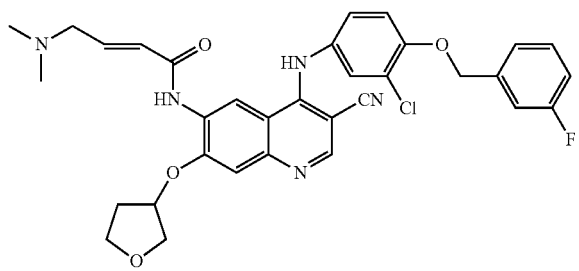 [SMILES: CN(C)C/C=C/C(=O)Nc1cc2c(Nc3ccc(OCc4cccc(F)c4)c(Cl)c3)c(C#N)cnc2cc1OC1CCOC1]

MS (M+1): 616

The compound was prepared as hydrochloride according to the process of Example 3 to determine H$^1$-NMR (CDCl$_3$, CH$_3$OH-d$_4$): δ 2.168-2.202 (m, 1H); 2.425-2.482 (m, 1H); 2.747 (s, 3H); 2.750 (s, 3H); 3.798-3.835 (m, 1H); 3.960-4.121 (m, 5H); 5.250 (br, 1H); 5.325 (s, 2H); 6.834-6.967 (m, 2H); 7.174-7.219 (m, 1H); 7.311-7.361 (m, 2H); 7.461 (q, 2H, J=7.2); 7.674 (s, 1H); 7.822 (s, 1H); 9.090 (s, 1H); 9.212 (s, 1H); 10.085 (s, 1H); 11.387 (s, 1H); 11.441 (s, 1H).

112

Example 10

(E)-N-(4-(4-(2-CHLOROBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

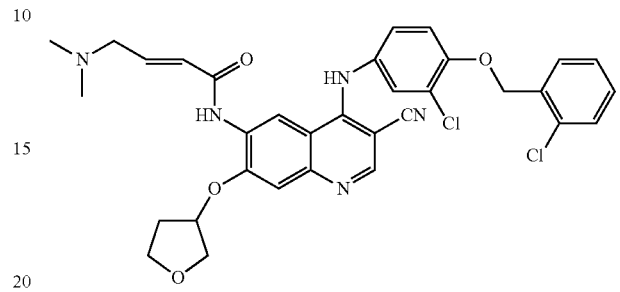

MS (M+1): 632

The compound was prepared as hydrochloride according to the process of Example 3 to determine H$^1$-NMR (DMSO-d$_6$): δ 2.148-2.213 (m, 1H); 2.399-2.452 (m, 1H); 2.746 (s, 3H); 2.757 (s, 3H); 3.804 (dd, 1H, J$_1$=8.0, J$_2$=13.6); 3.955-4.097 (m, 5H); 5.262 (br, 1H); 5.327 (s, 2H); 6.816-6.968 (m, 2H); 7.394-7.465 (m, 3H); 7.545-7.568 (m, 1H); 7.664-7.686 (m, 2H); 7.741 (s, 1H); 9.078 (s, 1H); 9.205 (s, 1H); 10.054 (s, 1H); 11.316 (br, 2H).

Example 11

(E)-N-(4-(4-(3-CHLOROBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

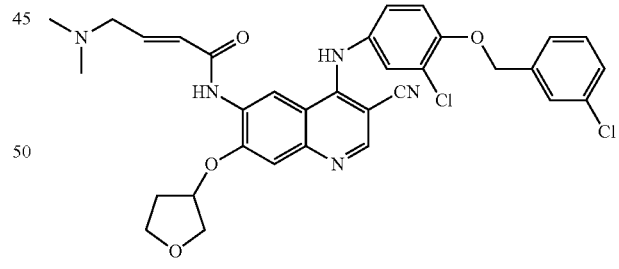

MS (M+1): 632

The compound was prepared as hydrochloride according to the process of Example 3 to determine H$^1$-NMR (DMSO-d$_6$): δ 2.150-2.211 (m, 1H); 2.385-2.454 (m, 1H); 2.743 (s, 3H); 2.751 (s, 3H); 3.801 (dd, 1H, J$_1$=8.0, J$_2$=13.2); 3.954-4.097 (m, 5H); 5.249 (br, 1H); 5.314 (s, 2H); 6.824-6.977 (m, 2H); 7.347 (d, 1H, J=8.8); 7.426-7.473 (m, 4H); 7.568 (s, 1H); 7.668 (d, 1H, J=2.4); 7.790 (s, 1H); 9.080 (s, 1H); 9.203 (s, 1H); 10.066 (s, 1H); 11.334 (s, 1H); 11.413 (br, 1H).

Example 12

(E)-N-(4-(4-(BENZYLOXY)-3-CHLOROPHE-NYLAMINO)-3-CYANO-7-(TETRAHYDRO-FURAN-3-YL-OXY)QUINOLIN-6-YL)-4-(DIM-ETHYLAMINO)-BUT-2-ENAMIDE

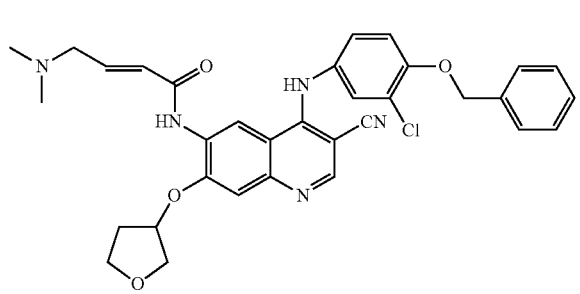 [SMILES: CN(C)C/C=C/C(=O)Nc1cc2c(Nc3ccc(OCc4ccccc4)c(Cl)c3)c(C#N)cnc2cc1OC1CCOC1]

MS (M+1): 598

The compound was prepared as hydrochloride according to the process of Example 3 to determine $H^1$-NMR (DMSO-$d_6$): δ 2.152-2.214 (m, 1H); 2.382-5.452 (m, 1H); 2.741 (s, 3H); 2.752 (s, 3H); 3.801 (dd, 1H, $J_1$=7.6, $J_2$=13.6); 3.936-4.091 (m, 5H); 5.254 (br, 1H); 5.282 (s, 2H); 6.818-6.975 (m, 2H); 7.345-7.379 (m, 2H); 7.408-7.446 (m, 3H); 7.495-7.513 (m, 2H); 7.642 (d, 1H, J=2.4); 7.778 (s, 1H); 9.055 (s, 1H); 9.195 (s, 1H); 10.028 (s, 1H); 11.292 (s, 1H); 11.418 (br, 1H).

Example 13

(E)-N-(4-(4-(2-CYANOBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

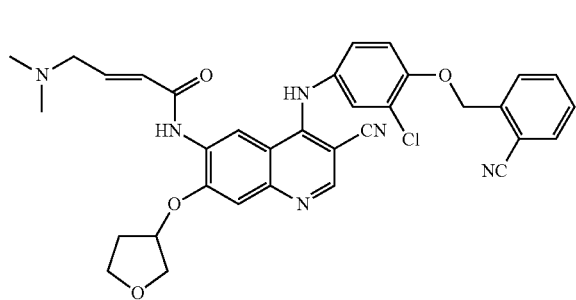 [SMILES: CN(C)C/C=C/C(=O)Nc1cc2c(Nc3ccc(OCc4ccccc4C#N)c(Cl)c3)c(C#N)cnc2cc1OC1CCOC1]

MS (M+1): 623

The compound was prepared as hydrochloride according to the process of Example 3 to determine $H^1$-NMR (DMSO-$d_6$): δ 2.150-2.211 (m, 1H); 2.374-2.443 (m, 1H); 2.749 (s, 3H); 2.759 (s, 3H); 3.805 (dd, 1H, $J_1$=7.6, $J_2$=13.2); 3.938-4.089 (m, 5H); 5.271 (br, 1H); 5.420 (s, 2H); 6.802-6.955 (m, 2H); 7.433 (s, 2H); 7.601-7.678 (m, 3H); 7.790 (s, 1H); 7.800 (s, 1H); 7.953 (d, 1H, J=8.0); 9.024 (s, 1H); 9.178 (s, 1H); 9.987 (s, 1H); 11.166 (br, 2H).

Example 14

(E)-N-(4-(4-(4-TERT-BUTYLBENZYLOXY)-3-CHLOROPHENYLAMINO)-3-CYANO-7-(TET-RAHYDROFURAN-3-YL-OXY)QUINOLIN-6-YL)-4-(DIMETHYLAMINO)-BUT-2-ENAMIDE

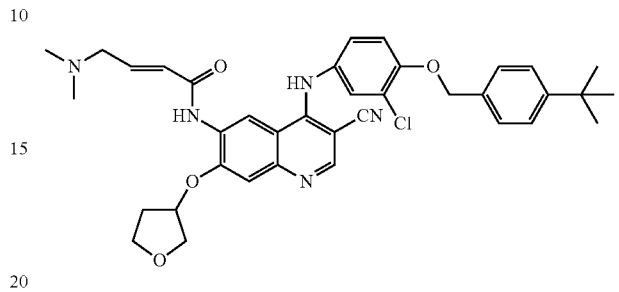

MS (M+1): 654

The compound was prepared as hydrochloride according to the process of Example 3 to determine $H^1$-NMR (DMSO-$d_6$): δ 1.268 (s, 9H); 2.121-2.181 (m, 1H), 2.353-2.422 (m, 1H); 2.713 (s, 3H); 2.724 (s, 3H); 3.771 (dd, 1H, $J_1$=8.0, $J_2$=13.6); 3.913-4.067 (m, 5H); 5.198 (s, 2H); 5.271 (br, 1H); 6.787-6.938 (m, 2H); 7.327-7.432 (s, 6H); 7.619 (d, 1H, J=2.8); 7.725 (s, 1H); 9.057 (s, 1H); 9.175 (s, 1H); 10.036 (s, 1H); 11.309 (br, 2H).

Example 15

(E)-N-(4-(4-(3-CYANOBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

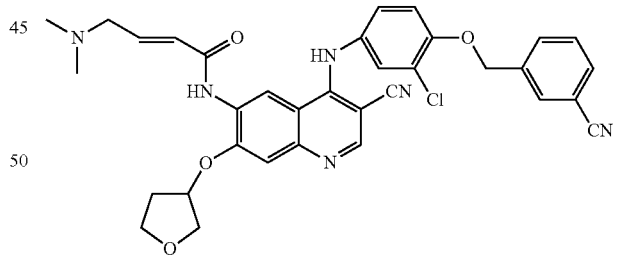

MS (M+1): 623

The compound was prepared as hydrochloride according to the process of Example 3 to determine $H^1$-NMR (DMSO-$d_6$): δ 2.150-2.197 (m, 1H); 2.380-2.451 (m, 1H); 2.748 (s, 3H); 2.758 (s, 3H); 3.803 (dd, 1H, $J_1$=8.0, $J_2$=13.6); 3.957-4.098 (m, 5H); 5.259 (br, 1H); 5.365 (s, 2H); 6.821-6.968 (m, 2H); 7.360 (d, 1H, J=8.8); 7.440 (d, 1H, J=8.8); 7.641-7.673 (m, 2H); 7.744 (br, 1H); 7.840 (s, 1H); 7.859 (s, 1H); 7.939 (s, 1H); 9.070 (s, 1H); 9.201 (s, 1H); 10.062 (s, 1H); 11.317 (br, 2H).

Example 16

(E)-N-(4-(4-(4-CHLOROBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

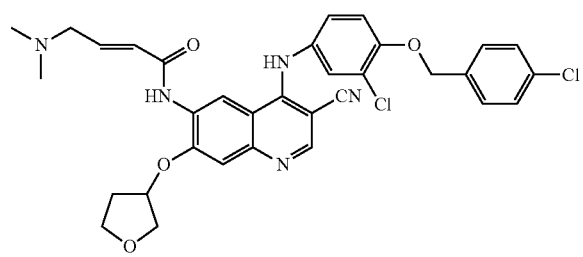 [SMILES: CN(C)C/C=C/C(=O)Nc1cc2c(Nc3ccc(OCc4ccc(Cl)cc4)c(Cl)c3)c(C#N)cnc2cc1OC1CCOC1]

MS (M+1): 632

The compound was prepared as hydrochloride according to the process of Example 3 to determine $H^1$-NMR (DMSO-$d_6$): δ 2.147-2.209 (m, 1H); 2.381-2.452 (m, 1H); 2.742 (s, 3H); 2.753 (s, 3H); 3.801 (dd, 1H, $J_1$=8.0, $J_2$=13.6); 3.942-4.096 (m, 5H); 5.253 (br, 1H); 5.290 (s, 2H); 6.818-6.972 (m, 2H); 7.345 (d, 1H, J=8.8); 7.429 (dd, 1H, $J_1$=2.4, $J_2$=8.8); 7.512 (dd, 1H, $J_1$=8.4, $J_2$=14.8); 7.655 (d, 1H, J=2.4); 7.763 (s, 1H); 9.074 (s, 1H); 9.198 (s, 1H); 10.059 (s, 1H); 11.305 (s, 1H); 11.360 (br, 1H).

Example 17

(E)-N-(4-(4-(2-METHYLBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

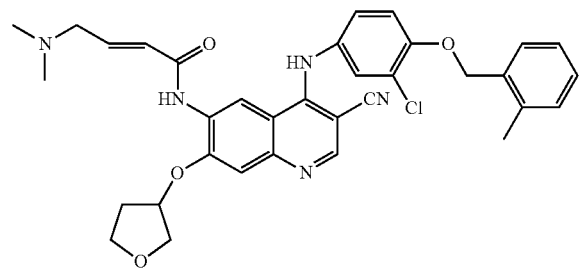 [SMILES: Cc1ccccc1COc1ccc(Nc2c(C#N)cnc3cc(OC4CCOC4)c(NC(=O)/C=C/CN(C)C)cc23)cc1Cl]

MS (M+1): 612

The compound was prepared as hydrochloride according to the process of Example 3 to determine $H^1$-NMR (DMSO-$d_6$): δ 2.164-2.195 (m, 1H); 2.368 (s, 3H); 2.403-2.454 (m, 1H); 2.744 (s, 6H); 3.774-3.809 (m, 1H); 3.955-4.097 (m, 5H); 5.260 (s, 3H); 6.824-6.975 (m, 2H); 7.236-7.283 (m, 3H); 7.413-7.498 (m, 3H); 7.651 (s, 1H); 7.780 (s, 1H); 9.082 (s, 1H); 9.208 (s, 1H); 10.069 (s, 1H); 11.348 (br, 2H).

Example 18

(E)-N-(4-(4-(3-METHYLBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

MS (M+1): 612

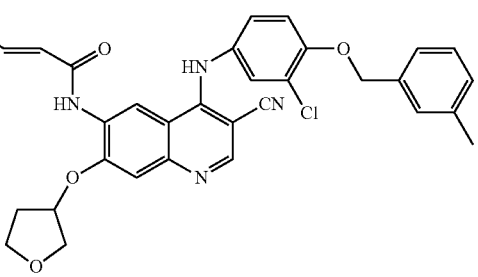

Example 19

(E)-N-(4-(4-(4-METHYLBENZYLOXY)-3-CHLO-ROPHENYLAMINO)-3-CYANO-7-(TETRAHY-DROFURAN-3-YL-OXY)QUINOLIN-6-YL)-4-(DIMETHYLAMINO)-BUT-2-ENAMIDE

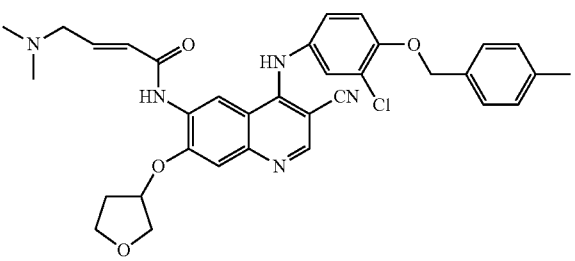

MS (M+1): 612

The compound was prepared as hydrochloride according to the process of Example 3 to determine $H^1$-NMR (DMSO-$d_6$): δ 2.148-2.194 (m, 1H); 2.325 (s, 3H); 2.396-2.448 (m, 1H); 2.743 (s, 3H); 2.754 (s, 3H); 3.801 (dd, 1H, $J_1$=8.0, $J_2$=13.6); 3.953-4.094 (m, 5H); 5.221 (s, 2H); 5.256 (br, 1H); 6.815-6.968 (m, 2H); 7.220 (s, 1H); 7.239 (s, 1H); 7.331-7.423 (m, 4H); 7.632 (d, 1H, J=2.4); 7.739 (s, 1H); 9.059 (s, 1H); 9.190 (s, 1H); 10.049 (s, 1H); 11.259 (br, 1H); 11.335 (br, 1H).

Example 20

(E)-N-(3-CYANO-4-((R)-1-PHENYLAMINO)-7-(TETRAHYDROFURAN-3-YL-OXY) QUINOLIN-6-YL)-4-(DIMETHYLAMINO)-BUT-2-ENAMIDE

MS (M+1): 486

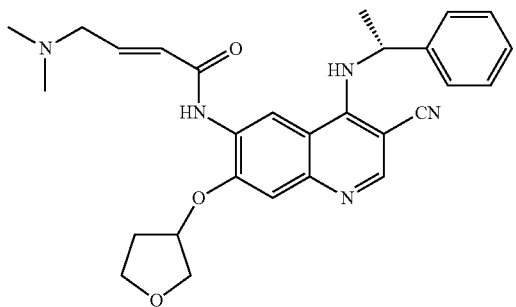 [SMILES: C[C@@H](Nc1c(C#N)cnc2cc(OC3CCOC3)c(NC(=O)/C=C/CN(C)C)cc12)c1ccccc1]

Example 21

(E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 599

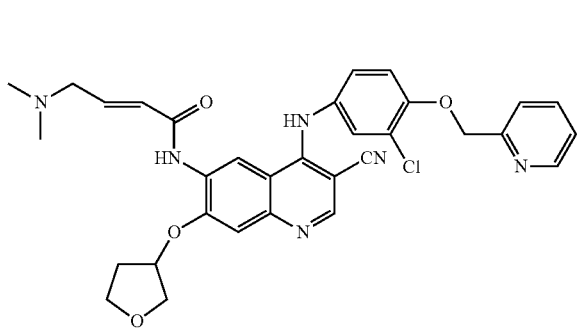

Example 22

N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)ACRYLAMIDE

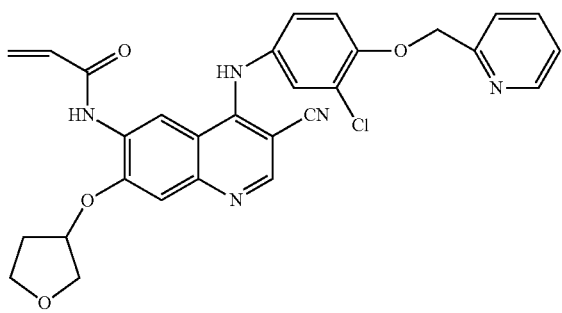 [SMILES: C=CC(=O)Nc1cc2c(Nc3ccc(OCc4ccccn4)c(Cl)c3)c(C#N)cnc2cc1OC1CCOC1]

To a reaction flask were added 6-amino-4-(3-chloro-4-(pyridin-2-yl-methoxy) phenylamino)-7-(tetrahydrofuran-3-yl-oxy)quinolin-3-carbonitrile (100 mg, 0.205 mmol), pyridine (0.3 ml), DMAP (20 mg) and THF (10 ml). The mixture was cooled to the temperature of 0° C. To the mixture was added acryloyl chloride (20 mg, 0.22 mmol). The resultant mixture was stirred for 30 min at the temperature of 0° C. Then the mixture was warmed to the room temperature and stirred for 5 hr. After the reaction finished, the resultant mixture was filtered and the filtrate was rotary-evaporated to dryness to give a solid. The solid was dissolved in ethyl acetate. The solution was washed with saturated sodium carbonate once, acetic acid solution (10%) once and saturated saline once, successively. The resulting solution was dried over anhydrous magnesium sulfate, filtered and rotary-evaporated to dryness to give a crude product. The product was purified with thin layer chromatography.

MS (M+1): 542.

The compounds of Examples 23-28 were prepared according to the process of Example 22.

Example 23

(E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)BUT-2-ENAMIDE

MS (M+1): 556

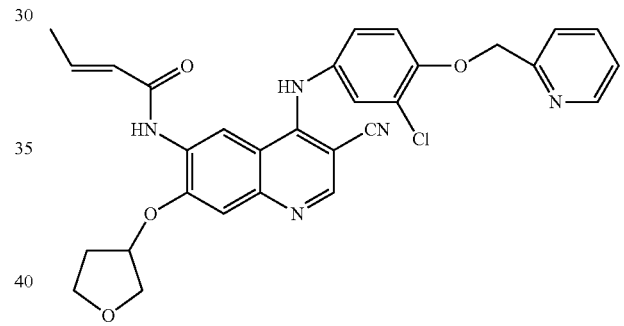

Example 24

N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-3-METHYLBUT-2-ENAMIDE

MS (M+1): 570

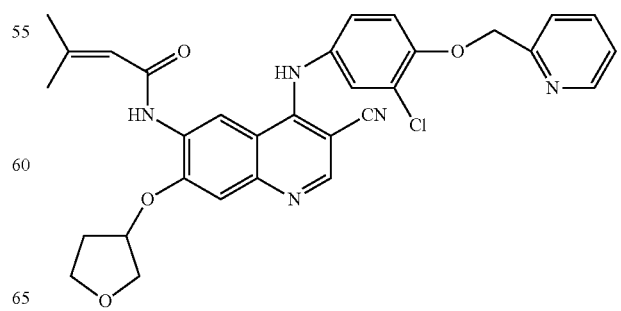

Example 25

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)PROPIOL-AMIDE

MS (M+1): 540

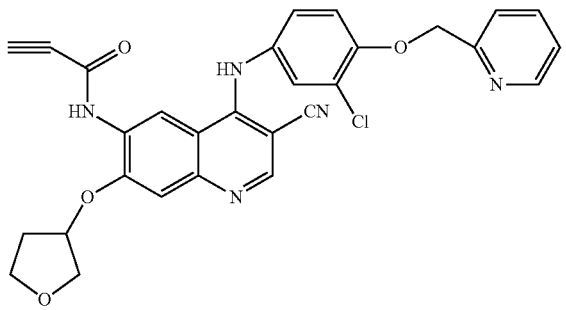 [SMILES: C#CC(=O)Nc1cc2c(Nc3ccc(OCc4ccccn4)c(Cl)c3)c(C#N)cnc2cc1OC1CCOC1]

Example 26

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)PROPIOL-AMIDE

MS (M+1): 544

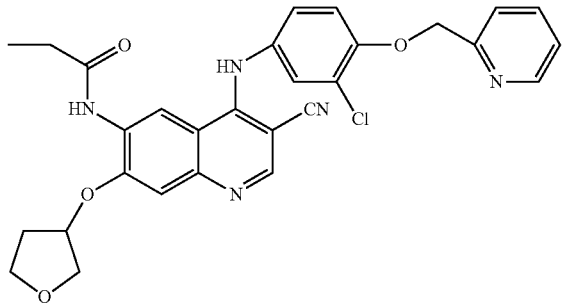 [SMILES: CCC(=O)Nc1cc2c(Nc3ccc(OCc4ccccn4)c(Cl)c3)c(C#N)cnc2cc1OC1CCOC1]

Example 27

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)ACET-AMIDE

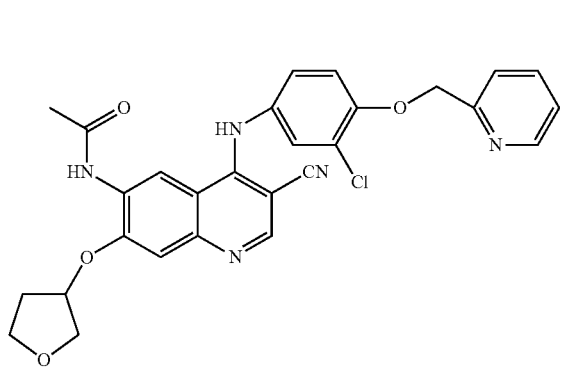 [SMILES: CC(=O)Nc1cc2c(Nc3ccc(OCc4ccccn4)c(Cl)c3)c(C#N)cnc2cc1OC1CCOC1]

MS (M+1): 530
$H^1$-NMR (DMSO-$d_6$): δ 2.181 (br, 4H), 62.326-2.393 (m, 1H); 3.805 (dd, 1H, $J_1$=7.2, $J_2$=12.8); 3.955 (dd, 1H, $J_1$=7.6, $J_2$=14.4); 4.017-4.058 (m, 2H); 5.279 (br, 1H); 5.319 (s, 2H); 7.303 (s, 1H); 7.375-7.444 (m, 2H); 7.521 (s, 1H); 7.593 (d, 1H, J=8.4); 7.893 (t, 1H, J=8.0); 8.617 (s, 1H); 8.752 (s, 1H); 8.967 (s, 1H); 9.442 (s, 1H).

Example 28

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)BENZ-AMIDE

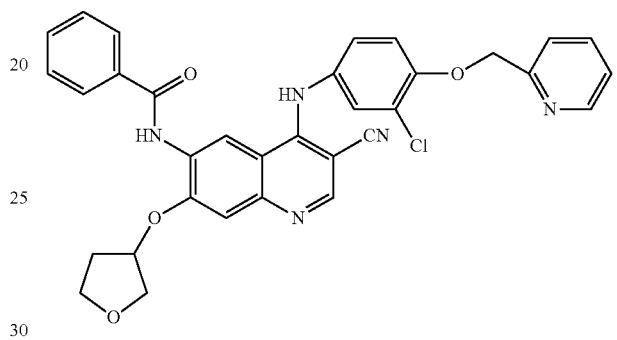

MS (M+1): 592
$H^1$-NMR (DMSO-$d_6$): δ 2.087-2.132 (m, 1H); 2.287-2.376 (m, 1H); 3.769-3.820 (m, 1H); 3.859-3.948 (m, 2H); 4.019 (dd, 1H, $J_1$=4.4; $J_2$=10.0); 5.298 (s, 2H); 5.348 (br, 1H); 7.234-7.267 (m, 2H); 7.360-7.390 (m, 1H); 7.438 (s, 1H) 7.449 (s, 1H); 7.556-7.650 (m, 4H); 7.877 (t, 1H, J=8.0); 7.889 (d, 2H, J=7.2); 8.324 (s, 1H); 8.527 (s, 1H); 8.603 (d, 1H, J=4.4); 8.821 (s, 1H); 9.757 (s, 1H); 9.808 (s, 1H).

Example 29

TERT-BUTYL 4-(2-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL-AMINO)-2-OXO ETHYLIDENE)PIPERIDINE-1-CARBOXYLATE

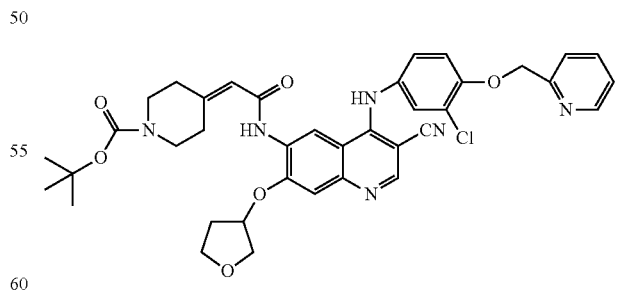

To a single-neck reaction flask (100 ml) were added 2-(1-(tert-butyloxycarbonyl)piperidin-4-ylidene)acetic acid (1 g) and anhydrous THF (20 ml). The mixture was stirred to dissolve and cooled to the temperature of −5° C. To the mixture were added isobutyl chloroformate (0.6 ml) and N-methylmorphine (0.5 ml). The resultant mixture was stirred for 20 min. 6-amino-4-(3-chloro-4-(pyridin-2-yl-methoxy) phenylamino)-7-(tetrahydrofuran-3-yl-oxy)quinolin-3-carbonitrile (2 g, 4.1 mmol) was dissolved in anhydrous pyridine (20 ml). The resulting solution was added into the reaction flask in an ice-water bath. After the reaction finished, the solvent was rotary-evaporated to dryness. To the residue were added chloroform and water. The solution was stood for separation. The chloroform layer was wash once with saturated saline solution, dried over anhydrous magnesium sulfate, filtered and rotary-evaporated to dryness to give a crude product. The product was recrystalized with ethanol.

MS (M+1): 711.

Example 30

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

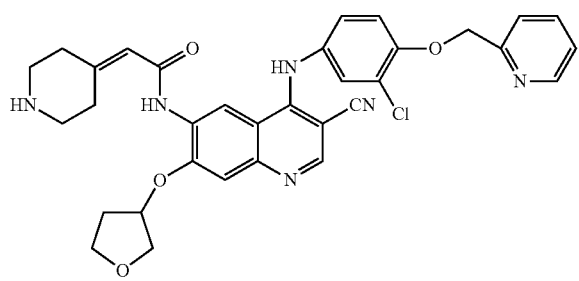 [SMILES: N#Cc1cnc2cc(OC3CCOC3)c(NC(=O)C=C3CCNCC3)cc2c1Nc1ccc(OCc2ccccn2)c(Cl)c1]

The product of Example 29 (100 mg) was dissolved in 20% TFA/DCM solution (20 ml). The solution was stirred for 2 hr at the room temperature. Then the solvent was rotary-evaporated to dryness. The residue was dissolved in chloroform. The organic phase was washed with staturated sodium carbonate once and saline solution once, successively. The resultant substance was dried over anhydrous magnesium sulfate and filtered. Then the solvent was rotary-evaporated to dryness to give the target compound.

MS (M+1): 611.

The compound was prepared as hydrochloride according to the process of Example 3 to determine, $H^1$-NMR (DMSO-$d_6$): δ 2.168-2.209 (m, 1H); 62.408-2.451 (m, 1H); 2.576 (bs, 2H); 3.133 (bs, 2H); 3.211 (s, 2H); 3.259 (s, 2H); 3.805-3.830 (m, 1H); 3.939-4.114 (m, 5H); 5.258 (br, 1H); 5.497 (s, 2H); 6.374 (s, 1H); 7.401 (d, 2H, J=8.4); 7.401 (d, 1H, J=8.4); 7.464 (d, 1H, J=8.4); 7.678 (br, 1H); 7.705 (s, 1H); 7.783-7.852 (m, 2H); 8.173-8.214 (m, 1H); 8.785 (s, 1H); 9.090 (s, 1H); 9.213 (s, 1H); 9.468 (br, 1H); 9.710 (s, 1H); 11.342 (br, 2H).

Example 31

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(1-METHYLPIPERIDIN-4-YLIDENE)ACETAMIDE

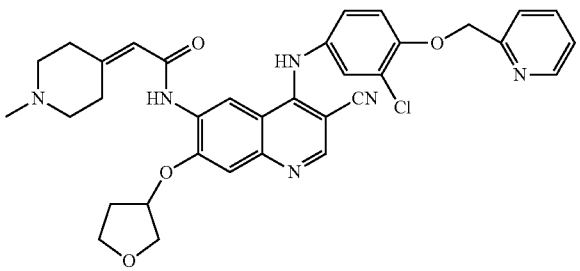 [SMILES: CN1CCC(=CC(=O)Nc2cc3c(Nc4ccc(OCc5ccccn5)c(Cl)c4)c(C#N)cnc3cc2OC2CCOC2)CC1]

To a single-neck reaction flask (50 ml) was added the product of Example 30 (20 mg). The product was dissolved in acetonitrile (10 ml). To the resultant solution were added anhydrous potassium carbonate powders (20 mg) and methyl iodide (5 mg). The resulting mixture was stirred at the room temperature. After the reaction finished, the resultant substance was filtered. The filtrate was rotary-evaporated to dryness to give a crude product. The crude product was purified with thin layer chromatography (developing solvent: chloroform:methanol=92:8).

MS (M+1): 625.

The compounds of Examples 32-37 were prepared according to the process of Example 31.

Example 32

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(1-ETH-YLPIPERIDIN-4-YLIDENE)ACETAMIDE

MS (M+1): 639

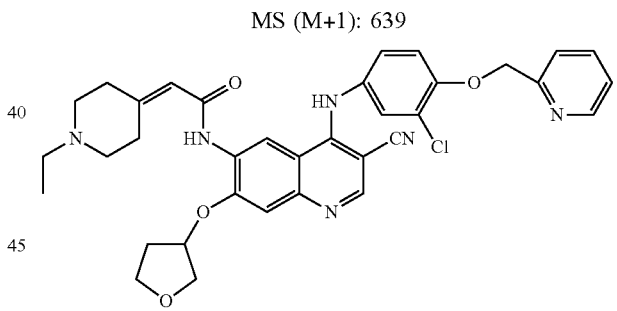

Example 33

2-(1-BENZYLPIPERIDIN-4-YLIDENE)-N-(4-(3-CHLORO-4-(PYRIDIN-2-YL-METHOXY)PHE-NYLAMINO)-3-CYANO-7-(TETRAHYDRO-FURAN-3-YL-OXY)QUINOLIN-6-YL) ACETAMIDE

MS (M+1): 701

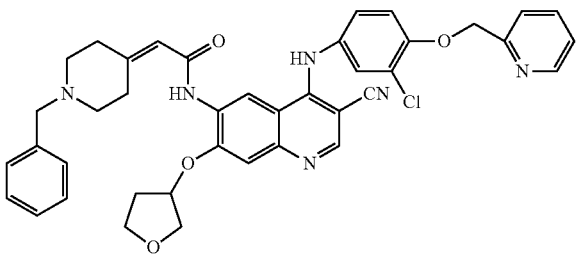 [SMILES: N#Cc1cnc2cc(OC3CCOC3)c(NC(=O)C=C3CCN(Cc4ccccc4)CC3)cc2c1Nc1ccc(OCc2ccccn2)c(Cl)c1]

Example 34

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(1-(2-METHOXYETHYL) PIPERIDIN-4-YLIDENE) ACETAMIDE

MS (M+1): 669

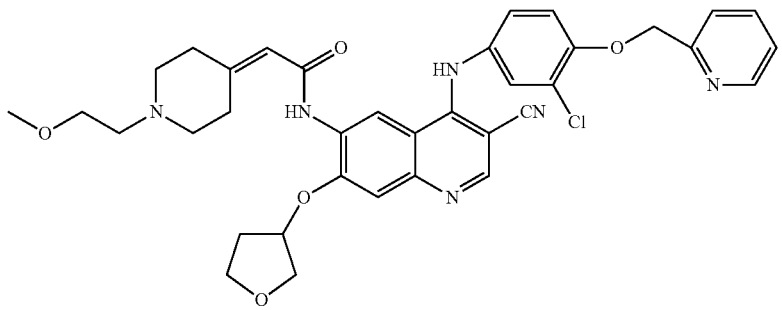 [SMILES: COCCN1CCC(=CC(=O)Nc2cc3c(Nc4ccc(OCc5ccccn5)c(Cl)c4)c(C#N)cnc3cc2OC2CCOC2)CC1]

Example 35

Methyl 2-(4-(2-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL-AMINO)-2-OXOETHYLIDENE)PIPERIDIN-1-YL)ACETATE

MS (M+1): 683

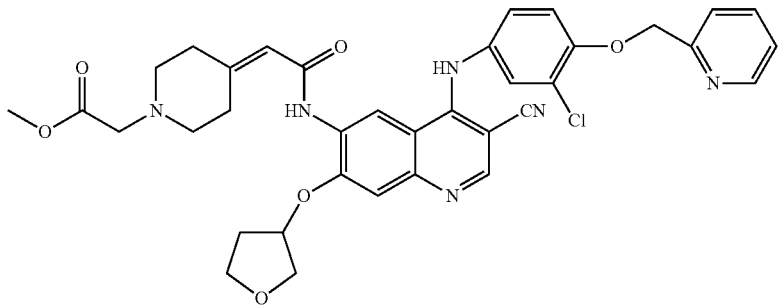 [SMILES: COC(=O)CN1CCC(=CC(=O)Nc2cc3c(Nc4ccc(OCc5ccccn5)c(Cl)c4)c(C#N)cnc3cc2OC2CCOC2)CC1]

Example 36

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(1-ISO-PROPYLPIPERIDIN-4-YLIDENE)ACETAMIDE

MS (M+1): 653

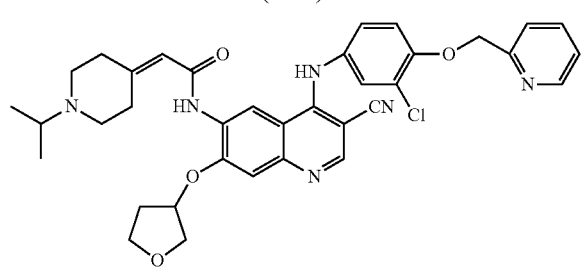

Example 37

N-(4-(3-CHLORO-4-(PYRIDIN-2-YL-METHOXY) PHENYLAMINO)-3-CYANO-7-(TETRAHYDRO-FURAN-3-YL-OXY)QUINOLIN-6-YL)-2-(1-(2-HYDROXYETHYL) PIPERIDIN-4-YLIDENE) ACETAMIDE

MS (M+1): 655

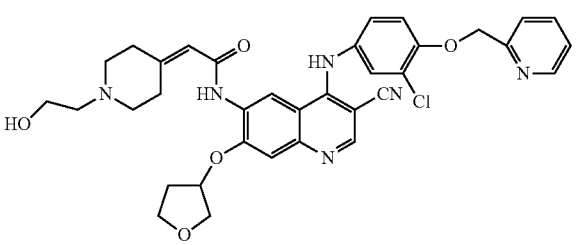 [SMILES: N#Cc1cnc2cc(OC3CCOC3)c(NC(=O)C=C3CCN(CCO)CC3)cc2c1Nc1ccc(OCc2ccccn2)c(Cl)c1]

Example 38

(E/Z)—N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-2-(PYRROLIDIN-3-YLIDENE)ACETAMIDE

MS (M+1): 597

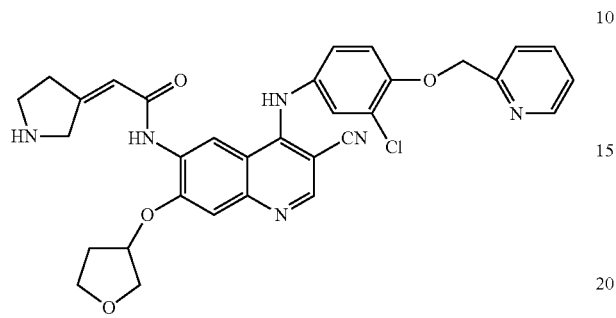

In accordance with the process of Examples 29 and 30, the target compound was prepared by replacing 2-(1-(tert-butoxycarbonyl)piperidin-4-ylidene)acetic acid with (E/Z)-2-(1-(tert-butoxycarbonyl)pyrrolin-3-ylidene)acetic acid.

Example 39

$N^1$-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-$N^4$-(2-(2-(DIMETHYLAMINO)ETHOXY)ETHYL)FUMARAMIDE

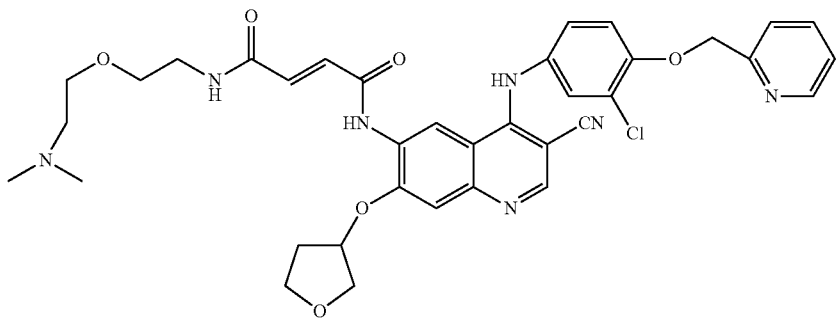 [SMILES: CN(C)CCOCCNC(=O)/C=C/C(=O)Nc1cc2c(Nc3ccc(OCc4ccccn4)c(Cl)c3)c(C#N)cnc2cc1OC1CCOC1]

To a single-neck reaction flask (50 ml) were added 6-amino-4-(3-chloro-4-(pyridin-2-yl-methoxy)phenylamino)-7-(tetrahydrofuran-3-yl-oxy)quinoline-3-carbonitrile (20 mg, 0.041 mmol), maleic acid (4 mg), pyridine (0.1 ml) and THF (5 ml), The mixture was stirred at the room temperature. After the reaction finished, the solvent was rotary-evaporated to dryness. The residue was purified with thin layer chromatography (developing solvent: chloroform:methanol:acetic acid=450:50:2). The resulting pure product was dissolved in anhydrous THF. Aminoethoxyethanol was added into the resultant solution. The mixture was cooled in an ice bath. DCC (8 mg) was dissolved in anhydrous THF (5 ml). The resulting solution was dropwise added into the reaction flask under continuously stirring. After the reaction finished, the solvent was rotary-evaporated to dryness to give a crude product. The crude product was dissolved in pyridine (5 ml). p-toluene sulfonyl chloride (7 mg) was added into the resultant solution. The mixture was stirred at the room temperature. After the reaction finished, the solvent was rotary-evaporated to dryness. The resulting crude product was dissolved in chloroform. The organic phase was washed with staturated sodium carbonate once, HCl (1 N) once and saturated saline solution once, successively. The resultant substance was dried over anhydrous magnesium sulfate, filtered and rotary-evaporated to dryness to give a product. The above resulting product was dissolved in pyridine (10 ml). Dimethylamine was added into the solution. The resultant mixture was stirred at the room temperature. After the reaction finished, the solvent was rotary-evaporated to dryness. The resultant substance was purified with thin layer chromatography, (developing solvent:chloroform:methanol=9:1) to give the targent compound.

MS (M+1): 700.

Example 40

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)-2-(1-(2-(2-(2-HYDROXYETHOXY)ETHYLAMINO)ACETYL)PIPERIDIN-4-YLIDENE) ACETAMIDE

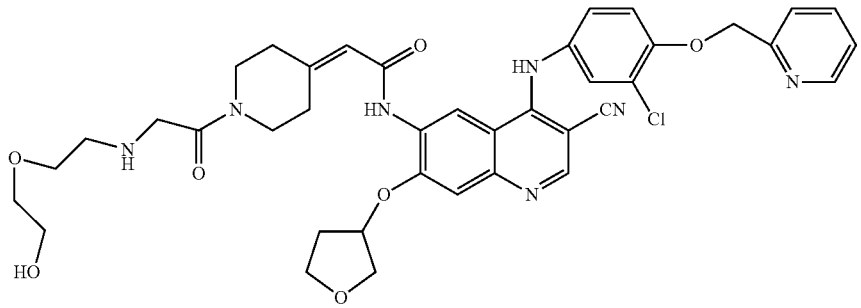 [SMILES: N#Cc1cnc2cc(OC3CCOC3)c(NC(=O)C=C3CCN(C(=O)CNCCOCCO)CC3)cc2c1Nc1ccc(OCc2ccccn2)c(Cl)c1]

To a single-neck reaction flask (50 ml) were added N-(4-(3-chloro-4-(pyridin-2-yl-methoxy)phenylamino)-3-cyano-7-(tetrahydrofuran-3-yl-oxy)quinolin-6-yl)-2-(piperidin-4-ylidene)acetamide (20 mg, 0.041 mmol) and anhydrous THF (10 ml). The solution was cooled in an ice bath. Chloroacetyl chloride (4.5 mg) and anhydrous triethylamine (0.02 ml) were added into the solution. The resultant mixture was continuously stirred. After the reaction finished, the solvent was rotary-evaporated to dryness. The residue was dissolved in chloroform. The solution was washed with water three times and with saturated saline solution once. The resultant solution was dried over anhydrous magnesium sulfate, filtered and rotary-evaporated to dryness. The above resulting crude product was dissolved in acetonitrile (10 ml). To the solution were added aminoethoxyethanol (4 mg) and triethylamine (0.2 ml). The mixture was stirred at the room temperature. After the reaction finished, the solvent was rotary-evaporated to dryness. The resultant substance was purified with thin layer chromatography (developing solvent:chloroform methanol=9:1.

MS (M+1): 756.

Example 41

N-(4-(3-CHLORO-4-(PYRIDIN-2-YL-METHOXY)PHENYLAMINO)-3-CYANO-7-(TETRAHYDRO-FURAN-3-YL-OXY)QUINOLIN-6-YL)-2-(1-(METHYLSULFONYL) PIPERIDIN-4-YLIDENE) ACETAMIDE

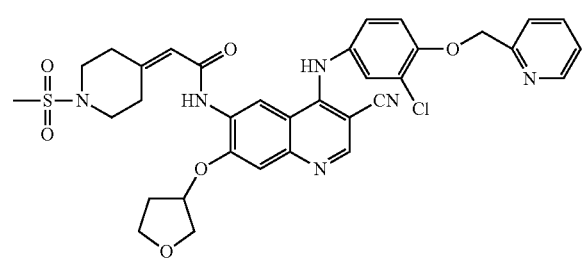 [SMILES: CS(=O)(=O)N1CCC(=CC(=O)Nc2cc3c(Nc4ccc(OCc5ccccn5)c(Cl)c4)c(C#N)cnc3cc2OC2CCOC2)CC1]

In accordance with the process of Example 22, the compound was prepared by replacing acryloyl chloride with methylsulfonyl chloride.

MS (M+1): 689.

The compounds of Examples 42-132 were prepared according to the processes of Examples 29 and 30.

Example 42

N-(4-(3-CHLORO-4-FLUOROPHENYLAMINO)-3-CYANO-7-(TETRAHYDROFURAN-3-YL-OXY)QUINOLIN-6-YL)-2-(PIPERIDIN-4-YLIDENE) ACETAMIDE

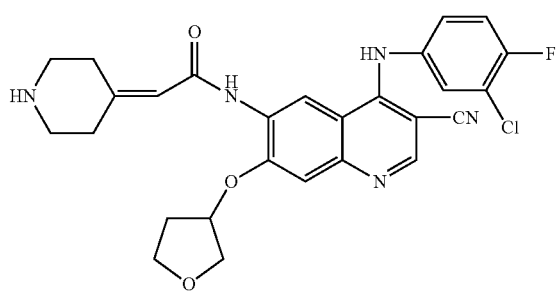 [SMILES: N#Cc1cnc2cc(OC3CCOC3)c(NC(=O)C=C3CCNCC3)cc2c1Nc1ccc(F)c(Cl)c1]

MS (M+1): 522

The compound was prepared as hydrochloride according to the process of Example 3 to determine $H^1$-NMR (DMSO-$d_6$): δ 2.143-2.214 (m, 1H); 62.372-2.443 (m, 1H); 2.561 (bs, 2H); 3.123 (bs, 2H); 3.169-3.240 (m, 4H); 3.803 (dd, 1H, $J_1$=8.0, $J_2$=13.6); 3.927-4.099 (m, 5H); 5.258 (br, 1H); 6.357 (s, 1H); 7.507 (br, 1H); 7.567 (t, 1H, J=9.0); 7.744-7.794 (m, 2H); 9.069 (s, 1H); 9.170 (s, 1H); 9.409 (br, 2H); 9.651 (s, 1H); 11.248 (s, 1H).

Example 43

N-(3-CYANO-4-(3-ETHYNYLPHENYLAMINO)-7-(TETRAHYDROFURAN-3-YL-OXY)QUINOLIN-6-YL)-2-(PIPERIDIN-4-YLIDENE)ACETAMIDE

MS (M+1): 494

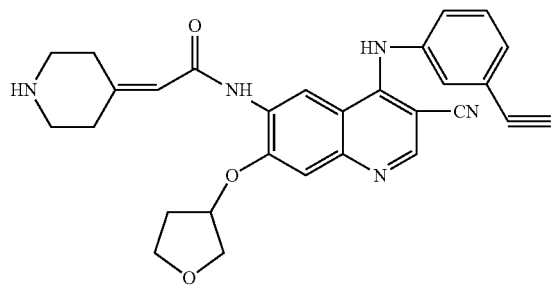 [SMILES: C#Cc1cccc(Nc2c(C#N)cnc3cc(OC4CCOC4)c(NC(=O)C=C4CCNCC4)cc23)c1]

Example 44

N-(4-(3-BROMOPHENYLAMINO)-3-CYANO-7-(TETRAHYDROFURAN-3-YL-OXY) QUINOLIN-6-YL)-2-(PIPERIDIN-4-YLIDENE)ACETAMIDE

MS (M+1): 548

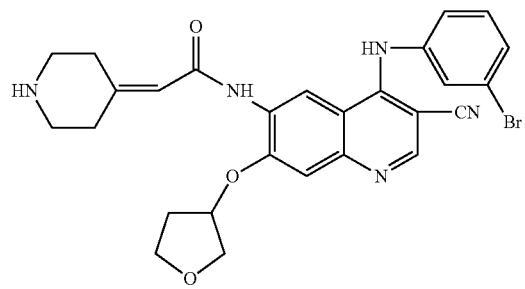 [SMILES: N#Cc1cnc2cc(OC3CCOC3)c(NC(=O)C=C3CCNCC3)cc2c1Nc1cccc(Br)c1]

Example 45

N-(4-(4-(2-FLUOROBENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 628

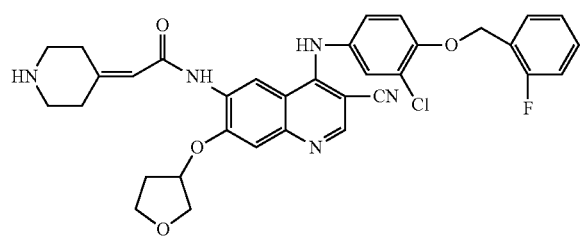

Example 46

N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 628

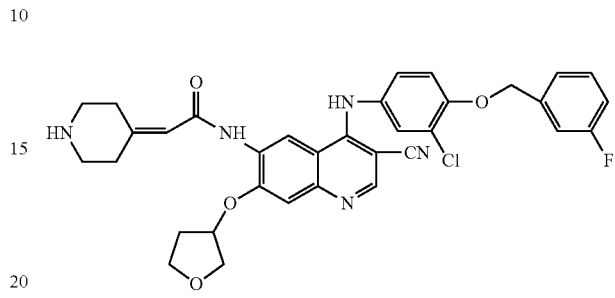

Example 47

N-(4-(4-(4-FLUOROBENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 628

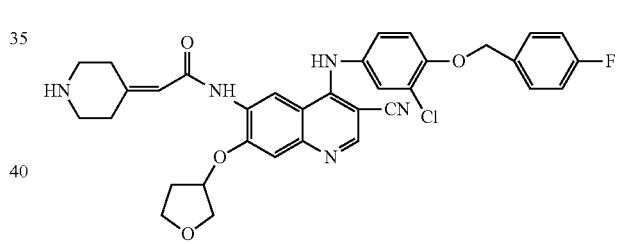

Example 48

N-(4-(4-(2-CHLOROBENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 644

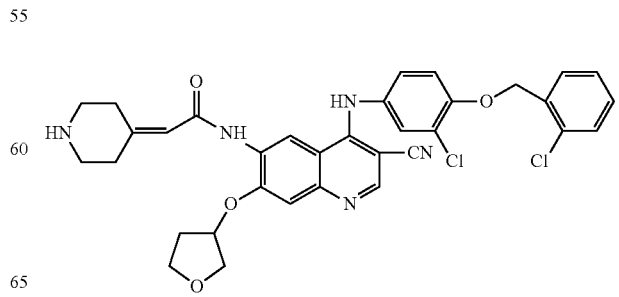

Example 49

N-(4-(4-(3-CHLOROBENZYLOXY)-3-CHLORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS/(M+1) 644

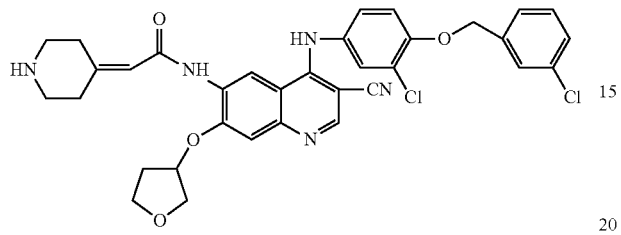

Example 50

N-(4-(4-(4-CHLOROBENZYLOXY)-3-CHLORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 644

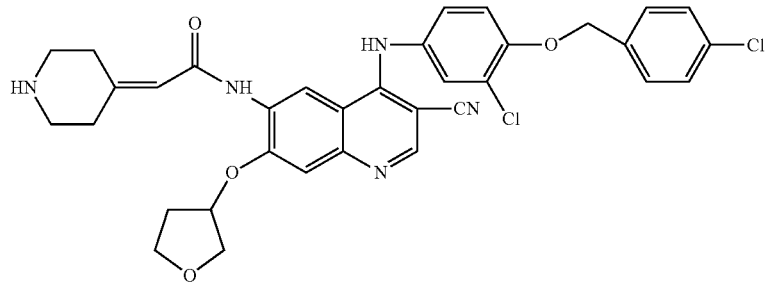

Example 51

N-(4-(4-(2-METHYLBENZYLOXY)-3-CHLORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 624

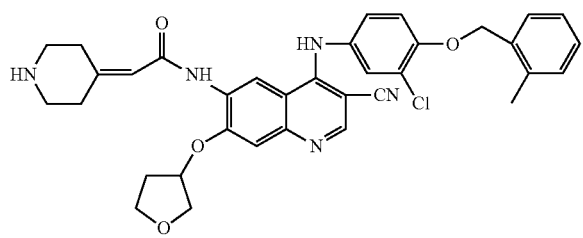

Example 52

N-(4-(4-(3-METHYLBENZYLOXY)-3-CHLORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 624

Example 53

N-(4-(4-(4-METHYLBENZYLOXY)-3-CHLORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 624

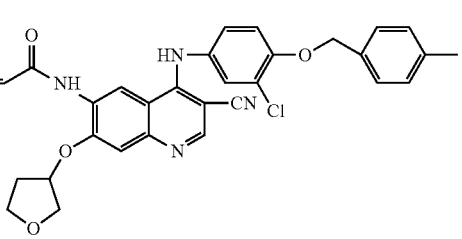

133

Example 54

N-(4-(4-(2-METHOXYBENZYLOXY)-3-CHLO-
ROPHENYLAMINO)-3-CYANO-7-(TETRAHY-
DROFURAN-3-YL-OXY)QUINOLIN-6-YL)-2-
(PIPERIDIN-4-YLIDENE) ACETAMIDE

MS (M+1): 640

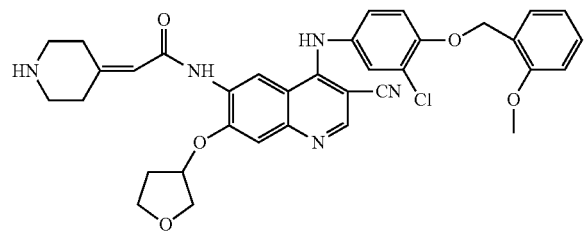 [SMILES: N#Cc1cnc2cc(OC3CCOC3)c(NC(=O)C=C3CCNCC3)cc2c1Nc1ccc(OCc2ccccc2Cl)c(Cl)c1]

Example 55

N-(4-(4-(3-METHOXYBENZYLOXY)-3-CHLO-
ROPHENYLAMINO)-3-CYANO-7-(TETRAHY-
DROFURAN-3-YL-OXY)QUINOLIN-6-YL)-2-
(PIPERIDIN-4-YLIDENE) ACETAMIDE

MS (M+1): 640

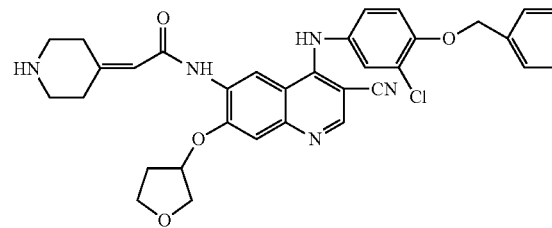

Example 56

N-(4-(4-(4-METHOXYBENZYLOXY)-3-CHLO-
ROPHENYLAMINO)-3-CYANO-7-(TETRAHY-
DROFURAN-3-YL-OXY)QUINOLIN-6-YL)-2-
(PIPERIDIN-4-YLIDENE) ACETAMIDE

MS (M+1): 640

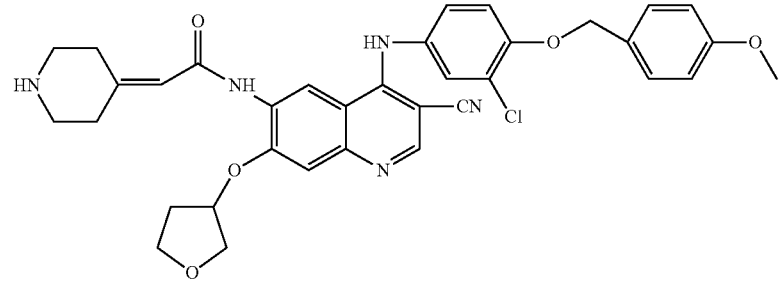 [SMILES: COc1ccc(COc2ccc(Nc3c(C#N)cnc4cc(OC5CCOC5)c(NC(=O)C=C5CCNCC5)cc34)cc2Cl)cc1]

134

Example 57

N-(4-(4-(2-CYANOBENZYLOXY)-3-CHLORO-
PHENYLAMINO)-3-CYANO-7-(TETRAHYDRO-
FURAN-3-YL-OXY)QUINOLIN-6-YL)-2-(PIPERI-
DIN-4-YLIDENE) ACETAMIDE

MS (M+1): 635

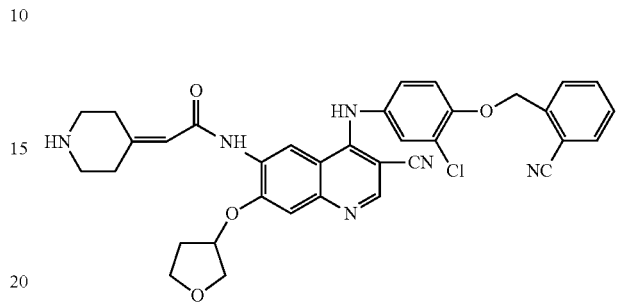

Example 58

N-(4-(4-(3-CYANOBENZYLOXY)-3-CHLORO-
PHENYLAMINO)-3-CYANO-7-(TETRAHYDRO-
FURAN-3-YL-OXY)QUINOLIN-6-YL)-2-(PIPERI-
DIN-4-YLIDENE) ACETAMIDE

MS (M+1): 635

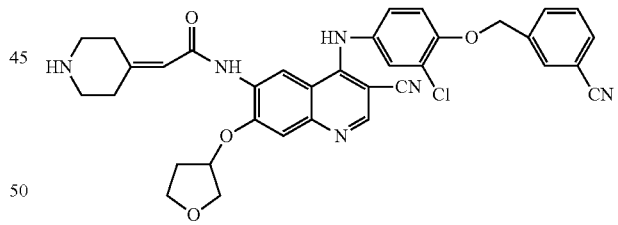

Example 59

N-(4-(4-(4-CYANOBENZYLOXY)-3-CHLORO-PHENYLAMINO)-3-CYANO-7-(TETRAHYDRO-FURAN-3-YL-OXY)QUINOLIN-6-YL)-2-(PIPERIDIN-4-YLIDENE) ACETAMIDE

MS (M+1): 635

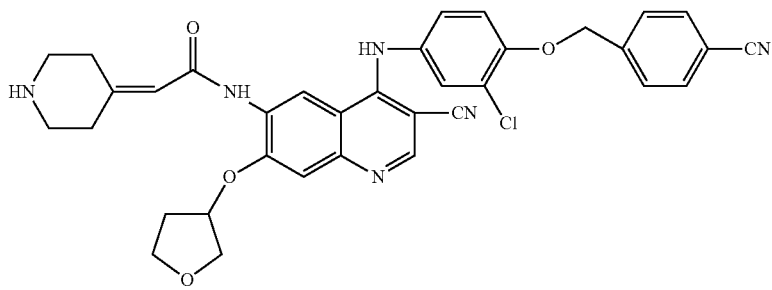 [SMILES: N#Cc1ccc(COc2ccc(Nc3c(C#N)cnc4cc(OC5CCOC5)c(NC(=O)C=C5CCNCC5)cc34)cc2Cl)cc1]

Example 60

N-(4-(4-(4-TERT-BUTYLBENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 666

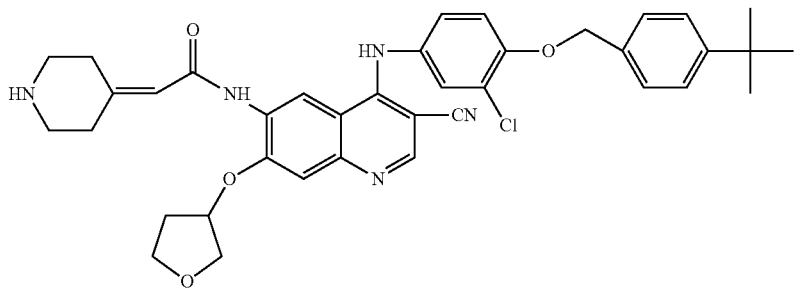 [SMILES: CC(C)(C)c1ccc(COc2ccc(Nc3c(C#N)cnc4cc(OC5CCOC5)c(NC(=O)C=C5CCNCC5)cc34)cc2Cl)cc1]

Example 61

N-(4-(4-(BENZYLOXY)-3-CHLOROPHENYLAMINO)-3-CYANO-7-(TETRAHYDROFURAN-3-YL-OXY)QUINOLIN-6-YL)-2-(PIPERIDIN-4-YLIDENE) ACETAMIDE

MS (M+1): 610

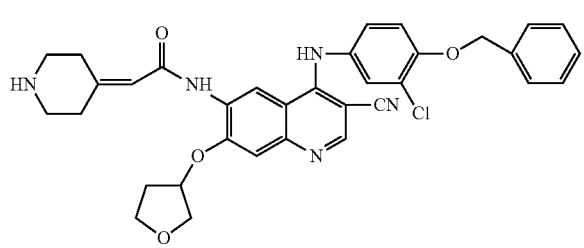 [SMILES: N#Cc1cnc2cc(OC3CCOC3)c(NC(=O)C=C3CCNCC3)cc2c1Nc1ccc(OCc2ccccc2)c(Cl)c1]

Example 62

N-(4-(1H-INDOL-5-YL-AMINO)-3-CYANO-7-(TETRAHYDROFURAN-3-YL-OXY) QUINOLIN-6-YL)-2-(PIPERIDIN-4-YLIDENE)ACETAMIDE

MS (M+1): 509

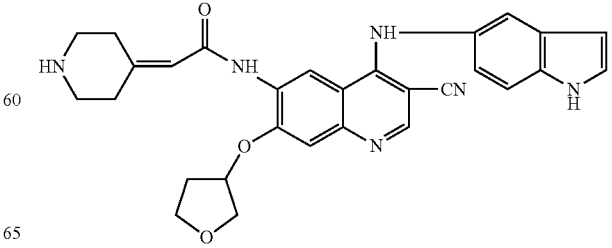

Example 63

N-(4-(4-(2-CHLOROBENZYLOXY)-3-FLUORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 628

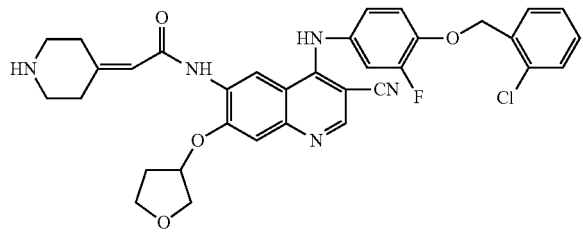

Example 64

N-(4-(4-(3-CHLOROBENZYLOXY)-3-FLUORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 628

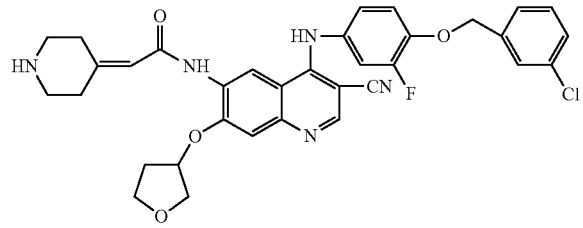 [SMILES: N#Cc1cnc2cc(OC3CCOC3)c(NC(=O)C=C3CCNCC3)cc2c1Nc1ccc(OCc2cccc(Cl)c2)c(F)c1]

Example 65

N-(4-(4-(4-CHLOROBENZYLOXY)-3-FLUORO-PHENYLAMINO)-3-CYANO-7-(TETRAHYDRO-FURAN-3-YL-OXY)QUINOLIN-6-YL)-2-(PIPERI-DIN-4-YLIDENE) ACETAMIDE

MS (M+1): 628

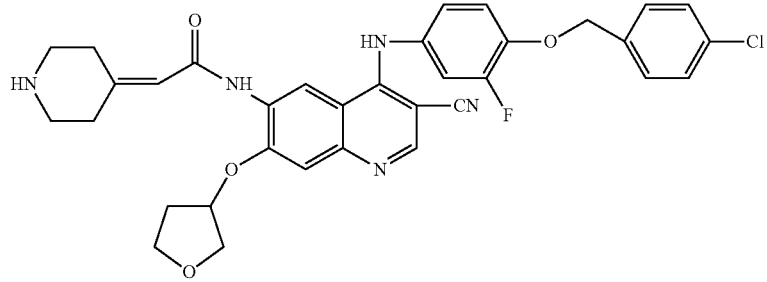

Example 66

N-(3-CYANO-4-((S)-1-PHENYLETHYLAMINO)-7-(TETRAHYDROFURAN-3-YL-OXY)QUINO-LIN-6-YL)-2-(PIPERIDIN-4-YLIDENE)ACET-AMIDE

MS (M+1): 498

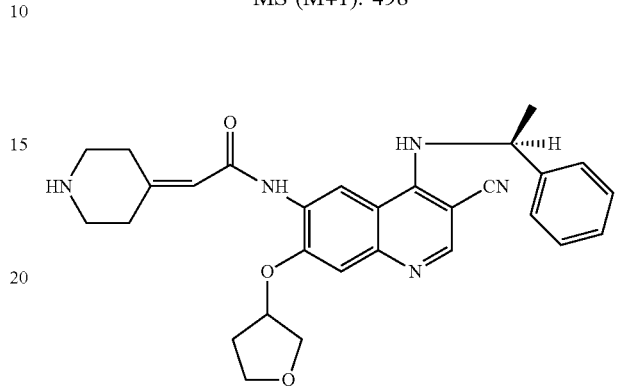

Example 67

N-(3-CYANO-4-((R)-1-PHENYLETHYLAMINO)-7-(TETRAHYDROFURAN-3-YL-OXY)QUINO-LIN-6-YL)-2-(PIPERIDIN-4-YLIDENE)ACET-AMIDE

MS (M+1): 498

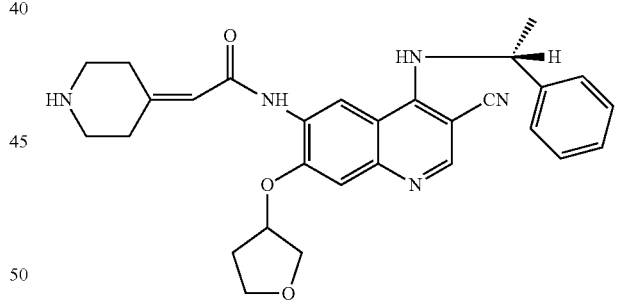

Example 68

N-(4-(1-BENZYL-1H-INDOL-5-YL-AMINO)-3-CYANO-7-(TETRAHYDROFURAN-3-YL-OXY)QUINOLIN-6-YL)-2-(PIPERIDIN-4-YLIDENE) ACETAMIDE

MS (M+1): 599

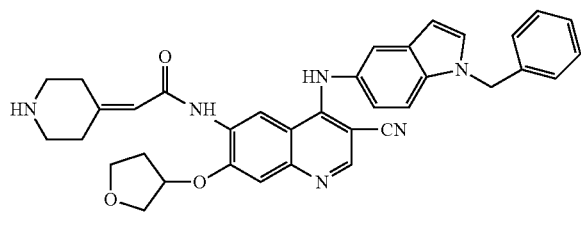 [SMILES: N#Cc1cnc2cc(OC3CCOC3)c(NC(=O)C=C3CCNCC3)cc2c1Nc1ccc2c(ccn2Cc2ccccc2)c1]

Example 69

N-(4-(1-(3-CYANOBENZYL)-1H-INDOL-5-YL-AMINO)-3-CYANO-7-(TETRAHYDROFURAN-3-YL-OXY)QUINOLIN-6-YL)-2-(PIPERIDIN-4-YLIDENE) ACETAMIDE

MS (M+1): 624

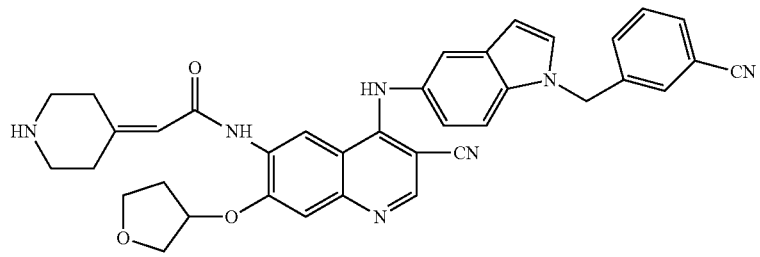 [SMILES: N#Cc1cccc(Cn2ccc3cc(Nc4c(C#N)cnc5cc(OC6CCOC6)c(NC(=O)C=C6CCNCC6)cc45)ccc32)c1]

Example 70

N-(4-(1-(3-METHOXYBENZYL)-1H-INDOL-5-YL-AMINO)-3-CYANO-7-(TETRAHYDROFURAN-3-YL-OXY)QUINOLIN-6-YL)-2-(PIPERIDIN-4-YLIDENE) ACETAMIDE

MS (M+1): 629

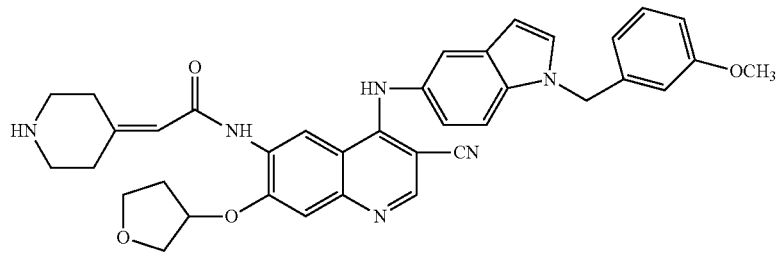 [SMILES: COc1cccc(Cn2ccc3cc(Nc4c(C#N)cnc5cc(OC6CCOC6)c(NC(=O)C=C6CCNCC6)cc45)ccc32)c1]

Example 71

N-(4-(1-(3-CHLOROBENZYL)-1H-INDOL-5-YL-AMINO)-3-CYANO-7-(TETRAHYDROFURAN-3-YL-OXY)QUINOLIN-6-YL)-2-(PIPERIDIN-4-YLIDENE) ACETAMIDE

MS (M+1): 633

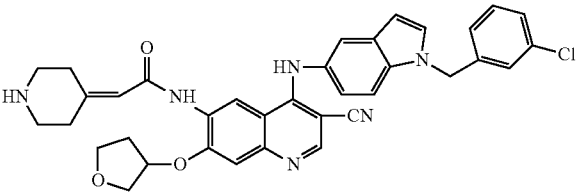 [SMILES: N#Cc1cnc2cc(OC3CCOC3)c(NC(=O)C=C3CCNCC3)cc2c1Nc1ccc2c(ccn2Cc2cccc(Cl)c2)c1]

Example 72

N-(3-CYANO-4-(INDOLIN-1-YL)-7-(TETRAHY-
DROFURAN-3-YL-OXY)QUINOLIN-6-YL)-2-
(PIPERIDIN-4-YLIDENE)ACETAMIDE

MS (M+1): 496

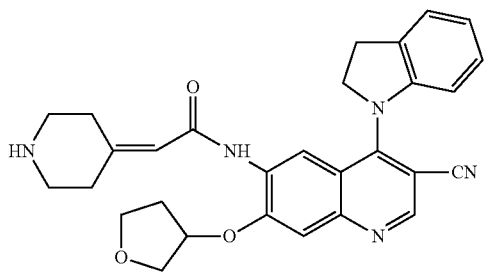 [SMILES: N#Cc1cnc2cc(OC3CCOC3)c(NC(=O)C=C3CCNCC3)cc2c1N1CCc2ccccc21]

Example 73

N-(4-(6-CHLOROINDOLIN-1-YL)-3-CYANO-7-
(TETRAHYDROFURAN-3-YL-OXY) QUINO-
LIN-6-YL)-2-(PIPERIDIN-4-YLIDENE)ACET-
AMIDE

MS (M+1): 530

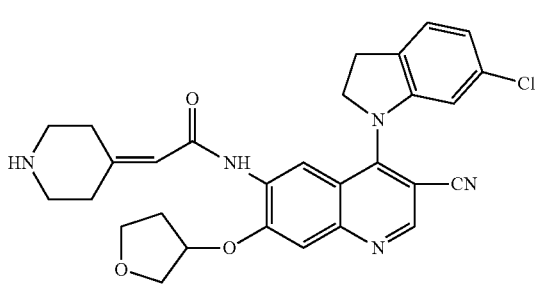 [SMILES: N#Cc1cnc2cc(OC3CCOC3)c(NC(=O)C=C3CCNCC3)cc2c1N1CCc2ccc(Cl)cc21]

Example 74

N-(3-CYANO-4-(6-FLUOROINDOLIN-1-YL)-7-
(TETRAHYDROFURAN-3-YL-OXY) QUINO-
LIN-6-YL)-2-(PIPERIDIN-4-YLIDENE)ACET-
AMIDE

MS (M+1) 514

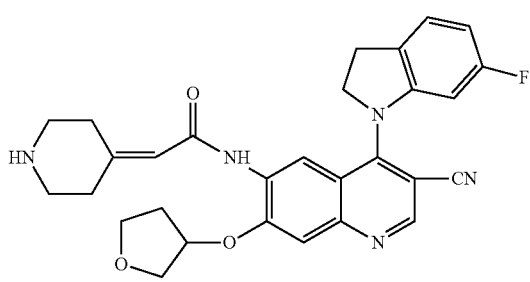 [SMILES: N#Cc1cnc2cc(OC3CCOC3)c(NC(=O)C=C3CCNCC3)cc2c1N1CCc2ccc(F)cc21]

Example 75

N-(4-(4-CHLOROINDOLIN-1-YL)-3-CYANO-7-
(TETRAHYDROFURAN-3-YL-OXY) QUINO-
LIN-6-YL)-2-(PIPERIDIN-4-YLIDENE)ACET-
AMIDE

MS (M+1) 530

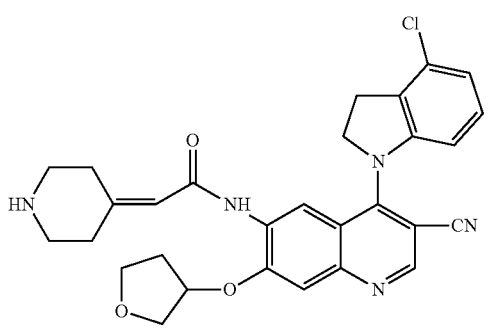 [SMILES: N#Cc1cnc2cc(OC3CCOC3)c(NC(=O)C=C3CCNCC3)cc2c1N1CCc2c(Cl)cccc21]

Example 76

N-(3-CYANO-4-(3,4-DIHYDROQUINOLIN-1(2H)-
YL)-7-(TETRAHYDROFURAN-3-YL-OXY)QUI-
NOLIN-6-YL)-2-(PIPERIDIN-4-YLIDENE) ACET-
AMIDE

MS (M+1): 510

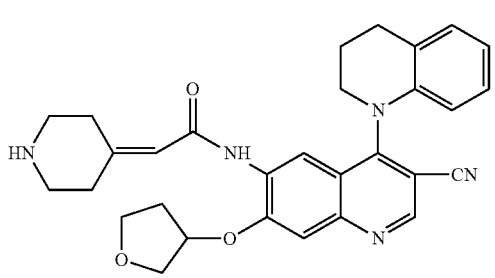 [SMILES: N#Cc1cnc2cc(OC3CCOC3)c(NC(=O)C=C3CCNCC3)cc2c1N1CCCc2ccccc21]

Example 77

N-(3-CYANO-4-(6-METHYL-3,4-DIHYDROQUI-
NOLIN-1(2H)-YL)-7-(TETRAHYDROFURAN-3-
YL-OXY)QUINOLIN-6-YL)-2-(PIPERIDIN-4-
YLIDENE) ACETAMIDE

MS (M+1): 524

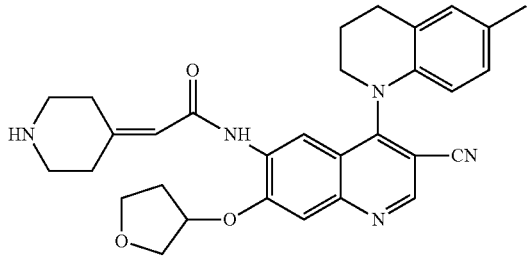 [SMILES: Cc1ccc2c(c1)CCCN2c1c(C#N)cnc2cc(OC3CCOC3)c(NC(=O)C=C3CCNCC3)cc12]

143

Example 78

N-(3-CYANO-7-(TETRAHYDROFURAN-3-YL-OXY)-4-(7-(TRIFLUOROMETHYL)-3,4-DIHYDROQUINOLIN-1 (2H)-YL)-QUINOLIN-6-YL)-2-(PIPERIDIN-4-YLIDENE) ACETAMIDE

MS (M+1): 578

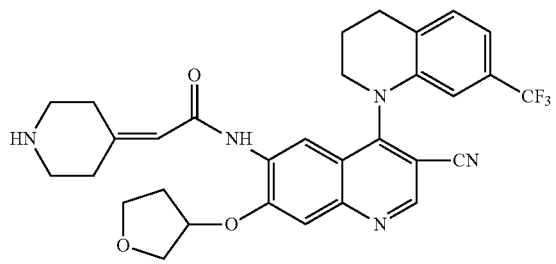 [SMILES: N#Cc1cnc2cc(OC3CCOC3)c(NC(=O)C=C3CCNCC3)cc2c1N1CCCc2ccc(C(F)(F)F)cc21]

Example 79

N-(4-(6-(BENZYLOXY)INDOLIN-1-YL)-3-CYANO-7-(TETRAHYDROFURAN-3-YL-OXY)QUINOLIN-6-YL)-2-(PIPERIDIN-4-YLIDENE) ACETAMIDE

MS (M+1): 602

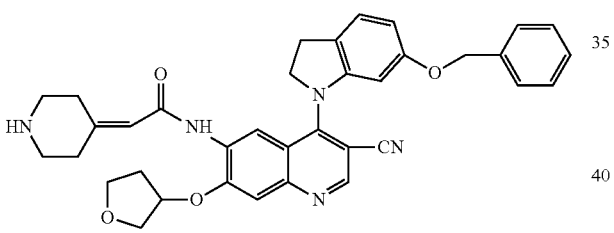

Example 80

METHYL 1-(3-CYANO-6-(2-(PIPERIDIN-4-YLIDENE)ACETAMIDO)-7-(TETRAHYDROFURAN-3-YL-OXY)QUINOLIN-4-YL)-INDOLINE-2-CARBOXYLATE

MS (M+1): 554

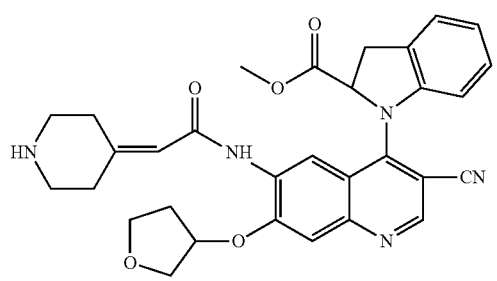 [SMILES: COC(=O)C1Cc2ccccc2N1c1c(C#N)cnc2cc(OC3CCOC3)c(NC(=O)C=C3CCNCC3)cc12]

144

Example 81

N-(3-CYANO-4-(2-(HYDROXYMETHYL)INDOLIN-1-YL)-7-(TETRAHYDROFURAN-3-YL-OXY)QUINOLIN-6-YL)-2-(PIPERIDIN-4-YLIDENE) ACETAMIDE

MS (M+1): 526

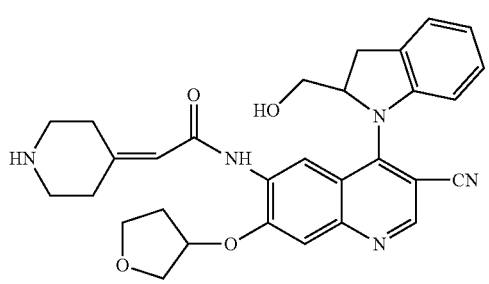 [SMILES: N#Cc1cnc2cc(OC3CCOC3)c(NC(=O)C=C3CCNCC3)cc2c1N1c2ccccc2CC1CO]

Example 82

N-(4-(6-(1HH-PYRROL-1-YL)INDOLIN-1-YL)-3-CYANO-7-(TETRAHYDROFURAN-3-YL-OXY)QUINOLIN-6-YL)-2-(PIPERIDIN-4-YLIDENE) ACETAMIDE

MS (M+1): 561

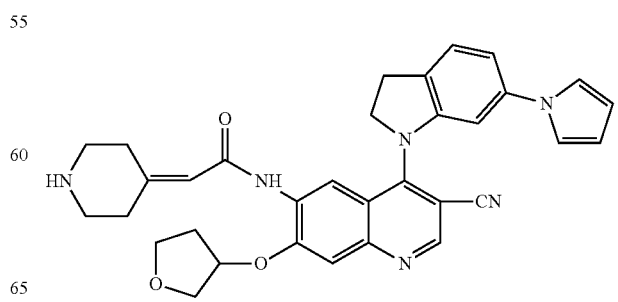

Example 83

N-(3-CYANO-4-(OCTAHYDROINDOL-1-YL)-7-(TETRAHYDROFURAN-3-YL-OXY) QUINOLIN-6-YL)-2-(PIPERIDIN-4-YLIDENE)ACETAMIDE

MS (M+1): 502

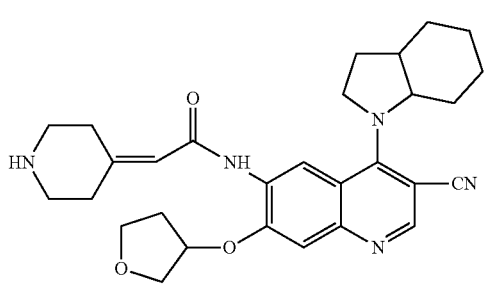 [SMILES: N#Cc1cnc2cc(OC3CCOC3)c(NC(=O)C=C3CCNCC3)cc2c1N1CCC2CCCCC21]

Example 84

N-(3-CYANO-4-(PYRIMIDIN-2-YL-AMINO)-7-(TETRAHYDROFURAN-3-YL-OXY) QUINOLIN-6-YL)-2-(PIPERIDIN-4-YLIDENE)ACETAMIDE

MS (M+1): 472

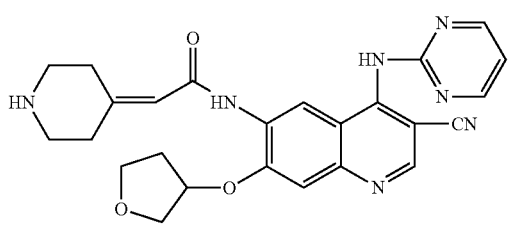 [SMILES: N#Cc1cnc2cc(OC3CCOC3)c(NC(=O)C=C3CCNCC3)cc2c1Nc1ncccn1]

Example 85

N-(2-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-5-YL) BENZAMIDE

MS (M+1): 591

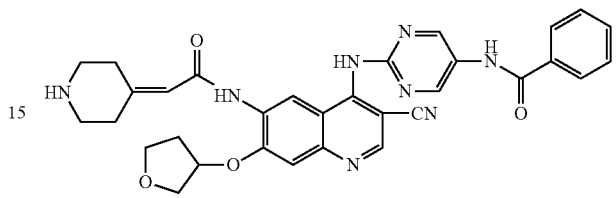

Example 86

N-(2-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-5-YL)-4-(DIMETHYLAMINO)BENZAMIDE

MS (M+1): 634

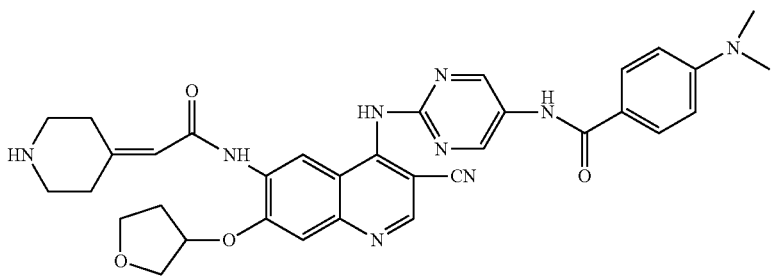 [SMILES: CN(C)c1ccc(C(=O)Nc2cnc(Nc3c(C#N)cnc4cc(OC5CCOC5)c(NC(=O)C=C5CCNCC5)cc34)nc2)cc1]

Example 87

N-(3-CYANO-4-(5-(PHENYLSULFONAMIDO)PYRIMIDIN-2-YL-AMINO)-7-(TETRAHYDROFURAN-3-YL-OXY)QUINOLIN-6-YL)-2-(PIPERIDIN-4-YLIDENE) ACETAMIDE

MS (M+1): 627

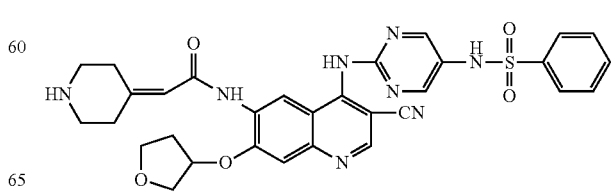

Example 88

N-(5-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-2-YL) BENZAMIDE

MS (M+1): 591

Example 90

N-(5-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-2-YL) THIOPHENE-2-CARBOXAMIDE

MS (M+1): 597

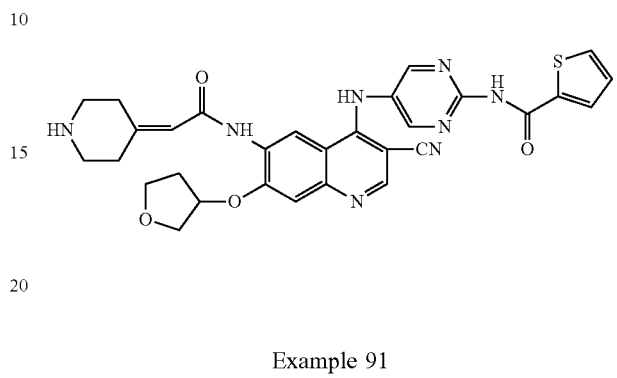

Example 91

N-(5-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-2-YL) CYCLOHEXYLCARBOXAMIDE

MS (M+1): 597

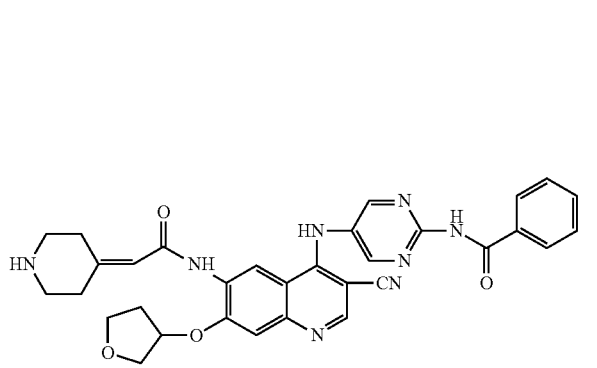 [SMILES: N#Cc1cnc2cc(OC3CCOC3)c(NC(=O)C=C3CCNCC3)cc2c1Nc1cnc(NC(=O)c2ccccc2)nc1]

Example 89

N-(5-(3-CYANO-6-(2-(PIPERIDIN-4-YLIDENE)ACETAMIDO)-7-(TETRAHYDROFURAN-3-YL-OXY)QUINOLIN-4-YL-AMINO)PYRIMIDIN-2-YL) FURAN-2-CARBOXAMIDE

MS (M+1): 581

Example 92

5-(3-CYANO-6-(2-(PIPERIDIN-4-YLIDENE)ACETAMIDO)-7-(TETRAHYDROFURAN-3-YL-OXY)QUINOLIN-4-YL-AMINO)-N-(4-METHOXYPHENYL)PYRIMIDIN-2-CARBOXAMIDE

MS (M+1): 621

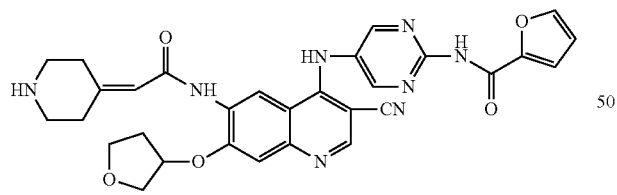

149

Example 93

N-(3-CYANO-4-(PYRIDIN-2-YL-AMINO)-7-(TETRAHYDROFURAN-3-YL-OXY) QUINOLIN-6-YL)-2-(PIPERIDIN-4-YLIDENE)ACETAMIDE

MS (M+1)-471

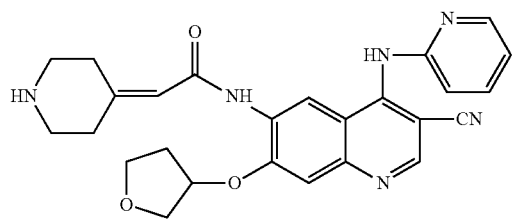 [SMILES: N#Cc1cnc2cc(OC3CCOC3)c(NC(=O)C=C3CCNCC3)cc2c1Nc1ccccn1]

Example 94

6-(3-CYANO-6-(2-(PIPERIDIN-4-YLIDENE)ACETAMIDO)-7-(TETRAHYDROFURAN-3-YL-OXY)QUINOLIN-4-YL-AMINO)-N-(4-METHOXYPTHENYL)NICOTINAMIDE

MS (M+1): 620

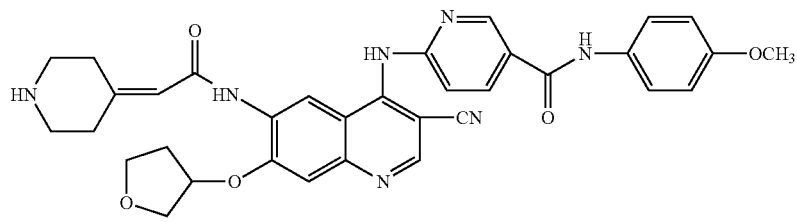 [SMILES: COc1ccc(NC(=O)c2ccc(Nc3c(C#N)cnc4cc(OC5CCOC5)c(NC(=O)C=C5CCNCC5)cc34)nc2)cc1]

Example 95

N-(3-CYANO-4-(PYRIDIN-3-YL-AMINO)-7-(TETRAHYDROFURAN-3-YL-OXY) QUINOLIN-6-YL)-2-(PIPERIDIN-4-YLIDENE)ACETAMIDE

MS (M+1): 471

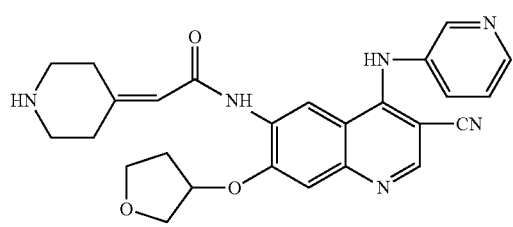 [SMILES: N#Cc1cnc2cc(OC3CCOC3)c(NC(=O)C=C3CCNCC3)cc2c1Nc1cccnc1]

150

Example 96

N-(3-CYANO-4-(PYRIDIN-4-YL-AMINO)-7-(TETRAHYDROFURAN-3-YL-OXY) QUINOLIN-6-YL)-2-(PIPERIDIN-4-YLIDENE)ACETAMIDE

MS (M+1): 471

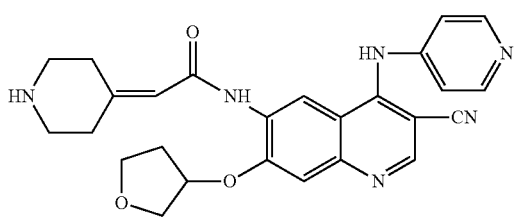 [SMILES: N#Cc1cnc2cc(OC3CCOC3)c(NC(=O)C=C3CCNCC3)cc2c1Nc1ccncc1]

Example 97

N-(4-(6-(BENZYLOXY)PYRIDIN-3-YL-AMINO)-3-CYANO-7-(TETRAHYDROFURAN-3-YL-OXY) QUINOLIN-6-YL)-2-(PIPERIDIN-4-YLIDENE) ACETAMIDE

MS (M+1): 577

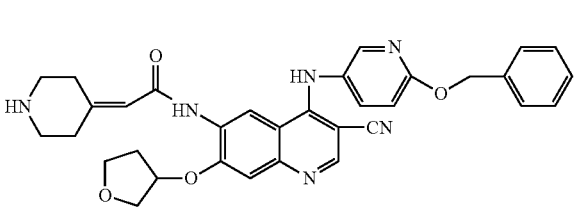 [SMILES: N#Cc1cnc2cc(OC3CCOC3)c(NC(=O)C=C3CCNCC3)cc2c1Nc1ccc(OCc2ccccc2)nc1]

Example 98

N-(3-CYANO-4-(PYRAZIN-2-YL-AMINO)-7-(TETRAHYDROFURAN-3-YL-OXY) QUINOLIN-6-YL)-2-(PIPERIDIN-4-YLIDENE)ACETAMIDE

MS (M+1) 472

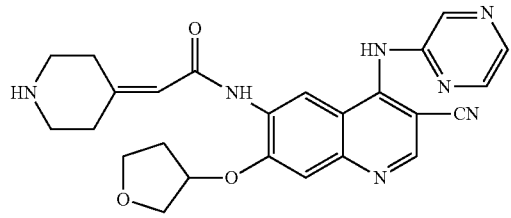 [SMILES: N#Cc1cnc2cc(OC3CCOC3)c(NC(=O)C=C3CCNCC3)cc2c1Nc1cnccn1]

Example 99

N-(4-(3-CHLORO-4-FLUOROPHENYLAMINO)-3-CYANO-7-(1-METHYLPIPERIDIN-4-YL-OXY) QUINOLIN-6-YL)-2-(PIPERIDIN-4-YLIDENE) ACETAMIDE

MS (M+1): 549

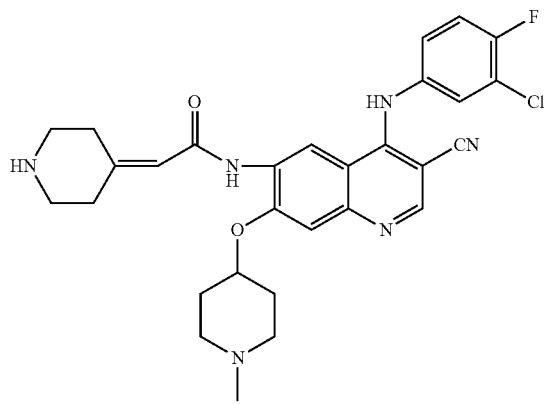 [SMILES: CN1CCC(Oc2cc3ncc(C#N)c(Nc4ccc(F)c(Cl)c4)c3cc2NC(=O)C=C2CCNCC2)CC1]

Example 100

N-(3-CYANO-4-(3-ETHYNYLPHENYLAMINO)-7-(1-METHYLPIPERIDIN-4-YL-OXY)QUINOLIN-6-YL)-2-(PIPERIDIN-4-YLIDENE)ACETAMIDE

MS (M+1): 521

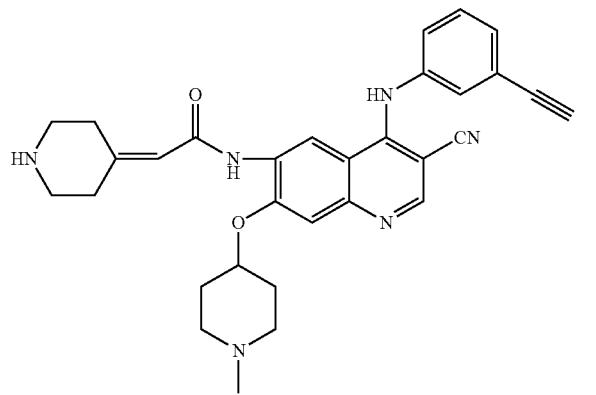 [SMILES: C#Cc1cccc(Nc2c(C#N)cnc3cc(OC4CCN(C)CC4)c(NC(=O)C=C4CCNCC4)cc23)c1]

Example 101

N-(4-(4-(BENZYLOXY)-3-CHLOROPHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 637

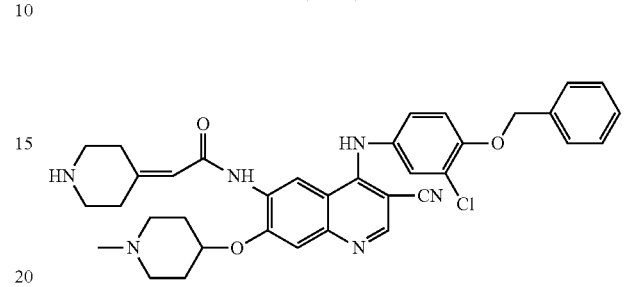

Example 102

N-(4-(4-(2-CHLOROBENZYLOXY)-3-CHLOROPHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 671

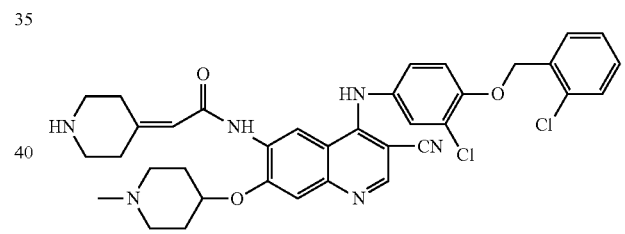

Example 103

N-(4-(4-(3-CHLOROBENZYLOXY)-3-CHLOROPHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 671

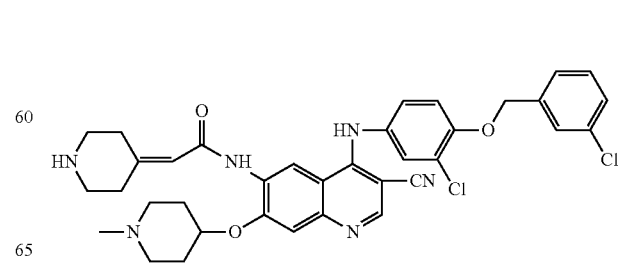

Example 104

N-(4-(4-(4-CHLOROBENZYLOXY)-3-CHLORO-
PHENYLAMINO)-3-CYANO-7-(1-METHYLPIP-
ERIDIN-4-YL-OXY)QUINOLIN-6-YL)-2-(PIPERI-
DIN-4-YLIDENE) ACETAMIDE

MS (M+1): 671

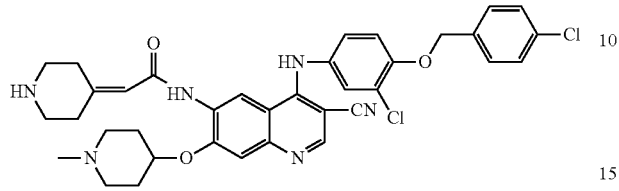

Example 105

N-(4-(4-(4-BROMOBENZYLOXY)-3-CHLORO-
PHENYLAMINO)-3-CYANO-7-(1-METHYLPIP-
ERIDIN-4-YL-OXY)QUINOLIN-6-YL)-2-(PIPERI-
DIN-4-YLIDENE) ACETAMIDE

MS (M+1): 715

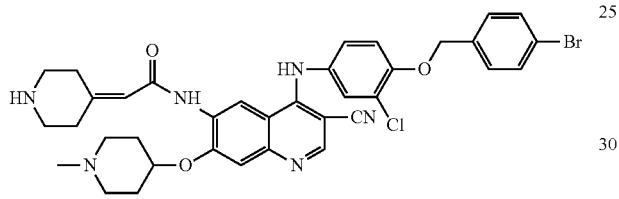

Example 106

N-(4-(4-(4-METHYLBENZYLOXY)-3-CHLORO-
PHENYLAMINO)-3-CYANO-7-(1-METHYLPIP-
ERIDIN-4-YL-OXY)QUINOLIN-6-YL)-2-(PIPERI-
DIN-4-YLIDENE) ACETAMIDE

MS (M+1): 651

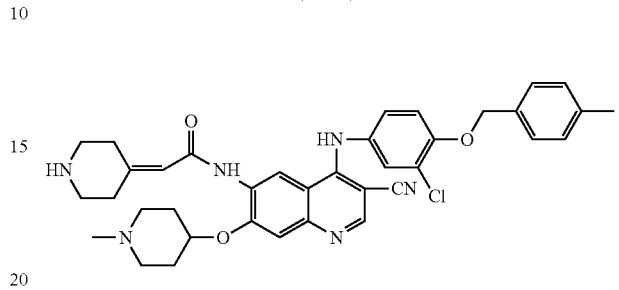

Example 107

N-(4-(4-(4-METHOXYBENZYLOXY)-3-CHLO-
ROPHENYLAMINO)-3-CYANO-7-(1-METHYL-
PIPERIDIN-4-YL-OXY)QUINOLIN-6-YL)-2-(PIP-
ERIDIN-4-YLIDENE) ACETAMIDE

MS (M+1): 667

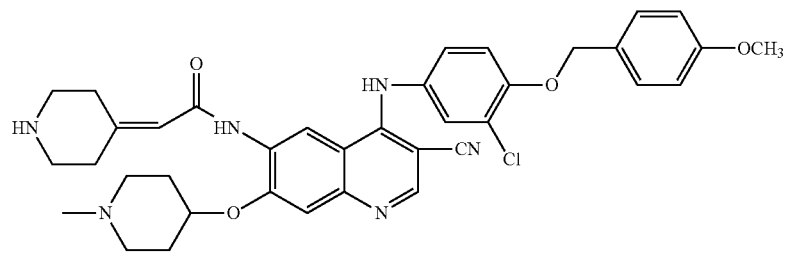 [SMILES: COc1ccc(COc2ccc(Nc3c(C#N)cnc4cc(OC5CCN(C)CC5)c(NC(=O)C=C5CCNCC5)cc34)cc2Cl)cc1]

Example 108

N-(4-(4-(4-CYANOBENZYLOXY)-3-CHLORO-
PHENYLAMINO)-3-CYANO-7-(1-METHYLPIP-
ERIDIN-4-YL-OXY)QUINOLIN-6-YL)-2-(PIPERI-
DIN-4-YLIDENE) ACETAMIDE

MS (M+1): 662

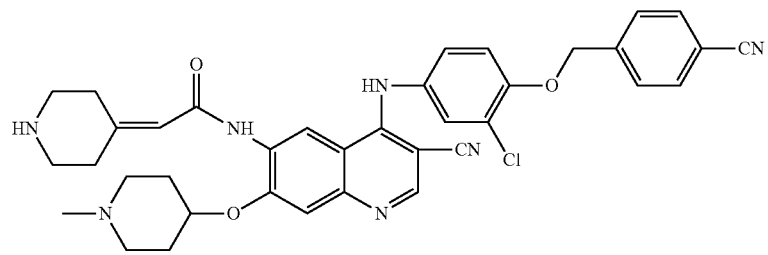 [SMILES: CN1CCC(Oc2cc3ncc(C#N)c(Nc4ccc(OCc5ccc(C#N)cc5)c(Cl)c4)c3cc2NC(=O)C=C2CCNCC2)CC1]

Example 109

N-(4-(4-(4-ETHYLBENZYLOXY)-3-CHLORO-PHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 665

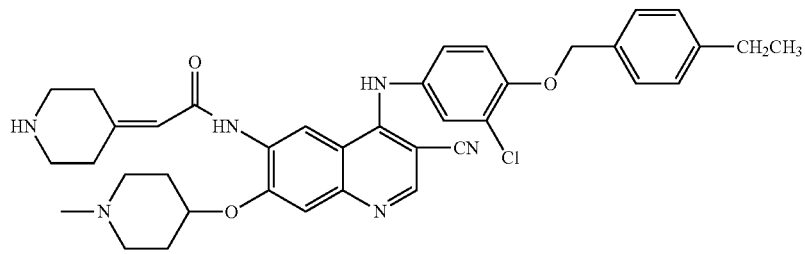 [SMILES: CCc1ccc(COc2ccc(Nc3c(C#N)cnc4cc(OC5CCN(C)CC5)c(NC(=O)C=C5CCNCC5)cc34)cc2Cl)cc1]

Example 110

N-(4-(4-(4-ETHOXYBENZYLOXY)-3-CHLORO-PHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 681

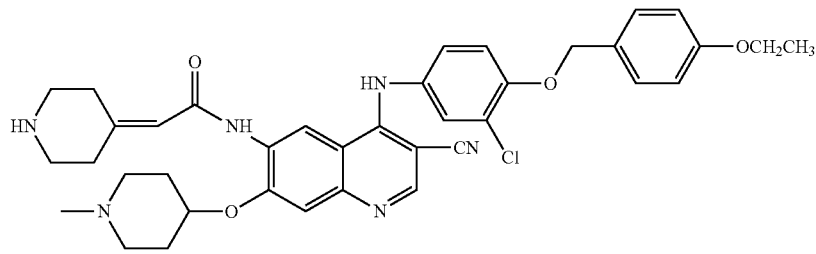 [SMILES: CCOc1ccc(COc2ccc(Nc3c(C#N)cnc4cc(OC5CCN(C)CC5)c(NC(=O)C=C5CCNCC5)cc34)cc2Cl)cc1]

Example 111

N-(4-(3-CHLORO-4-PHENOXYPHENYLAMINO)-3-CYANO-7-(1-METHYLPIPERIDIN-4-YL-OXY)QUINOLIN-6-YL)-2-(PIPERIDIN-4-YLIDENE) ACETAMIDE

MS (M+1): 623

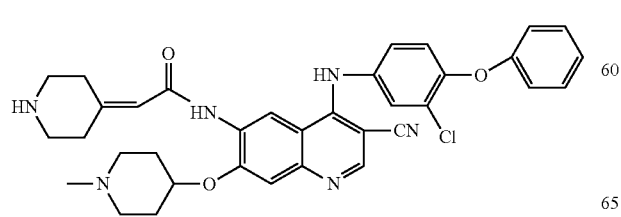

Example 112

N-(3-CYANO-7-(1-METHYLPIPERIDIN-4-YL-OXY)-4-(PYRIDIN-2-YL-AMINO) QUINOLIN-6-YL)-2-(PIPERIDIN-4-YLIDENE)ACETAMIDE

MS (M+1): 498

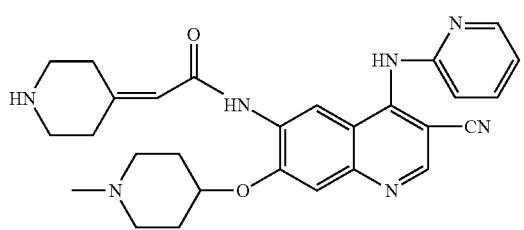 [SMILES: CN1CCC(Oc2cc3ncc(C#N)c(Nc4ccccn4)c3cc2NC(=O)C=C2CCNCC2)CC1]

Example 113

N-(3-CYANO-7-(1-METHYLPIPERIDIN-4-YL-OXY)-4-(PYRIDIN-3-YL-AMINO) QUINOLIN-6-YL)-2-(PIPERIDIN-4-YLIDENE)ACETAMIDE

MS (M+1): 498

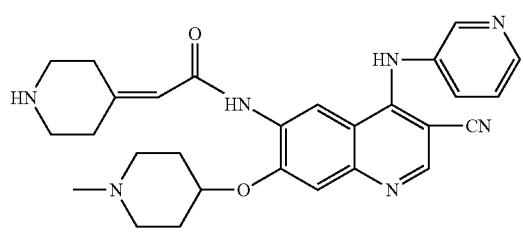 [SMILES: CN1CCC(Oc2cc3ncc(C#N)c(Nc4cccnc4)c3cc2NC(=O)C=C2CCNCC2)CC1]

Example 114

N-(3-CYANO-7-(1-METHYLPIPERIDIN-4-YL-OXY)-4-(PYRIDIN-4-YL-AMINO) QUINOLIN-6-YL)-2-(PIPERIDIN-4-YLIDENE)ACETAMIDE

MS (M+1): 498

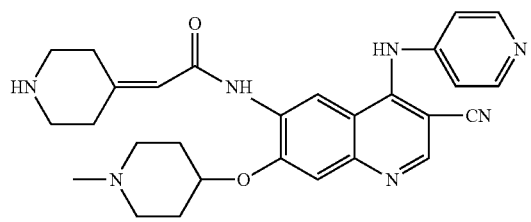 [SMILES: CN1CCC(Oc2cc3ncc(C#N)c(Nc4ccncc4)c3cc2NC(=O)C=C2CCNCC2)CC1]

Example 115

N-(4-(6-(BENZYLOXY)PYRIDIN-3-YL-AMINO)-3-CYANO-7-(1-METHYLPIPERIDIN-4-YL-OXY) QUINOLIN-6-YL)-2-(PIPERIDIN-4-YLIDENE) ACETAMIDE

MS (M+1): 604

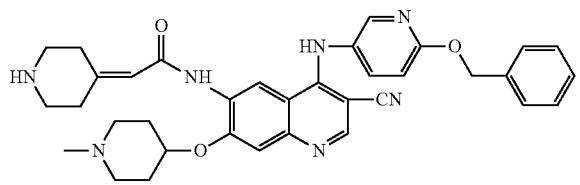 [SMILES: CN1CCC(Oc2cc3ncc(C#N)c(Nc4ccc(OCc5ccccc5)nc4)c3cc2NC(=O)C=C2CCNCC2)CC1]

Example 116

N-(4-(3-CHLORO-4-FLUOROPHENYLAMINO)-3-CYANO-7-(PYRIDIN-4-YL-OXY) QUINOLIN-6-YL)-2-(PIPERIDIN-4-YLIDENE)ACETAMIDE

MS (M+1): 529

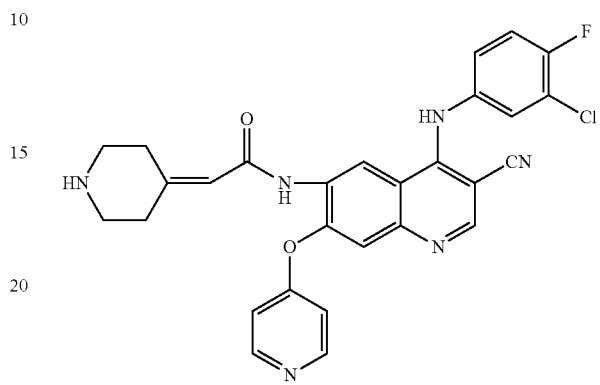

Example 117

N-(3-CYANO-4-(3-ETHYNYLPHENYLAMINO)-7-(PYRIDIN-4-YL-OXY)QUINOLIN-6-YL)-2-(PIPERIDIN-4-YLIDENE)ACETAMIDE

MS (M+1): 501

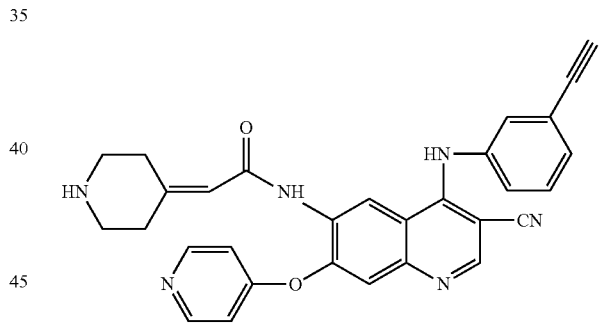

Example 118

N-(3-CYANO-4-(4-PHENOXYPHENYLAMINO)-7-(PYRIDIN-4-YL-OXY)QUINOLIN-6-YL)-2-(PIPERIDIN-4-YLIDENE)ACETAMIDE

MS (M+1): 569

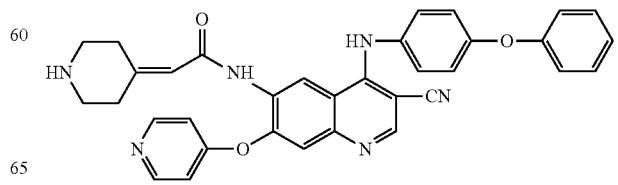

Example 119

N-(4-(4-(BENZYLOXY)PHENYLAMINO)-3-CYANO-7-(PYRIDIN-4-YL-OXY) QUINOLIN-6-YL)-2-(PIPERIDIN-4-YLIDENE)ACETAMIDE

MS (M+1): 583

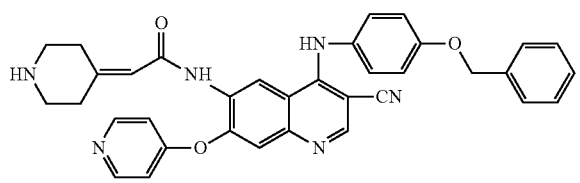 [SMILES: N#Cc1cnc2cc(Oc3ccncc3)c(NC(=O)C=C3CCNCC3)cc2c1Nc1ccc(OCc2ccccc2)cc1]

Example 120

N-(4-(4-(2-CHLOROBENZYLOXY)-3-CHLOROPHENYLAMINO)-3-CYANO-7-(PYRIDIN-4-YL-OXY)QUINOLIN-6-YL)-2-(PIPERIDIN-4-YLIDENE)ACETAMIDE

MS (M+1): 651

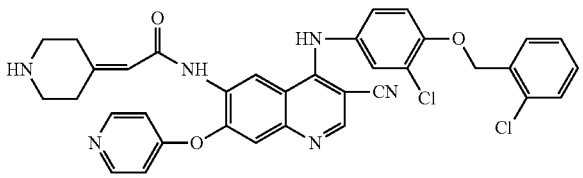 [SMILES: N#Cc1cnc2cc(Oc3ccncc3)c(NC(=O)C=C3CCNCC3)cc2c1Nc1ccc(OCc2ccccc2Cl)c(Cl)c1]

Example 121

N-(4-(4-(4-METHYLBENZYLOXY)-3-CHLOROPHENYLAMINO)-3-CYANO-7-(PYRIDIN-4-YL-OXY)QUINOLIN-6-YL)-2-(PIPERIDIN-4-YLIDENE)ACETAMIDE

MS (M+1): 631

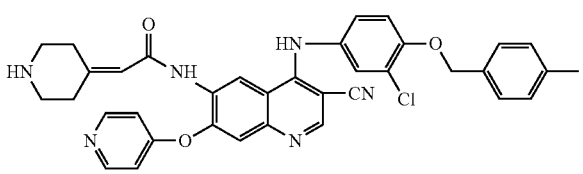 [SMILES: Cc1ccc(COc2ccc(Nc3c(C#N)cnc4cc(Oc5ccncc5)c(NC(=O)C=C5CCNCC5)cc34)cc2Cl)cc1]

Example 122

N-(4-(4-(4-METHOXYBENZYLOXY)PHENYLAMINO)-3-CYANO-7-(PYRIDIN-4-YL-OXY) QUINOLIN-6-YL)-2-(PIPERIDIN-4-YLIDENE) ACETAMIDE

MS (M+1): 613

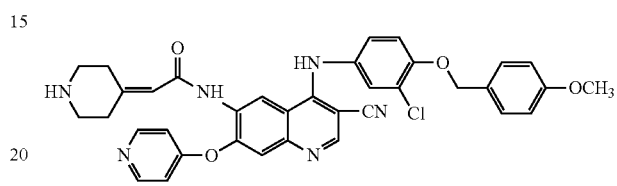

Example 123

N-(4-(4-(3-CYANOBENZYLOXY)-3-CHLOROPHENYLAMINO)-3-CYANO-7-(PYRIDIN-4-YL-OXY)QUINOLIN-6-YL)-2-(PIPERIDIN-4-YLIDENE)ACETAMIDE

MS (M+1): 642

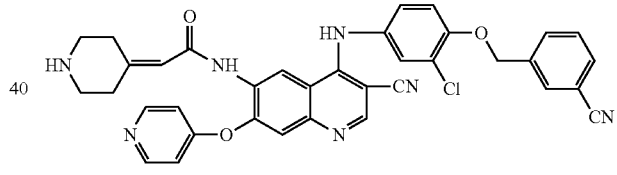

Example 124

N-(3-CYANO-4-(PYRIDINE-2-YL-AMINO)-7-(PYRIDIN-4-YL-OXY) QUINOLIN-6-YL)-2-(PIPERIDIN-4-YLIDENE)ACETAMIDE

MS (M+1): 478

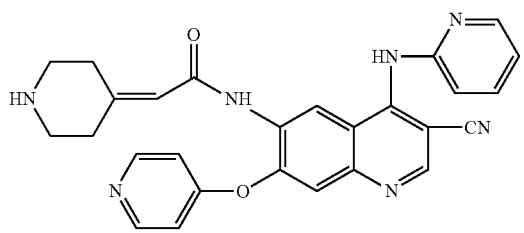 [SMILES: N#Cc1cnc2cc(Oc3ccncc3)c(NC(=O)C=C3CCNCC3)cc2c1Nc1ccccn1]

Example 125

N-(3-CYANO-7-(PYRIDIN-4-YL-OXY)-4-(PYRIMIDIN-2-YL-AMINO) QUINOLIN-6-YL)-2-(PIPERIDIN-4-YLIDENE)ACETAMIDE

MS (M+1) 479

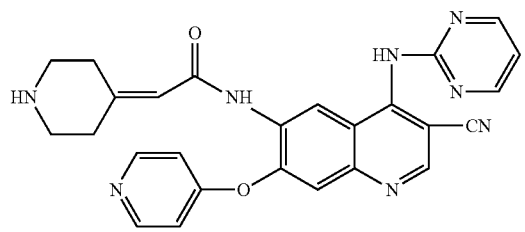 [SMILES: N#Cc1cnc2cc(Oc3ccncc3)c(NC(=O)C=C3CCNCC3)cc2c1Nc1ncccn1]

Example 126

N-(4-(6-(BENZYLOXY)PYRIDIN-3-YL-AMINO)-3-CYANO-7-(PYRIDIN-4-YL-OXY) QUINOLIN-6-YL)-2-(PIPERIDIN-4-YLIDENE)ACETAMIDE

MS (M+1): 584

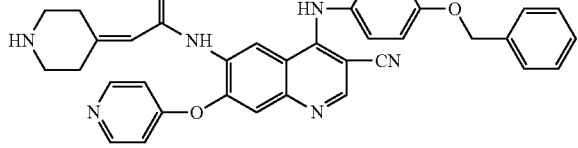

Example 127

N-(4-(6-(3-CHLOROBENZYLOXY)PYRIDIN-3-YL-AMINO)-3-CYANO-7-(PYRIDIN-4-YL-OXY) QUINOLIN-6-YL)-2-(PIPERIDIN-4-YLIDENE) ACETAMIDE

MS (M+1): 618

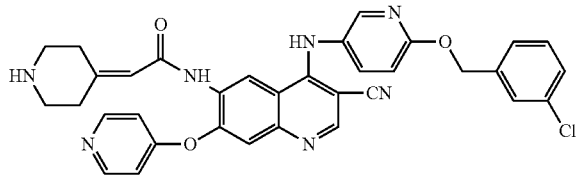 [SMILES: N#Cc1cnc2cc(Oc3ccncc3)c(NC(=O)C=C3CCNCC3)cc2c1Nc1ccc(OCc2cccc(Cl)c2)nc1]

Example 128

N-(3-CYANO-4-(6-(PHENOXYPYRIDIN-3-YL-AMINO)-7-(PYRIDIN-4-YL-OXY) QUINOLIN-6-YL)-2-(PIPERIDIN-4-YLIDENE)ACETAMIDE

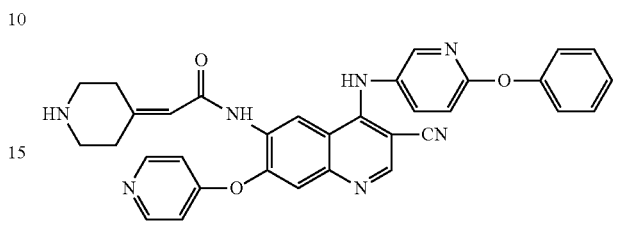

Example 129

N-(4-(3-CHLORO-4-(PYRIDINE-2-YL-METHOXY)PHENYLAMINO)-3-CYANO-7-(PYRIDIN-4-YL-OXY)QUINOLIN-6-YL)-2-(PIPERIDIN-4-YLIDENE)ACETAMIDE

MS (M+1): 611

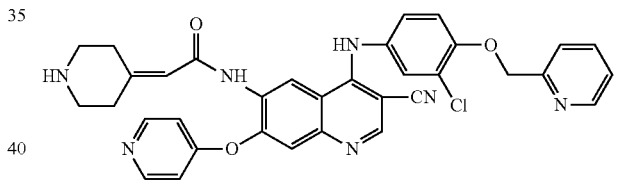

Example 130

(E/Z)—N-(3-CYANO-4-(6-(PHENOXYPYRIDIN-3-YL-AMINO)-7-(PYRIDIN-4-YL-OXY)QUINOLIN-6-YL)-2-(PYRROLIDIN-3-YLIDENE)ACETAMIDE

MS (M+1): 556

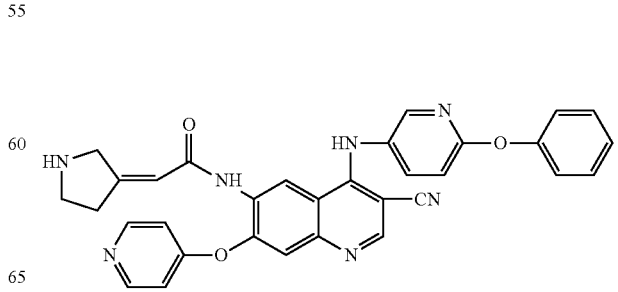

Example 131

(E/Z)—N-(3-CYANO-7-(1-METHYLPIPERIDIN-4-YL-OXY)-4-(6-(PHENOXYPYRIDIN-3-YL-AMINO)QUINOLIN-6-YL)-2-(PYRROLIDIN-3-YLIDENE)ACETAMIDE

MS (M+1): 576

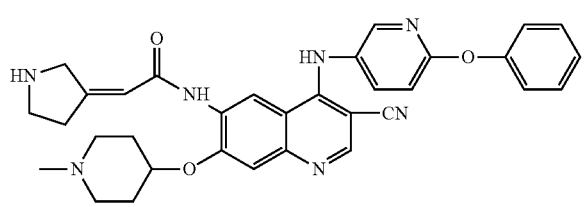 [SMILES: CN1CCC(Oc2cc3ncc(C#N)c(Nc4ccc(Oc5ccccc5)nc4)c3cc2NC(=O)/C=C2/CCNC2)CC1]

Example 132

(E/Z)—N-(3-CYANO-4-(6-(PHENOXYPYRIDIN-3-YL-AMINO)-7-(TETRAHYDROFUR AN-3-YL-OXY)QUINOLIN-6-YL)-2-(PYRROLIDIN-3-YLIDENE)ACETAMIDE

MS (M+1): 549

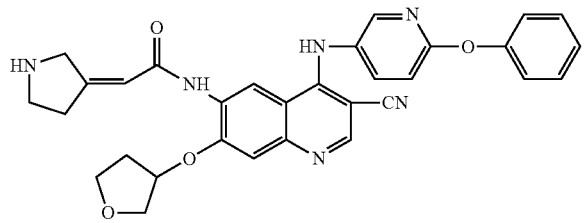 [SMILES: N#Cc1cnc2cc(OC3CCOC3)c(NC(=O)/C=C3/CCNC3)cc2c1Nc1ccc(Oc2ccccc2)nc1]

Example 133

4-(3-CHLORO-4-(PYRIDIN-2-YL-METHOXY)PHENYLAMINO)-6-METHOXY-7-(TETRAHYDROFURAN-3-YL-OXY)QUINOLINE-3-CARBONITRILE

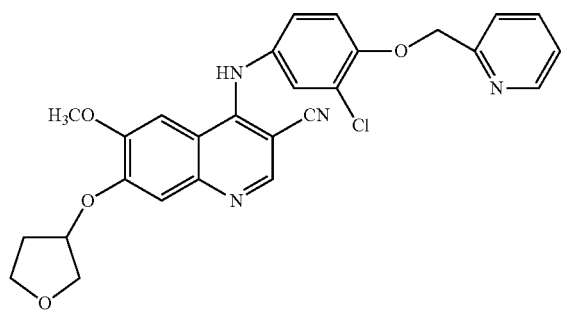 [SMILES: COc1cc2c(Nc3ccc(OCc4ccccn4)c(Cl)c3)c(C#N)cnc2cc1OC1CCOC1]

The target compound was prepared according to the process disclosed in Chinese patent No. ZL 03815201.0.

MS (M+1): 503.

Example 134

4-(3-CHLORO-4-(PYRIDIN-2-YL-METHOXY)PHENYLAMINO)-6-(PIPERIDIN-1-YL)-7-(TETRAHYDROFURAN-3-YL-OXY)QUINOLINE-3-CARBONITRILE

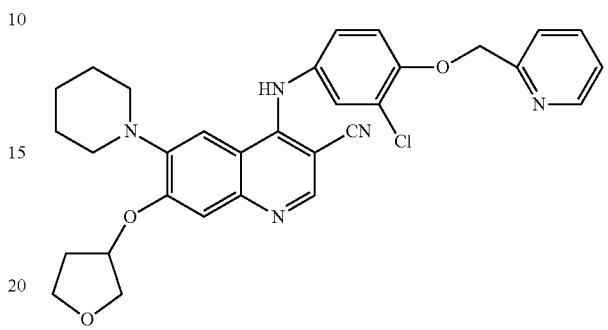

To a single-neck reaction flask (50 ml) were added 6-amino-4-(3-chloro-4-(pyridin-2-yl-methoxy)phenylamino)-7-(tetrahydrofuran-3-yl-oxy)quinolin-3-carbonitril e (20 mg, 0.041 mmol), anhydrous potassium carbonate powder (10 mg) and chloroform (5 ml). To the flask was added 1,5-dibromopentane (10 mg). The mixture was stirred at the room temperature. After the reaction finished, the mixture was filtered. The filtrate was rotary-evaporated to dryness. The residue was purified with thin layer chromatography (developing solvent:chloroform:methanol=9:1) to give a pure product.

MS (M+1): 556.

The compounds of Examples 135-137 were prepared according to the process disclosed in Chinese patent No. ZL 03815201.0.

Example 135

4-(3-CHLORO-4-(PYRIDIN-2-YL-METHOXY)PHENYLAMINO)-6-(2-METHOXYETHOXY)-7-(TETRAHYDROFURAN-3-YL-OXY)QUINOLINE-3-CARBONITRILE

MS (M+1): 547

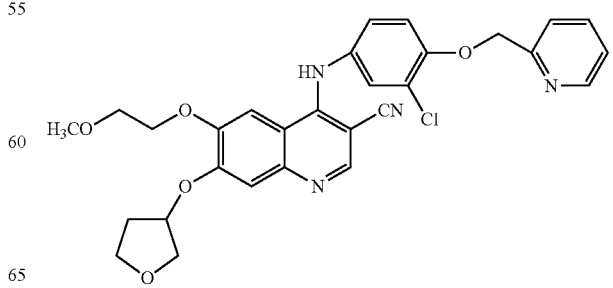

Example 136

4-(3-CHLORO-4-(PYRIDIN-2-YL-METHOXY)
PHENYLAMINO)-6-(2-(2-METHOXYETHOXY)
ETHOXY)-7-(TETRAHYDROFURAN-3-YL-
OXY) QUINOLINE-3-CARBONITRILE

MS (M+1): 591

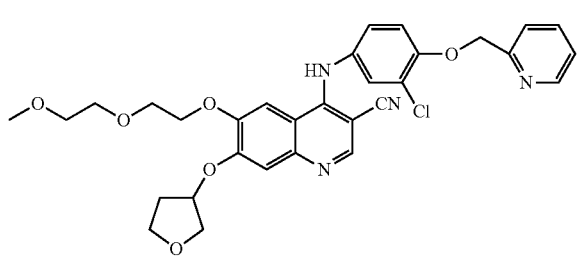 [SMILES: COCCOCCOc1cc2c(Nc3ccc(OCc4ccccn4)c(Cl)c3)c(C#N)cnc2cc1OC1CCOC1]

Example 137

4-(3-CHLORO-4-(PYRIDIN-2-YL-METHOXY)
PHENYLAMINO)-6-(2-MORPHOLINOETH-
OXY)-7-(TETRAHYDROFURAN-3-YL-OXY)
QUINOLINE-3-CARBONITRILE

MS (M+1): 602

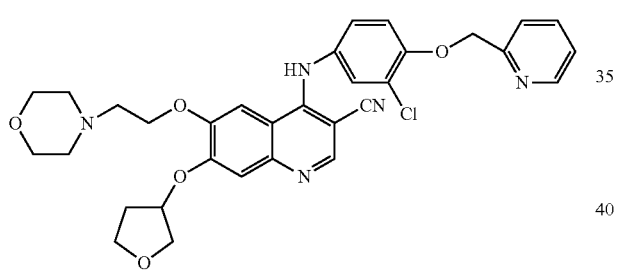

The compounds of Examples 138-206 were prepared according to the process of Example 2.

Example 138

(S,E)-N-(4-(3-CHLORO-4-(PYRIDIN-2-YL-
METHOXY)PHENYLAMINO)-3-CYANO-7-(TET-
RAHYDROFURAN-3-YL-OXY)QUINOLIN-6-
YL)-4-(DIMETHYLAMINO)-BUT-2-ENAMIDE

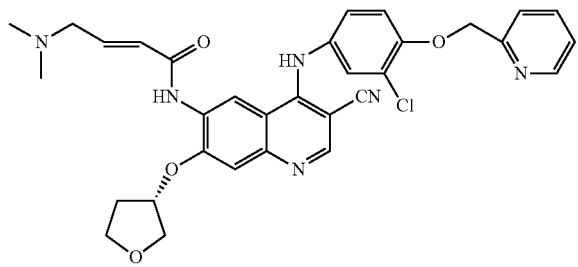 [SMILES: CN(C)C/C=C/C(=O)Nc1cc2c(Nc3ccc(OCc4ccccn4)c(Cl)c3)c(C#N)cnc2cc1O[C@H]1CCOC1]

MS (M+1): 599

The compound was prepared as hydrochloride according to the process of Example 3 so as to determine the specific rotation (the measurement conditions: 20° C., sodium lamp, D light, 589 nm): +51.4°

Example 139

(R,E)-N-(4-(3-CHLORO-4-(PYRIDIN-2-YL-
METHOXY)PHENYLAMINO)-3-CYANO-7-(TET-
RAHYDROFURAN-3-YL-OXY)QUINOLIN-6-
YL)-4-(DIMETHYLAMINO)-BUT-2-ENAMIDE

MS (M+1): 599

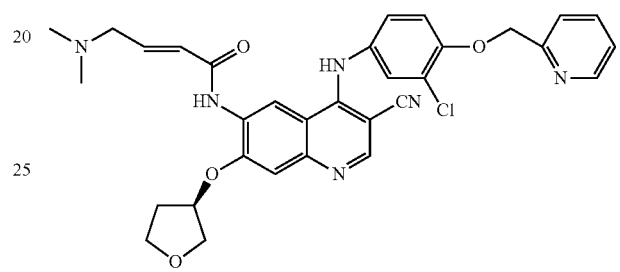

Example 140

(S,E)-N-(3-CYANO-4-(3-ETHYNYLPHE-
NYLAMINO)-7-(TETRAHYDROFURAN-3-YL-
OXY)QUINOLIN-6-YL)-4-(DIMETHYLAMINO)-
BUT-2-ENAMIDE

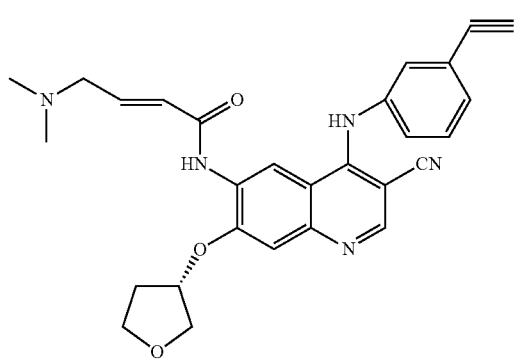 [SMILES: C#Cc1cccc(Nc2c(C#N)cnc3cc(O[C@H]4CCOC4)c(NC(=O)/C=C/CN(C)C)cc23)c1]

MS (M+1): 482

The compound was prepared as hydrochloride according to the process of Example 3 to determine $H^1$-NMR (DMSO-$d_6$): δ 2.144-2.232 (m, 1H); 2.375-2.469 (m, 1H); 2.741 (s, 3H); 2.756 (s, 3H); 3.765-3.837 (dd, 1H, $J_1$=10.8; $J_2$=16.0); 3.930-4.109 (m, 5H); 4.327 (s, 1H); 5.246 (br, 1H); 6.839-6.997 (m, 2H); 7.508-7.511 (m, 3H); 7.576 (s, 1H); 7.848 (s, 1H); 9.080 (s, 1H); 9.226 (s, 1H); 10.081 (s, 1H); 11.356 (br, 1H); 11.505 (br, 1H).

Specific rotation (the measurement conditions: 20° C., sodium lamp, D light, 589 nm): +10.3°

Example 141

(R,E)-N-(3-CYANO-4-(3-ETHYNYLPHE-
NYLAMINO)-7-(TETRAHYDROFURAN-3-YL-
OXY)QUINOLIN-6-YL)-4-(DIMETHYLAMINO)-
BUT-2-ENAMIDE

MS (M+1): 482

Example 143

(S,E)-N-(3-CYANO-4-(3-ETHYNYLPHE-
NYLAMINO)-7-(TETRAHYDROFURAN-3-YL-
OXY)QUINOLIN-6-YL)-4-(DIETHYLAMINO)-
BUT-2-ENAMIDE

MS (M+1): 510

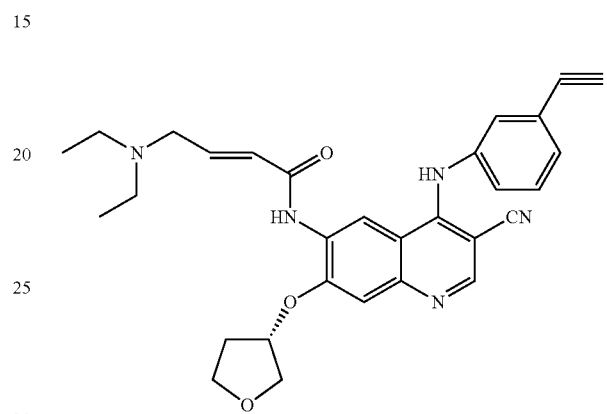

Example 142

(S,E)-N-(4-(3-CHLORO-4-FLUOROPHE-
NYLAMINO)-3-CYANO-7-(TETRAHYDRO-
FURAN-3-YL-OXY)QUINOLIN-6-YL)-4-(DIM-
ETHYLAMINO)-BUT-2-ENAMIDE

Example 144

(S,E)-N-(3-CYANO-4-(3-ETHYNYLPHE-
NYLAMINO)-7-(TETRAHYDROFURAN-3-YL-
OXY)QUINOLIN-6-YL)-4-(PIPERIDIN-1-YL)-
BUT-2-ENAMIDE

MS (M+1): 522

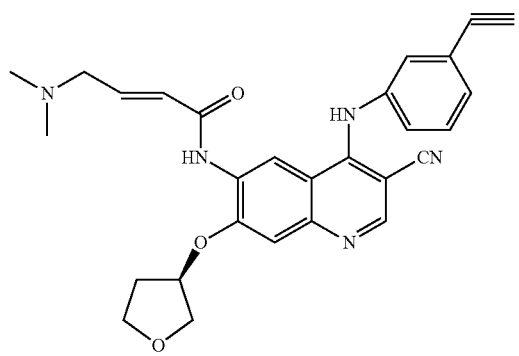 [SMILES: C#Cc1cccc(Nc2c(C#N)cnc3cc(O[C@@H]4CCOC4)c(NC(=O)/C=C/CN(C)C)cc23)c1]

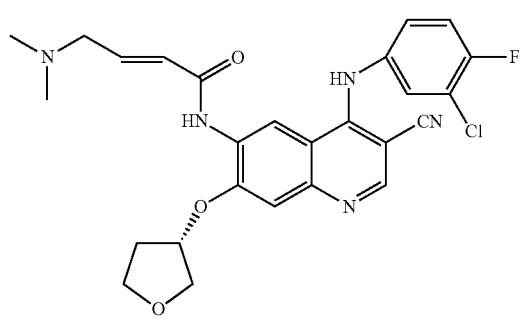 [SMILES: CN(C)C/C=C/C(=O)Nc1cc2c(Nc3ccc(F)c(Cl)c3)c(C#N)cnc2cc1O[C@H]1CCOC1]

MS (M+1): 510

The compound was prepared as hydrochloride according to the process of Example 3 so as to determine the specific rotation (the measurement conditions: 20° C., sodium lamp, D light, 589 nm): +21.2°

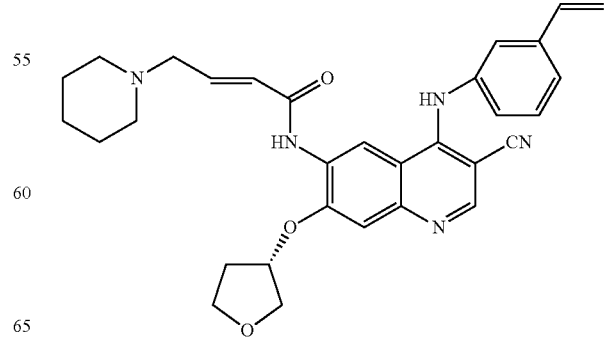

169

Example 145

(S,E)-N-(3-CYANO-4-(3-ETHYNYLPHE-
NYLAMINO)-7-(TETRAHYDROFURAN-3-YL-
OXY)QUINOLIN-6-YL)-4-(MORPHOLIN-4-YL)-
BUT-2-ENAMIDE

MS (M+1): 524

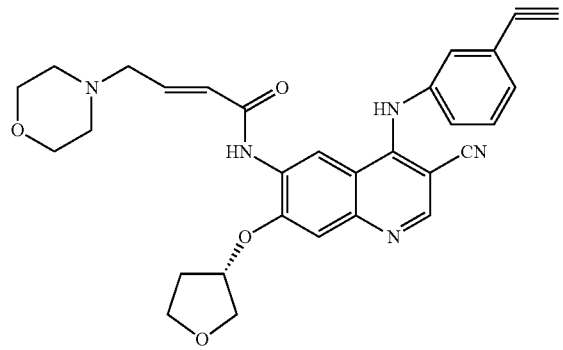 [SMILES: C#Cc1cccc(Nc2c(C#N)cnc3cc(O[C@H]4CCOC4)c(NC(=O)/C=C/CN4CCOCC4)cc23)c1]

Example 146

(S,E)-N-(3-CYANO-4-(3-ETHYNYLPHE-
NYLAMINO)-7-(TETRAHYDROFURAN-3-YL-
OXY)QUINOLIN-6-YL)-4-(TERT-BUTY-
LAIMINO)-BUT-2-ENAMIDE

MS (M+1): 510

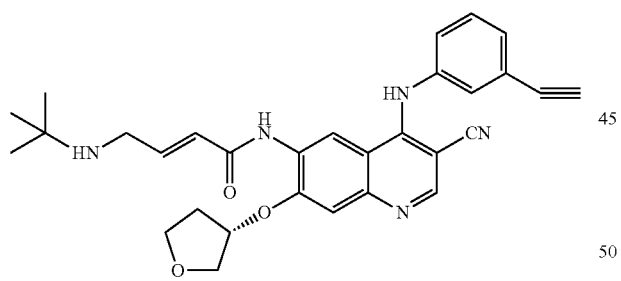

170

Example 147

(S,E)-N-(3-CYANO-4-(3-ETHYNYLPHE-
NYLAMINO)-7-(TETRAHYDROFURAN-3-YL-
OXY)QUINOLIN-6-YL)-4-(BENZYLAMINO)-
BUT-2-ENAMIDE

MS (M+1): 544

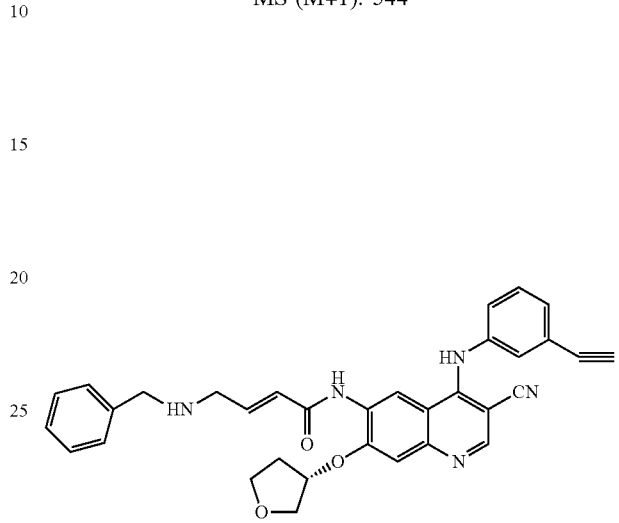

Example 148

(S,E)-N-(3-CYANO-4-(3-ETHYNYLPHE-
NYLAMINO)-7-(TETRAHYDROFURAN-3-YL-
OXY)QUINOLIN-6-YL)-4-(6-HYDROXYHEXY-
LAIMINO)-BUT-2-ENAMIDE

MS (M+1): 552

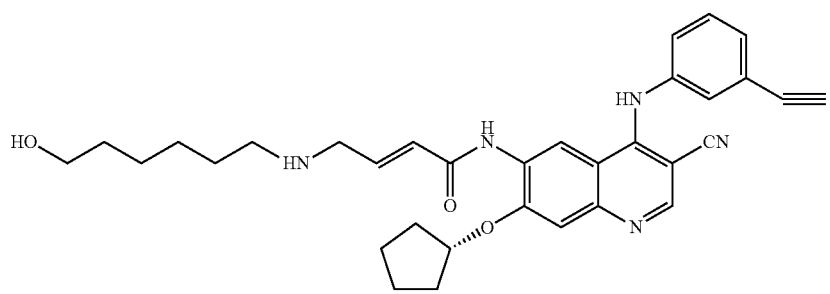

Example 149

(S,E)-N-(3-CYANO-4-(3-ETHYNYLPHE-NYLAMINO)-7-(TETRAHYDROFURAN-3-YL-OXY)QUINOLIN-6-YL)-4-(N-METHYLBENZY-LAMINO)-BUT-2-ENAMIDE

MS (M+1): 558

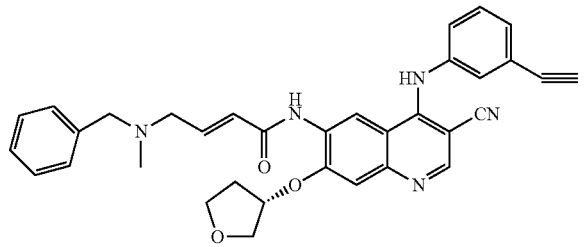 [SMILES: C#Cc1cccc(Nc2c(C#N)cnc3cc(O[C@H]4CCOC4)c(NC(=O)/C=C/CN(C)Cc4ccccc4)cc23)c1]

Example 150

(S,E)-N-(4-(3-CHLORO-4-(PYRIDIN-2-YL-METHOXY)PHENYLAMINO)-3-CYANO-7-(TET-RAHYDROFURAN-3-YL-OXY)QUINOLIN-6-YL)-4-(DIETHYLAMINO)-BUT-2-ENAMIDE

MS (M+1): 627

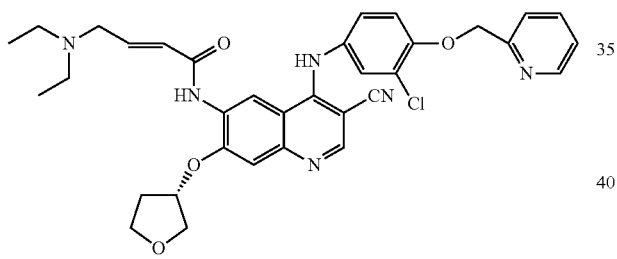

Example 151

(S,E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(PIPERIDIN-1-YL)-BUT-2-ENAMIDE

MS (M+1): 639

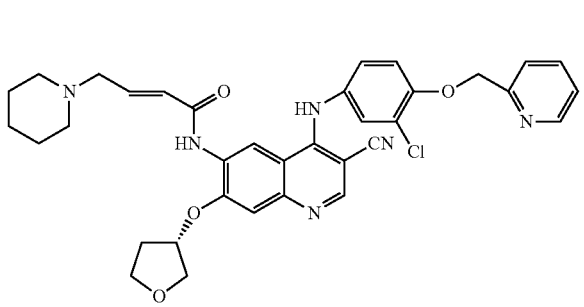 [SMILES: N#Cc1cnc2cc(O[C@H]3CCOC3)c(NC(=O)/C=C/CN3CCCCC3)cc2c1Nc1ccc(OCc2ccccn2)c(Cl)c1]

Example 152

(S,E)-N-(4-(3-CHLORO-4-(PYRIDIN-2-YL-METHOXY)PHENYLAMINO)-3-CYANO-7-(TET-RAHYDROFURAN-3-YL-OXY)QUINOLIN-6-YL)-4-(MORPHOLIN-4-YL)-BUT-2-ENAMIDE

MS (M+1): 641

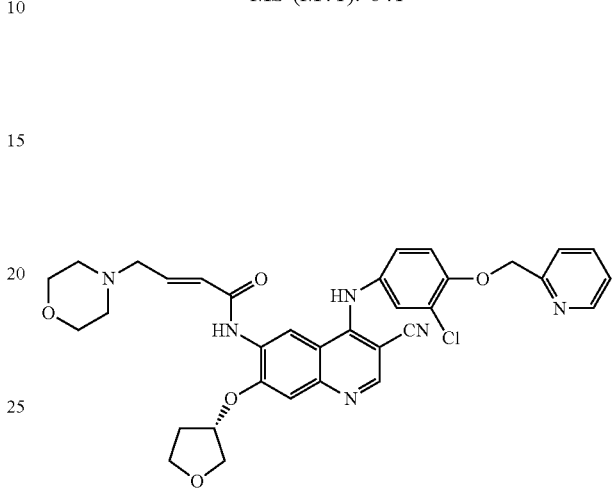

Example 153

(S,E)-N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(TERT-BUTYLAMINO)-BUT-2-ENAMIDE

MS (M+1): 627

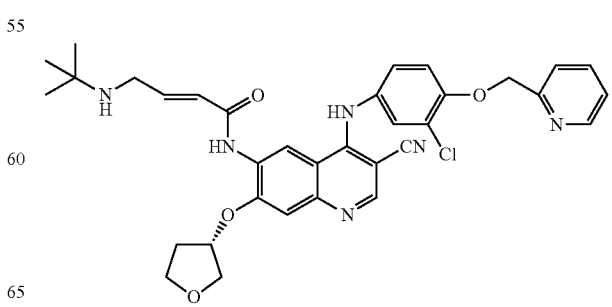

Example 154

(S,E)-N-(4-(3-CHLORO-4-(PYRIDIN-2-YL-METHOXY)PHENYLAMINO)-3-CYANO-7-(TETRAHYDROFUTAN-3-YL-OXY)QUINOLIN-6-YL)-4-(6-HYDROXYHEXYL AMINO)-BUT-2-ENAMIDE

MS (M+1): 671

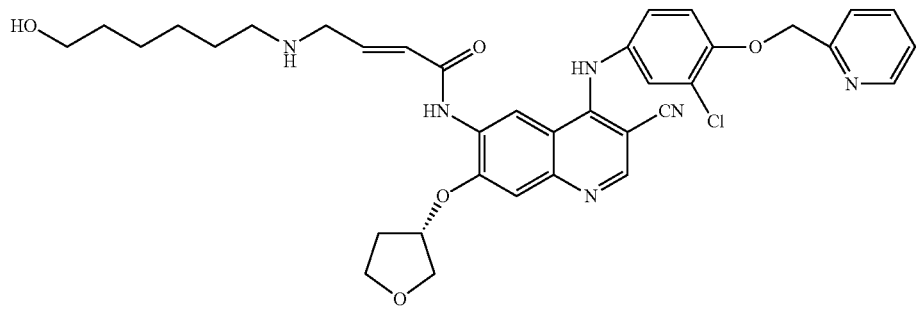 [SMILES: N#Cc1cnc2cc(O[C@H]3CCOC3)c(NC(=O)/C=C/CNCCCCCCO)cc2c1Nc1ccc(OCc2ccccn2)c(Cl)c1]

Example 155

(S,E)-N-(4-(4-(BENZYLOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 564

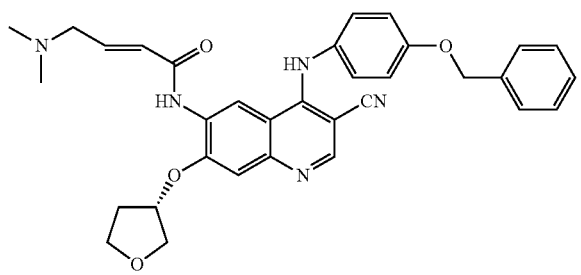

Example 156

(S,E)-N-(4-(3-BROMOPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1) 536

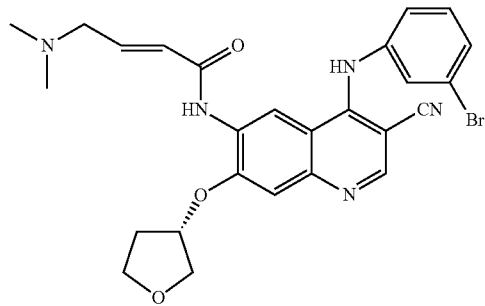 [SMILES: CN(C)C/C=C/C(=O)Nc1cc2c(Nc3cccc(Br)c3)c(C#N)cnc2cc1O[C@H]1CCOC1]

Example 157

(S,E)-N-(4-(4-(2-FLUOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 616

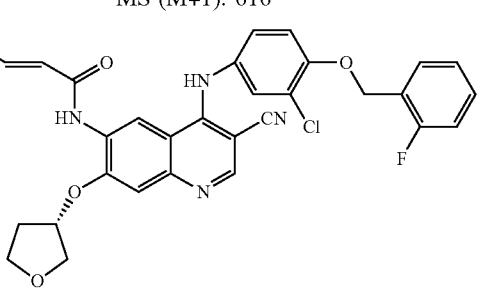

Example 158

(S,E)-N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 616

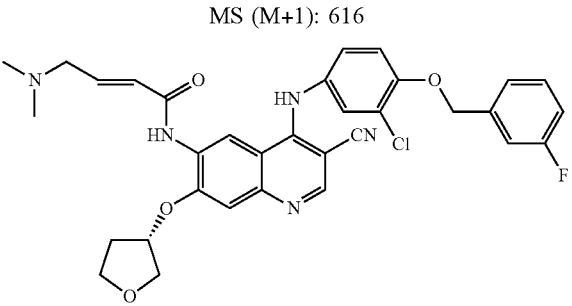

Example 159

(S,E)-N-(4-(4-(2-CHLOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 632

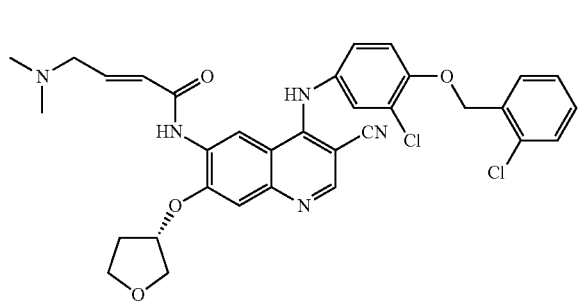 [SMILES: CN(C)C/C=C/C(=O)Nc1cc2c(Nc3ccc(OCc4ccccc4Cl)c(Cl)c3)c(C#N)cnc2cc1O[C@H]1CCOC1]

Example 160

(S,E)-N-(4-(4-(3-CHLOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 632

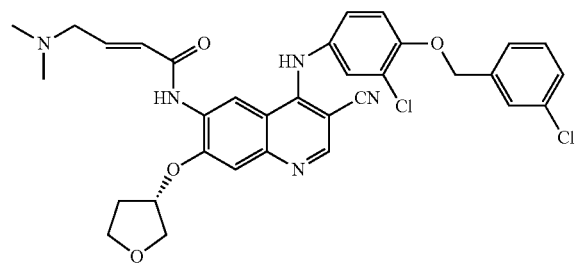

Example 161

(S,E)-N-(4-(4-(BENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 598

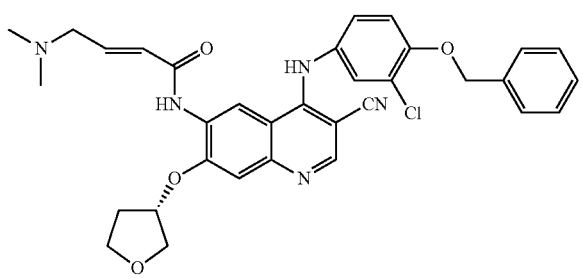

Example 162

(S,E)-N-(4-(4-(2-CYANOBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 623

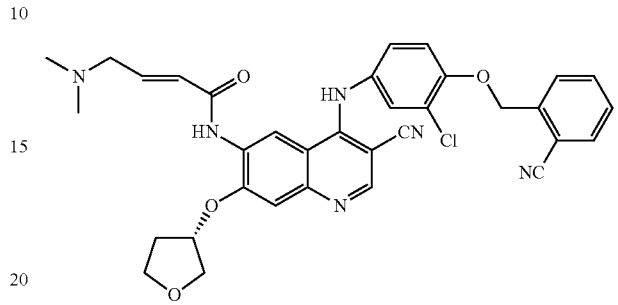

Example 163

(S,E)-N-(4-(4-(4-TERT-BUTYLBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 654

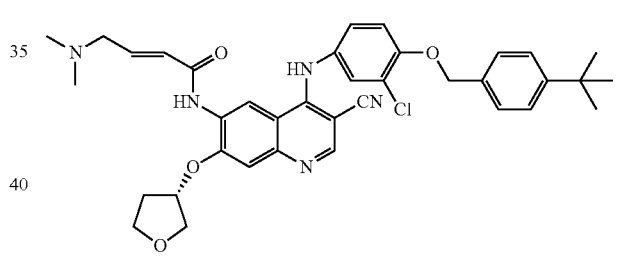

Example 164

(S,E)-N-(4-(4-(3-CYANOBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 623

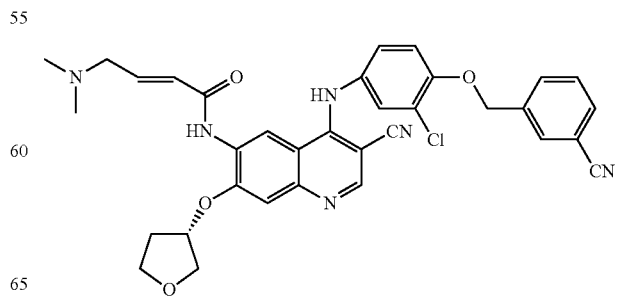

Example 165

(S,E)-N-(4-(4-(4-CHLOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 632

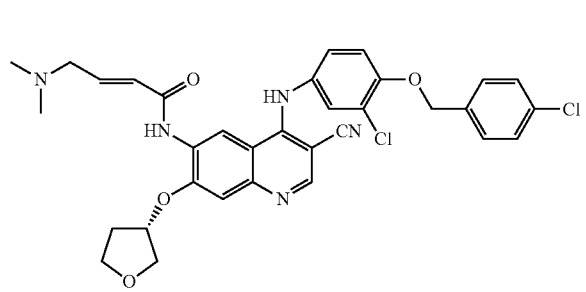 [SMILES: CN(C)C/C=C/C(=O)Nc1cc2c(Nc3ccc(OCc4ccc(Cl)cc4)c(Cl)c3)c(C#N)cnc2cc1O[C@H]1CCOC1]

Example 166

(S,E)-N-(4-(4-(2-METHYLBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 612

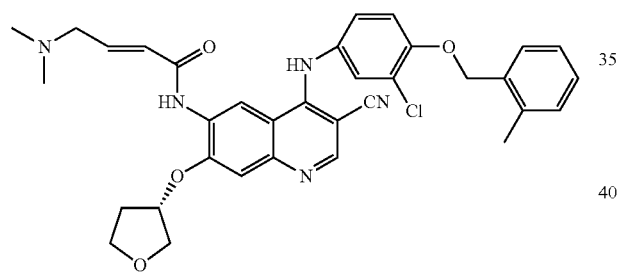

Example 167

(S,E)-N-(4-(4-(4-METHYLBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 612

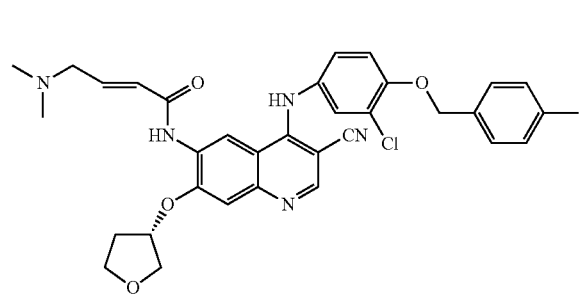

Example 168

(S,E)-N-(4-(3-CHLORO-4-FLUOROPHENYLAMINO)-3-CYANO-7-(TETRAHYDROFURAN-3-YL-OXY)QUINOLIN-6-YL)-4-(DIETHYLAMINO)-BUT-2-ENAMIDE

MS (M+1) 538

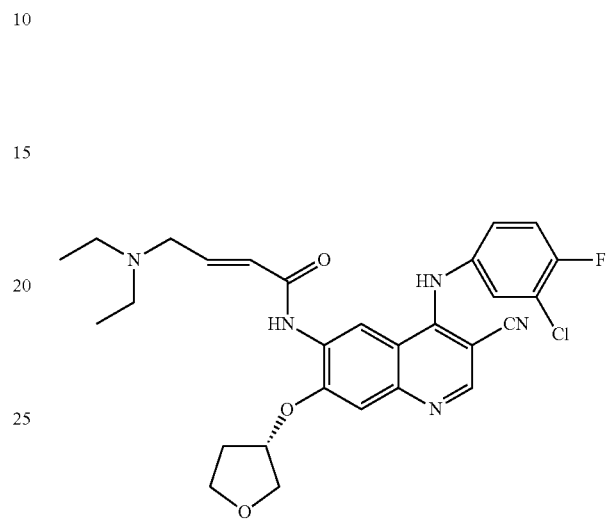

Example 169

(S,E)-N-(4-(3-CHLORO-4-FLUOROPHENYLAMINO)-3-CYANO-7-(TETRAHYDROFURAN-3-YL-OXY)QUINOLIN-6-YL)-4-(PIPERIDIN-1-YL)-BUT-2-ENAMIDE

MS (M+1): 550

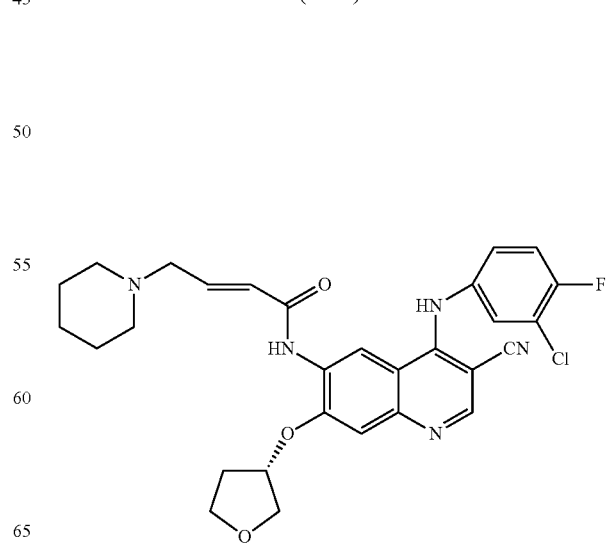

Example 170

(S,E)-N-(4-(3-CHLORO-4-FLUOROPHE-NYLAMINO)-3-CYANO-7-(TETRAHYDRO-FURAN-3-YL-OXY)QUINOLIN-6-YL)-4-(MORPHOLIN-4-YL)-BUT-2-ENAMIDE

MS (M+1): 552

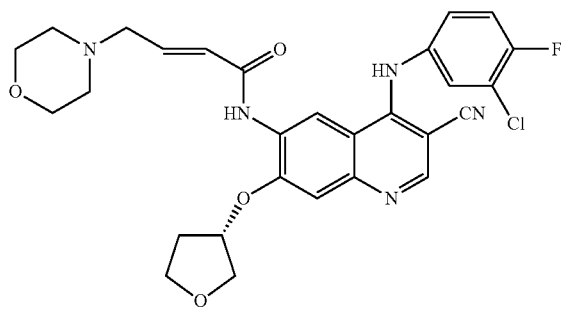 [SMILES: N#Cc1cnc2cc(O[C@H]3CCOC3)c(NC(=O)/C=C/CN3CCOCC3)cc2c1Nc1ccc(F)c(Cl)c1]

Example 171

(S,E)-N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-4-(DIETHYLAMINO)-BUT-2-ENAMIDE

MS (M+1): 644

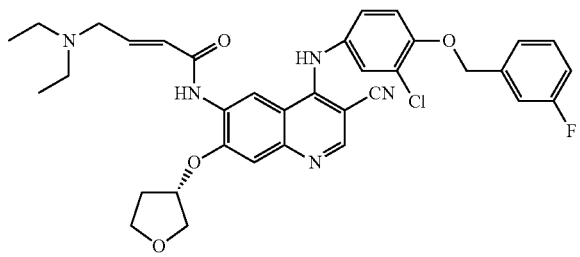 [SMILES: CCN(CC)C/C=C/C(=O)Nc1cc2c(Nc3ccc(OCc4cccc(F)c4)c(Cl)c3)c(C#N)cnc2cc1O[C@H]1CCOC1]

Example 172

(S,E)-N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-4-(PIPERIDIN-1-YL)-BUT-2-ENAMIDE

MS (M+1): 656

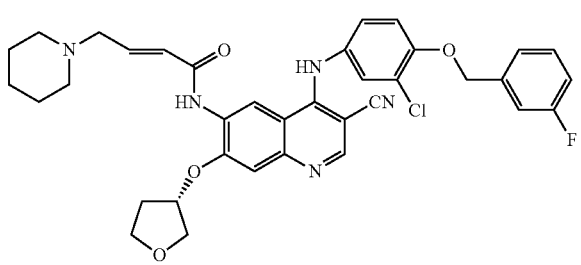 [SMILES: N#Cc1cnc2cc(O[C@H]3CCOC3)c(NC(=O)/C=C/CN3CCCCC3)cc2c1Nc1ccc(OCc2cccc(F)c2)c(Cl)c1]

Example 173

(S,E)-N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-4-(MORPHOLIN-4-YL)-BUT-2-ENAMIDE

MS (M+1): 658

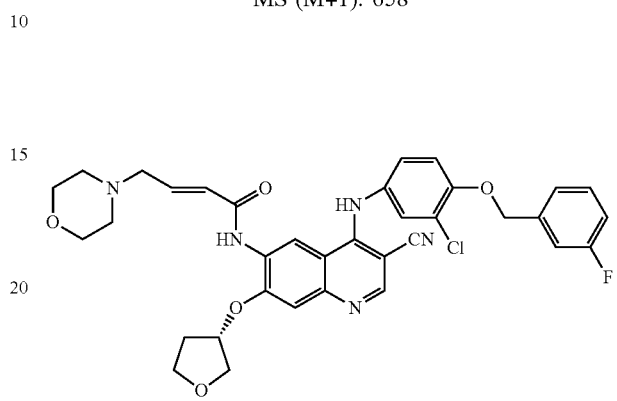

Example 174

(E)-N-(4-(3-CHLORO-4-FLUOROPHE-NYLAMINO)-3-CYANO-7-(PYRIDIN-3-YL-OXY)QUINOLIN-6-YL)4-(DIMETHYLAMINO)-BUT-2-ENAMIDE

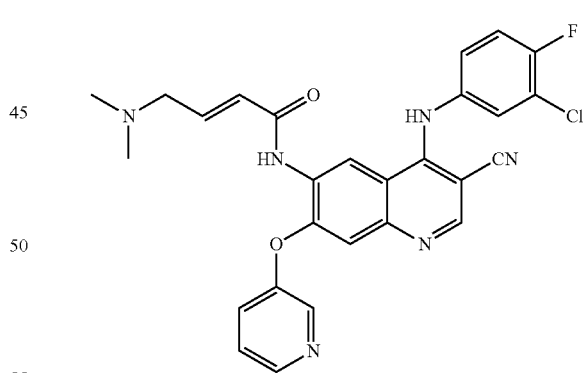

MS (M+1): 517.

The compound was prepared as hydrochloride according to the process of Example 3 to determine, $H^1$-NMR (DMSO-$d_6$): δ 2.732 (s, 3H); 2.744 (s, 3H); 3.945 (t, 2H, $J_1$=6.0); 3.955-4.097 (m, 5H); 6.784-6.989 (m, 2H); 7.544-7.621 (m, 3H); 7.781-7.853 (m, 2H); 8.029 (dd, 1H, $J_1$=1.6, $J_2$=8.8); 8.695 (d, 1H, J=4.8); 8.773 (d, 1H, J=2.8); 9.079 (s, 1H); 9.346 (s, 1H); 10.739 (s, 1H); 11.428 (br, 1H).

Example 175

(E/Z)—N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 600

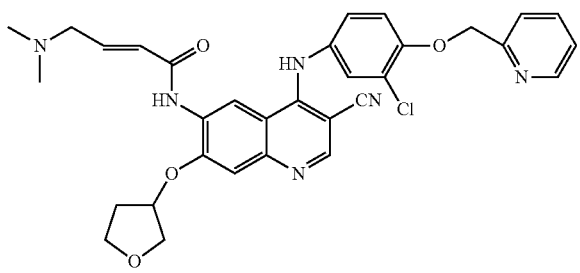

Example 176

(E/Z)—N-(4-(3-CHLORO-4-FLUOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 510

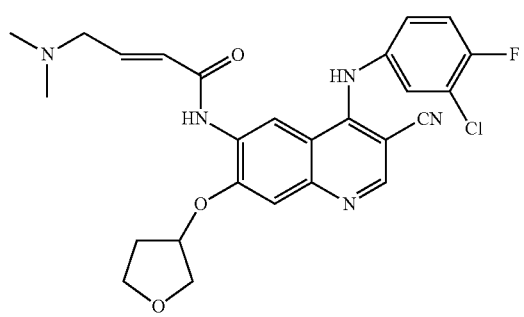 [SMILES: CN(C)C/C=C/C(=O)Nc1cc2c(Nc3ccc(F)c(Cl)c3)c(C#N)cnc2cc1OC1CCOC1]

Example 177

(E/Z)—N-(3-CYANO-4-(3-ETHYNYLPHENYLAMINO)-7-(TETRAHYDROFURAN-3-YL-OXY)QUINOLIN-6-YL)-4-(DIMETHYLAMINO)-BUT-2-ENAMIDE

MS (M+1): 482

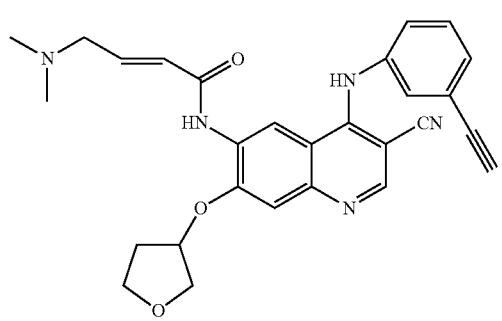 [SMILES: C#Cc1cccc(Nc2c(C#N)cnc3cc(OC4CCOC4)c(NC(=O)/C=C/CN(C)C)cc23)c1]

Example 178

(E/Z)—N-(4-(4-(BENZYLOXY)PHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 564

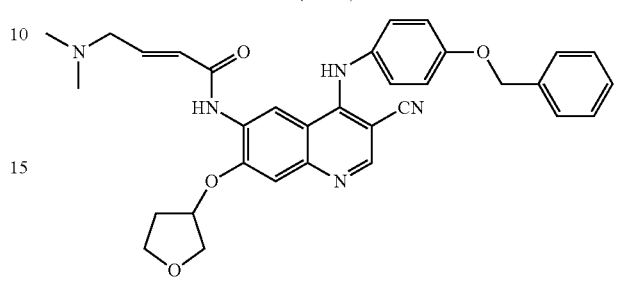

Example 179

(E/Z)—N-(4-(3-BROMOPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 536

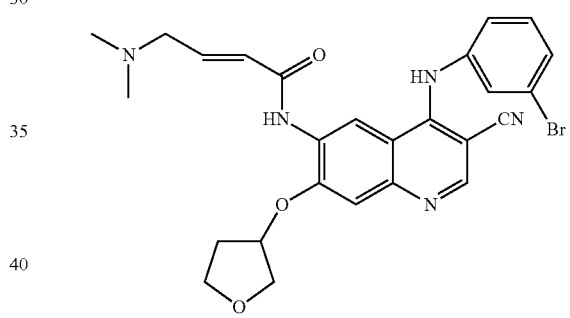

Example 180

(E/Z)—N-(4-(4-(3-FLUOROBENZYLOXY)-3-CHLOROPHENYLAMINO)-3-CYANO-7-(TETRAHYDROFURAN-3-YL-OXY)QUINOLIN-6-YL)-4-(DIMETHYLAMINO)-BUT-2-ENAMIDE

MS (M+1): 616

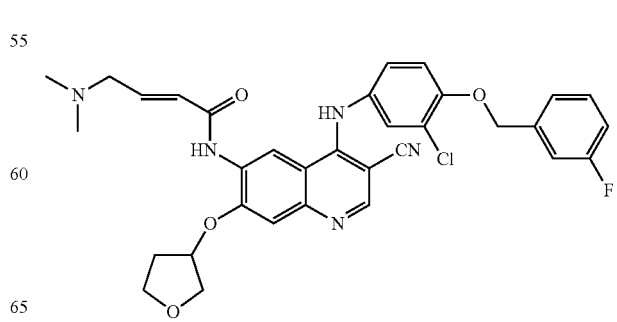

Example 181

(S,E/Z)—N-(3-CYANO-4-(3-ETHYNYLPHE-NYLAMINO)-7-(TETRAHYDROFURAN-3-YL-OXY)QUINOLIN-6-YL)-4-(DIETHYLAMINO)-BUT-2-ENAMIDE

MS (M+1): 510

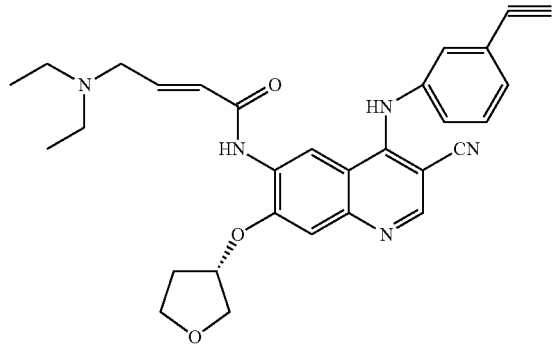 [SMILES: C#Cc1cccc(Nc2c(C#N)cnc3cc(O[C@H]4CCOC4)c(NC(=O)/C=C/CN(CC)CC)cc23)c1]

Example 182

(S,E/Z)—N-(3-CYANO-4-(3-ETHYNYLPHE-NYLAMINO)-7-(TETRAHYDROFURAN-3-YL-OXY)QUINOLIN-6-YL)-4-(PIPERIDIN-1-YL)-BUT-2-ENAMIDE

MS (M+1): 522

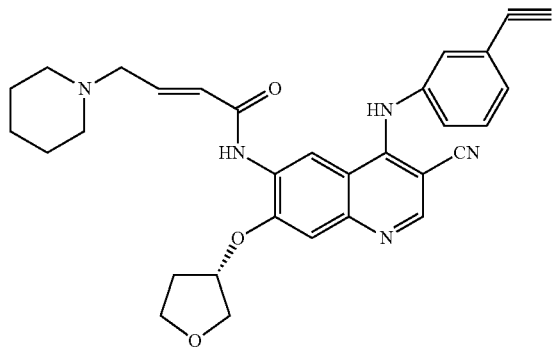 [SMILES: C#Cc1cccc(Nc2c(C#N)cnc3cc(O[C@H]4CCOC4)c(NC(=O)/C=C/CN4CCCCC4)cc23)c1]

Example 183

(S,E/Z)—N-(3-CYANO-4-(3-ETHYNYLPHE-NYLAMINO)-7-(TETRAHYDROFURAN-3-YL-OXY)QUINOLIN-6-YL)-4-(MORPHOLIN-4-YL)-BUT-2-ENAMIDE

MS (M+1): 524

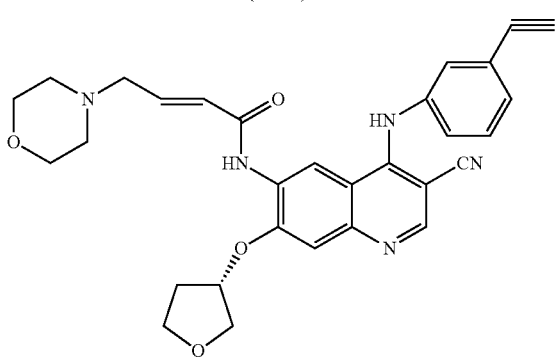

Example 184

(S,E/Z)—N-(4-(3-CHLORO-4-(PYRIDIN-2-YL-METHOXY)PHENYLAMINO)-3-CYANO-7-(TET-RAHYDROFURAN-3-YL-OXY)QUINOLIN-6-YL)-4-(DIETHYLAMINO)-BUT-2-ENAMIDE

MS (M+1): 627

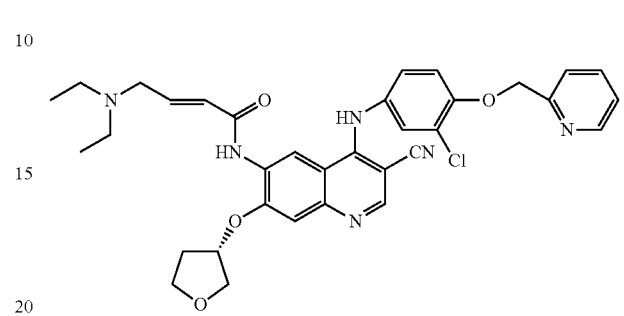

Example 185

(S,E/Z)—N-(4-(3-CHLORO-4-(PYRIDIN-2-YL-METHOXY)PHENYLAMINO)-3-CYANO-7-(TET-RAHYDROFURAN-3-YL-OXY)QUINOLIN-6-YL)-4-(PIPERIDIN-1-YL)-BUT-2-ENAMIDE

MS (M+1): 629

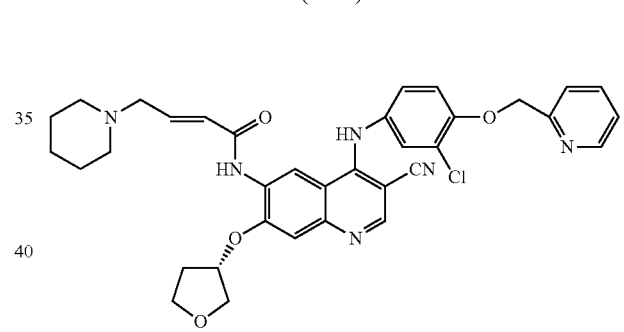

Example 186

(S,E/Z)—N-(4-(3-CHLORO-4-(PYRIDIN-2-YL-METHOXY)PHENYLAMINO)-3-CYANO-7-(TET-RAHYDROFURAN-3-YL-OXY)QUINOLIN-6-YL)-4-(MORPHOLIN-4-YL)-BUT-2-ENAMIDE

MS (M+1): 641

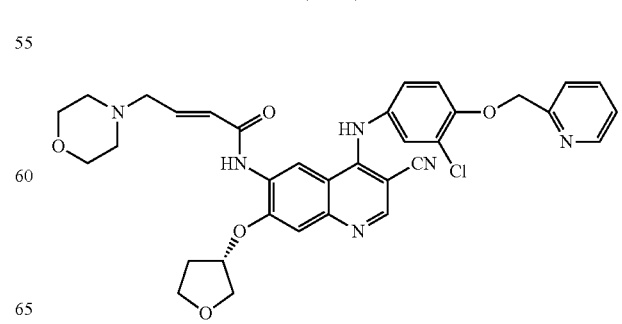

Example 187

(S,E/Z)—N-(4-(3-CHLORO-4-(PYRIDIN-2-YL-METHOXY)PHENYLAMINO)-3-CYANO-7-(TETRAHYDROFURAN-3-YL-OXY)QUINOLIN-6-YL)-4-(2-METHOXYETHYLAMINO)-BUT-2-ENAMIDE

MS (M+1): 629

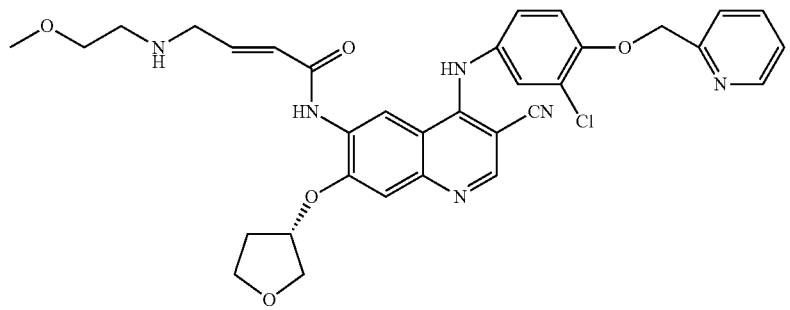 [SMILES: COCCNC/C=C/C(=O)Nc1cc2c(Nc3ccc(OCc4ccccn4)c(Cl)c3)c(C#N)cnc2cc1O[C@H]1CCOC1]

Example 188

(S,E)-N-(3-CYANO-4-(3-ETHYNYLPHENYLAMINO)-7-(TETRAHYDROFURAN-3-YL-OXY)QUINOLIN-6-YL)-4-(DIETHANOLAMINO)-BUT-2-ENAMIDE

MS (M+1): 542

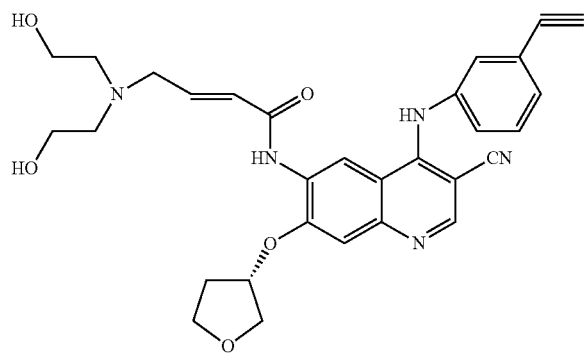 [SMILES: C#Cc1cccc(Nc2c(C#N)cnc3cc(O[C@H]4CCOC4)c(NC(=O)/C=C/CN(CCO)CCO)cc23)c1]

Example 189

(S,E)-N-(3-CYANO-4-(3-ETHYNYLPHENYLAMINO)-7-(TETRAHYDROFURAN-3-YL-OXY)QUINOLIN-6-YL)-4-(N-METHYL-METHOXYETHYLAMINO)-BUT-2-ENAMIDE

MS (M+1): 526

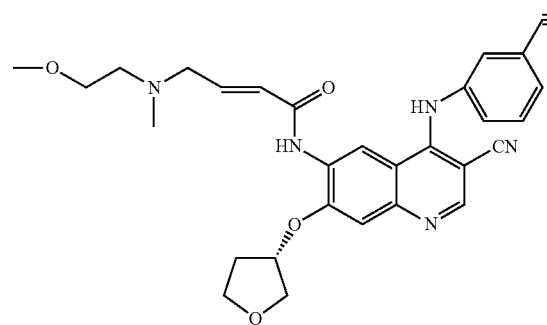

Example 190

(S,E)-N-(3-CYANO-4-(3-ETHYNYLPHENYLAMINO)-7-(TETRAHYDROFURAN-3-YL-OXY)QUINOLIN-6-YL)-4-(N-METHYLETHANOLAMINO)-BUT-2-ENAMIDE

MS (M+1): 512

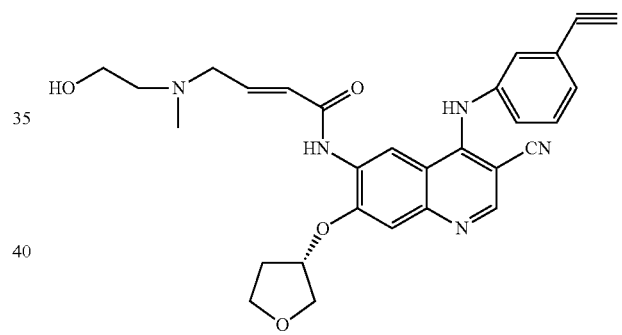

Example 191

(S,E)-N-(3-CYANO-4-(3-ETHYNYLPHENYLAMINO)-7-(TETRAHYDROFURAN-3-YL-OXY)QUINOLIN-6-YL)-4-(DIMETHOXYETHYLAMINO)-BUT-2-ENAMIDE

MS (M+1): 570

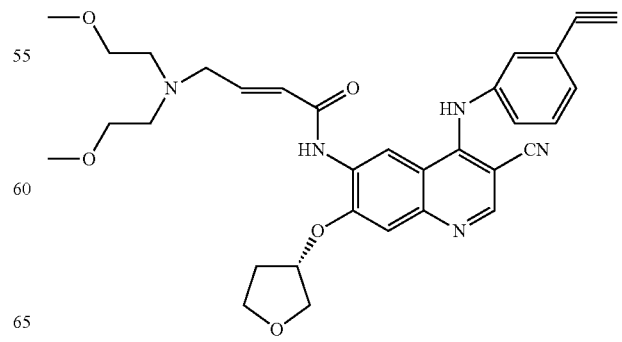

187

Example 192

(S,E)-N-(3-CYANO-4-(3-CHLORO-4-FLUORO-
PHENYLAMINO)-7-(TETRAHYDROFURAN-3-
YL-OXY)QUINOLIN-6-YL)-4-(DIETHANO-
LAMINO)-BUT-2-ENAMIDE

MS (M+1): 570

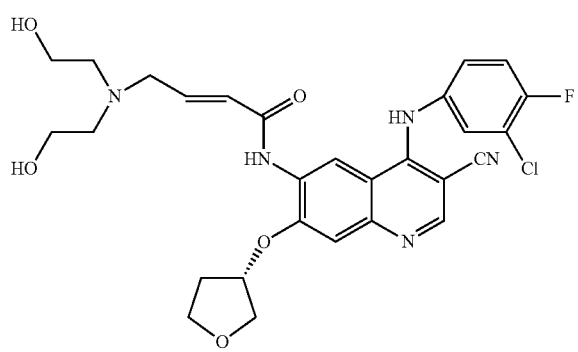 [SMILES: N#Cc1cnc2cc(O[C@H]3CCOC3)c(NC(=O)/C=C/CN(CCO)CCO)cc2c1Nc1ccc(F)c(Cl)c1]

Example 193

(S,E)-N-(3-CYANO-4-(3-CHLORO-4-FLUORO-
PHENYLAMINO)-7-(TETRAHYDROFURAN-3-
YL-OXY)QUINOLIN-6-YL)-4-(N-METHYL-
METHOXYETHYLAMINO)-BUT-2-ENAMIDE

MS (M+1): 554

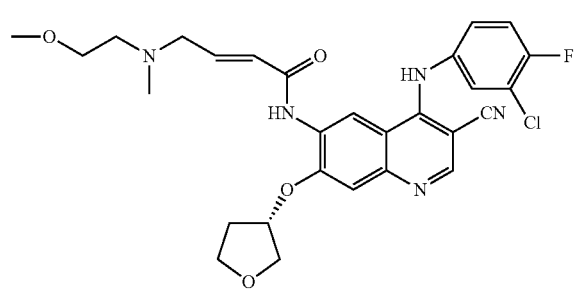 [SMILES: COCCN(C)C/C=C/C(=O)Nc1cc2c(Nc3ccc(F)c(Cl)c3)c(C#N)cnc2cc1O[C@H]1CCOC1]

188

Example 194

(S,E)-N-(3-CYANO-4-(3-CHLORO-4-FLUORO-
PHENYLAMINO)-7-(TETRAHYDROFURAN-3-
YL-OXY)QUINOLIN-6-YL)-4-(N-METHYL-
ETHANOLAMINO)-BUT-2-ENAMIDE

MS (M+1): 540

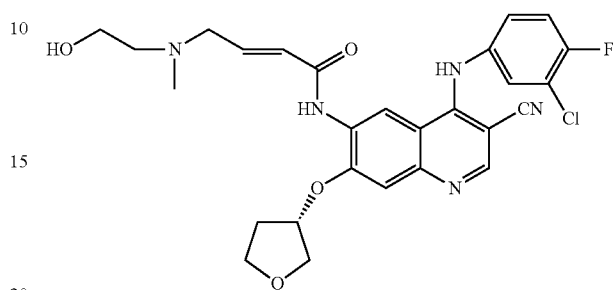

Example 195

(S,E)-N-(3-CYANO-4-(3-CHLORO-4-FLUORO-
PHENYLAMINO)-7-(TETRAHYDROFURAN-3-
YL-OXY)QUINOLIN-6-YL)-4-(DIMETHOXY-
ETHYLAMINO)-BUT-2-ENAMIDE

MS (M+1): 598

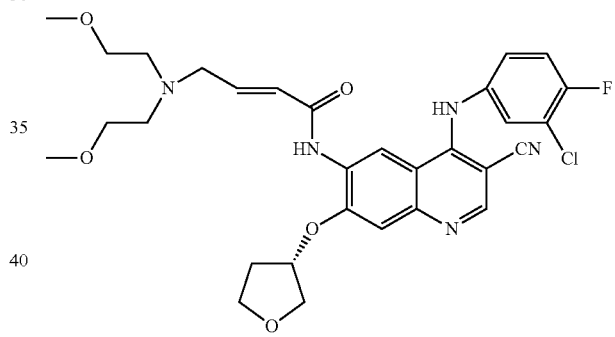

Example 196

(S,E)-N-(3-CYANO-4-(4-(3-FLUOROBENZY-
LOXY)-3-CHLOROPHENYLAMINO)-7-(TETRA-
HYDROFURAN-3-YL-OXY) QUINOLIN-6-YL)-
4-(DIETHANOLAMINO)-BUT-2-ENAMIDE

MS (M+1): 676

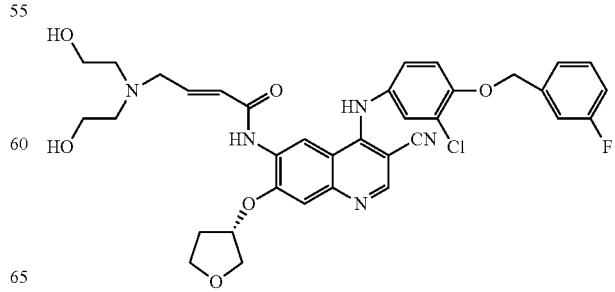

Example 197

(S,E)-N-(3-CYANO-4-(4-(3-FLUOROBENZY-LOXY)-3-CHLOROPHENYLAMINO)-7-(TETRA-HYDROFURAN-3-YL-OXY) QUINOLIN-6-YL)-4-(N-METHYLMETHOXYETHYLAMINO)-BUT-2-ENAMIDE

MS (M+1): 660

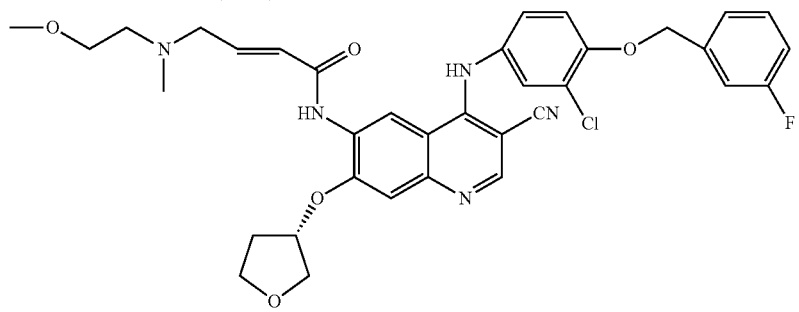 [SMILES: COCCN(C)C/C=C/C(=O)Nc1cc2c(Nc3ccc(OCc4cccc(F)c4)c(Cl)c3)c(C#N)cnc2cc1O[C@H]1CCOC1]

Example 198

(S,E)-N-(3-CYANO-4-(4-(3-FLUOROBENZY-LOXY)-3-CHLOROPHENYLAMINO)-7-(TETRA-HYDROFURAN-3-YL-OXY) QUINOLIN-6-YL)-4-(N-METHYLETHANOLAMINO)-BUT-2-ENAMIDE

MS (M+1): 646

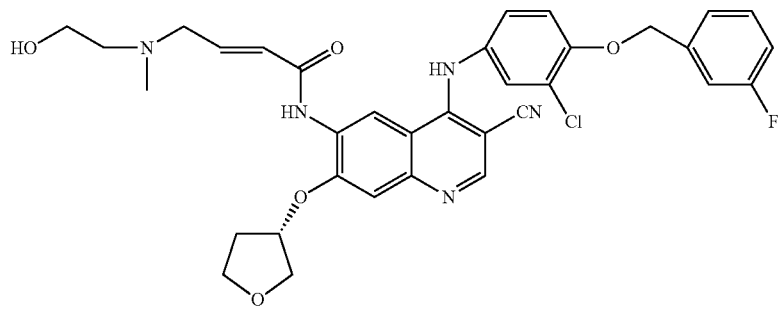 [SMILES: CN(C/C=C/C(=O)Nc1cc2c(Nc3ccc(OCc4cccc(F)c4)c(Cl)c3)c(C#N)cnc2cc1O[C@H]1CCOC1)CCO]

Example 199

(S,E)-N-(3-CYANO-4-(4-(3-FLUOROBENZY-LOXY)-3-CHLOROPHENYLAMINO)-7-(TETRA-HYDROFURAN-3-YL-OXY) QUINOLIN-6-YL)-4-(DIMETHOXYETHYLAMINO)-BUT-2-ENAMIDE

MS (M+1): 704

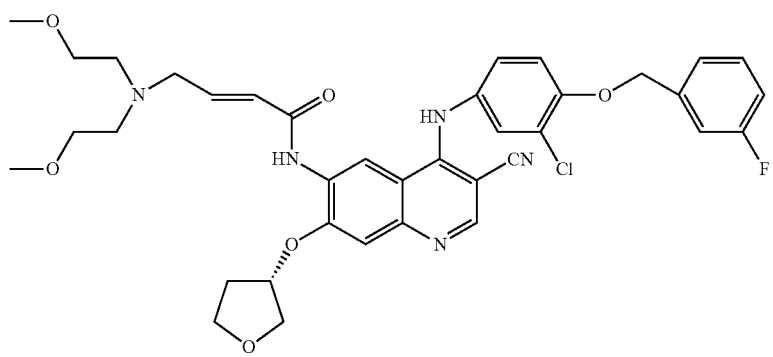 [SMILES: COCCN(C/C=C/C(=O)Nc1cc2c(Nc3ccc(OCc4cccc(F)c4)c(Cl)c3)c(C#N)cnc2cc1O[C@H]1CCOC1)CCOC]

Example 200

(S,E)-N-(3-CYANO-4-(3-CHLORO-4-(PYRIDIN-2-YL-METHOXY)PHENYLAMINO)-7-(TETRAHY-DROFURAN-3-YL-OXY)QUINOLIN-6-YL)-4-(DIETHANOLAMINO)-BUT-2-ENAMIDE

MS (M+1): 589

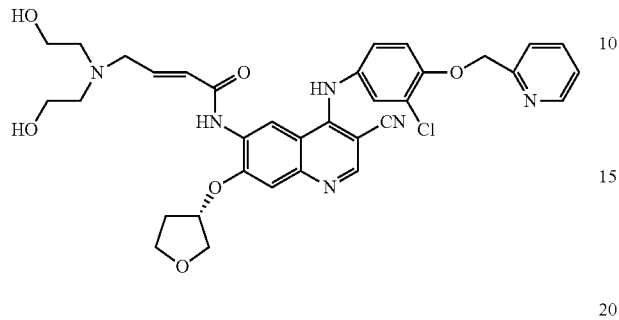

Example 201

(S,E)-N-(3-CYANO-4-(3-CHLORO-4-(PYRIDIN-2-YL-METHOXY)PHENYLAMINO)-7-(TETRAHY-DROFURAN-3-YL-OXY)QUINOLIN-6-YL)-4-(N-METHYLMETHOXY ETHYLAMINO)-BUT-2-ENAMIDE

MS (M+1): 643

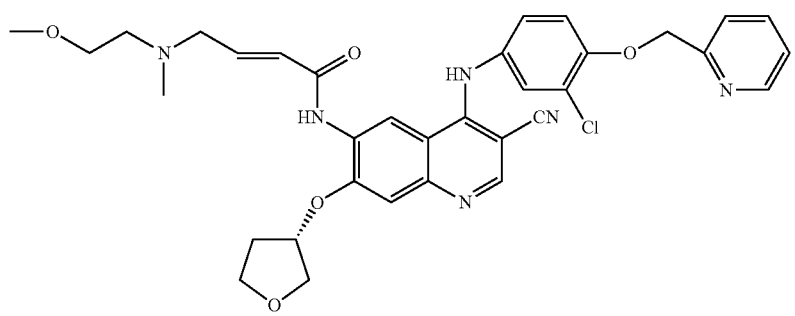 [SMILES: COCCN(C)C/C=C/C(=O)Nc1cc2c(Nc3ccc(OCc4ccccn4)c(Cl)c3)c(C#N)cnc2cc1O[C@H]1CCOC1]

Example 202

(S,E)-N-(3-CYANO-4-(3-CHLORO-4-(PYRIDIN-2-YL-METHOXY)PHENYLAMINO)-7-(TETRAHY-DROFURAN-3-YL-OXY)QUINOLIN-6-YL)-4-(N-METHYLETHANOL AMINO)-BUT-2-ENAMIDE

MS (M+1): 639

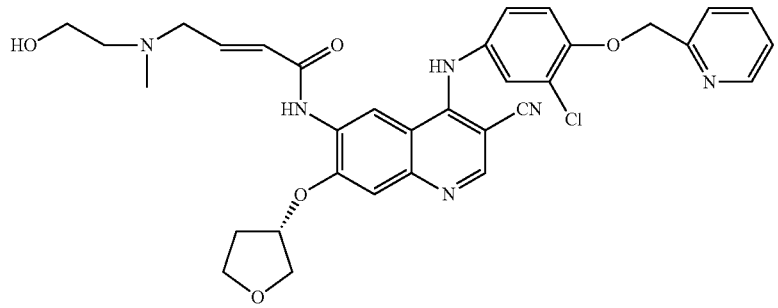 [SMILES: CN(C/C=C/C(=O)Nc1cc2c(Nc3ccc(OCc4ccccn4)c(Cl)c3)c(C#N)cnc2cc1O[C@H]1CCOC1)CCO]

Example 203

(S,E)-N-(3-CYANO-4-(3-CHLORO-4-(PYRIDIN-2-YL-METHOXY)PHENYLAMINO)-7-(TETRAHYDROFUTAN-3-YL-OXY)QUINOLIN-6-YL)-4-(DIMETHOXYETHYL AMINO)-BUT-2-ENAMIDE

MS (M+1): 687

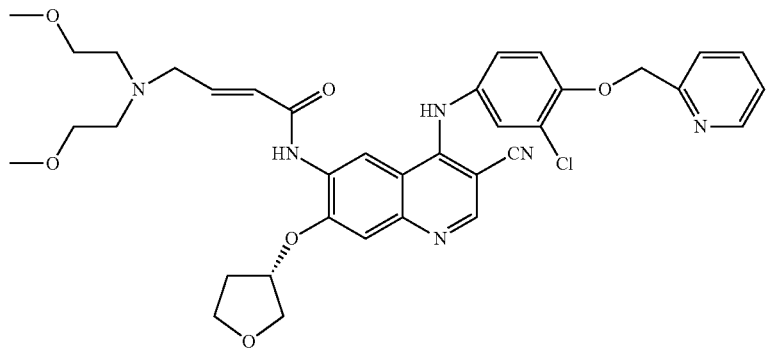 [SMILES: COCCN(C/C=C/C(=O)Nc1cc2c(Nc3ccc(OCc4ccccn4)c(Cl)c3)c(C#N)cnc2cc1O[C@H]1CCOC1)CCOC]

Example 204

(S,E)-N-(3-CYANO-4-(3-CHLORO-4-(PYRIDIN-2-YL-METHOXY)PHENYLAMINO)-7-(TETRAHYDROFURAN-3-YL-OXY)QUINOLIN-6-YL)-4-(6-HYDROXYHEXYL AMINO)-BUT-2-ENAMIDE

MS (M+1): 671

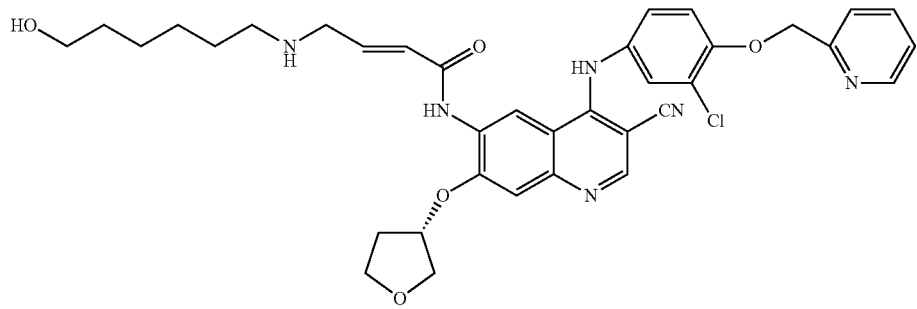 [SMILES: N#Cc1cnc2cc(O[C@H]3CCOC3)c(NC(=O)/C=C/CNCCCCCCO)cc2c1Nc1ccc(OCc2ccccn2)c(Cl)c1]

Example 205

(S,E)-N-(3-CYANO-4-(3-CHLORO-4-FLUOROPHENYLAMINO)-7-(TETRAHYDROFURAN-3-YL-OXY)QUINOLIN-6-YL)-4-(6-HYDROXYHEXYLAMINO)-BUT-2-ENAMIDE

MS (M+1): 582

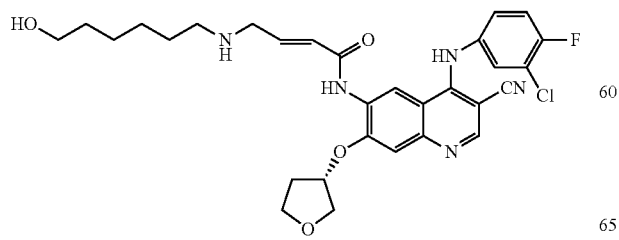

Example 206

(S,E)-N-(3-CYANO-4-(4-(3-FLUOROBENZY-LOXY)-3-CHLOROPHENYLAMINO)-7-(TETRA-HYDROFURAN-3-YL-OXY)QUINOLIN-6-YL)-4-(6-HYDROXYHEXYLAMINO)-BUT-2-ENAMIDE

MS (M+1): 688

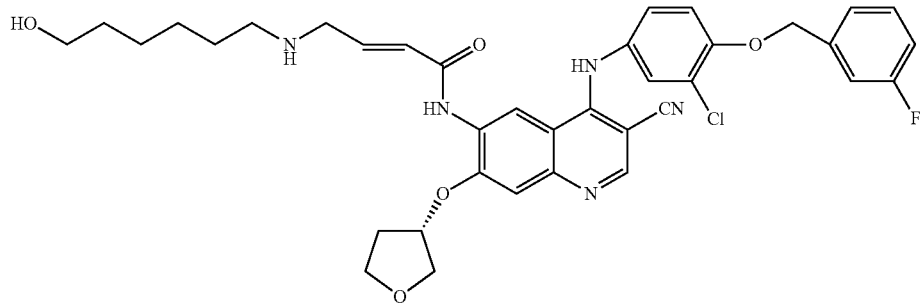 [SMILES: N#Cc1cnc2cc(O[C@H]3CCOC3)c(NC(=O)/C=C/CNCCCCCCO)cc2c1Nc1ccc(OCc2cccc(F)c2)c(Cl)c1]

Example 207

(S,E)-N-(3-CYANO-4-(3-ETHYNYLPHE-NYLAMINO)-7-(TETRAHYDROFURAN-3-YL-OXY)QUINOLIN-6-YL)-4-(N-METHYL-6-AMINO-1-HEXANOLYL)-BUT-2-ENAMIDE

MS (M+1): 566

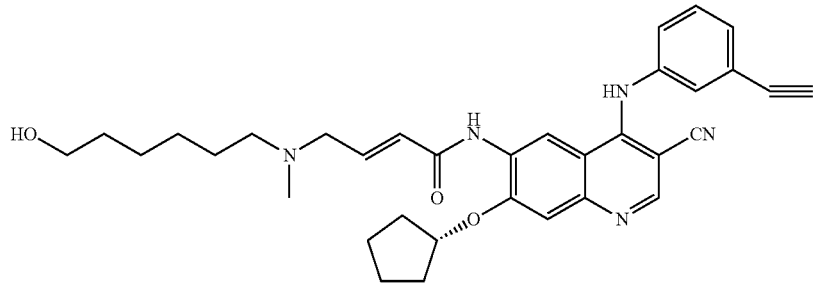

(S,E)-N-(3-cyano-4-(3-ethynylphenylamino)-7-(tetrahydrofuran-3-yl-oxy)quinolin-6-yl)-4-(6-amino-1-hexanolyl)-but-2-enamide (552 mg, 0.001 mol) was dissolved in DMF (15 ml). The solution was stirred homogeneously. To the solution were added methyl iodide (156 mg (1.1 mmol), anhydrous potassium carbonate (276 mg, 2 mmol) and tetrabutyl ammonium iodide (11 mg, 0.03 mmol). The resulting mixture was stirred in the dark at the room temperature. After 48 hr, the reaction was stopped. The reaction solution was added into saturated sodium bicarbonate (150 ml). The mixture was extracted with ethyl acetate (150 ml) once. The organic phase was retained. Anhydrous magnesium sulfate was added into the organic phase for half-hour. After half-hour, the drying agent was removed. The organic phase was concentrated in vacuo to give a yellow solid. The solid was purified with column chromatography (eluent: chloroform:methanol=9:1) to give a yellow solid (342 mg). Yield: 60.5%.

The compounds of Examples 208-210 were prepared according to the process of Example 207.

Example 208

(S,E)-N-(3-CYANO-4-(3-CHLORO-4-FLUORO-PHENYLAMINO)-7-(TETRAHYDROFURAN-3-YL-OXY)QUINOLIN-6-YL)-4-(N-METHYL-6-AMINO-1-HEXANOLYL)-BUT-2-ENAMIDE

MS (M+1): 596

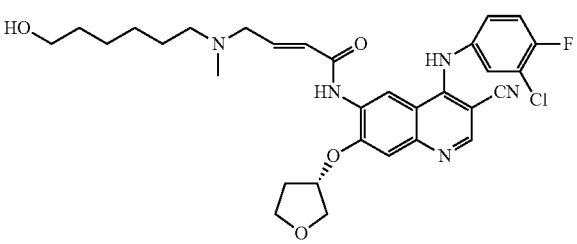 [SMILES: CN(C/C=C/C(=O)Nc1cc2c(Nc3ccc(F)c(Cl)c3)c(C#N)cnc2cc1O[C@H]1CCOC1)CCCCCCO]

Example 209

(S,E)-N-(3-CYANO-4-(4-(3-FLUOROBENZYLOXY)-3-CHLOROPHENYLAMINO)-7-(TETRAHYDROFURAN-3-YL-OXY)QUINOLIN-6-YL)-4-(N-METHYL-6-AMINO-1-HEXANOLYL)-BUT-2-ENAMIDE

MS (M+1): 702

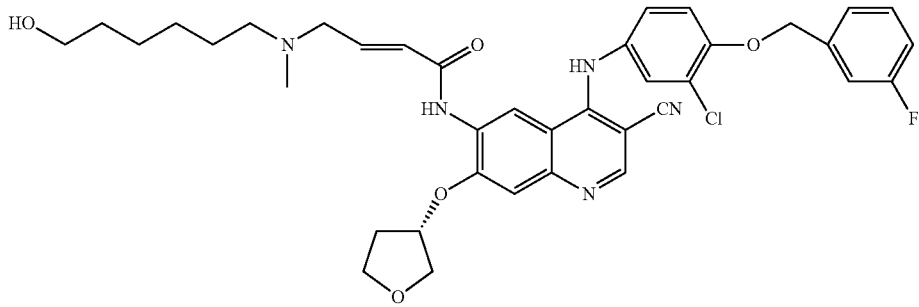 [SMILES: CN(C/C=C/C(=O)Nc1cc2c(Nc3ccc(OCc4cccc(F)c4)c(Cl)c3)c(C#N)cnc2cc1O[C@H]1CCOC1)CCCCCCO]

Example 210

(S,E)-N-(3-CYANO-4-(3-CHLORO-4-(PYRIDIN-2-YL-METHOXY)PHENYLAMINO)-7-(TETRAHYDROFURAN-3-YL-OXY)QUINOLIN-6-YL)-4-(N-METHYL-6-AMINO-1-HEXANOLYL)-BUT-2-ENAMIDE

MS (M+1): 485

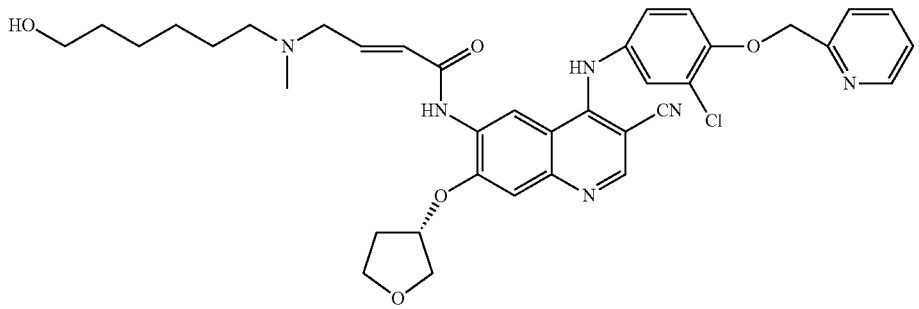

BIOLOGICAL EXAMPLES

Abbreviations used in the following Biological Examples are as follows: EGFR-TK: intracellular epidermal growth factor receptor phosphorylase; A431 (human epithelial gland cancer cell strain); A549: human lung cancer cell strain; LoVo: human intestinal cancer cell strain; NCI-H460: human large cell lung cancer cell strain; NCI-N87: human gastric cancer cell strain; Sk-Br-3: human breast cancer cell strain; SW620: human colorectal cancer cell strain; BT-474: human breast cancer cell strain; CCRF-CEM/T: human acute lymphocytic cell leukemia cell resistant to paclitaxel; Fadu: human head and neck cancer cell strain; BxPC-3: human pancreatic cancer cell strain; AsPC-1: human pancreatic cancer cell strain; SK-OV-3: human ovarian cancer cell strain; NCI-H358: human non-small cell lung cancer cell strain; NCI-H1650: human non-small cell lung cancer cell strain; MDA-MB-453: human breast cancer cell strain; PGT: polyglutamic acid tyrosine; PBS: phosphate buffer, pH 7.4; ATP: triphosadenine; TKB: tyrosine kinase reaction buffer; SDS: sodium dodecyl sulfate; PBST: PBS containing 0.05% Tween 20; BSA: bovine serum albumin; HRP: horseradish peroxidase; TMB: 3,3',5,5'-tetramethyl benzidine; DTT: dithiothreitol; $ddH_2O$: double distilled water; MTT: tetrazole; DMEM: Dulbecco's Modified Eagle's Medium; F12: F-12 Nutrient Mixture (Ham); EDTA: ethylene diamine tetraacetic acid; RPMI-1640: RPMI-1640 Medium; FBS: fetal bovine serum; SRB: sulforhodamine; Tris: trihydroxy methyl amino methane; EMEM: Minimum Essential Medium with Earle's salts; NEAA: non-essential amino acid; McCoy's 5A: McCoy's 5A Medium; HEPEs: hydroxyethylpiperazine ethanesulfonic acids; DMSO: dimethyl sulfoxide.

Biological Example 1

A431 Cell Growth Inhibition Test (MTT Assay)

I. Assay Materials
  1. Cell strains: A431 (human epithelial adenocarcinoma cell strains);
  2. MTT; antitumor compounds; DMSO II. Reagents and Consumable Materials
  Culture medium: 45% DMEM, 45% F12+10% FBS;
  Pancreatin (0.25% (w/v) solution was formulated with PBS, 0.53 mM of EDTA was added in the formulation);
  PBS;
  96-well culture plate III. Assay Process
  1. A plate (10 cm) of cells in logarithmic growth phase normally cultured was collected;

2. The culture solution was sucked out. The plate was washed with 5 ml of PBS 1-2 times;

3. PBS was sucked out, and 2 ml of 0.25% pancreatin was added to infiltrate the cells for 1 min;

4. The pancreatin was sucked out, and the culture plate was placed in an incubator. Digestion was carried out for about 15 min at 37° C.;

5. 4 ml of complete culture solution was added in the culture plate to stop the digestion. The cells were carefully scoured with micropipette (1 ml) to give a uniform cell suspension. The suspension was implanted into a 96-well cell culture plate by 2500 cells/100 μl per well. The culture plate was incubated overnight under 5% $CO_2$ at 37° C. In day 2, 100 μl of culture solution comprising the compound was added in each well, and further incubated for 68 h under 5% $CO_2$ at 37° C.

6. The culture solution was sucked out;

7. 100 μl of serum-free culture solution containing 0.5 mg/ml MTT was added in each well, and incubated for 4 h;

8. The culture solution was carefully sucked out;

9. 100 μl of DMSO was added into each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD value of cells after normal growth in control wells without a compound;

n: OD value of cells after growth in test wells with a compound;

NC: Background OD value of blank wells without a compound and cells;

$IC_{50}$: concentration of a compound where inhibition ratio was 50%. $IC_{50}$ values were fitted with Origin7.5.

TABLE 1

Growth Inhibition Ratio of Some Compounds (1 μM) in Examples on A431 Cells

| Compound | Growth Inhibition Ratio (%) | Compound | Growth Inhibition Ratio (%) | Compound | Growth Inhibition Ratio (%) |
|---|---|---|---|---|---|
| Example 3 | 85 | Example 4 | 80 | Example 5 | 85 |
| Example 8 | 91 | Example 9 | 90 | Example 13 | 89 |
| Example 15 | 91 | Example 138 | 89 | Example 139 | 90 |
| Example 140 | 87 | Example 141 | 80 | Example 142 | 75 |
| Example 143 | 70 | Example 150 | 84 | Example 155 | 82 |
| Example 157 | 72 | Example 158 | 77 | Example 166 | 69 |
| Example 167 | 75 | Example 176 | 79 | Example 177 | 81 |
| Example 180 | 73 | Example 185 | 70 | Example 190 | 79 |

TABLE 2

Growth Inhibition Activity ($IC_{50}$) of Some Compounds in Examples on A431 Cells

| Compounds | $IC_{50}$ (μM) | Compounds | $IC_{50}$ (μM) | Compounds | $IC_{50}$ (μM) |
|---|---|---|---|---|---|
| Example 4 | 0.068 | Example 5 | 0.024 | Example 7 | 0.160 |
| Example 8 | 0.145 | Example 9 | 0.135 | Example 10 | 0.222 |
| Example 11 | 0.184 | Example 12 | 0.147 | Example 13 | 0.158 |
| Example 174 | 0.95 | Example 15 | 0.37 | Example 16 | 0.358 |
| Example 17 | 0.194 | Example 19 | 0.39 | Example 21 | 0.081 |
| Example 138 | 0.062 | Example 139 | 0.093 | Example 140 | 0.026 |
| Example 141 | 0.050 | Example 142 | 0.045 | Example 143 | 0.059 |
| Example 144 | 0.026 | Example 145 | 0.071 | Example 146 | 0.053 |
| Example 149 | 0.089 | Example 150 | 0.027 | Example 151 | 0.061 |
| Example 152 | 0.062 | Example 153 | 0.053 | Example 154 | 0.162 |

Biological Example 2

BT-474 Cell Growth Inhibition Test (SRB Assay)

I. Assay Materials

1. Cell strains: BT-474 (human breast tumor cell strains);

2. SRB: available from Sigmaaldrich, goods number: S9012, lot number: 047K3751. SRB was reserved at the room temperature. 0.4% (w/v) of working solution was formulated with 1% of glacial acetic acid. The solution was reserved at the temperature of 4° C.; anti-tumor compounds; DMSO.

II. Reagents and Consumable Materials

Culture medium (90% EMEM+10% FBS+0.1 mM NEAA, reserved at 4° C.);

Pancreatin (0.25% (w/v) solution was formulated with PBS, 0.53 mM of EDTA was added in the formulation);

PBS;

FBS (fetal bovine serum);

Tris;

Glacial acetic acid;

96-well cell culture plate

III. Assay Process

1. A plate (10 cm) of cells in logarithmic growth phase normally cultured was collected. The culture solution was sucked out. The plate was washed with 5 mL of PBS 1-2 times;

2. PBS was sucked out, and 1.5 m of 0.25% pancreatin was added to infiltrate the cells for 30 s;

3. The pancreatin was sucked out. The culture plate was pleaced in an incubator. Digestion was carried out for about 5 min at 37° C.;

4. 3 mL of complete culture solution was added to the culture plate to stop the digestion. The cells were carefully scoured with micropipette (1 ml) to give a uniform single cell suspension;

5. Cell suspension was counted. The suspension was diluted to 1×10⁵/ml. The resulting suspension was developed uniformly on a plate. The plate was incubated under 5% $CO_2$ at 37° C. overnight. In day 2, 80 μL of complete culture medium was added in each well and then 20 μL of culture solution comprising a compound was added. The mixture was incubated for 70 h under 5% $CO_2$ at 37° C.

6. The culture solution was sucked out. 100 uL of TCA fixed cells which were diluted to 10% were added to each well. The plate was kept in a refrigerator for 1 h at 4° C.

7. TCA stationary liquid was sucked out. Each well was washed with 150 μL of $ddH_2O$ five times;

8. After the stationary liquid was cleansed, the plate was dried in the air at the room temperature;

9. 60 μL of SRB staining solution was added in each well. The well was stained for 15 min at the room temperature;

10. The SRB staining solution was sucked out. Each well was washed with 150 μL of 1% glacial acetic acid five times;

11. After the SRB staining solution was cleansed, the plate was dried in the air at the room temperature;
12. 100 μL of 10 mM Tris was added in each well. The plate was vibrated to dissolve out SRB;
13. OD values were determined at 570 nM.

IV. Assay Results

1. Calculation of Relative Inhibition Ratio

The inhibition ratio of a compound on cell growth=(PC−n)/(PC−NC)×100% wherein:

PC: OD value of cells after normal growth in control wells without a compound;

n: OD value of cells after growth in test wells with a compound;

NC: Background OD values of blank wells without a compound and cells;

$IC_{50}$: Concentration of a compound where inhibition ratio was 50%. $IC_{50}$ values were fitted with Origin7.5.

TABLE 3

Growth Inhibition Ratio of Some Compounds (1 μM) in Examples on BT-474 Cells

| Compounds | Growth Inhibition Ratio (%) | Compounds | Growth Inhibition Ratio (%) | Compounds | Growth Inhibition Ratio (%) |
|---|---|---|---|---|---|
| Example 4 | 79 | Example 5 | 85 | Example 8 | 79 |
| Example 9 | 78 | Example 13 | 75 | Example 15 | 71 |
| Example 16 | 72 | Example 138 | 82 | Example 139 | 81 |
| Example 140 | 85 | Example 141 | 89 | Example 142 | 89 |
| Example 143 | 87 | Example 145 | 75 | Example 147 | 75 |
| Example 149 | 79 | Example 150 | 82 | Example 151 | 80 |
| Example 152 | 78 | Example 156 | 70 | Example 158 | 82 |
| Example 162 | 80 | Example 166 | 69 | Example 167 | 75 |
| Example 168 | 86 | Example 169 | 80 | Example 171 | 84 |
| Example 172 | 62 | Example 173 | 67 | Example 176 | 89 |
| Example 177 | 87 | Example 180 | 78 | Example 181 | 87 |
| Example 183 | 75 | Example 184 | 83 | Example 186 | 80 |
| Example 189 | 85 | Example 192 | 85 | Example 198 | 78 |
| Example 201 | 80 | Example 203 | 82 | Example 205 | 75 |

TABLE 4

Growth Inhibition Activity ($IC_{50}$) of Some Compounds in Examples on BT-474 Cells

| Compounds | $IC_{50}$ (μM) | Compounds | $IC_{50}$ (μM) | Compounds | $IC_{50}$ (μM) |
|---|---|---|---|---|---|
| Example 4 | 0.140 | Example 5 | 0.041 | Example 7 | 0.309 |
| Example 9 | 0.0052 | Example 10 | 0.0099 | Example 11 | 0.0079 |
| Example 12 | 0.008 | Example 13 | 0.011 | Example 189 | 0.108 |
| Example 15 | 0.0081 | Example 16 | 0.035 | Example 17 | 0.017 |
| Example 19 | 0.032 | Example 190 | 0.267 | Example 21 | 0.0036 |
| Example 138 | 0.003 | Example 139 | 0.0039 | Example 140 | 0.033 |
| Example 141 | 0.096 | Example 142 | 0.133 | Example 143 | 0.149 |
| Example 144 | 0.129 | Example 145 | 0.654 | Example 146 | 0.236 |
| Example 149 | 0.212 | Example 150 | 0.0049 | Example 151 | 0.0065 |
| Example 152 | 0.0104 | Example 153 | 0.0072 | Example 154 | 0.012 |
| Example 191 | 0.390 | | | | |

Biological Example 3

A549 Cell Growth Inhibition Test (MTT Assay)

I. Assay Materials

1. Cell strains: A4549 (human lung cancer cell strains);
2. MTT; antitumor compounds; DMSO.

II. Reagents and Consumable Materials

Culture medium: 90% F12K+10% FBS;
Pancreatin (0.25% (w/v) solution was formulated with PBS, 0.53 mM of EDTA was added in the formulation);
PBS;
96-well culture plate III. Assay Process 1. A plate (10 cm) of cells in logarithmic growth phase normally cultured was collected;
2. The culture solution was sucked out. The plate was washed with 5 ml of PBS 1-2 times;
3. PBS was sucked out. 2 ml of 0.25% pancreatin was added to infiltrate the cells for 1 min;
4. The pancreatin was sucked out. The culture plate was placed in an incubator. Digestion was carried out for about 2 min at 37° C.;
5. 4 ml of complete culture solution was added to the culture plate to stop the digestion. The cells were carefully scoured with micropipette (1 ml) to give a uniform cell suspension. The suspension was implanted into a 96-well cell culture plate by 2500 cells/100 μl per well. The culture plate was incubated overnight under 5% $CO_2$ at 37° C. In day 2, 100 μl of culture solution comprising a compound was added in each well, and further incubated for 72 h under 5% $CO_2$ at 37° C.
6. The culture solution was sucked out;
7. 100 μl of serum-free culture solution containing 0.5 mg/ml MTT was added in each well, and incubated for 3 h;
8. The culture solution was carefully sucked out;
9. 100 μl of DMSO was added in each well and vibrated to dissolve;
10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD value of cells after normal growth in control wells without a compound;

n: OD value of cells after growth in test wells with s compound;

NC: Background OD value of blank wells without s compound and cells;

$IC_{50}$: Concentration of a compound where inhibition ratio was 50%. $IC_{50}$ values were fitted with Origin7.5.

TABLE 5

Growth Inhibition Activity ($IC_{50}$) of Some Compounds in Examples on A549 Cells

| Compounds | $IC_{50}$ (μM) | Compounds | $IC_{50}$ (μM) | Compounds | $IC_{50}$ (μM) |
|---|---|---|---|---|---|
| Example 4 | 1.25 | Example 5 | 1.3 | Example 7 | 3 |
| Example 8 | 1.7 | Example 9 | 1.7 | Example 10 | 2.3 |
| Example 11 | 1.6 | Example 12 | 2 | Example 13 | 1.1 |
| Example 14 | 1.5 | Example 15 | 3.9 | Example 16 | 3.4 |
| Example 17 | 2.4 | Example 19 | 2 | Example 21 | 0.9 |
| Example 153 | 6.4 | Example 138 | 1.5 | Example 139 | 0.6 |
| Example 140 | 1.6 | Example 141 | 0.8 | Example 142 | 1.5 |
| Example 143 | 1.5 | Example 144 | 1 | Example 145 | 6.7 |
| Example 146 | 7 | Example 150 | 3.8 | Example 151 | 3.7 |
| Example 174 | 3.7 | | | | |

Biological Example 4

LoVo Cell Growth Inhibition Test (MTT Assay)

I. Assay Materials

1. Cell strains: LoVo (human intestinal cancer cell strains);
2. MTT; antitumor compounds; DMSO.

II. Reagents and Consumable Materials

Culture medium: 90% RPMI-1640+10% FBS;

Pancreatin (0.25% (w/v) solution was formulated with PBS, and 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 2 ml of 0.25% pancreatin was added to infiltrate the cells for 1 min;

4. The pancreatin was sucked out. The culture plate was placed in an incubator. Digestion was carried out for about 4 min at 37° C.;

5. 4 ml of complete culture solution was added in the culture plate to stop the digestion. The cells were carefully scoured with micropipette (1 ml) to give a uniform cell suspension. The suspension was implanted into a 96-well cell culture plate by 3000-4000 cells/100 µl per well. The culture plate was incubated overnight under 5% $CO_2$ at 37° C. In day 2, 100 µl of culture solution comprising a compound was added into each well, and further incubated for 72 h under 5% $CO_2$ at 37° C.

6. The culture solution was sucked out;

7. 100 µl of serum-free culture solution containing 0.5 mg/ml MTT was added in each well, and incubated for 4 h;

8. The culture solution was carefully sucked out;

9. 100 µl of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD value of cells after normal growth in control wells without a compound;

n: OD value of cells after growth in test wells with a compound;

NC: Background OD value of blank wells without a compound and cells;

$IC_{50}$: Concentration of a compound where inhibition ratio was 50%. $IC_{50}$ values were fitted with Origin7.5.

TABLE 6

Growth Inhibition Activity ($IC_{50}$) of Some Compounds in Examples on LoVo Cells

| Compounds | $IC_{50}$ (µM) | Compounds | $IC_{50}$ (µM) | Compounds | $IC_{50}$ (µM) |
|---|---|---|---|---|---|
| Example 4 | 8.0 | Example 5 | 8.57 | Example 7 | 7.0 |
| Example 8 | 1.7 | Example 9 | 1.58 | Example 10 | 2.0 |
| Example 11 | 1.6 | Example 12 | 2.0 | Example 13 | 2.0 |
| Example 14 | 1.3 | Example 15 | 2.2 | Example 16 | 1.8 |
| Example 17 | 2.0 | Example 19 | 2.0 | Example 21 | 2.0 |
| Example 138 | 2.1 | Example 139 | 2.2 | Example 140 | 8.8 |
| Example 141 | 7.63 | Example 142 | 8.83 | Example 143 | 7.5 |
| Example 144 | 3.3 | Example 153 | 5.6 | Example 149 | 2.3 |
| Example 150 | 2.2 | Example 151 | 1.9 | Example 152 | 6.6 |

Biological Example 5

NCI-H460 Cell Growth Inhibition Test (MTT Assay)

I. Assay Materials

1. Cell strains: NCI-H460 (human large cell lung cancer cell strains);

2. MTT; antitumor compounds; DMSO

II. Reagents and Consumable Materials

Culture medium: 90% RPMI-1640+10% FBS;

Pancreatin (0.25% (w/v) solution was formulated with PBS, and 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 2 ml of 0.25% pancreatin was added to infiltrate the cells for 1 min;

4. The pancreatin was sucked out. The culture plate was placed in an incubator. Digestion was carried out for about 2 min at 37° C.;

5. 4 ml of complete culture solution was added to the culture plate to stop the digestion. The cells were carefully scoured with micropipette (1 ml) to give a uniform cell suspension. The suspension was implanted into a 96-well cell culture plate by 2500 cells/100 µl per well. The culture plate was incubated overnight under 5% $CO_2$ at 37° C. In day 2, 100 µl of culture solution comprising a compound was added in each well, and further incubated for 72 h under 5% $CO_2$ at 37° C.

6. The culture solution was sucked out;

7. 100 µl of serum-free culture solution containing 0.5 mg/ml MTT was added in each well, and incubated for 3 h;

8. The culture solution was carefully sucked out;

9. 100 µl of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD value of cells after normal growth in control wells without a compound;

n: OD value of cell after growth in test wells with a compound;

NC: Background OD values of blank wells without a compound and cells;

$IC_{50}$: Concentration of a compound where inhibition ratio was 50%. $IC_{50}$ values were fitted with Origin7.5.

TABLE 7

Growth Inhibition Activity ($IC_{50}$) of Some Compounds in Examples on NCI-H460 Cells

| Compounds | $IC_{50}$ (µM) | Compounds | $IC_{50}$ (µM) | Compounds | $IC_{50}$ (µM) |
|---|---|---|---|---|---|
| Example 4 | 1.6 | Example 5 | 1.2 | Example 7 | 0.94 |
| Example 8 | 1.2 | Example 9 | 1.7 | Example 10 | 1.7 |
| Example 11 | 1.5 | Example 12 | 0.97 | Example 13 | 1.8 |
| Example 14 | 0.94 | Example 15 | 1.4 | Example 16 | 1.1 |
| Example 17 | 1.5 | Example 19 | 1.1 | Example 21 | 2.7 |

TABLE 7-continued

Growth Inhibition Activity (IC$_{50}$) of Some
Compounds in Examples on NCI-H460 Cells

| Compounds | IC$_{50}$ (μM) | Compounds | IC$_{50}$ (μM) | Compounds | IC$_{50}$ (μM) |
|---|---|---|---|---|---|
| Example 174 | 3.0 | Example 46 | 4.0 | Example 138 | 2.2 |
| Example 140 | 1.1 | Example 141 | 2.9 | Example 142 | 1.04 |

Biological Example 6

NCI-N87 Cell Growth Inhibition Test (MTT Assay)

I. Assay Materials
 1. Cell strains: NCI-N87 (human gastric carcinoma cell strains);
 MTT; antitumor compounds; DMSO
II. Reagents and Consumable Materials
 Culture medium: 90% RPMI-1640+10% FBS;
 Pancreatin (0.25% (w/v) solution was formulated with PBS, and 0.53 mM of EDTA was added in the formulation);
 PBS;
 96-well culture plate
III. Assay Process
 1. A plate (10 cm) of cells in logarithmic growth phase normally cultured was collected;
 2. The culture solution was sucked out. The plate was washed with 5 ml of PBS 1-2 times;
 3. PBS was sucked out. 1.5 ml of 0.25% pancreatin was added to infiltrate the cells for 1 min;
 4. The pancreatin was sucked out. The culture plate was placed in an incubator. Digestion was carried out for about 12 min at 37° C.;
 5. 4.5 ml of complete culture solution was added to the culture plate to stop the digestion. The cells were carefully scoured with micropipette (1 ml) to give a uniform cell suspension. The suspension was implanted into a 96-well cell culture disc by 17000 cells/100 μl per well. The culture plate was incubated overnight under 5% CO$_2$ at 37° C. In day 2, 100 μl of culture solution comprising a compound was added in each well, and further incubated for 72 h under 5% CO$_2$ at 37° C.
 6. The culture solution was sucked out;
 7. 100 μl of serum-free culture solution containing 0.5 mg/ml MTT was added in each well, and incubated for 3 h;
 8. The culture solution was carefully sucked out;
 9. 100 μl of DMSO was added in each well and vibrated to dissolve;
 10. OD values were determined at 490 nM.
IV. Results and Treatments
 1. Calculation of Relative Inhibition Ratio
 The inhibition ratio of a compound on cell growth=(PC−n)/(PC−NC)×100%
 wherein:
 PC: OD value of cells after normal growth in control wellswithout a compound;
 n: OD value of cells after growth in test wellswith a compound;
 NC: Background OD value of blank wellswithout a compound and cells;
 IC$_{50}$: Concentration of a compound where inhibition ratio was 50%. IC$_{50}$ values were fitted with Origin7.5.

TABLE 8

Growth Inhibition Activity (IC$_{50}$) of Some
Compounds in Examples on NCI-N87 Cells

| Compounds | IC$_{50}$ (μM) | Compounds | IC$_{50}$ (μM) | Compounds | IC$_{50}$ (μM) |
|---|---|---|---|---|---|
| Example 4 | 0.079 | Example 5 | 0.022 | Example 7 | 0.113 |
| Example 8 | 0.0056 | Example 9 | 0.0086 | Example 10 | 0.011 |
| Example 11 | 0.011 | Example 12 | 0.0061 | Example 13 | 0.0044 |
| Example 153 | 0.015 | Example 15 | 0.0071 | Example 16 | 0.026 |
| Example 17 | 0.021 | Example 19 | 0.032 | Example 154 | 0.041 |
| Example 21 | 0.0068 | Example 138 | 0.0044 | Example 139 | 0.0072 |
| Example 140 | 0.015 | Example 141 | 0.032 | Example 142 | 0.075 |
| Example 143 | 0.089 | Example 144 | 0.098 | Example 145 | 0.346 |
| Example 146 | 0.189 | Example 149 | 0.111 | Example 150 | 0.0066 |
| Example 151 | 0.016 | Example 152 | 0.020 | | |

Biological Example 7

Sk-Br-3 Cell Growth Inhibition Test (SRB Assay)

I. Assay Materials
 1. Cell strains: Sk-Br-3 (human breast cancer cell strains);
 2. SRB: available from Sigmaaldrich, goods number: S9012, lot number: 047K3751. SRB was reserved at the room temperature. 0.4% (w/v) of working solution was formulated with 1% of glacial acetic acid. The solution was reserved at 4° C.; anti-tumor compounds; DMSO
II. Reagents and Consumable Materials
 Culture medium: 90% DMEM+10% FBS;
 Pancreatin (0.25% (w/v) solution was formulated with PBS, 0.53 mM of EDTA was added in the formulation);
 PBS;
 Tris;
 Glacial acetic acid;
 96-well culture plate
III. Assay Process
 1. A plate (10 cm) of cells in logarithmic growth phase normally cultured was collected. The culture solution was sucked out. The plate was washed with 5 mL of PBS 1-2 times;
 2. PBS was sucked out. 1.5 m of 0.25% pancreatin was added to infiltrate the cells for 30 s;
 3. The pancreatin was sucked out. The culture plate was placed in an incubator. Digestion was carried out for about 1.5-2 min at 37° C.;
 4. 4 mL of complete culture solution was added to the culture plate to stop the digestion. The cells were carefully scoured with micropipette (1 ml) to give a uniform single cell suspension;
 5. Cell suspension was counted. The suspension was diluted to 1×10$^5$/ml. The resulting suspension was developed uniformly on a plate by 10000 cells/100 μl per well. The culture plate was incubated overnight under 5% CO$_2$ at 37° C. In day 2, 100 μl of culture solution comprising a compound was added in each well, and further incubated for 91 h under 5% CO$_2$ at 37° C.
 6. The culture solution was sucked out. 100 uL of TCA fixed cells which were diluted to 10% were added to each well. The plate was kept in a refrigerator for 1 h at 4° C.
 7. TCA stationary liquid was sucked out. Each well was washed with 150 μL of ddH$_2$O five times;
 8. After the stationary liquid was cleansed, the plate was dried in the air at the room temperature;
 9. 60 μL of SRB staining solution was added in each well. The well was stained for 15 min at the room temperature;

10. The SRB staining solution was sucked out. Each well was washed with 150 μL of 1% glacial acetic acid five times;

11. After the SRB staining solution was cleansed, the plate was dried in the air at the room temperature;

12. 100 μL of 10 mM Tris was added in each well. The plate was vibrated to dissolve out SRB;

13. OD values were determined at 570 nM.

IV. Results and Treatments

1. Calculation of Relative Inhibition Ratio

To: OD values of the starting content of cells when the cells were developed on a plate;

PC: OD values of cells after normal growth in control wells without a compound;

Ti: OD values of cells after growth in test wells with a compound;

NC: Background OD values of blank well without a compound and cells (1) If Ti>To, it shows that cells still grow after a compound was added.

Therefore:

Ratio of cells in test wells to normal wells (% of control cell growth)
=(Ti−To)/(PC−To)×100%

Ratio $GI_{50}$ was concentration of a compound at the point of 50%.

(2) If Ti<To, it shows that cells gradually die after a compound was added.

Therefore:

Ratio of killed cells to inoculated cells (% of killed cells)
=(Ti−To)/(To−NC)×100%

$LC_{50}$ was concentration point of a compound when half of the starting inoculated concentration was reached.

(3) If Ti=To, it shows that in the presence of a compound, both growth and death of cells tended to balance. Concentration of a compound at this point is defined as TGI (total growth inhibition).

TABLE 9

Growth Inhibition Activity ($GI_{50}$) of Some Compounds in Examples on Sk-Br-3 Cells

| Compounds | $GI_{50}$ (μM) | Compounds | $GI_{50}$ (μM) | Compounds | $GI_{50}$ (μM) |
|---|---|---|---|---|---|
| Example 4 | 0.148 | Example 5 | 0.024 | Example 7 | 0.213 |
| Example 9 | 0.015 | Example 10 | 0.006 | Example 14 | 0.924 |
| Example 16 | 0.036 | Example 17 | 0.007 | Example 19 | 0.063 |
| Example 21 | 0.0041 | Example 154 | 0.038 | Example 138 | 0.0038 |
| Example 139 | 0.0052 | Example 140 | 0.022 | Example 141 | 0.039 |
| Example 142 | 0.117 | Example 143 | 0.231 | Example 144 | 0.202 |
| Example 145 | 0.831 | Example 146 | 0.823 | Example 149 | 0.644 |
| Example 150 | 0.011 | Example 151 | 0.017 | Example 152 | 0.019 |
| Example 153 | 0.0068 | | | | |

Biological Example 8

SW620 Cell Growth Inhibition Test (SRB Assay)

I. Assay Materials

Cell strains: SW620 (human colorectal cancer cell strains);

SRB: available from Sigmaaldrich, goods number: S9012, lot number: 047K3751. RT was reserved at the room temperature. 0.4% (w/v) of working solution was formulated with 1% of glacial acetic acid. The solution was reserved at 4° C.; anti-tumor compounds; DMSO.

II. Reagents and Consumable Materials

Culture medium: 90% L15+10% FBS;

Pancreatin (0.25% (w/v) solution was formulated with PBS, 0.53 mM of EDTA was added in the formulation);

PBS;

Tris;

Glacial acetic acid;

96-well culture plate

III. Assay Process

1. A plate (10 cm) of cells in logarithmic growth phase normally cultured was collected. The culture solution was sucked out. The plate was washed with 5 mL of PBS 1-2 times;

2. PBS was sucked out. 1.5 m of 0.25% pancreatin was added to infiltrate the cells for 30 s;

3. The pancreatin was sucked out. The culture plate was placed in an incubator. Digestion was carried out for about 1.5-2 min at 37° C.;

4. 4 mL of complete culture solution was added to the culture plate to stop the digestion. The cells were carefully scoured with micropipette (1 ml) to give a uniform single cell suspension;

5. Cell suspension was counted. The suspension was diluted to $1.5 \times 10^5$/ml. The resulting suspension was developed uniformly on a plate by 15000 cells/100 μl per well. The culture plate was incubated overnight under 5% $CO_2$ at 37° C. In day 2, 100 μl of culture solution comprising a compound was added in each well, and further incubated for 91 h under 5% $CO_2$ at 37° C.;

6. The culture solution was sucked out. 100 uL of TCA fixed cells which were diluted to 10% were added to each well. The plate was kept in a refrigerator for 1 h at 4° C.

7. TCA stationary liquid was sucked out. Each well was washed with 150 μL of $ddH_2O$ five times;

8. After the stationary liquid was cleansed, the plate was dried in the air at the room temperature;

9. 60 μL of SRB staining solution was added in each well. The well was stained for 15 min at the room temperature;

10. The SRB staining solution was sucked out. Each well was washed with 150 μL of 1% glacial acetic acid five times;

11. After the SRB staining solution was cleansed, the plate was dried in the air at the room temperature;

12. 100 μL of 10 mM Tris was added in each well, the plate was vibrated to dissolve out SRB;

13. OD values were determined at 570 nM.

IV. Results and Treatments

1. Calculation of Relative Inhibition Ratio

To: OD values of the starting content of cells when the cells were developed on a plate;

PC: OD values of cells after normal growth in control wells without a compound;

Ti: OD values of cells after growth in test wells with a compound;

NC: Background OD values of blank wells without a compound and cells (1) If Ti>To, it shows that cells still grow after a compound was added.

Therefore:

Ratio of cells in test wells to normal wells (% of control cell growth)
=(Ti−To)/(PC−To)×100%

Ratio $GI_{50}$ was concentration of a compound at the point of 50%.

(2) If Ti<To, it shows that cells gradually die after a compound was added.

Therefore:

Ratio of killed cells to inoculated cells (% of killed cell)
=(Ti−To)/(To−NC)×100%

$LC_{50}$ was concentration point of a compound when half of the starting inoculated concentration was reached.

(3) If Ti=To, it shows that in the presence of a compound, both growth and death of cells tended to balance. Concentration of a compound at this point is defined as TGI (total growth inhibition).

TABLE 10

Growth Inhibition Activity ($GI_{50}$) of Some Compounds in Examples on SW620 Cells

| Compounds | $GI_{50}$ (μM) | Compounds | $GI_{50}$ (μM) | Compounds | $GI_{50}$ (μM) |
|---|---|---|---|---|---|
| Example 4 | 3.5 | Example 5 | 1.68 | Example 9 | 2.1 |
| Example 21 | 1.78 | Example 138 | 1.78 | Example 139 | 1.9 |
| Example 140 | 2.3 | Example 141 | 1.4 | Example 142 | 2.3 |

Biological Example 9

CCRF-CEM/T Cell Growth Inhibition Test (MTT Assay)

I. Assay Materials

Cell strains: CCRF-CEM/T (human acute lymphocytic cell leukemia cells);

MTT; antitumor compounds; DMSO

II. Reagents and Consumable Materials

Culture medium: 90% RPMI-1640+10% FBS;

PBS;

96-well cell culture plate;

triple lysate solution: 10% SDS, 5% isobutanol, 0.012M HCl.

III. Assay Process

1. Cells were cultured to exponential phase. The cells were suspension cells;

2. The cells were collected by centrifuge. The resulting cells were resuspended in a complete culture medium to a desired concentration. The cells suspension was implanted into a 96-well cell culture plate by 20000 cells per well. A compound was added in the wellsuch that the final volume of the system was 120 al. The system was further incubated for 72 h under 5% $CO_2$ at 37° C.

7. 30 μl of serum-free culture solution containing 2.5 mg/ml MTT was added in each well, and incubated for 3 h;

8. 150 μl of triple lysate solution was added in each well and placed to dissolve at the room temperature;

9. OD values were determined at 570 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells;

$IC_{50}$: Concentration of a compound where inhibition ratio was 50%. $IC_{50}$ values were fitted with Origin7.5.

TABLE 11

Growth Inhibition Activity ($IC_{50}$) of Some Compounds in Examples on CCRF-CEM/T Cells

| Compounds | $IC_{50}$ (μM) | Compounds | $IC_{50}$ (μM) | Compounds | $IC_{50}$ (μM) |
|---|---|---|---|---|---|
| Example 2 | 1.8 | Example 4 | 5.8 | Example 5 | 9 |
| Example 158 | 1.1 | Example 138 | 5.6 | Example 139 | 1.4 |
| Example 140 | 7.9 | Example 141 | 9.1 | Example 142 | 6.6 |
| Example 150 | 3.76 | Example 151 | 3.6 | | |

Biological Example 10

Fadu Cell Growth Inhibition Test (MTT Assay)

I. Assay Materials

Cell strains: Fudu (human head and neck cancer cell strains);

MTT; antitumor compounds; DMSO

II. Reagents and Consumable Materials

Culture medium: 90% EMEM+10% FBS;

Pancreatin (0.25% (w/v) solution was formulated with PBS, 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 1.5 ml of 0.25% pancreatin was added to infiltrate the cells for 1 min;

4. The pancreatin was sucked out. The culture plate was placed in an incubator. Digestion was carried out for about 5 min at 37° C.;

5. 4.5 ml of complete culture solution was added to the culture plate to stop the digestion. The cells were carefully scoured with micropipette (1 ml) to give a uniform cell suspension. The suspension was implanted into a 96-well cell culture plate by 6000 cells/100 μl per well. The culture plate was incubated overnight under 5% $CO_2$ at 37° C. In day 2, 100 μl of culture solution comprising a compound was added in each well, and further incubated for 72 h under 5% $CO_2$ at 37° C.

6. The culture solution was sucked out;

7. 100 μl of serum-free culture solution containing 0.5 mg/ml MTT was added in each well, and incubated for 3 h;

8. The culture solution was carefully sucked out;

9. 100 μl of DMSO was added in each welland vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without s compound and cells;

$IC_{50}$: Concentration of a compound where inhibition ratio was 50%. $IC_{50}$ values were fitted with Origin7.5.

TABLE 12

Growth Inhibition Activity (IC$_{50}$) of Somes Compounds in Examples on Fadu Cells

| Compounds | IC$_{50}$ (μM) | Compounds | IC$_{50}$ (μM) | Compounds | IC$_{50}$ (μM) |
|---|---|---|---|---|---|
| Example 2 | 149 | Example 4 | 331 | Example 143 | 127 |
| Example 7 | 474 | Example 8 | 188 | Example 9 | 219 |
| Example 11 | 187 | Example 12 | 202 | Example 13 | 300 |
| Example 15 | 260 | Example 138 | 101 | Example 139 | 201 |
| Example 144 | 103 | Example 145 | 194 | Example 146 | 200 |
| Example 149 | 163 | Example 150 | 207 | Example 151 | 244 |
| Example 152 | 170 | Example 153 | 231 | Example 154 | 324 |
| Example 142 | 115 | Example 158 | 119 | | |

Biological Example 11

BxPc-3 Cell Growth Inhibition Test (MTT Assay)

I. Assay Materials

Cell strains: BxPC-3 (human pancreatic cancer cell strains);

MTT; antitumor compounds; DMSO

II. Reagents and Consumable Materials

Culture medium: 90% RPMI-1640+10% FBS;

Pancreatin (0.25% (w/v) solution was formulated with PBS, 0.53 mM of EDTA was added in the formulation);

PBS;

96-well culture plate

III. Assay Process

1. A plate (10 cm) of cells in logarithmic growth phase normally cultured was collected;

2. The culture solution was sucked out. was added into The plate was washed with 5 ml of PBS 1-2 times;

3. PBS was sucked out. 1.5 ml of 0.25% pancreatin was added to infiltrate the cells for 1 min;

4. The pancreatin was sucked out. The culture plate was placed in an incubator. Digestion was carried out for about 5 min at 37° C.;

5. 4.5 ml of complete culture solution was added to the culture plate to stop the digestion. The cells were carefully scoured with micropipette (1 ml) to give a uniform cell suspension. The suspension was implanted into a 96-well cell culture plate by 5000 cells/100 μl per well. The culture plate was incubated overnight under 5% CO$_2$ at 37° C. In day 2, 100 μl of culture solution comprising a compound was added in each well, and further incubated for 72 h under 5% CO$_2$ at 37° C.

6. The culture solution was sucked out;

7. 100 μl of serum-free culture solution containing 0.5 mg/ml MTT was added in each well, and incubated for 3 h;

8. The culture solution was carefully sucked out;

9. 100 μl of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells;

IC$_{50}$: Concentration of a compound where inhibition ratio was 50%. IC$_{50}$ values were fitted with Origin7.5.

TABLE 13

Growth Inhibition Activity (IC$_{50}$) of Some Compounds in Examples on BxPc-3 Cells

| Compounds | IC$_{50}$ (μM) | Compounds | IC$_{50}$ (μM) | Compounds | IC$_{50}$ (μM) |
|---|---|---|---|---|---|
| Example 131 | 306 | Example 138 | 337 | Example 139 | 188 |
| Example 142 | 416 | | | | |

Biological Example 12

AsPC-1 Cell Growth Inhibition Test (MTT Assay)

I. Assay Materials

Cell strains: AsPC-1 (human pancreatic cancer cell strains);

MTT; antitumor compounds; DMSO

II. Reagents and Consumable Materials

Culture medium: 90% RPMI-1640+10% FBS;

Pancreatin (0.25% (w/v) solution was formulated with PBS, 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 1.5 ml of 0.25% pancreatin was added to infiltrate the cells for 1 min;

4. The pancreatin was sucked out. The culture plate was placed in an incubator. Digestion was carried out for about 7.5 min at 37° C.;

5. 4.5 ml of complete culture solution was added to the culture plate to stop the digestion. The cells were carefully scoured with micropipette (1 ml) to give a uniform cell suspension. The suspension was implanted into a 96-well cell culture plate by 8000 cells/100 μl per well. The culture plate was incubated overnight under 5% CO$_2$ at 37° C. In day 2, 100 μl of culture solution comprising a compound was added in each well, and further incubated for 72 h under 5% CO$_2$ at 37° C.

6. The culture solution was sucked out;

7. 100 μl of serum-free culture solution containing 0.5 mg/ml MTT was added in each well, and incubated for 3 h;

8. The culture solution was carefully sucked out;

9. 100 μl of DMSO was added in each welland vibrated to dissolve;

10. OD values were determined at 490 nM.

IV Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells;

IC$_{50}$: Concentration of a compound where inhibition ratio was 50%. IC$_{50}$ values were fitted with Origin7.5.

TABLE 14

Growth Inhibition Activity (IC$_{50}$) of Some Compounds in Examples on AsPC-1 Cells

| Compounds | IC$_{50}$ (µM) | Compounds | IC$_{50}$ (µM) | Compounds | IC$_{50}$ (µM) |
|---|---|---|---|---|---|
| Example 2 | 0.77 | Example 4 | 1 | Example 142 | 1.5 |
| Example 150 | 0.895 | Example 8 | 0.878 | Example 9 | 0.458 |
| Example 11 | 1.2 | Example 12 | 1.2 | Example 13 | 0.922 |
| Example 14 | 1.4 | Example 15 | 1.1 | Example 16 | 0.81 |
| Example 17 | 1 | Example 19 | 0.621 | Example 10 | 1 |
| Example 138 | 1 | Example 139 | 0.422 | | |
| Example 151 | 0.81 | Example 158 | 0.44 | | |

Biological Example 13

SK-OV-3 Cell Growth Inhibition Test (MTT Assay)

I. Assay Materials

Cell strains: SK-OV-3 (human ovarian cancer cell strains);

MTT; antitumor compounds; DMSO.

II. Reagents and Consumable Materials

Culture medium: 90% McCoy's 5A+10% FBS;

Pancreatin (0.25% (w/v) solution was formulated with PBS, 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 1.5 ml of 0.25% pancreatin was added to infiltrate the cells for 1 min;

4. The pancreatin was sucked out. The culture plate was placed in an incubator. Digestion was carried out for about 5 min at 37° C.;

5. 4.5 ml of complete culture solution was added to the culture plate to stop the digestion. T the cells were carefully scoured with micropipette (1 ml) to give a uniform cell suspension. The suspension was implanted into a 96-well cell culture disc by 4000 cells/100 µl per well. The culture plate was incubated overnight under 5% CO$_2$ at 37° C. In day 2, 100 µl of culture solution comprising a compound was added in each well, and further incubated for 72 h under 5% CO$_2$ at 37° C.

6. The culture solution was sucked out;

7. 100 µl of serum-free culture solution containing 0.5 mg/ml MTT was added in each well, and incubated for 3 h;

8. The culture solution was carefully sucked out;

9. 100 µl of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wellswith a compound;

NC: Background OD values of blank wells without a compound and cells;

IC$_{50}$: Concentration of a compound where inhibition ratio was 50%. IC$_{50}$ values were fitted with Origin7.5.

TABLE 15

Growth Inhibition Activity (IC$_{50}$) of Some Compounds in Examples on SK-OV-3 Cells

| Compounds | IC$_{50}$ (µM) | Compounds | IC$_{50}$ (µM) | Compounds | IC$_{50}$ (µM) |
|---|---|---|---|---|---|
| Example 2 | 331 | Example 4 | 409 | Example 5 | 195 |
| Example 9 | 469 | Example 138 | 457 | Example 139 | 371 |
| Example 140 | 286 | Example 141 | 283 | Example 142 | 553 |
| Example 189 | 312 | | | | |

Biological Example 14

NCI-H358 Cell Growth Inhibition Test (MTT Assay)

I. Assay Materials

Cell strains: NCI-H358 (human non-small cell lung cancer cell strains);

MTT; antitumor compounds; DMSO

II. Reagents and Consumable Materials

Culture medium: 90% RPMI-1640+10% FBS;

Pancreatin (0.25% (w/v) solution was formulated with PBS, 0.53 mM of EDTA was added in the formulation);

PBS;

96-well culture plate

III. Assay Process

1. A plate (10 cm) of cells in logarithmic growth phase normally cultured was collected;

2. The culture solution was sucked out. The plate was washed with 5 ml of PBS 1-2 times;

3. PBS was sucked out. 1.5 ml of 0.25% pancreatin was added to infiltrate the cells for 1 min;

4. The culture plate was placed in an incubator. Digestion was carried out for about 5 min at 37° C.;

5. 3 ml of complete culture solution was added to the culture plate to stop the digestion. The cells were carefully scoured with micropipette (1 ml) to give a uniform cell suspension. The suspension was implanted into a 96-well cell culture plate by 10000 cells/100 µl per well. The culture plate was incubated overnight under 5% CO$_2$ at 37° C. In day 2, 100 µl of culture solution comprising a compound was added in each well, and further incubated for 72 h under 5% CO$_2$ at 37° C.

6. The culture solution was sucked out;

7. 100 µl of serum-free culture solution containing 0.5 mg/ml MTT was added in each well, and incubated for 3 h;

8. The culture solution was carefully sucked out;

9. 100 µl of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells;

$IC_{50}$: Concentration of a compound where inhibition ratio was 50%. $IC_{50}$ values were fitted with Origin7.5.

TABLE 16

Growth Inhibition Activity ($IC_{50}$) of Some Compounds in Examples on NCI-H358 Cells

| Compounds | $IC_{50}$ (μM) | Compounds | $IC_{50}$ (μM) | Compounds | $IC_{50}$ (μM) |
|---|---|---|---|---|---|
| Example 138 | 54 | Example 153 | 78 | Example 188 | 110 |

Biological Example 15

NCI-H1650 Cell Growth Inhibition Test (SRB Assay)

I. Assay Materials
1. Cell strains: NCI-H1650 (human non-small cell lung cancer cell strains);
2. SRB, 0.4% (w/v) working solution was formulated with 1% glacial acetic acid and reserved at 4° C.; antitumor compounds; DMSO II. Reagents and Consumable Materials
Culture medium: 90% RPMI1640+10% FBS;
Pancreatin (0.25% (w/v) solution was formulated with PBS, 0.53 mM of EDTA was added in the formulation);
PBS;
Tris;
Glacial acetic acid;
96-well culture plate III. Assay Process
1. A plate (10 cm) of cells in logarithmic growth phase normally cultured was collected;
2. The culture solution was sucked out. The plate was washed with 5 mL of PBS 1-2 times;
3. 1.5 mL of 0.25% pancreatin was added to the plate to infiltrate the cells;
4. The pancreatin was sucked out. The culture plate was placed in an incubator. Digestion was carried out for about 3 min at 37° C.;
5. 4 mL of complete culture solution was added to the culture plate to stop the digestion. The cells were carefully scoured with micropipette (1 ml) to give a uniform single cell suspension. The suspensin was implanted into a 96-well cell culture plate by 6000 cells/100 μl per well. The culture plate was incubated overnight under 5% $CO_2$ at 37° C. In day 2, 100 μl of culture solution comprising a compound was added in each well, and further incubated for 72 h under 5% $CO_2$ at 37° C.;
6. The culture solution was sucked out. 100 uL of TCA fixed cells which were diluted to 10% were added to each well. The plate was kept in a refrigerator for 1 h at 4° C.
7. TCA stationary liquid was sucked out. Each well was washed with 150 μL of dd$H_2O$ five times;
8. After the stationary liquid was cleansed, the plate was dried in the air at the room temperature;
9. 60 μL of SRB staining solution was added in each well. The well was stained for 15 min at the room temperature;
10. The SRB staining solution was sucked out. Each well was washed with 150 μL of 1% glacial acetic acid five times;
11. After the SRB staining solution was cleansed, the plate was dried in the air at the room temperature; 12. 100 μL of 10 mM Tris was added in each well, the plate was vibrated to dissolve out SRB;
13. OD values were determined at 570 nM.

IV. Results and Treatments
1. Calculation of Relative Inhibition Ratio
The inhibition ratio of a compound on cell growth=(PC−n)/(PC−NC)×100%
wherein:
PC: OD values of cells after normal growth in control wells without a compound;
n: OD values of cells after growth in test wells with a compound;
NC: Background OD values of blank wells without a compound and cells;
$IC_{50}$: Concentration of a compound where inhibition ratio was 50%. $IC_{50}$ values were fitted with Origin7.5.

TABLE 17

Growth Inhibition Activity ($IC_{50}$) of Some Compounds in Examples on NCI-H1650 Cells

| Compounds | $IC_{50}$ (μM) | Compounds | $IC_{50}$ (μM) | Compounds | $IC_{50}$ (μM) |
|---|---|---|---|---|---|
| Example 9 | 636 | Example 138 | 1100 | Example 139 | 1130 |
| Example 3 | 819 | Example 158 | 760 | | |

Biological Example 16

MDA-MB-453 Cell Growth Inhibition Test (SRB Assay)

I. Assay Materials
Cell strains: MDA-MB-453 (human breast cancer cell strains);
SRB: 0.4% (w/v) working solution was formulated with 1% glacial acetic acid, reserved at 4° C.; antitumor compounds; DMSO II. Reagents and Consumable Materials
Culture medium: 90% L15+10% FBS;
pancreatin (0.25% (w/v) solution was formulated with PBS, 0.53 mM of EDTA was added in the formulation);
PBS;
96-well culture plate III. Assay Process
1. A plate (10 cm) of cells in logarithmic growth phase normally cultured was collected;
2. The culture solution was sucked out. The plate was washed with 5 mL of PBS 1-2 times;
3. 1.5 mL of 0.25% pancreatin was added to the plate to infiltrate the cells;
4. The pancreatin was sucked out. The culture plate was placed in an incubator. Digestion was carried out for about 3 min at 37° C.;
5. 4 mL of complete culture solution was added to the culture plate to stop the digestion. The cells were carefully scoured with micropipette (1 ml) to give a uniform single cell suspension. The suspension was implanted into a 96-well cell culture plate by 7000 cells/100 μl per well. The culture plate was incubated overnight under 5% $CO_2$ at 37° C. In day 2, 100 μl of culture solution comprising a compound was added in each well, and further incubated for 72 h under 5% $CO_2$ at 37° C.;
6. The culture solution was sucked out. 100 uL of TCA fixed cells which were diluted to 10% were added to each well. The plate was kept in a refrigerator for 1 h at 4° C.
7. TCA stationary liquid was sucked out. Each well was washed with 150 μL of dd$H_2O$ five times;

8. After the stationary liquid was cleansed, the plate was dried in the air at the room temperature;

9. 60 μL of SRB staining solution was added in each well. The well was stained for 15 min at the room temperature;

10. The SRB staining solution was sucked out. Each well was washed with 150 μL of 1% glacial acetic acid five times;

11. After the SRB staining solution was cleansed, the plate was dried in the air at the room temperature;

12. 100 μL of 10 mM Tris was added in each well. The plate was vibrated to dissolve out SRB;

13. OD values were determined at 570 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells;

$IC_{50}$: Concentration of a compound where inhibition ratio was 50%. $IC_{50}$ values were fitted with Origin7.5.

TABLE 18

Growth Inhibition Activity ($IC_{50}$) or Some Compounds in Examples on MDA-MB-453 Cells

| Compounds | $IC_{50}$ (μM) | Compounds | $IC_{50}$ (μM) |
|---|---|---|---|
| Example 5 | 505 | Example 189 | 523 |

Biological Example 17

Inhibition Test on EGFR-TK

I. Operation Procedures 1. 2 mg/ml of PGT was diluted with PBS to 0.2 mg/ml. The resulting solution was added into elisa plate by 50 μl per well. The plate was placed in a refrigerator at 4° C. and coated overnight.

2. The coating solution was discarded to stop coating. The plate was washed three times with PBS, and then beaten to dryness.

3. The elisa plate was placed in a refrigerator at 4° C., drained out and stood for 2 h.

4. The mother liquid of aqueous solution of each compound was diluted with double distilled water to four folds, i.e. a desirable concentration. Then, the compound was diluted and added in the corresponding elisa well by 25 μl/well.

5. 4 nM of ATP solution was diluted with double distilled water to 50 folds and then sufficiently mixed. The resulting solution was separately added in each elisa well by 25 μl per well (except for the negative control).

6. EGFR kinase was diluted with 2×TKB to 800 folds. The solution was added in elisa well with 50 μl per well. Then, the enzyme reaction began. The elisa plate was immediately placed on a micro-oscillator and shaked to react for 20 min at the room temperature.

7. 2% of SDS was added in the elisa well to stop the reaction by adding 100 μl of SDS into each well. The solution was sufficiently mixed on the micro-oscillator to sufficiently mix for about 5 min.

8. The reaction solution was sucked out. The plate was washed four times with PBST. After the plate was beaten to dryness, 0.25 μg/ml of mice anti-phosphorylation tyrosine-HRP antibody which was diluted with blocking solution (3% solution of BSA in PBST) was added in the plate by 100 μl per well. The mixture was reacted for 30 min at the room temperature.

9. The antibody reaction solution was sucked out. The plate was washed four times with PBST. After the plate was beated to dryness, TMB peroxidase substrate was added to the plate by 100 μl/well. The mixture reacted in the dark for 15 min at the room temperature.

10. 100 μl of 2N $H_2SO_4$ was added in the plate to stop chromogenic reaction. After the bubbles were cleansed, OD values were determined in ELIASA at 450 nm.

11. Formula for calculating inhibition percentage:

$$\text{Inhibition \%} = 100 - \frac{\text{Reading of Infrared Reader (Drug)}}{\text{Reading of Infrared Reader (Blank)}} \times 100$$

$EC_{50}$ values of some compounds were given in Table 1.

TABLE 19

Inhibition Activity ($EC_{50}$) of Some Compounds in Examples on EGFR-TK phosphorylation

| Compounds | $EC_{50}$ (μM) | Compounds | $EC_{50}$ (μM) | Compounds | $EC_{50}$ (μM) |
|---|---|---|---|---|---|
| Example 4 | 42 | Example 5 | 44 | Example 9 | 135 |
| Example 46 | 25 | Example 138 | 110 | Example 21 | 154 |

Biological Example 18

Inhibition Activity Assay on Her2 Enzyme

I. Assay Materials

1. Her2 kinase, Cell Signaling Tech, #7382, Lot. 2, reserved at −80° C.;

2. Elisa plate, Nunc Maxisorp, 442404;

3. Test compounds and control compounds were prepared by applicants;

II. Assay Reagemts

1. PBS: 8 g/L NaCl, 0.2 g/L KCl, 2.9 g/L $Na_2HPO_4$ $12H_2O$, 0.2 g/L $KH_2PO_4$;

2. PBST: PBS+0.05% (v/v) Tween 20;

3. Confining liquid: 3% of BSA in PBS; 4. HEPEs buffer (2×): 50 mM HEPEs, 20 mM $MgCl_2$, 0.1 mM $MnCl_2$, 0.2 mM $Na_3VO_4$, adjusted to pH of 7.4 with NaOH;

5. PGT, Sigma, Cat#P0275): 2 mg/ml of stock solution was prepared by dissolving PBS, reserved at −20° C.

6. ATP: 4 nM of stock solution was prepared by dissolving dd$H_2O$, reserved at −20° C.;

7. Mice anti-phosphorylation tyrosine-HRP: Invitrogen-037720, 0.5 mg/ml, reserved at 4° C.;

8. TMB: Cell Signaling Tech, Cat #7004L;

9. DTT: 2.5 M of stock solution was prepared with dd$H_2O$, reserved at −20° C. Before use, 2×HEPEs buffer was added in the solution to the final concentration of 1.25 mM.

III. Assay Equipment

1. ELIASA, Bio-Rad, Model-680;

2. Plate washer, Bio-Rad, Model-1575;

3. 4° C. refrigerator, Frestech, Model-BCD-213KC;

4. Micro oscillator, Shanghai Yarong Biochemisty Instrument Plant, Model MM-I;
5. −80° C. refrigerator, Haier, Model DW-86L386.

IV. Assay Process 1. 2 mg/ml of PGT was diluted with PBS to 0.2 mg/ml. 60 µl of the resulting solution was added in each well. The elisa plate was placed in a refrigerator at 4° C. and coated overnight;
2. The coating solution was discarded to stop the coating. The plate was washed four times with PBS, and then beaten to dryness;
3. The elisa plate was placed in a refrigerator at 4° C., drained out and stood for 3 h.
4. 2 nM of aqueous solution of each compound was diluted with ddH$_2$O to a desirable concentration. Then, the solution was added in the corresponding elisa well by 25 µl/well;
5. 2 nM of ATP solution was diluted with ddH$_2$O to 25 folds and then sufficiently mixed. The resulting solution was separately added in each elisa well by 25 µl per well (25 µl ddH$_2$O was added in the negative control);
6. Her2 kinase was diluted with 2×TKB to 800 folds. The resulting solution was added in the elisa well by 50 µl per well. Then, the enzyme reaction began. Moreover, the elisa plate was immediately placed in a micro-oscillator. The reaction is carried out for 8 min at the temperature of 4° C.;
7. 2% of SDS was added in the elisa well to stop the reaction by adding 100 µl of SDS in each well. The solution was sufficiently mixed on the micro-oscillator to sufficiently mix for about 5 min;
8. The reaction solution was sucked out. The plate was washed four times with PBST. After the plate was beaten to dryness, 0.25 µg/ml of mice anti-phosphorylation tyrosine-HRP which was diluted with confining liquid was added in the plate by 100 µl per well, and then reacted for 30 min at the room temperature.
9. The antibody reaction solution was sucked out. The plate was washed six times with PBST. After the plate was beaten to dryness, TMB peroxidase substrate was added in the plate with 100 al/well, and then reacted in the dark for 15 min at the room temperature;
10. 100 µl of 2N H$_2$SO$_4$ was added in the solution to stop the chromogenic reaction. After the bubbles were cleansed, the solution was measured in elisa at 450 nm.

V. Data Processing Method

OD values were converted in relative inhibition ratios according to following formula:

Relative inhibition ratio=[1−(experiment values−NC mean values)/(PC mean values−NC mean values)]×100% wherein:
PC: Group of cells that grow normally in control wells without a compound;
NC: Blank group without a compound and cells.
The inhibition activity of some compounds on Her-2 were measured as given in Table 2.

TABLE 20

Inhibition Activity (EC$_{50}$) of Some Compounds in Examples on Her-2

| Compounds | EC$_{50}$ (µM) | Compounds | EC$_{50}$ (µM) | Compounds | EC$_{50}$ (µM) |
|---|---|---|---|---|---|
| Example 4 | 161 | Example 5 | 96 | Example 9 | 221 |
| Example 21 | 234 | Example 42 | 291 | Example 138 | 244 |
| Example 140 | 110 | | | | |

In view of the above, the compounds of the invention have excellent inhibition activity on receptor tyrosine kinase, especially erbB family, more specially EGFR and Her 2.

All the patents, patent application publications, patent applications and non-patent publications cited in the present description are incorporated herein by reference in their entirety.

From the forging, it will be appreciated, although specific embodiments of the present invention have been described herein for purposes of illustration, various modifications may be made without deviating from the spirit and scope of the present invention. Therefore, the scope of the present invention is only defined by the pending claims.

What is claimed is:

1. A method for treating tumor in a mammal, comprising administering to the mammal a therapeutically effective amount of a compound of formula I, a stereoisomer thereof, a tautomer thereof, or a mixture thereof, or a pharmaceutically acceptable salt thereof,

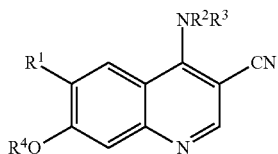

wherein:
R$^1$ is selected from the group consisting of substituted or unsubstituted alkenylacylamino and substituted or unsubstituted alkynylacylamino;
R$^2$ and R$^3$ are each independently selected from the group consisting of hydrogen, substituted or unsubstituted aralkyl, substituted or unsubstituted aryl, and substituted or unsubstituted heteroaryl; wherein R$^2$ and R$^3$ are not both hydrogen;
or R$^2$ and R$^3$ together with nitrogen atom to which they are attached form substituted or unsubstituted heterocyclyl; and
R$^4$ is substituted or unsubstituted heterocyclyl or substituted or unsubstituted heteroaryl;
wherein the tumor is selected from the group consisting of sarcoma; sinus tumor; urogenital system cancer; esophageal cancer; liver cancer; kidney cancer; endocrine cancer; skin cancer; melanoma; and brain or central nervous system cancer.

2. The method of claim 1, wherein R$^4$ is tetrahydrofuranyl.

3. The method of claim 1,
wherein:
R$^1$ is selected from the group consisting of C$_2$-C$_6$ alkenylacylamino and C$_2$-C$_6$ alkynylacylamino; and
one of R$^2$ and R$^3$ is H, while the other one is selected from the group consisting of C$_7$-C$_{24}$ aralkyl, C$_6$-C$_{18}$ aryl, and C$_5$-C$_{18}$ heteroaryl, wherein the aryl is optionally substituted with a substituent selected from the group consisting of C$_2$-C$_6$ alkynyl, halogen, C$_7$-C$_{24}$ aralkyloxy, C$_6$-C$_{24}$ heteroaralkyloxy, C$_6$-C$_{18}$ aryloxy and C$_5$-C$_{18}$ heteroaryloxy, and wherein the heteroaryl is optionally substituted with a substituent selected from the group consisting of C$_7$-C$_{24}$ aralkyl, C$_6$-C$_{18}$ arylacylamino, C$_6$-C$_{18}$ arylsulfonylamino, C$_5$-C$_{18}$ heteroarylacylamino, C$_3$-C$_{10}$ cycloalkylacylamino, C$_6$-C$_{18}$ arylaminoacyl, $C_7$-$C_{24}$ aralkyloxy, $C_6$-$C_{24}$ heteroaralkyloxy and $C_6$-$C_{18}$ aryloxy.

4. The method of claim 1, wherein:

$R^1$ is $C_2$-$C_6$ alkenylacylamino; and one of $R^2$ and $R^3$ is H, while the other one is selected from the group consisting of $C_7$-$C_{24}$ aralkyl, and $C_6$-$C_{18}$ aryl, wherein the aryl is optionally substituted with a substituent selected from the group consisting of $C_2$-$C_6$ alkynyl, halogen, $C_7$-$C_{24}$ aralkyloxy, $C_6$-$C_{18}$ aryloxy, $C_5$-$C_{18}$ heteroaryloxy, and $C_6$-$C_{24}$ heteroaralkyloxy.

5. The method of claim 1, wherein:

$R^1$ is $C_2$-$C_6$ alkenylacylamino; and one of $R^2$ and $R^3$ is H, while the other one is selected from the group consisting of $C_7$-$C_{24}$ aralkyl, and $C_6$-$C_{18}$ aryl, wherein the aryl is optionally substituted with a substituent selected from the group consisting of $C_2$-$C_6$ alkynyl, halogen, $C_7$-$C_{24}$ aralkyloxy, and $C_6$-$C_{24}$ heteroaralkyloxy.

6. The method of claim 1, wherein:

$R^1$ is selected from the group consisting of 4-(dimethylamino)-but-2-enamido, 4-(diethylamino)-but-2-enamido, 4-(piperidin-1-yl)-but-2-enamido, 4-(morpholin-4-yl)-but-2-enamido, 4-(tert-butylamino)-but-2-enamido, 4-(benzylamino)-but-2-enamido, 4-(N-methylbenzylamino)-but-2-enamido, 4-(6-hydroxyhexylamino)-but-2-enamido, 4-(2-methoxyethylamino)-but-2-enamido, 2-(piperidin-4-ylidene)acetamido, 2-(1-methylpiperidin-4-ylidene)acetamido, 2-(1-ethylpiperidin-4-ylidene)acetamide, 2-(1-(2-methoxyehtyl)piperdin-4-ylidene)acetamido, 4-(diethanolamino)-but-2-enamido, 4-(N-methyl-methoxylethylamino)-but-2-enamido, 4-(N-methyl-ethanolamino)-but-2-enamido, 4-(dimethoxylethyl-amino)-but-2-enamido, 4-(N-methyl-6-amino-1-hexanolyl)-but-2-enamido, acrylamido, but-2-enamido, 3-methyl-but-2-enamido, and 2-(pyrrolidin-3-ylidene)acetamido.

7. The method of claim 1, wherein:

$R^1$ is $C_2$-$C_6$ alkenylacylamino; and one of $R^2$ and $R^3$ is H, while the other one is $C_6$-$C_{18}$ aryl, wherein the aryl is optionally substituted with a substituent selected from the group consisting of halogen, $C_6$-$C_{24}$ heteroaralkyloxy, $C_2$-$C_6$ alkynyl, and $C_7$-$C_{24}$ aralkyloxy.

8. The method of claim 1, wherein:

$R^1$ is $C_2$-$C_6$ alkenylacylamino; and $R^2$ and $R^3$ together with nitrogen atom to which they are attached form substituted or unsubstituted $C_3$-$C_{18}$ heterocyclyl.

9. The method of claim 7, wherein:

$R^1$ is 2-(piperidin-4-ylidene)acetamide.

10. A method for treating tumor in a mammal, comprising administering to the mammal a therapeutically effective amount of a compound of formula I, or a pharmaceutically acceptable salt thereof,

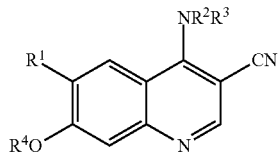

I wherein:

$R^1$ is $C_2$-$C_6$ alkenylacylamino;

one of $R^2$ and $R^3$ is H, while the other one is selected from the group consisting of $C_6$-$C_{18}$ aryl, and $C_5$-$C_{18}$ heteroaryl, wherein the aryl is optionally substituted with a substituent selected from the group consisting of $C_2$-$C_6$ alkynyl, halogen, $C_7$-$C_{24}$ aralkyloxy, and $C_6$-$C_{18}$ aryloxy, and wherein the heteroaryl is optionally substituted with a substituent selected from the group consisting of $C_7$-$C_{24}$ aralkyloxy, and $C_6$-$C_{18}$ aryloxy; and $R^4$ is hexahydropyridinyl optionally substituted with $C_1$-$C_6$ alkyl;

wherein the tumor is selected from the group consisting of sarcoma; sinus tumor; urogenital system cancer; esophageal cancer; liver cancer; kidney cancer; endocrine cancer; skin cancer; melanoma; and brain or central nervous system cancer.

11. The method of claim 10, wherein:

$R^1$ is 2-(piperidin-4-ylidene)acetamide; and one of $R^2$ and $R^3$ is H, while the other one is selected from the group consisting of $C_6$-$C_{18}$ aryl, and $C_5$-$C_{18}$ heteroaryl, wherein the aryl is optionally substituted with a substituent selected from the group consisting of $C_2$-$C_6$ alkynyl, halogen, $C_7$-$C_{24}$ aralkyloxy, and $C_6$-$C_{18}$ aryloxy, and wherein the heteroaryl is optionally substituted with $C_7$-$C_{24}$ aralkyloxy.

12. A method for treating tumor in a mammal, comprising administering to the mammal a therapeutically effective amount of a compound of formula I, or a pharmaceutically acceptable salt thereof,

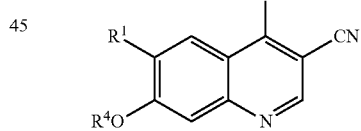

I wherein:

$R^1$ is $C_2$-$C_6$ alkenylacylamino;

one of $R^2$ and $R^3$ is H, while the other one is selected from the group consisting of $C_6$-$C_{18}$ aryl, $C_5$-$C_{18}$ heteroaryl, wherein the aryl is optionally substituted with substituent selected from the group consisting of $C_2$-$C_6$ alkynyl, halogen, $C_7$-$C_{24}$ aralkyloxy, $C_6$-$C_{24}$ heteroaralkyloxy, and $C_6$-$C_{18}$ aryloxy, and wherein the heteroaryl is optionally substituted with substituent selected from the group consisting of $C_7$-$C_{24}$ aralkyloxy and $C_6$-$C_{18}$ aryloxy; and $R^4$ is pyridinyl;

wherein the tumor is selected from the group consisting of sarcoma; sinus tumor; urogenital system cancer; esophageal cancer; liver cancer; kidney cancer; endocrine cancer; skin cancer; melanoma; and brain or central nervous system cancer.

13. The method of claim 12, wherein:
$R^1$ is 2-(piperidin-4-ylidene)acetamido; and
one of $R^2$ and $R^3$ is H, while the other one is selected from the group consisting of $C_6$-$C_{18}$ aryl, and $C_5$-$C_{18}$ heteroaryl, wherein the aryl is optionally substituted with a substituent selected from the group consisting of $C_2$-$C_6$ alkynyl, halogen, $C_7$-$C_{24}$ aralkyloxy, $C_6$-$C_{24}$ heteroaralkyloxy, and $C_6$-$C_{18}$ aryloxy, and wherein the heteroaryl is optionally substituted with a substituent selected from the group consisting of $C_7$-$C_{24}$ aralkyloxy, and $C_6$-$C_{18}$ aryloxy.

14. The method of claim 12, wherein:
$R^1$ is 2-(pyrrolidin-3-ylidene)acetamido; and
one of $R^2$ and $R^3$ is H, while the other one is $C_5$-$C_{18}$ heteroaryl substituted with $C_6$-$C_{18}$ aryloxy.

15. The method of claim 12, wherein:
$R^1$ is 4-(diethylamino)-but-2-eneamido, or 4-(dimethylamino)-but-2-enamido; and
one of $R^2$ and $R^3$ is H, while the other one is $C_6$-$C_{18}$ aryl substituted with halogen.

16. A method for treating tumor in a mammal, comprising administering to the mammal a therapeutically effective amount of a compound or a pharmaceutically acceptable salt thereof, selected from the group consisting of:

- (E)-4-bromo-N-(4-(3-chloro-4-(pyridin-2-yl-methoxy) phenylamino)-3-cyano-7-(tetrahydrofuran-3-yl-oxy) quinolin-6-yl)but-2-enamide;
- (E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-but-2-enamide;
- (E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-but-2-enamide hydrochloride;
- (E)-N-(4-(3-chloro-4-fluorophenylamino)-3-cyano-7-(tetrahydrofuran-3-yl-oxy)quinolin-6-yl)-4-(dimethylamino)-but-2-enamide;
- (E)-N-(3-cyano-4-(3-ethynylphenylamino)-7-(tetrahydrofuran-3-yl-oxy) quinolin-6-yl)-4-(dimethylamino)-but-2-enamide;
- (E)-N-(4-(4-(benzyloxy)phenylamino)-3-cyano-7-(tetrahydrofuran-3-yl-oxy) quinolin-6-yl)-4-(dimethylamino)-but-2-enamide;
- (E)-N-(4-(3-bromophenylamino)-3-cyano-7-(tetrahydrofuran-3-yl-oxy) quinolin-6-yl)-4-(dimethylamino)-but-2-enamide;
- (E)-N-(4-(4-(2-fluorobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(3-fluorobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(2-chlorobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(3-chlorobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(benzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(2-cyanobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(4-tert-butylbenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(3-cyanobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(4-chlorobenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(2-methylbenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(3-methylbenzyloxy)-3-chlorophenylamino)-3-cyano-7-(tetrahydrofuran-3-yl-oxy)quinolin-6-yl)-4-(dimethylamino)-but-2-enamide;
- (E)-N-(4-(4-(4-methylbenzyloxy)-3-chlorophenylamino)-3-cyano-7-(tetrahydrofuran-3-yl-oxy)quinolin-6-yl)-4-(dimethylamino)-but-2-enamide;
- (E)-N-3-cyano-4-((R)-1-phenylamino)-7-(tetrahydrofuran-3-yl-oxy)quinolin-6-yl)-4-(dimethylamino)-but-2-enamide;
- (E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-but-2-enamide;
- N-(4-(3-chloro-4-(pyridin-2-yl-methoxy)phenylamino)-3-cyano-7-(tetrahydrofuran-3-yl-oxy)quinolin-6-yl) acrylamide;
- (E)-N-(4-(3-chloro-4-(pyridin-2-yl-methoxy)phenylamino)-3-cyano-7-(tetrahydrofuran-3-yl-oxy)quinolin-6-yl)but-2-enamide;
- N-(4-(3-chloro-4-(pyridin-2-yl-methoxy)phenylamino)-3-cyano-7-(tetrahydrofuran-3-yl-oxy)quinolin-6-yl)-3-methylbut-2-enamide;
- N-(4-(3-chloro-4-(pyridin-2-yl-methoxy)phenylamino)-3-cyano-7-(tetrahydrofuran-3-yl-oxy)quinolin-6-yl) propiolamide;
- tert-butyl 4-(2-(4-(3-chloro-4-(pyridin-2-yl-methoxy) phenylamino)-3-cyano-7-(tetrahydrofuran-3-yl-oxy) quinolin-6-yl-amino)-2-oxoethylidene)piperidine-1-carboxylate;
- N-(4-(3-chloro-4-(pyridin-2-yl-methoxy)phenylamino)-3-cyano-7-(tetrahydrofuran-3-yl-oxy)quinolin-6-yl)-2-(piperidin-4-ylidene)acetamide;
- N-(4-(3-chloro-4-(pyridin-2-yl-methoxy)phenylamino)-3-cyano-7-(tetrahydrofuran-3-yl-oxy)quinolin-6-yl)-2-(1-methylpiperidin-4-ylidene)acetamide;
- N-(4-(3-chloro-4-(pyridin-2-yl-methoxy)phenylamino)-3-cyano-7-(tetrahydrofuran-3-yl-oxy)quinolin-6-yl)-2-(1-ethylpiperidin-4-ylidene)acetamide;
- 2-(1-benzylpiperidin-4-ylidene)-N-(4-(3-chloro-4-(pyridin-2-yl-methoxy) phenylamino)-3-cyano-7-(tetrahydrofuran-3-yl-oxy)quinolin-6-yl)acetamide;
- N-(4-(3-chloro-4-(pyridin-2-yl-methoxy)phenylamino)-3-cyano-7-(tetrahydrofuran-3-yl-oxy)quinolin-6-yl)-2-(1-(2-methoxyethyl)piperidin-4-ylidene)acetamide;
- methyl 2-(4-(2-(4-(3-chloro-4-(pyridin-2-yl-methoxy) phenylamino)-3-cyano-7-(tetrahydrofuran-3-yl-oxy) quinolin-6-yl-amino)-2-oxoethylidene)piperidin-1-yl) acetate;
- N-(4-(3-chloro-4-(pyridin-2-yl-methoxy)phenylamino)-3-cyano-7-(tetrahydrofuran-3-yl-oxy)quinolin-6-yl)-2-(1-isopropylpiperidin-4-ylidene)acetamide;
- N-(4-(3-chloro-4-(pyridin-2-yl-methoxy)phenylamino)-3-cyano-7-(tetrahydrofuran-3-yl-oxy)quinolin-6-yl)-2-(1-(2-hydroxyethyl)piperidin-4-ylidene) acetamide;
- (E/Z)—N-(4-(3-chloro-4-(pyridin-2-yl-methoxy)phenylamino)-3-cyano-7-(tetrahydrofuran-3-yl-oxy)quinolin-6-yl)-2-(pyrrolidin-3-ylidene)acetamide;

N$^1$-(4-(3-chloro-4-(pyridin-2-yl-methoxy)phenylamino)-3-cyano-7-(tetrahydrofuran-3-yl-oxy)quinolin-6-yl)-N$^4$-(2-(2-(dimethylamino)ethoxy)ethyl) fumaramide;

N-(4-(3-chloro-4-(pyridin-2-yl-methoxy)phenylamino)-3-cyano-7-(tetrahydrofuran-3-yl-oxy)quinolin-6-yl)-2-(1-(2-(2-(2-hydroxyethoxy)ethylamino)acetyl) piperidin-4-ylidene)acetamide;

N-(4-(3-chloro-4-(pyridin-2-yl-methoxy)phenylamino)-3-cyano-7-(tetrahydrofuran-3-yl-oxy)quinolin-6-yl)-2-(1-(methylsulfonyl)piperidin-4-ylidene) acetamide;

N-(4-(3-chloro-4-fluorophenylamino)-3-cyano-7-(tetrahydrofuran-3-yl-oxy) quinolin-6-yl)-2-(piperidin-4-ylidene)acetamide;

N-(3-cyano-4-(3-ethynylphenylamino)-7-(tetrahydrofuran-3-yl-oxy)quinolin-6-yl)-2-(piperidin-4-ylidene) acetamide;

N-(4-(3-bromophenylamino)-3-cyano-7-(tetrahydrofuran-3-yl-oxy)quinolin-6-yl)-2-(piperidin-4-ylidene) acetamide;

N-(4-(4-(2-fluorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-fluorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-fluorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(2-chlorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-chlorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-chlorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(2-methylbenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-methylbenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-methylbenzyloxy)-3-chlorophenylamino)-3-cyano-7-(tetrahydrofuran-3-yl-oxy)quinolin-6-yl)-2-(piperidin-4-ylidene)acetamide;

N-(4-(4-(2-methoxybenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-methoxybenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-methoxybenzyloxy)-3-chlorophenylamino)-3-cyano-7-(tetrahydrofuran-3-yl-oxy)quinolin-6-yl)-2-(piperidin-4-ylidene)acetamide;

N-(4-(4-(2-cyanobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-cyanobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-cyanobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-tert-butylbenzyloxy)-3-chlorophenylamino)-3-cyano-7-(tetrahydrofuran-3-yl-oxy)quinolin-6-yl)-2-(piperidin-4-ylidene)acetamide;

N-(4-(4-(benzyloxy)-3-chlorophenylamino)-3-cyano-7-(tetrahydrofuran-3-yl-oxy)quinolin-6-yl)-2-(piperidin-4-ylidene)acetamide;

N-(4-(4-(2-chlorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(3-chlorobenzyloxy)-3-chlorophenylamino)-3-cyano-7-(tetrahydrofuran-3-yl-oxy)quinolin-6-yl)-2-(piperidin-4-ylidene)acetamide;

N-(4-(4-(4-chlorobenzyloxy)-3-chlorophenylamino)-3-cyano-7-(tetrahydrofuran-3-yl-oxy)quinolin-6-yl)-2-(piperidin-4-ylidene)acetamide;

N-(3-cyano-4-((S)-1-phenylethylamino)-7-(tetrahydrofuran-3-yl-oxy)quinolin-6-yl)-2-(piperidin-4-ylidene) acetamide;

N-(3-cyano-4-((R)-1-phenylethylamino)-7-(tetrahydrofuran-3-yl-oxy) quinolin-6-yl)-2-(piperidin-4-ylidene) acetamide;

N-(4-(1-benzyl-1H-indol-5-yl-amino)-3-cyano-7-(tetrahydrofuran-3-yl-oxy) quinolin-6-yl)-2-(piperidin-4-ylidene)acetamide;

N-(4-(1-(3-cyanobenzyl)-1H-indol-5-yl-amino)-3-cyano-7-(tetrahydrofuran-3-yl-oxy)quinolin-6-yl)-2-(piperidin-4-ylidene)acetamide;

N-(4-(1-(3-methoxybenzyl)-1H-indol-5-yl-amino)-3-cyano-7-(tetrahydrofuran-3-yl-oxy)quinolin-6-yl)-2-(piperidin-4-ylidene)acetamide;

N-(4-(1-(3-chlorobenzyl)-1H-indol-5-yl-amino)-3-cyano-7-(tetrahydrofuran-3-yl-oxy)quinolin-6-yl)-2-(piperidin-4-ylidene)acetamide;

N-(3-cyano-4-(indolin-1-yl)-7-(tetrahydrofuran-3-yl-oxy)quinolin-6-yl)-2-(piperidin-4-ylidene)acetamide;

N-(4-(6-chloroindolin-1-yl)-3-cyano-7-(tetrahydrofuran-3-yl-oxy)quinolin-6-yl)-2-(piperidin-4-ylidene)acetamide;

N-(3-cyano-4-(6-fluoroindolin-1-yl)-7-(tetrahydrofuran-3-yl-oxy)quinolin-6-yl)-2-(piperidin-4-ylidene)acetamide;

N-(4-(4-chloroindolin-1-yl)-3-cyano-7-(tetrahydrofuran-3-yl-oxy)quinolin-6-yl)-2-(piperidin-4-ylidene)acetamide;

N-(3-cyano-4-(3,4-dihydroquinolin-1 (2H)-yl)-7-(tetrahydrofuran-3-yl-oxy) quinolin-6-yl)-2-(piperidin-4-ylidene)acetamide;

N-(3-cyano-4-(6-methyl-3,4-dihydroquinolin-1 (2H)-yl)-7-(tetrahydrofuran-3-yl-oxy)quinolin-6-yl)-2-(piperidin-4-ylidene)acetamide;

N-(3-cyano-7-(tetrahydrofuran-3-yl-oxy)-4-(7-(trifluoromethyl)-3,4-dihydroquinolin-1 (2H)-yl)-quinolin-6-yl)-2-(piperidin-4-ylidene)acetamide;

N-(4-(6-(benzyl oxy)indolin-1-yl)-3-cyano-7-(tetrahydrofuran-3-yl-oxy) quinolin-6-yl)-2-(piperidin-4-ylidene)acetamide;

methyl 1-(3-cyano-6-(2-(piperidin-4-ylidene)acetamido)-7-(tetrahydrofuran-3-yl-oxy)quinolin-4-yl)-indoline-2-carboxylate;

N-(3-cyano-4-(2-(hydroxymethyl)indolin-1-yl)-7-(tetrahydrofuran-3-yl-oxy) quinolin-6-yl)-2-(piperidin-4-ylidene)acetamide;

N-(4-(6-(1H-pyrrol-1-yl)indolin-1-yl)-3-cyano-7-(tetrahydrofuran-3-yl-oxy) quinolin-6-yl)-2-(piperidin-4-ylidene)acetamide;

N-(3-cyano-4-(octahydroindol-1-yl)-7-(tetrahydrofuran-3-yl-oxy)quinolin-6-yl)-2-(piperidin-4-ylidene)acetamide;

N-(3-cyano-4-(pyrimidin-2-yl-amino)-7-(tetrahydrofuran-3-yl-oxy)quinolin-6-yl)-2-(piperidin-4-ylidene)acetamide;
N-(2-(3-cyano-6-(2-(piperidin-4-ylidene)acetamido)-7-(tetrahydrofuran-3-yl-oxy)quinolin-4-yl-amino)pyrimidin-5-yl)benzamide;
N-(2-(3-cyano-6-(2-(piperidin-4-ylidene)acetamido)-7-(tetrahydrofuran-3-yl-oxy)quinolin-4-yl-amino)pyrimidin-5-yl)-4-(dimethylamino)benzamide;
N-(3-cyano-4-(5-(phenylsulfonamido)pyrimidin-2-yl-amino)-7-(tetrahydrofuran-3-yl-oxy)quinolin-6-yl)-2-(piperidin-4-ylidene)acetamide;
N-(5-(3-cyano-6-(2-(piperidin-4-ylidene)acetamido)-7-(tetrahydrofuran-3-yl-oxy)quinolin-4-yl-amino)pyrimidin-2-yl)benzamide;
N-(5-(3-cyano-6-(2-(piperidin-4-ylidene)acetamido)-7-(tetrahydrofuran-3-yl-oxy)quinolin-4-yl-amino)pyrimidin-2-yl)furan-2-carboxamide;
N-(5-(3-cyano-6-(2-(piperidin-4-ylidene)acetamido)-7-(tetrahydrofuran-3-yl-oxy)quinolin-4-yl-amino)pyrimidin-2-yl)thiophene-2-carboxamide;
N-(5-(3-cyano-6-(2-(piperidin-4-ylidene)acetamido)-7-(tetrahydrofuran-3-yl-oxy)quinolin-4-yl-amino)pyrimidin-2-yl)cyclohexylcarboxamide;
5-(3-cyano-6-(2-(piperidin-4-ylidene)acetamido)-7-(tetrahydrofuran-3-yl-oxy)quinolin-4-yl-amino)-N-(4-methoxyphenyl)pyrimidin-2-carboxamide;
N-(3-cyano-4-(pyridin-2-yl-amino)-7-(tetrahydrofuran-3-yl-oxy)quinolin-6-yl)-2-(piperidin-4-ylidene)acetamide;
6-(3-cyano-6-(2-(piperidin-4-ylidene)acetamido)-7-(tetrahydrofuran-3-yl-oxy)quinolin-4-yl-amino)-N-(4-methoxyphenyl)nicotinamide;
N-(3-cyano-4-(pyridin-3-yl-amino)-7-(tetrahydrofuran-3-yl-oxy)quinolin-6-yl)-2-(piperidin-4-ylidene)acetamide;
N-(3-cyano-4-(pyridin-4-yl-amino)-7-(tetrahydrofuran-3-yl-oxy)quinolin-6-yl)-2-(piperidin-4-ylidene)acetamide;
N-(4-(6-(benzyloxy)pyridin-3-yl-amino)-3-cyano-7-(tetrahydrofuran-3-yl-oxy)quinolin-6-yl)-2-(piperidin-4-ylidene)acetamide;
N-(3-cyano-4-(pyrazin-2-yl-amino)-7-(tetrahydrofuran-3-yl-oxy)quinolin-6-yl)-2-(piperidin-4-ylidene)acetamide;
N-(4-(3-chloro-4-fluorophenylamino)-3-cyano-7-(1-methylpiperidin-4-yl-oxy)quinolin-6-yl)-2-(piperidin-4-ylidene)acetamide;
N-(3-cyano-4-(3-ethynylphenylamino)-7-(1-methylpiperidin-4-yl-oxy) quinolin-6-yl)-2-(piperidin-4-ylidene)acetamide;
N-(4-(4-(benzyloxy)-3-chlorophenylamino)-3-cyano-7-(1-methylpiperidin-4-yl-oxy)quinolin-6-yl)-2-(piperidin-4-ylidene)acetamide;
N-(4-(4-(2-chlorobenzyloxy)-3-chlorophenylamino)-3-cyano-7-(1-methylpiperidin-4-yl-oxy)quinolin-6-yl)-2-(piperidin-4-ylidene)acetamide;
N-(4-(4-(3-chlorobenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-chlorobenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-bromobenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-methylbenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-methoxybenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-cyanobenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-ethylbenzyloxy)-3-chlorophenylamino)-3-cyano-7-(1-methylpiperidin-4-yl-oxy)quinolin-6-yl)-2-(piperidin-4-ylidene)acetamide;
N-(4-(4-(4-ethoxybenzyloxy)-3-chlorophenylamino)-3-cyano-7-(1-methylpiperidin-4-yl-oxy)quinolin-6-yl)-2-(piperidin-4-ylidene)acetamide;
N-(4-(3-chloro-4-phenoxyphenylamino)-3-cyano-7-(1-methylpiperidin-4-yl-oxy)quinolin-6-yl)-2-(piperidin-4-ylidene)acetamide;
N-(3-cyano-7-(1-methylpiperidin-4-yl-oxy)-4-(pyridin-2-yl-amino)quinolin-6-yl)-2-(piperidin-4-ylidene)acetamide;
N-(3-cyano-7-(1-methylpiperidin-4-yl-oxy)-4-(pyridin-3-yl-amino)quinolin-6-yl)-2-(piperidin-4-ylidene)acetamide;
N-(3-cyano-7-(1-methylpiperidin-4-yl-oxy)-4-(pyridin-4-yl-amino)quinolin-6-yl)-2-(piperidin-4-ylidene)acetamide;
N-(4-(6-(benzyloxy)pyridin-3-yl-amino)-3-cyano-7-(1-methylpiperidin-4-yl-oxy)quinolin-6-yl)-2-(piperidin-4-ylidene)acetamide;
N-(4-(3-chloro-4-fluorophenylamino)-3-cyano-7-(pyridin-4-yl-oxy)quinolin-6-yl)-2-(piperidin-4-ylidene)acetamide;
N-(3-cyano-4-(3-ethynylphenylamino)-7-(pyridin-4-yl-oxy)quinolin-6-yl)-2-(piperidin-4-ylidene)acetamide;
N-(3-cyano-4-(4-phenoxyphenylamino)-7-(pyridin-4-yl-oxy)quinolin-6-yl)-2-(piperidin-4-ylidene)acetamide;
N-(4-(4-(benzyloxy)phenylamino)-3-cyano-7-(pyridin-4-yl-oxy)quinolin-6-yl)-2-(piperidin-4-ylidene)acetamide;
N-(4-(4-(2-chlorobenzyloxy)-3-chlorophenylamino)-3-cyano-7-(pyridin-4-yl-oxy)quinolin-6-yl)-2-(piperidin-4-ylidene)acetamide;
N-(4-(4-(4-methylbenzyloxy)-3-chlorophenylamino)-3-cyano-7-(pyridin-4-yl-oxy)quinolin-6-yl)-2-(piperidin-4-ylidene)acetamide;
N-(4-(4-(4-methoxybenzyloxy)phenylamino)-3-cyano-7-(pyridin-4-yl-oxy) quinolin-6-yl)-2-(piperidin-4-ylidene)acetamide;
N-(4-(4-(3-cyanobenzyloxy)-3-chlorophenylamino)-3-cyano-7-(pyridin-4-yl-oxy)quinolin-6-yl)-2-(piperidin-4-ylidene)acetamide;
N-(3-cyano-4-(pyridine-2-yl-amino)-7-(pyridin-4-yl-oxy)quinolin-6-yl)-2-(piperidin-4-ylidene)acetamide;
N-(3-cyano-7-(pyridin-4-yl-oxy)-4-(pyrimidin-2-yl-amino)quinolin-6-yl)-2-(piperidin-4-ylidene)acetamide;
N-(4-(6-(benzyloxy)pyridin-3-yl-amino)-3-cyano-7-(pyridin-4-yl-oxy) quinolin-6-yl)-2-(piperidin-4-ylidene)acetamide;
N-(4-(6-(3-chlorobenzyloxy)pyridin-3-yl-amino)-3-cyano-7-(pyridin-4-yl-oxy)quinolin-6-yl)-2-(piperidin-4-ylidene)acetamide;
N-(3-cyano-4-(6-(phenoxypyridin-3-yl-amino)-7-(pyridin-4-yl-oxy)quinolin-6-yl)-2-(piperidin-4-ylidene)acetamide;

N-(4-(3-chloro-4-(pyridine-2-yl-methoxy)phenylamino)-3-cyano-7-(pyridin-4-yl-oxy)quinolin-6-yl)-2-(piperidin-4-ylidene)acetamide;

(E/Z)—N-(3-cyano-4-(6-(phenoxypyridin-3-yl-amino)-7-(pyridin-4-yl-oxy) quinolin-6-yl)-2-(pyrrolidin-3-ylidene)acetamide;

(E/Z)—N-(3-cyano-7-(1-methylpiperidin-4-yl-oxy)-4-(6-(phenoxypyridin-3-yl-amino)quinolin-6-yl)-2-(pyrrolidin-3-ylidene)acetamide;

(E/Z)—N-(3-cyano-4-(6-(phenoxypyridin-3-yl-amino)-7-(tetrahydrofuran-3-yl-oxy)quinolin-6-yl)-2-(pyrrolidin-3-ylidene)acetamide;

(S,E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-but-2-enamide;

(R,E)-N-(4-(3-chloro-4-(pyridin-2-yl-methoxy)phenylamino)-3-cyano-7-(tetrahydrofuran-3-yl-oxy)quinolin-6-yl)-4-(dimethylamino)-but-2-enamide;

(S,E)-N-(3-cyano-4-(3-ethynylphenylamino)-7-(tetrahydrofuran-3-yl-oxy) quinolin-6-yl)-4-(dimethylaimino)-but-2-enamide;

(R,E)-N-(3-cyano-4-(3-ethynylphenylamino)-7-(tetrahydrofuran-3-yl-oxy) quinolin-6-yl)-4-(dimethylaimino)-but-2-enamide;

(S,E)-N-(4-(3-chloro-4-fluorophenylamino)-3-cyano-7-(tetrahydrofuran-3-yl-oxy)quinolin-6-yl)-4-(dimethylamino)-but-2-enamide;

(S,E)-N-(3-cyano-4-(3-ethynylphenylamino)-7-(tetrahydrofuran-3-yl-oxy) quinolin-6-yl)-4-(diethylamino)-but-2-enamide;

(S,E)-N-(3-cyano-4-(3-ethynylphenylamino)-7-(tetrahydrofuran-3-yl-oxy) quinolin-6-yl)-4-(piperidin-1-yl)-but-2-enamide;

(S,E)-N-(3-cyano-4-(3-ethynylphenylamino)-7-(tetrahydrofuran-3-yl-oxy) quinolin-6-yl)-4-(morpholin-4-yl)-but-2-enamide;

(S,E)-N-(3-cyano-4-(3-ethynylphenylamino)-7-(tetrahydrofuran-3-yl-oxy) quinolin-6-yl)-4-(tert-butylaimino)-but-2-enamide;

(S,E)-N-(3-cyano-4-(3-ethynylphenylamino)-7-(tetrahydrofuran-3-yl-oxy) quinolin-6-yl)-4-(benzylamino)-but-2-enamide;

(S,E)-N-(3-cyano-4-(3-ethynylphenylamino)-7-(tetrahydrofuran-3-yl-oxy) quinolin-6-yl)-4-(6-hydroxyhexylaimino)-but-2-enamide;

(S,E)-N-(3-cyano-4-(3-ethynylphenylamino)-7-(tetrahydrofuran-3-yl-oxy) quinolin-6-yl)-4-(N-methylbenzylamino)-but-2-enamide;

(S,E)-N-(4-(3-chloro-4-(pyridin-2-yl-methoxy)phenylamino)-3-cyano-7-(tetrahydrofuran-3-yl-oxy)quinolin-6-yl)-4-(diethylamino)-but-2-enamide;

(S,E)-N-(4-(3-chloro-4-(pyridin-2-yl-methoxy)phenylamino)-3-cyano-7-(tetrahydrofuran-3-yl-oxy)quinolin-6-yl)-4-(piperidin-1-yl)-but-2-enamide;

(S,E)-N-(4-(3-chloro-4-(pyridin-2-yl-methoxy)phenylamino)-3-cyano-7-(tetrahydrofuran-3-yl-oxy)quinolin-6-yl)-4-(morpholin-4-yl)-but-2-enamide;

(S,E)-N-(4-(3-chloro-4-(pyridin-2-yl-methoxy)phenylamino)-3-cyano-7-(tetrahydrofuran-3-yl-oxy)quinolin-6-yl)-4-(tert-butylamino)-but-2-enamide;

(S,E)-N-(4-(3-chloro-4-(pyridin-2-yl-methoxy)phenylamino)-3-cyano-7-(tetrahydrofuran-3-yl-oxy)quinolin-6-yl)-4-(6-hydroxyhexylamino)-but-2-enamide;

(S,E)-N-(4-(4-(benzyloxy)phenylamino)-3-cyano-7-(tetrahydrofuran-3-yl-oxy)quinolin-6-yl)-4-(dimethylamino)-but-2-enamide;

(S,E)-N-(4-(3-bromophenylamino)-3-cyano-7-(tetrahydrofuran-3-yl-oxy) quinolin-6-yl)-4-(dimethylamino)-but-2-enamide;

(S,E)-N-(4-(4-(2-fluorobenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(3-fluorobenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(2-chlorobenzyloxy)-3-chlorophenylamino)-3-cyano-7-(tetrahydrofuran-3-yl-oxy)quinolin-6-yl)-4-(dimethylaimino)-but-2-enamide;

(S,E)-N-(4-(4-(3-chlorobenzyloxy)-3-chlorophenylamino)-3-cyano-7-(tetrahydrofuran-3-yl-oxy)quinolin-6-yl)-4-(dimethylaimino)-but-2-enamide;

(S,E)-N-(4-(4-(benzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(2-cyanobenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(4-tert-butylbenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(3-cyanobenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(4-chlorobenzyloxy)-3-chlorophenylamino)-3-cyano-7-(tetrahydrofuran-3-yl-oxy)quinolin-6-yl)-4-(dimethylaimino)-but-2-enamide;

(S,E)-N-(4-(4-(2-methylbenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(4-(4-methylbenzyloxy)-3-chlorophenylamino)-3-cyano-7-(tetrahydrofuran-3-yl-oxy)quinolin-6-yl)-4-(dimethylamino)-but-2-enamide;

(S,E)-N-(4-(3-chloro-4-fluorophenylamino)-3-cyano-7-(tetrahydrofuran-3-yl-oxy)quinolin-6-yl)-4-(diethylamino)-but-2-enamide;

(S,E)-N-(4-(3-chloro-4-fluorophenylamino)-3-cyano-7-(tetrahydrofuran-3-yl-oxy)quinolin-6-yl)-4-(piperidin-1-yl)-but-2-enamide;

(S,E)-N-(4-(3-chloro-4-fluorophenylamino)-3-cyano-7-(tetrahydrofuran-3-yl-oxy)quinolin-6-yl)-4-(morpholin-4-yl)-but-2-enamide;

(S,E)-N-(4-(4-(3-fluorobenzyloxy)-3-chlorophenylamino)-3-cyano-7-(tetrahydrofuran-3-yl-oxy)quinolin-6-yl)-4-(diethylamino)-but-2-enamide;

(S,E)-N-(4-(4-(3-fluorobenzyloxy)-3-chlorophenylamino)-3-cyano-7-(tetrahydrofuran-3-yl-oxy)quinolin-6-yl)-4-(piperidin-1-yl)-but-2-enamide;

(S,E)-N-(4-(4-(3-fluorobenzyloxy)-3-chlorophenylamino)-3-cyano-7-(tetrahydrofuran-3-yl-oxy)quinolin-6-yl)-4-(morpholin-4-yl)-but-2-enamide;

(E)-N-(4-(3-chloro-4-fluorophenylamino)-3-cyano-7-(pyridin-3-yl-oxy) quinolin-6-yl)4-(dimethylamino)-but-2-enamide;

(E/Z)—N-(4-(3-chloro-4-(pyridin-2-yl-methoxy)phenylamino)-3-cyano-7-(tetrahydrofuran-3-yl-oxy)quinolin-6-yl)-4-(dimethylaimino)-but-2-enamide;

(E/Z)—N-(4-(3-chloro-4-fluorophenylamino)-3-cyano-7-(tetrahydrofuran-3-yl-oxy)quinolin-6-yl)-4-(dimethylamino)-but-2-enamide;

(E/Z)—N-(3-cyano-4-(3-ethynylphenylamino)-7-(tetrahydrofuran-3-yl-oxy) quinolin-6-yl)-4-(dimethylaimino)-but-2-enamide;

(E/Z)—N-(4-(4-(benzyloxy)phenylamino)-3-cyano-7-(tetrahydrofuran-3-yl-oxy)quinolin-6-yl)-4-(dimethylaimino)-but-2-enamide;
(E/Z)—N-(4-(3-bromophenylamino)-3-cyano-7-(tetrahydrofuran-3-yl-oxy) quinolin-6-yl)-4-(dimethylamino)-but-2-enamide;
(E/Z)—N-(4-(4-(3-fluorobenzyloxy)-3-chlorophenylamino)-3-cyano-7-(tetrahydrofuran-3-yl-oxy)quinolin-6-yl)-4-(dimethylamino)-but-2-enamide;
(S,E/Z)—N-(3-cyano-4-(3-ethynylphenylamino)-7-(tetrahydrofuran-3-yl-oxy) quinolin-6-yl)-4-(diethylamino)-but-2-enamide;
(S,E/Z)—N-(3-cyano-4-(3-ethynylphenylamino)-7-(tetrahydrofuran-3-yl-oxy) quinolin-6-yl)-4-(piperidin-1-yl)-but-2-enamide;
(S,E/Z)—N-(3-cyano-4-(3-ethynylphenylamino)-7-(tetrahydrofuran-3-yl-oxy) quinolin-6-yl)-4-(morpholin-4-yl)-but-2-enamide;
(S,E/Z)—N-(4-(3-chloro-4-(pyridin-2-yl-methoxy)phenylamino)-3-cyano-7-(tetrahydrofuran-3-yl-oxy)quinolin-6-yl)-4-(diethylamino)-but-2-enamide;
(S,E/Z)—N-(4-(3-chloro-4-(pyridin-2-yl-methoxy)phenylamino)-3-cyano-7-(tetrahydrofuran-3-yl-oxy)quinolin-6-yl)-4-(piperidin-1-yl)-but-2-enamide;
(S,E/Z)—N-(4-(3-chloro-4-(pyridin-2-yl-methoxy)phenylamino)-3-cyano-7-(tetrahydrofuran-3-yl-oxy)quinolin-6-yl)-4-(morpholin-4-yl)-but-2-enamide;
(S,E/Z)—N-(4-(3-chloro-4-(pyridin-2-yl-methoxy)phenylamino)-3-cyano-7-(tetrahydrofuran-3-yl-oxy)quinolin-6-yl)-4-(2-methoxyethylamino)-but-2-enamide;
(S,E)-N-(3-cyano-4-(3-ethynylphenylamino)-7-(tetrahydrofuran-3-yl-oxy) quinolin-6-yl)-4-(diethanolamino)-but-2-enamide
(S,E)-N-(3-cyano-4-(3-ethynylphenylamino)-7-(tetrahydrofuran-3-yl-oxy) quinolin-6-yl)-4-(N-methylmethoxyethylamino)-but-2-enamide;
(S,E)-N-(3-cyano-4-(3-ethynylphenylamino)-7-(tetrahydrofuran-3-yl-oxy) quinolin-6-yl)-4-(N-methylethanolamino)-but-2-enamide;
(S,E)-N-(3-cyano-4-(3-ethynylphenylamino)-7-(tetrahydrofuran-3-yl-oxy) quinolin-6-yl)-4-(dimethoxyethylamino)-but-2-enamide;
(S,E)-N-(3-cyano-4-(3-ethynylphenylamino)-7-(tetrahydrofuran-3-yl-oxy) quinolin-6-yl)-4-(N-methyl-6-amino-1-hexanolyl)-but-2-enamide;
(S,E)-N-(3-cyano-4-(3-chloro-4-fluoro-phenylamino)-7-(tetrahydrofuran-3-yl-oxy)quinolin-6-yl)-4-(diethanolamino)-but-2-enamide;
(S,E)-N-(3-cyano-4-(3-chloro-4-fluoro-phenylamino)-7-(tetrahydrofuran-3-yl-oxy)quinolin-6-yl)-4-(N-methylmethoxyethylamino)-but-2-enamide;
(S,E)-N-(3-cyano-4-(3-chloro-4-fluoro-phenylamino)-7-(tetrahydrofuran-3-yl-oxy)quinolin-6-yl)-4-(N-methylethanolamino)-but-2-enamide;
(S,E)-N-(3-cyano-4-(3-chloro-4-fluoro-phenylamino)-7-(tetrahydrofuran-3-yl-oxy)quinolin-6-yl)-4-(dimethoxyethylamino)-but-2-enamide;
(S,E)-N-(3-cyano-4-(3-chloro-4-fluoro-phenylamino)-7-(tetrahydrofuran-3-yl-oxy)quinolin-6-yl)-4-(N-methyl-6-amino-1-hexanolyl)-but-2-enamide;
(S,E)-N-(3-cyano-4-(4-(3-fluorobenzyloxy)-3-chlorophenylamino)-7-(tetrahydrofuran-3-yl-oxy)quinolin-6-yl)-4-(diethanolamino)-but-2-enamide;
(S,E)-N-(3-cyano-4-(4-(3-fluorobenzyloxy)-3-chlorophenylamino)-7-(tetrahydrofuran-3-yl-oxy)quinolin-6-yl)-4-(N-methylmethoxyethylamino)-but-2-enamide;
(S,E)-N-(3-cyano-4-(4-(3-fluorobenzyloxy)-3-chlorophenylamino)-7-(tetrahydrofuran-3-yl-oxy)quinolin-6-yl)-4-(N-methylethanolamino)-but-2-enamide;
(S,E)-N-(3-cyano-4-(4-(3-fluorobenzyloxy)-3-chlorophenylamino)-7-(tetrahydrofuran-3-yl-oxy)quinolin-6-yl)-4-(dimethoxyethylamino)-but-2-enamide;
(S,E)-N-(3-cyano-4-(4-(3-fluorobenzyloxy)-3-chlorophenylamino)-7-(tetrahydrofuran-3-yl-oxy)quinolin-6-yl)-4-(N-methyl-6-amino-1-hexanolyl)-but-2-enamide;
(S,E)-N-(3-cyano-4-(3-chloro-4-(pyridin-2-yl-methoxy) phenylamino)-7-(tetrahydrofuran-3-yl-oxy)quinolin-6-yl)-4-(diethanolamino)-but-2-enamide;
(S,E)-N-(3-cyano-4-(3-chloro-4-(pyridin-2-yl-methoxy) phenylamino)-7-(tetrahydrofuran-3-yl-oxy)quinolin-6-yl)-4-(N-methylmethoxyethylamino)-but-2-enamide;
(S,E)-N-(3-cyano-4-(3-chloro-4-(pyridin-2-yl-methoxy) phenylamino)-7-(tetrahydrofuran-3-yl-oxy)quinolin-6-yl)-4-(N-methylethanolamino)-but-2-enamide;
(S,E)-N-(3-cyano-4-(3-chloro-4-(pyridin-2-yl-methoxy) phenylamino)-7-(tetrahydrofuran-3-yl-oxy)quinolin-6-yl)-4-(dimethoxyethylamino)-but-2-enamide; and
(S,E)-N-(3-cyano-4-(3-chloro-4-(pyridin-2-yl-methoxy) phenylamino)-7-(tetrahydrofuran-3-yl-oxy)quinolin-6-yl)-4-(N-methyl-6-amino-1-hexanol)-but-2-enamide;
wherein the tumor is selected from the group consisting of sarcoma; sinus tumor; urogenital system cancer; esophageal cancer; liver cancer; kidney cancer; endocrine cancer; skin cancer; melanoma; and brain or central nervous system cancer.

17. The method of claim 1, wherein the stereoisomer is a cis-trans-isomer.

18. The method of any one of claims 1, 10, 12, and 16, wherein the sarcoma is selected from the group consisting of osteosarcoma, angiosarcoma, and fibrosarcoma.

19. The method of any one of claims 1, 10, 12, and 16, wherein the urogenital system cancer is selected from the group consisting of ureter cancer, bladder cancer, and prostate cancer.

20. The method of any one of claims 1, 10, 12, and 16, wherein the central nervous system cancer is glioma.

* * * * *